(12) United States Patent
Dushin et al.

(10) Patent No.: US 10,967,068 B2
(45) Date of Patent: Apr. 6, 2021

(54) STABILITY-MODULATING LINKERS FOR USE WITH ANTIBODY DRUG CONJUGATES

(71) Applicants: PFIZER INC., New York, NY (US); RINAT NEUROSCIENCE CORP., South San Franciso, CA (US)

(72) Inventors: Russell George Dushin, Old Lyme, CT (US); Pavel Strop, San Mateo, CA (US); Magdalena Grazyna Dorywalska, Redwood City, CA (US); Ludivine Moine, Uncasville, CT (US)

(73) Assignees: PFIZER INC., New York, NY (US); RINAT NEUROSCIENCE CORP., New York, NY (US)

( * ) Notice: Subject to any disclaimer, the term of this patent is extended or adjusted under 35 U.S.C. 154(b) by 247 days.

(21) Appl. No.: 15/504,801

(22) PCT Filed: Aug. 14, 2015

(86) PCT No.: PCT/IB2015/056211
§ 371 (c)(1),
(2) Date: Feb. 17, 2017

(87) PCT Pub. No.: WO2016/030791
PCT Pub. Date: Mar. 3, 2016

(65) Prior Publication Data
US 2018/0140714 A1 May 24, 2018

Related U.S. Application Data

(60) Provisional application No. 62/042,901, filed on Aug. 28, 2014.

(51) Int. Cl.
*A61K 47/65* (2017.01)
*A61K 47/64* (2017.01)
*A61K 47/68* (2017.01)
*A61K 39/00* (2006.01)

(52) U.S. Cl.
CPC .............. *A61K 47/65* (2017.08); *A61K 47/64* (2017.08); *A61K 47/6803* (2017.08); *A61K 2039/505* (2013.01); *C07K 2317/94* (2013.01); *C07K 2319/01* (2013.01); *C07K 2319/35* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,500,362 A | 3/1996 | Robinson et al. | |
| 5,663,149 A | 9/1997 | Pettit et al. | |
| 5,821,337 A | 10/1998 | Carter et al. | |
| 6,214,345 B1 | 4/2001 | Firestone et al. | |
| 7,754,681 B2 | 7/2010 | Feng | |
| 2013/0122020 A1 | 5/2013 | Liu et al. | |
| 2013/0129753 A1 | 5/2013 | Doroski et al. | |
| 2013/0230543 A1 | 9/2013 | Pons | |

FOREIGN PATENT DOCUMENTS

| | | | |
|---|---|---|---|
| CN | 101837130 A | | 9/2010 |
| EP | 0 081 783 | * | 2/1983 |
| WO | 9852976 | | 11/1998 |
| WO | 0034317 | | 6/2000 |
| WO | 2012059882 A2 | | 5/2012 |
| WO | WO2012-059882 | * | 10/2012 |
| WO | 2013068946 A2 | | 5/2013 |
| WO | 2015/015401 A9 | | 2/2015 |
| WO | 2015015448 A2 | | 2/2015 |
| WO | 2015110935 A1 | | 7/2015 |

OTHER PUBLICATIONS

Greene et al. (Protective groups in organic synthesis, Third Edition, copywright 1999).*
Bloom et al., "Intrachain disulfide bond in the core hinge region of human IgG4.", Protein Science, 1997, 6: 407-415.
Boger et al., "CC-1065 and the duocarmycins: Unraveling the keys to a new class of naturally derived DNA alkylating agents.", Proc. Natl. Acad., Sci., 1995, 92: 3642-3649.
Capel et al., "Heterogeneity of Human IgG Fc Receptors." Immunomethods, 1994, 4: 25-34.
Chari et al., "Antibody-Drug Conjugates: An Emerging Concept in Cancer Therapy." Angew. Chem. Int. Ed., 2014, 53: 3796-3827.
Clynes et al., "Fc receptors are required in passive and active immunity to melanoma." Proc. Natl. Acad. Sci., 1998, 95: 652-656.
DeHaas et al., "FCγ receptors of phagocytes." J Lab Clin Med, 1995, 126, 4: 330-341.
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity." Bioconjugate Chem., 2002, 13:855-869.
Edelman et al., "The Cobalent Structure of an Entire γG Immunoglobulin Molecule*." Biochemistry, 1969, 63: 78-85.
Farias et al., "Mass Spectrometric Characterization of Transglutaminase Based Site-Specific Antibody-Drug Conjugates." Bioconjugate Chemistry, 2014, 25: 240-250.
Gazzano-Santoro et al., "A non-radioactive complement-dependent cytotoxicity assay for anti-CD20 monoclonal antibody." Journal of Immunological Methods, 1997, 202: 163-171.
Guyer et al., "Immunoglobulin Binding by Mouse Intestinal Epithelial Cell Receptors." Journal of Immunology, 1976, 117: 587-593.

(Continued)

*Primary Examiner* — James H Alstrum-Acevedo
*Assistant Examiner* — Tara L Martinez
(74) *Attorney, Agent, or Firm* — Pfizer Inc.

(57) ABSTRACT

The present invention provides stability-modulated antibody-drug conjugates, stability-modulating linker components used to make these stability-modulated antibody-drug conjugates, therapeutic methods using stability-modulated antibody-drug conjugates, and methods of making stability modulating linkers and stability-modulated antibody-drug conjugates.

2 Claims, 10 Drawing Sheets

Specification includes a Sequence Listing.

(56) References Cited

OTHER PUBLICATIONS

Harris, "Production of humanized monoclonal antibodies for in vivo imaging and therapy." Biochemical Society Transactions, 1995, 23, 1035-1038.
Humphreys et al., "Formation of dimeric Fabs in *Escherichia coli*: effect of hinge size and isotype, presence of interchain disulphide bond, Fab' expression levels, tail piece sequences and growth conditions." Journal of Immunological Methods, 1997, 209: 193-202.
Hurle et al., "Protein engineering techniques for antibody humanization." Current Opinion in Biotechnology, 1994, 5: 428-433.
Jones et al., "Replacing the complementarity-determining regions in a human antibody with those from a mouse." Nature, 1986, 321: 522-525.
Kostelny et al., "Formation of a bispecific antibody by the use of leucine zippers." Journal of Immunology, 1992, 148: 1547-1553.
Lambert, "Drug-conjugated antibodies for the treatment of cancer." British Journal of Clinical Pharmacology, 2013, 76:2, 248-262.
Morrison et al., "Chimeric human antibody molecules: Mouse antigen-binding domains with human constant region domains." Proc. Natl. Acad. Sci., 1984, 81: 6851-6855.
Nimmerjahn et al., "A Newly Discovered Fc Receptor that Explains IgG-Isotype Disparities in Effector Responses." Immunity, 2005, 23: 2-4.
Petit et al., "Specific Activities of Dolastatin 10 and Peptide Derivatives against Cryptococcus neoformans." Antimicrobial Agents and Chemotherapy, 1998, 42, 11: 2961-2965.
Presta, "Antibody engineering." Current Opinion in Structural Biology, 1992, 2: 593-596.
Ravetch et al., "Fc Receptors." Annu. Rev. Immunol, 1991, 9: 957-492.
Remillard et al., "Antimitotic activity of the potent tumor inhibitor maytansine." Science, 1975, 189: 1002-1005.
Riechmann et al., "Reshaping human antibodies for therapy." Nature, 1988, 332: 323-327.
Senter et al., "The discovery and development of brentuximab vedotin for use in relapsed Hodgkin lymphoma and systemic anaplastic large cell lymphoma." Nature Biotechnology, 2012, 30, 7: 631-637.
Songsivilai et al., "Bispecific antibody: a tool for diagnosis and treatment of disease." Clin. exp. Immunol., 1990, 79: 315-321.
Strop et al., "Location Matters: Site of Conjugation Modulates Stability and Pharmacokinetics of Antibody Drug Conjugates." Chemistry and Biology, 2013, 20: 161-167.
Strop et al., "Generating Bispecific Human IgG1 and IgG2 Antibodies from Any Antibody Pair." Journal of Molecular Biology, 2012, 420: 204-219.
Vaswani et al., "Humanized antibodies as potential therapeutic drugs." Annals of Allergy, Asthma & Immunology, 1998, 81: 105-119.

\* cited by examiner

SEQUENCE LISTING

<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Leu Leu Gln Gly Gly
1               5

<210> SEQ ID NO 2

```
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Leu Leu Gln Gly
1

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Leu Ser Leu Ser Gln Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Gly Gly Gly Leu Leu Gln Gly Gly
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Gly Leu Leu Gln Gly
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Gly Ser Pro Leu Ala Gln Ser His Gly Gly
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Gly Leu Leu Gln Gly Gly Gly
1               5

<210> SEQ ID NO 8
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 8

Gly Leu Leu Gln Gly Gly
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct

<400> SEQUENCE: 9

Gly Leu Leu Gln
1

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Leu Leu Gln Leu Leu Gln Gly Ala
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Construct

<400> SEQUENCE: 11

Leu Leu Gln Gly Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

Leu Leu Gln Tyr Gln Gly Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

Leu Leu Gln Gly Ser Gly
1               5

<210> SEQ ID NO 14
<211> LENGTH: 6
<212> TYPE: PRT
```

<213> ORGANISM: Artificial Sequence
<220> FEATURE:
<223> OTHER INFORMATION: Synthetic Construct

<400> SEQUENCE: 14

Leu Leu Gln Tyr Gln Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Leu Leu Gln Leu Leu Gln Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic Construct

<400> SEQUENCE: 16

Ser Leu Leu Gln Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Leu Leu Gln Leu Gln
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Construct

<400> SEQUENCE: 18

Leu Leu Gln Leu Leu Gln
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Leu Leu Gln Gly Arg
1               5

<210> SEQ ID NO 20
<211> LENGTH: 6
<212> TYPE: PRT
<213> ORGANISM: Artificial Sequence

```
<220> FEATURE:
<223> OTHER INFORMATION: Synthetic Construct

<400> SEQUENCE: 20

Leu Leu Gln Gly Pro Pro
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Leu Leu Gln Gly Pro Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Construct

<400> SEQUENCE: 22

Gly Gly Leu Leu Gln Gly Pro Pro
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Gly Gly Leu Leu Gln Gly Ala
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Construct

<400> SEQUENCE: 24

Leu Leu Gln Gly Ala
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Leu Leu Gln Gly Pro Gly Lys
1               5

<210> SEQ ID NO 26
<211> LENGTH: 6
<212> TYPE: PRT
<213> ORGANISM: Artificial Sequence
<220> FEATURE:
```

```
<223> OTHER INFORMATION: Synthetic Construct

<400> SEQUENCE: 26

Leu Leu Gln Gly Pro Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Leu Leu Gln Gly Pro
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic Construct

<400> SEQUENCE: 28

Leu Leu Gln Pro
1

<210> SEQ ID NO 29
<211> LENGTH: 6
<212> TYPE: PRT
<213> ORGANISM: Artificial Sequence
<220> FEATURE:
<223> OTHER INFORMATION: Synthetic Construct

<400> SEQUENCE: 29

Leu Leu Gln Pro Gly Lys
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Leu Leu Gln Ala Pro Gly Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Leu Leu Gln Gly Ala Pro Gly
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 32

Leu Leu Gln Gly Ala Pro
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Construct

<400> SEQUENCE: 33

Leu Leu Gln Gly Pro Ala
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Construct

<400> SEQUENCE: 34

Leu Leu Gln Gly Pro Pro
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic Construct

<400> SEQUENCE: 35

Gly Gly Leu Leu Gln Gly Pro Pro
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Construct

<400> SEQUENCE: 36

Leu Leu Gln Leu Gln Gly
1               5

<210> SEQ ID NO 37
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa = Leu, Ala, Gly, Ser, Val, Phe, Tyr, His,
      Arg, Asn, Glu, Asp, Cys, Gln, Ile, Met, Pro, Thr, Lys, or Trp
<220> FEATURE:
<221> NAME/KEY: misc_feature
<222> LOCATION: (4)..(4)
<223> OTHER INFORMATION: Xaa = Leu, Ala, Gly, Ser, Val, Phe, Tyr, His,
      Arg, Asn, Glu, Asp, Cys, Gln, Ile, Met, Pro, Thr, Lys, or Trp

<400> SEQUENCE: 37

Xaa Xaa Gln Xaa
```

```
1
<210> SEQ ID NO 38
<211> LENGTH: 4
<212> TYPE: PRT
<213> ORGANISM: Artificial
<220> FEATURE:
<223> OTHER INFORMATION: Synthetic Construct

<400> SEQUENCE: 38

Gly Phe Leu Gly
1

<210> SEQ ID NO 39
<211> LENGTH: 4
<212> TYPE: PRT
<213> ORGANISM: Artificial
<220> FEATURE:
<223> OTHER INFORMATION: Synthetic Construct

<400> SEQUENCE: 39

Ala Leu Ala Leu
1
```

STABILITY-MODULATING LINKERS FOR USE WITH ANTIBODY DRUG CONJUGATES

CROSS-REFERENCE TO RELATED APPLICATIONS

This Application is the national stage filing under 35 U.S.C. 371 of Patent Cooperation Treaty Patent Application No. PCT/B2015/056211, filed Aug. 14, 2015, which claims the benefit of U.S. Provisional Application No. 62/042,901 filed on Aug. 28, 2014, the contents of each of which are hereby incorporated by reference in their entirety.

FIELD

The present invention relates to linkers used in connection with antibody-drug conjugates (ADCs) which are able to up- and down-modulate the extracellular and/or intracellular stability of antibody-drug conjugates. The invention also relates to therapeutic uses and treatment regimens employing such clinically advantageous stability-modulated antibody-drug conjugates. Finally, the invention relates to methods of making stability modulating linkers and stability-modulated antibody-drug conjugates.

REFERENCE TO SEQUENCE LISTING

This application contains a Sequence Listing which has been submitted electronically in ASCII format and is hereby incorporated by reference in it its entirety. Said ASCII copy, created on Jan. 10, 2019, is named PC72108A_SEQ_LISTING_ST25.txt and is 8 bytes in size.

BACKGROUND

Antibody therapy provides targeted therapeutic treatment in patients with various disorders, such as cancers and immunological diseases, and therefore has played an important role in biological research. Different approaches of targeted antibody therapy, including antibody-drug conjugates (ADCs), have been explored. Chari, R. V., Miller, M. L., and Widdison, W. C. (2014) Antibody-drug conjugates: an emerging concept in cancer therapy. Angewandte Chemie 53, 3796-827; Senter, P. D., and Sievers, E. L. (2012) The discovery and development of ADCETRIS® (brentuximab vedotin) for use in relapsed Hodgkin lymphoma and systemic anaplastic large cell lymphoma. Nature biotechnology 30, 631-7; Lambert, J. M. (2013) Drug-conjugated antibodies for the treatment of cancer. British journal of clinical pharmacology 76, 248-62.

In the case of ADCs (also called immunoconjugates in certain contexts) small molecule "payloads", which are often cytotoxic small molecules (drug moieties), are covalently linked (conjugated) to antibodies for targeted local delivery of the drug moieties to tumors. Conventional conjugating methods for ADCs include chemical modification through either the lysine side chain amines, or through the cysteine sulfhydryl groups activated by reducing the interchain disulfide bonds. Brentuximab vedotin and KADCYLA® (ado-trastuzumab emtansine) are two examples of ADCs using these conventional methods.

Enzymatic approaches using a transglutaminase for making ADCs have also been explored. Transglutaminases belong to a family of enzymes that catalyze acyl addition to a primary amine. Conjugation using a transglutaminase provides the advantages of high selectivity, simplified reaction procedures, and mild reaction conditions. See, e.g., Strop et al., Chemistry & Biology, 20:161-167 (2013); and Farias et al., Bioconj. Chem. 25(2):240-250 (2014). US2013-0230543 and US2013-0122020 describe transglutaminase-mediated site-specific conjugation of antibodies and small molecules.

Conventional ADC conjugation methods result in ADCs having an inherent stability in a given biological system. Delivery of the payload at the desired site, typically a tumor, is dependent upon the properties of the payload, the covalent linker, the antibody and the biological system into which the ADC is introduced. Often, a significant amount of the payload is released prematurely from a less than optimally-stable ADC, for instance in the plasma, and thus necessitates higher ADC dosing levels in order to achieve the desired exposure to payload at the tumor site. In other circumstances use of an overly stable ADC results in less than optimal payload release activity within the targeted tumor cells.

Proteolytically cleavable peptide-based linkages that employ the p-aminobenzyloxycarbonyl (PABC) immolation element have been widely used in antibody-drug conjugate (ADC) research since their introduction in 2002 (Dubowchik, G. M. et al. Bioconjugate Chem. 2002, 13, 855-869). Such linkages purportedly undergo cleavage upon internalization into antigen-targeted cells and exposure of the ADC to the degradative proteolytic environment found in endosomal and lysosomal organelles. Cysteine-linked variants of these dipeptide-PABC linkers have been patented (U.S. Pat. No. 6,214,345 B2), and it has been demonstrated that amine-containing versions of these and other linkages are appropriate for site-specific conjugations to glutamine residues using enzymatic conjugations promoted by microbial transglutaminase, as well as the use of aglycosylated antibodies and engineered antibody variants that undergo efficient conjugations using this enzymatic conjugation approach (WO2012/059882 A2).

All publications, patents, and patent applications cited herein are hereby incorporated by reference herein in their entirety for all purposes to the same extent as if each individual publication, patent, and patent application were specifically and individually indicated to be so incorporated by reference. In the event that one or more of the incorporated literature and similar materials differs from or contradicts this application, including but not limited to defined terms, term usage, described techniques, or the like, this application controls.

SUMMARY

The present invention relates generally to ADCs, typically made by employing a transglutaminase-mediated conjugation, having stability properties which are altered by the presence of a modulating moiety on the ADCs' linkers. The inventors have surprisingly discovered that such a modulating moiety positioned at a specific position on an ADC linker, and more specifically certain chemical features incorporated into these modulating moieties, has the ability to either increase or decrease the stability of the ADC as desired such that a great or lesser proportion of the ADC payload is released at the desired site of action.

Thus, herein that specific substitutions on the amine-containing conjugation handle, which are often acylated derivatives of lysine, are provided which can have a profound effect upon the in vitro plasma stability and in vivo exposure of the resulting ADCs. It is demonstrated that conjugate stability can be modulated by varying the nature of the substituents present on the amine-containing conjugation handles, and further, that the substituent can be chosen to optimize the stability of each unique conjugation site. This invention therefore permits the fine-tuning of ADC stability in vivo, and hence allows for the modulation of parameters that affect both in vivo efficacy and safety, and therefore permits the optimization of the therapeutic index of ADCs.

DETAILED DESCRIPTION

Figure 1A:
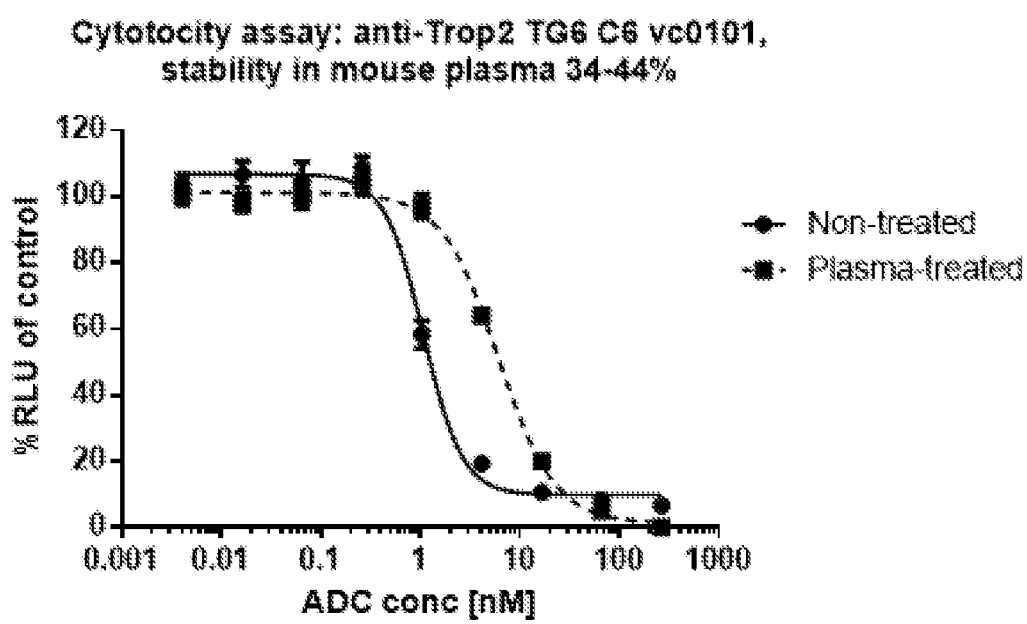
FIGS. 1A through 1I show in vitro cytotoxicity studies of chimeric anti-Trop2 antibodies conjugated at a range of sites with the amino-caproyl (C6) vcAur0101 cytotoxic payload.
Figure 1B:
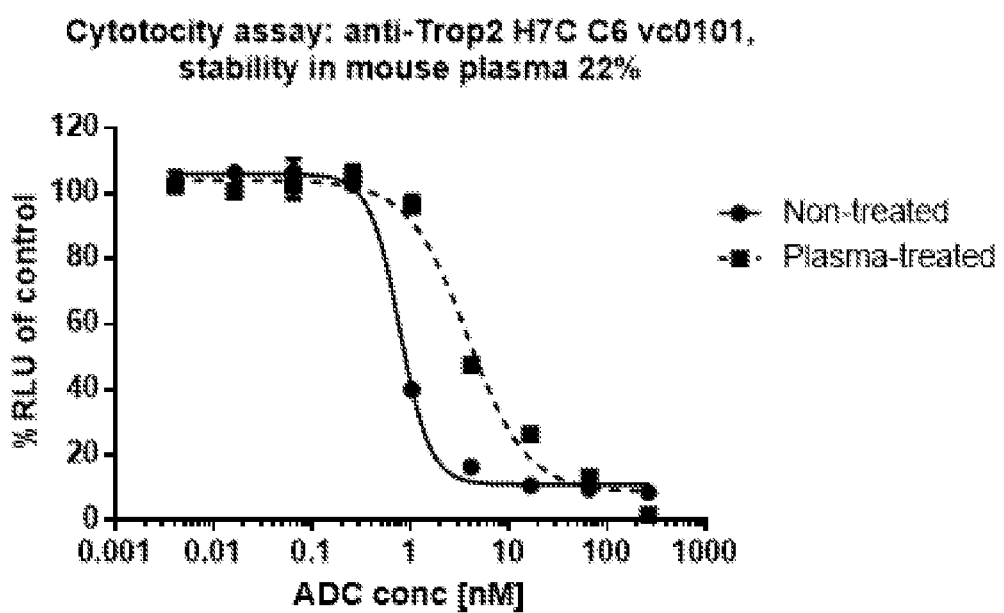
Figure 1C:
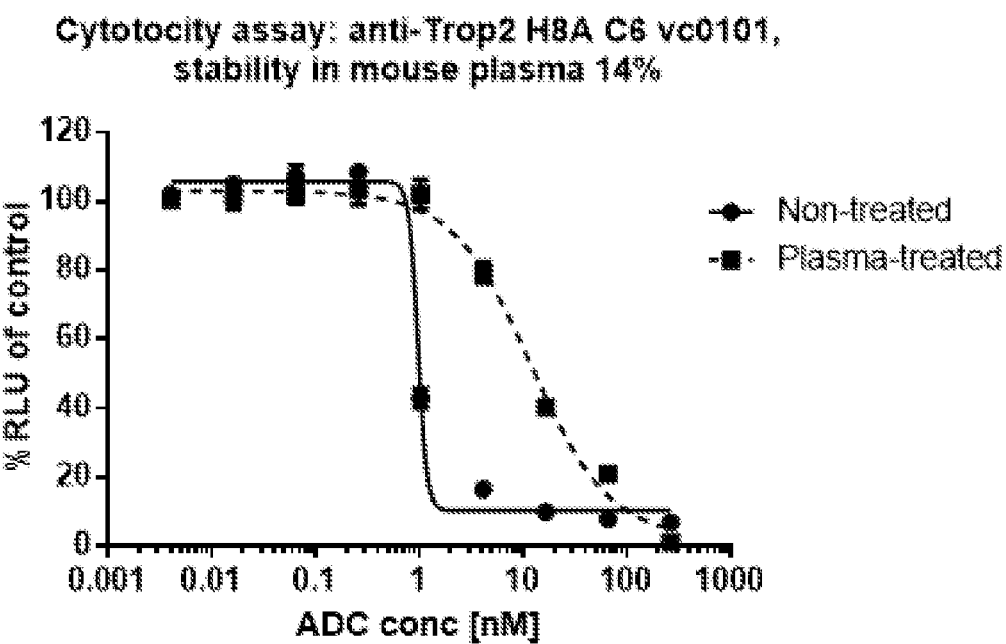
Figure 1D:
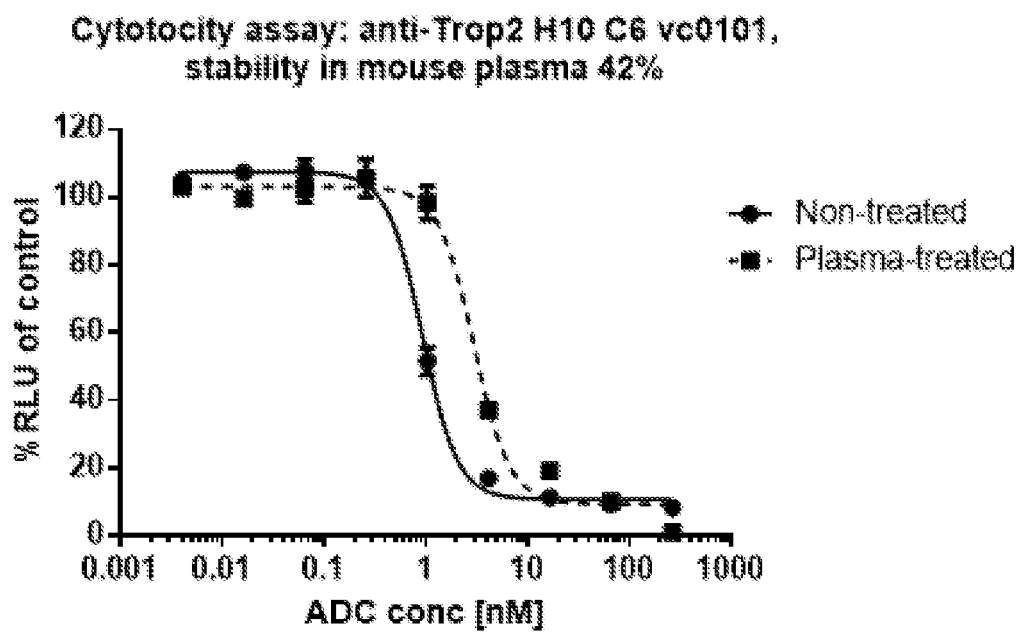
Figure 1E:
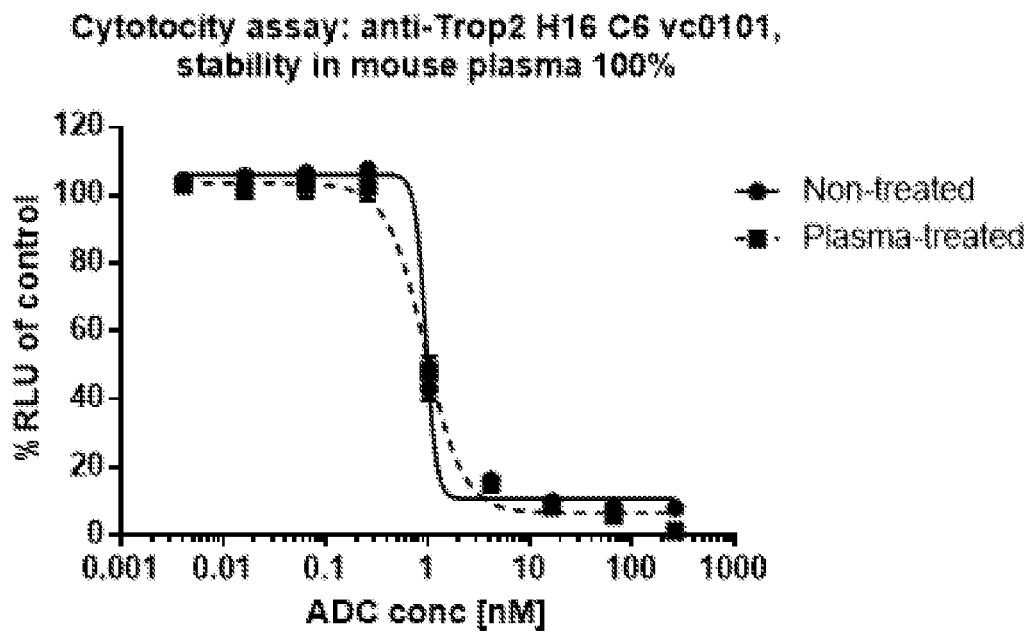
Figure 1F:
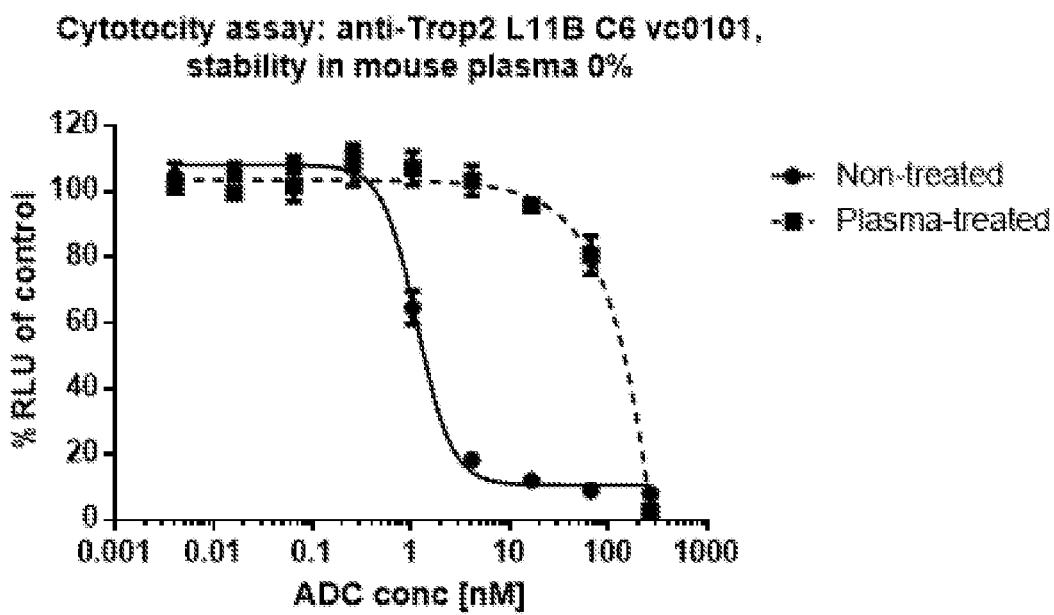
Figure 1G:
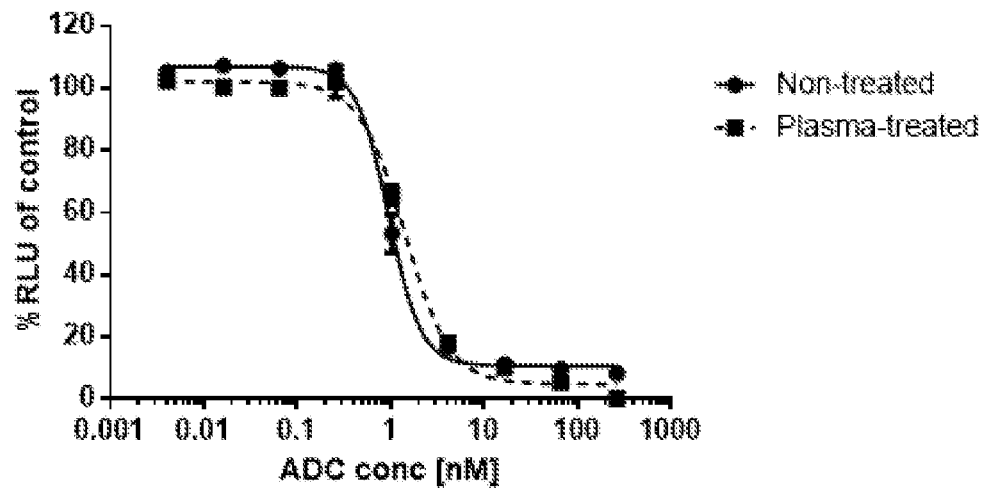
Figure 1H:
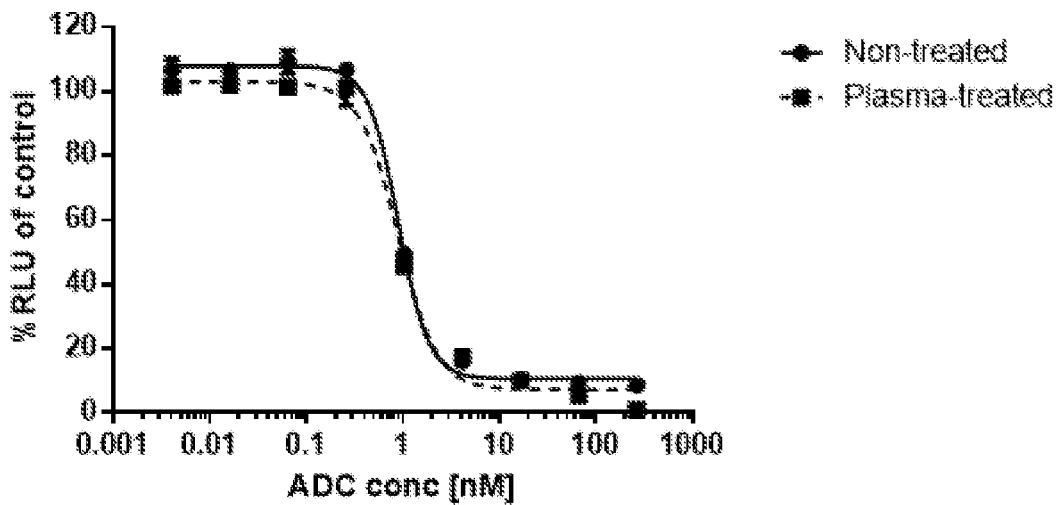
Figure 1I:
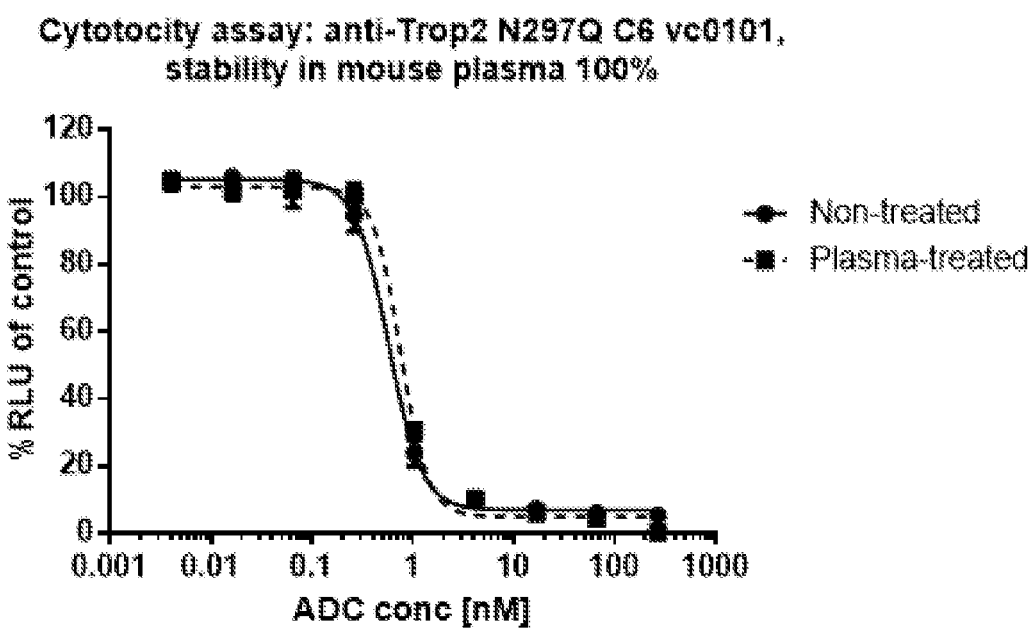
Figure 1J:
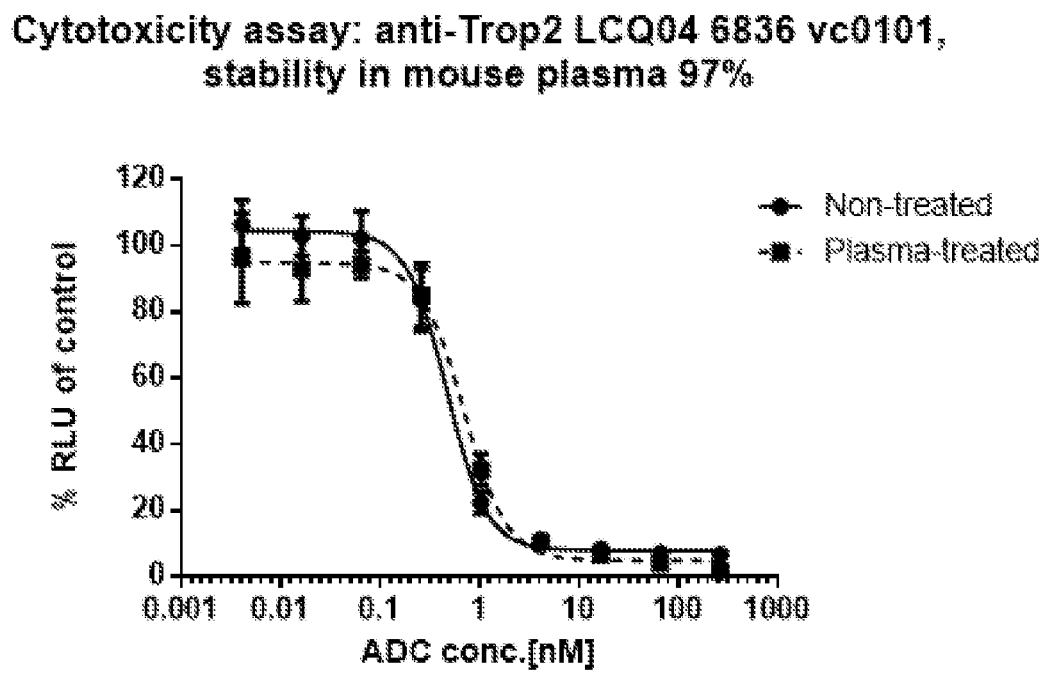
FIGS. 1J through 1O show in vitro cytotoxicity studies of chimeric anti Trop2 antibodies conjugated at the sites LCQ04 and L11B with the linker-payloads of Examples 2, 3, and 5.
Figure 1K:
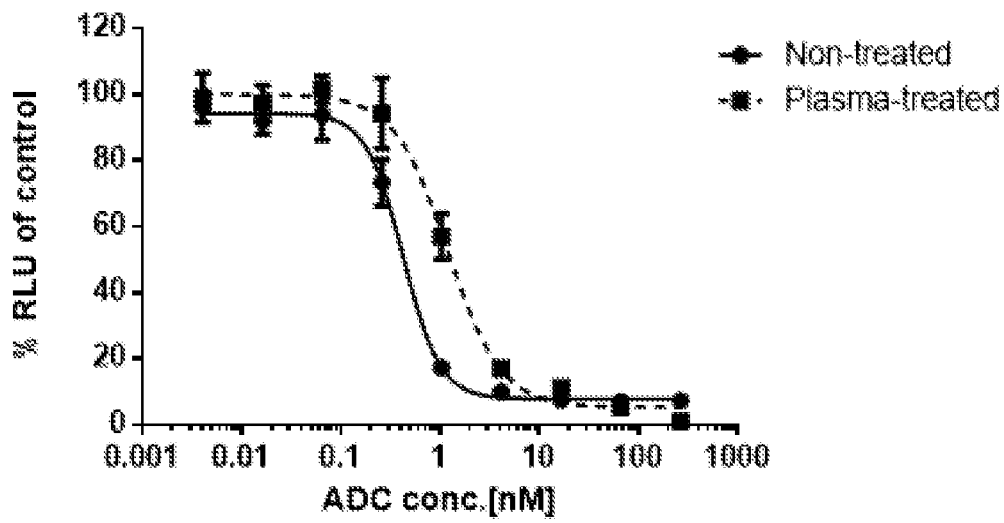
Figure 1L:
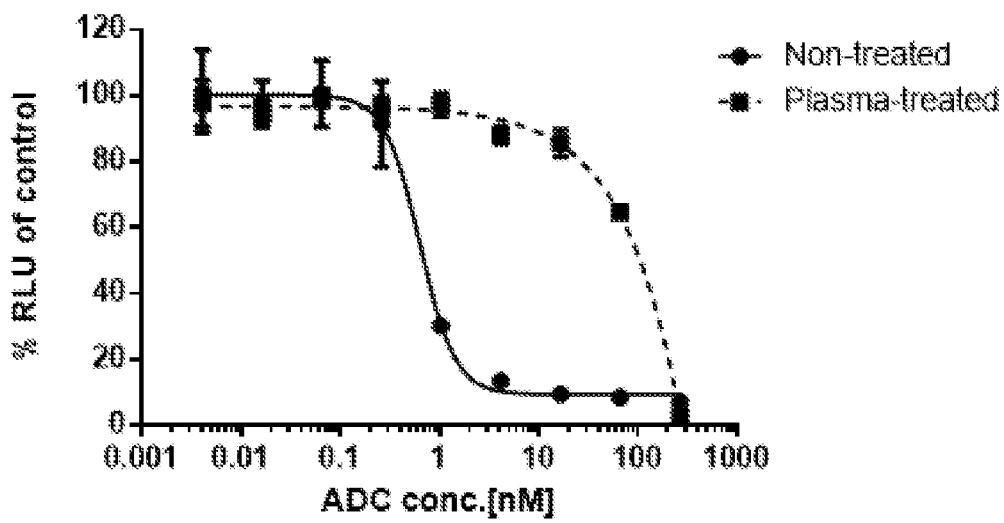
Figure 1M:
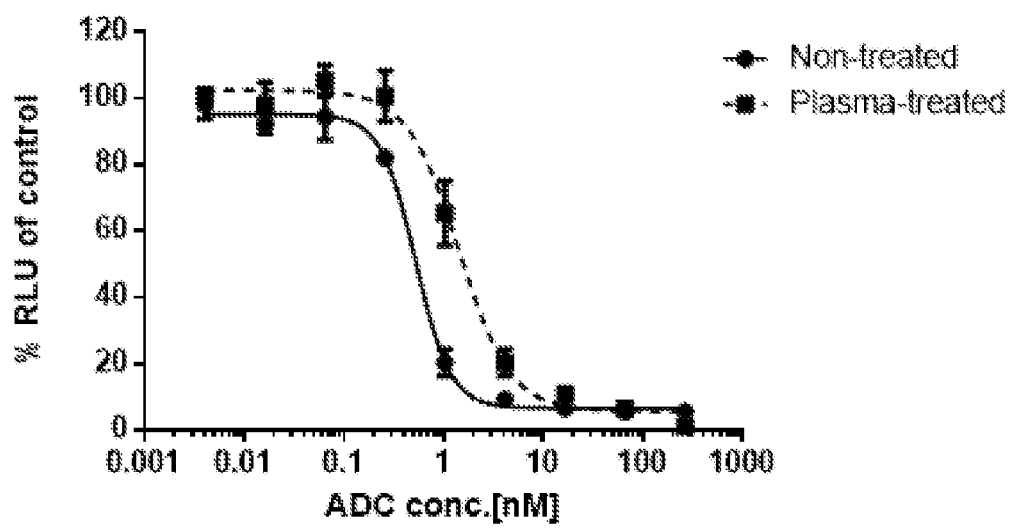
Figure 1N:
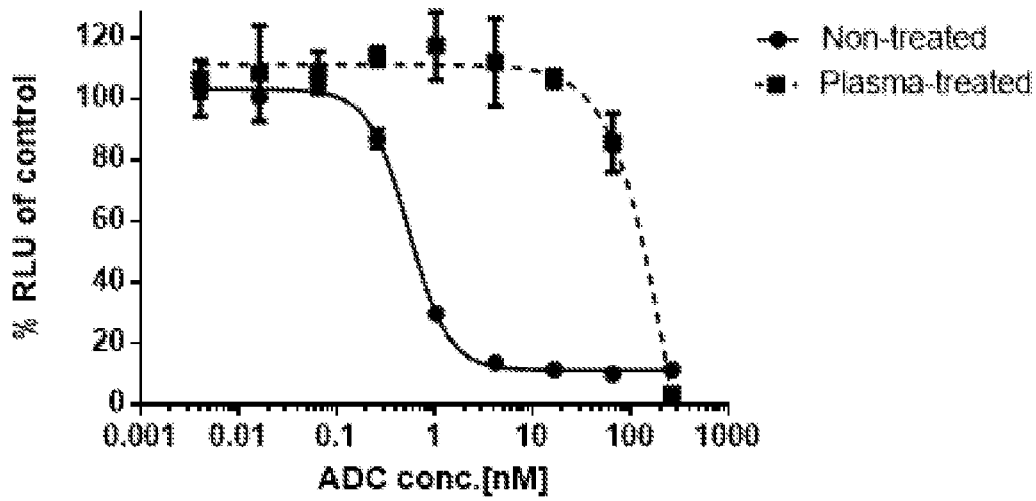
Figure 1O:
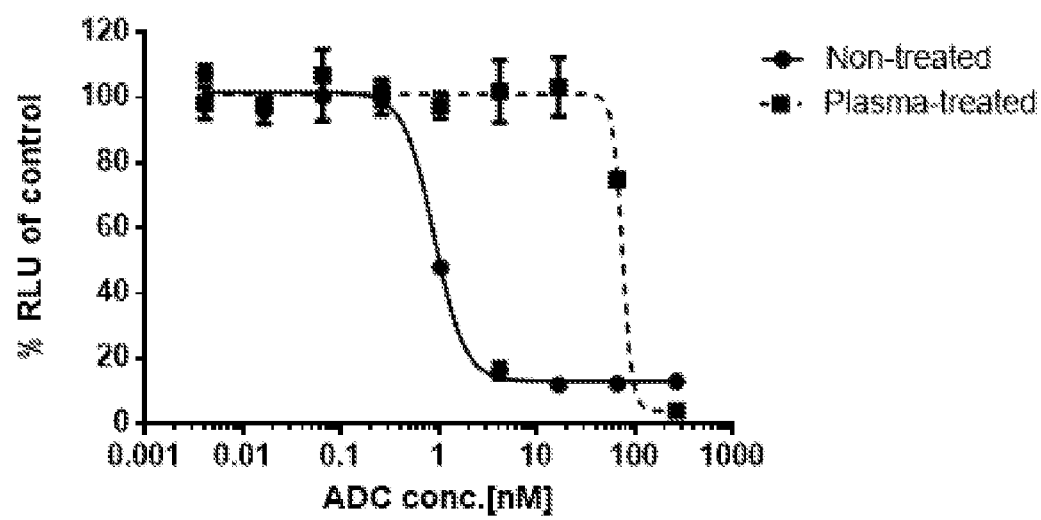
Figure 2A:
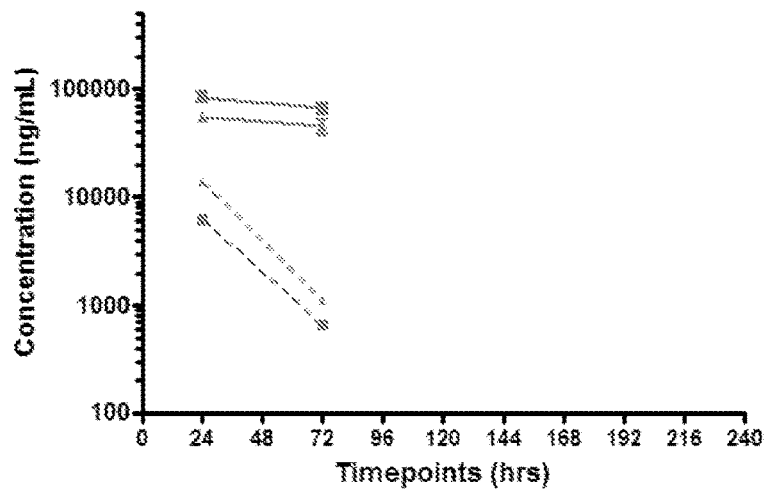
FIG. 2 shows the in vivo stability of the Example 12 and 14 ADC compounds (FIG. 2A); the Example 16 and 13 ADC compounds (FIG. 2B); and the Example 11, 18 and 17 ADC compounds (FIG. 2C), linked via the LCQ04 site on the Trop2 antibody. Dashed lines represent payload concentration, solid lines represent antibody concentration.
Figure 2B:
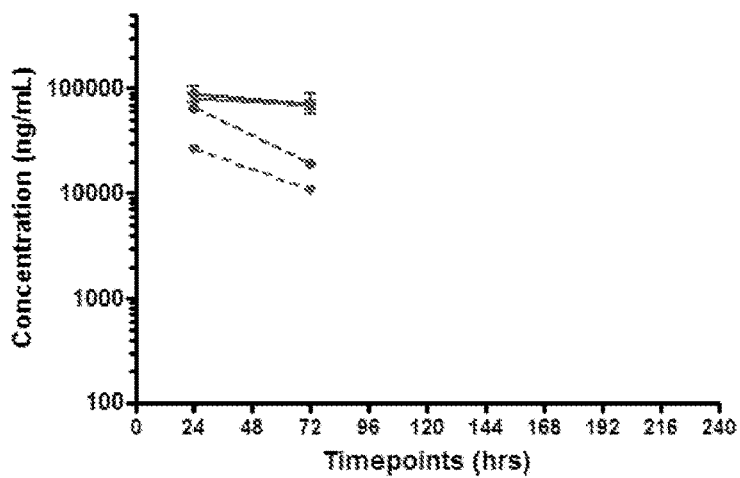
Figure 2C:
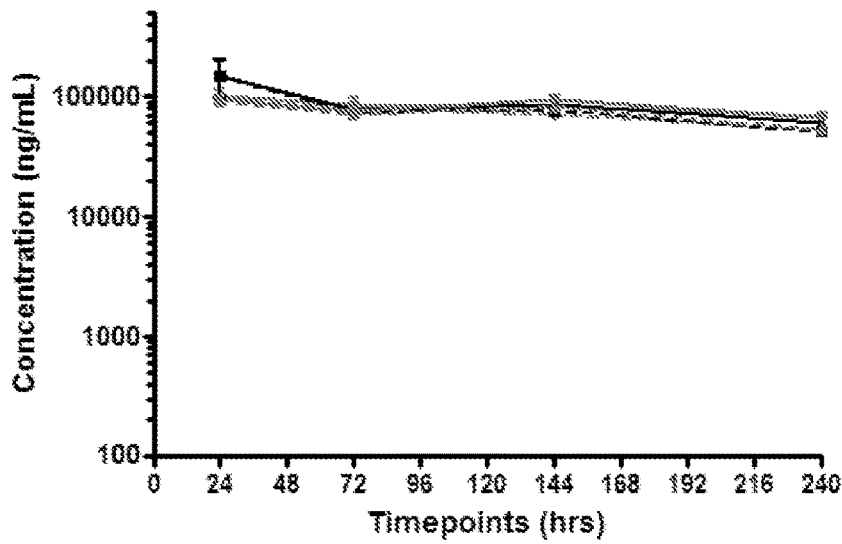

The present invention relates generally to antibody-drug conjugates (ADCs) having a designed degree of stability. Specifically, the invention provides compounds of Formula (I):

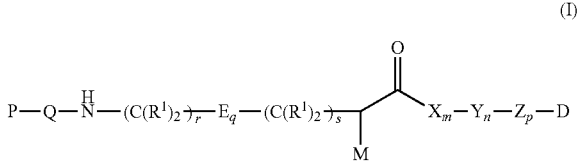

(I)

wherein:
M is a stability modulator;
P is a peptide sequence which includes one or more glutamine residues;
Q is one of said glutamine residues present in P;
each E is independently selected from the group consisting of: $-C(R^1)_2-$, $-O-C(R^1)_2-C(R^1)_2-$ where r is at least 2, and $-C(R^1)_2-C(R^1)_2-O-$ where s is at least 1;
each $R^1$ is independently selected from the group consisting of: H, $C_1$-$C_6$ straight or branched alkyl, $C_2$-$C_6$ straight or branched alkenyl, and $C_2$-$C_6$ straight or branched alkynyl;
each X is independently an amino acid, where each amino acid X is the same or is different;
each Y is independently an amino acid, where each amino acid Y is the same or is different;
each Z is independently a spacer element, where each spacer element is the same or is different;
m is 0-5, n is 1-5, p is 0-2, q is 0-10, r is 0-2, and s is 0-2, where q+r+s=2 or more; and
D is a cytotoxic agent or other therapeutic agent, or D is an imaging agent.

Embodiments of the invention also include compounds of Formula (II):

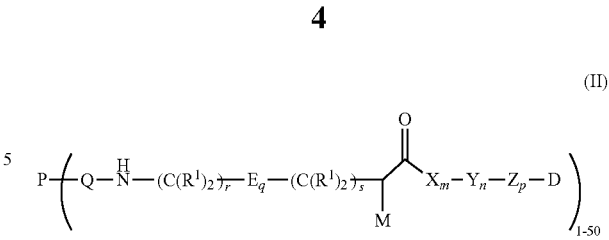

(II)

wherein:
M is a stability modulator;
P is a peptide sequence which includes one or more glutamine residues;
Q is one of said glutamine residues present in P;
each E is independently selected from the group consisting of: $-C(R^1)_2-$, $-O-C(R^1)_2-C(R^1)_2-$ where r is at least 2, and $-C(R^1)_2-C(R^1)_2-O-$ where s is at least 1;
each $R^1$ is independently selected from the group consisting of: H, $C_1$-$C_6$ straight or branched alkyl, $C_2$-$C_6$ straight or branched alkenyl, and $C_2$-$C_6$ straight or branched alkynyl;
each X is independently an amino acid, where each amino acid X is the same or is different;
each Y is independently an amino acid, where each amino acid Y is the same or is different;
each Z is independently a spacer element, where each spacer element is the same or is different;
m is 0-5, n is 1-5, p is 0-2, q is 0-10, r is 0-2, and s is 0-2, where q+r+s=2 or more; and
D is a cytotoxic agent or other therapeutic agent, or D is an imaging agent.

Additional embodiments include compounds of Formula (III):

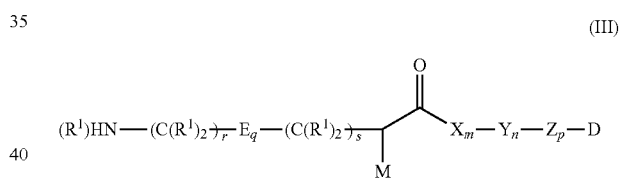

(III)

useful for manufacture of antibody drug conjugates, wherein:
M is a stability modulator;
each E is independently selected from the group consisting of: $-C(R^1)_2-$, $-O-C(R^1)_2-C(R^1)_2-$ where r is at least 2, and $-C(R^1)_2-C(R^1)_2-O-$ where s is at least 1;
each $R^1$ is independently selected from the group consisting of: H, $C_1$-$C_6$ straight or branched alkyl, $C_2$-$C_6$ straight or branched alkenyl, and $C_2$-$C_6$ straight or branched alkynyl;
each X is independently an amino acid, where each amino acid X is the same or is different;
each Y is independently an amino acid, where each amino acid Y is the same or is different;
each Z is independently a spacer element, where each spacer element is the same or is different;
m is 0-5, n is 1-5, p is 0-2, q is 0-10, r is 0-2, and s is 0-2, where q+r+s=2 or more; and
D is a cytotoxic agent or other therapeutic agent, or D is an imaging agent.

Embodiments of the invention include compounds as described herein wherein M is -$M^1$-$M^2$, where $M^1$ is $-NR^1-C(O)-$, $-NR^1-S(O)_2-$, or is absent, and $M^2$ is selected from the group consisting of: substituted methyl, $-C_2$-$C_{20}$ alkyl, $-C_1$-$C_{20}$ heteroalkyl, $-C_2$-$C_6$ alkenyl, $-C_2$-$C_6$ alkynyl, $C_1$-$C_6$ alkoxy, carboxy, $-N(R^1)_2$, $-C_6$-

$C_{14}$ aryl, —$C_6$-$C_{14}$ heteroaryl, —$C_1$-$C_{10}$ heterocyclyl, and —$C_3$-$C_{10}$ carbocyclyl, and where $M^2$ is optionally further substituted with one or more substituents selected from the group consisting of: —$C_1$-$C_6$ alkyl, —$C_1$-$C_6$ alkenyl, —$C_1$-$C_6$ alkynyl, halo, $C_1$-$C_6$ alkoxy, hydroxyl, —$N(R^1)_2$, —$C(O)$ $N(R^1)_2$, —$NO_2$, —$C_6$-$C_{14}$ aryl, —$C_6$-$C_{14}$ heteroaryl, —$C_1$-$C_{10}$ heterocyclyl, —$C_3$-$C_{10}$ carbocyclyl, carboxy, —SH, —S($C_1$-$C_6$ alkyl), —S($C_6$-$C_{14}$ aryl), —S($C_6$-$C_{14}$ heteroaryl), —S($C_1$-$C_{10}$ heterocyclyl), —S($C_3$-$C_{10}$ carbocyclyl), —$C_1$-$C_8$ alkyl-C(O)—$C_1$-$C_8$ alkyl, —$C_1$-$C_8$ alkyl-C(O)—H, —$C_1$-$C_8$ alkyl-C(O)—O—$C_1$-$C_8$ alkyl, —$NR^1$—C(O)—N $(R^1)_2$, —$C_1$-$C_8$ alkyl-O—C(O)—$N(R^1)_2$, —$C_1$-$C_8$ alkyl-S $(O)_2$—$N(R^1)_2$, —$C_1$-$C_8$ alkyl-S$(O)_2$—OH, —$C_1$-$C_8$ alkyl-S $(O)_2$—$C_1$-$C_8$ alkyl, and —$C_1$-$C_8$ alkyl-S(O)—$C_1$-$C_8$ alkyl; provided that $M^2$ is not unsubstituted methyl when $M^1$ is —NH—C(O)— and —$(C(R^1)_2)_r$-$E_q$-$(C(R^1)_2)_s$— is a straight chain $C_4$-alkyl.

Embodiments of the invention include compounds as described herein wherein M is -$M^1$-$M^2$, where $M^1$ is —$NR^1$—C(O)—, —$NR^1$—S(O)$_2$—, or is absent, and $M^2$ is selected from the group consisting of: —$C_2$-$C_{10}$ alkyl, —$C_1$-$C_{10}$ heteroalkyl, —$C_6$-$C_{14}$ aryl, —$C_6$-$C_{14}$ heteroaryl, —$C_1$-$C_{10}$ heterocyclyl, and —$C_3$-$C_{10}$ carbocyclyl, and where $M^2$ is optionally further substituted with one or more substituents selected from the group consisting of: —$C_1$-$C_6$ alkyl, halo, —$C_6$-$C_{14}$ aryl, and —$C_6$-$C_{14}$ heteroaryl.

Additional embodiments include compounds as described herein wherein $M^2$ is selected from the group consisting of:

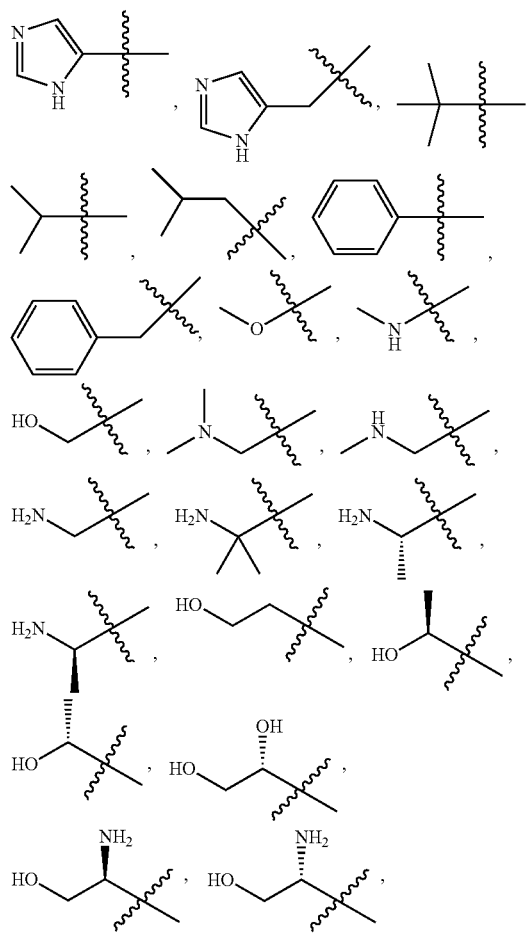

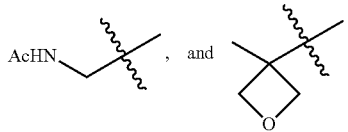

In some embodiments, the ADC of the present invention comprises a lysine-based linker system with a modified acyl modulating moiety where the modified acyl modulating moiety is:

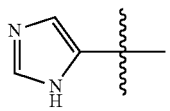

In some embodiments, the ADC of the present invention comprises a lysine-based linker system with a modified acyl modulating moiety where the modified acyl modulating moiety is:

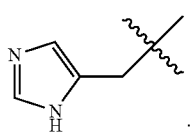

In some embodiments, the ADC of the present invention comprises a lysine-based linker system with a modified acyl modulating moiety where the modified acyl modulating moiety is:

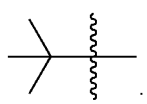 [SMILES: *C(C)(C)C]

In some embodiments, the ADC of the present invention comprises a lysine-based linker system with a modified acyl modulating moiety where the modified acyl modulating moiety is:

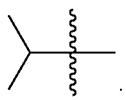

In some embodiments, the ADC of the present invention comprises a lysine-based linker system with a modified acyl modulating moiety where the modified acyl modulating moiety is:

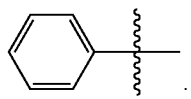

In some embodiments, the ADC of the present invention comprises a lysine-based linker system with a modified acyl modulating moiety is:

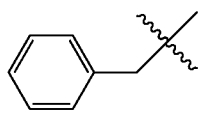 [SMILES: *Cc1ccccc1]

In some embodiments, the ADC of the present invention comprises a lysine-based linker system with a modified acyl modulating moiety where the modified acyl modulating moiety is:

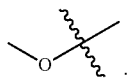

In some embodiments, the ADC of the present invention comprises a lysine-based linker system with a modified acyl modulating moiety where the modified acyl modulating moiety is:

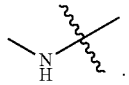

In some embodiments, the ADC of the present invention comprises a lysine-based linker system with a modified acyl modulating moiety where the modified acyl modulating moiety is:

In some embodiments, the ADC of the present invention comprises a lysine-based linker system with a modified acyl modulating moiety where the modified acyl modulating moiety is:

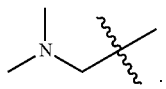

In some embodiments, the ADC of the present invention comprises a lysine-based linker system with a modified acyl modulating moiety where the modified acyl modulating moiety is:

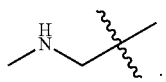

In some embodiments, the ADC of the present invention comprises a lysine-based linker system with a modified acyl modulating moiety is:

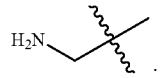

In some embodiments, the ADC of the present invention comprises a lysine-based linker system with a modified acyl modulating moiety where the modified acyl modulating moiety is:

In some embodiments, the ADC of the present invention comprises a lysine-based linker system with a modified acyl modulating moiety where the modified acyl modulating moiety is:

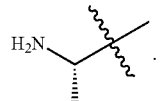

In some embodiments, the ADC of the present invention comprises a lysine-based linker system with a modified acyl modulating moiety where the modified acyl modulating moiety is:

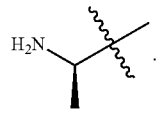

In some embodiments, the ADC of the present invention comprises a lysine-based linker system with a modified acyl modulating moiety where the modified acyl modulating moiety is:

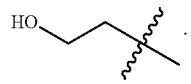

In some embodiments, the ADC of the present invention comprises a lysine-based linker system with a modified acyl modulating moiety where the modified acyl modulating moiety is:

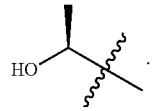

In some embodiments, the ADC of the present invention comprises a lysine-based linker system with a modified acyl modulating moiety where the modified acyl modulating moiety is:

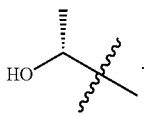

In some embodiments, the ADC of the present invention comprises a lysine-based linker system with a modified acyl modulating moiety where the modified acyl modulating moiety is:

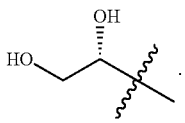

In some embodiments, the ADC of the present invention comprises a lysine-based linker system with a modified acyl modulating moiety where the modified acyl modulating moiety is:

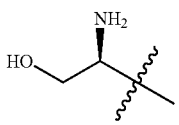

In some embodiments, the ADC of the present invention comprises a lysine-based linker system with a modified acyl modulating moiety where the modified acyl modulating moiety is:

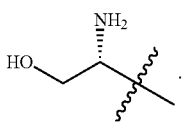

In some embodiments, the ADC of the present invention comprises a lysine-based linker system with a modified acyl modulating moiety where the modified acyl modulating moiety is:

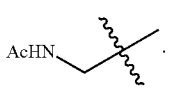

In some embodiments, the ADC of the present invention comprises a lysine-based linker system with a modified acyl modulating moiety where the modified acyl modulating moiety is:

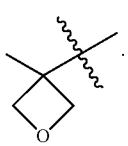 [SMILES: *C1(C)COC1]

In some embodiments there is provided a method of modulating the in vivo stability of an ADC, said method comprising the steps of: selecting modulator M capable of modulating the extracellular stability of said compound; incorporating said modulator M into said conjugate; and administering said conjugate to a patient.

In some embodiments stability is modulated such that the ratio of cytotoxic agent released outside of target cells compared to cytotoxic agent released within target cells is increased.

In some embodiments stability is modulated such that the ratio of cytotoxic agent released outside of target cells compared to cytotoxic agent released within target cells is decreased.

In some embodiments stability is modulated such that the ratio of cytotoxic agent released inside of target cells compared to cytotoxic agent released outside of target cells is increased.

In some embodiments stability is modulated such that the ratio of cytotoxic agent released inside of target cells compared to cytotoxic agent released outside of target cells is decreased.

In some embodiments, the methods provided herein further comprise a purification step, wherein the ADC is purified by a chromatography step.

In some embodiments, the transglutaminase is a microbial, purified, or engineered transglutaminase.

In another aspect, the invention provides a method of treating a cancer in a subject in need thereof, comprising administering to the subject an effective amount of a pharmaceutical composition comprising an ADC or ADCs as described herein.

In another aspect, the invention provides a method of inhibiting tumor growth or progression in a subject in need thereof, comprising administering to the subject an effective amount of a pharmaceutical composition comprising the ADC as described herein.

In another aspect, the invention provides a method of diagnosing cancer in a subject suspected of suffering from cancer, comprising a) contacting a sample of the subject with the ADC as described herein under conditions that result in binding of the ADC with a cancer-related protein, and b) determining binding of the ADC to the cancer-related protein.

In some embodiments, the antibody in the ADC as described herein is a monoclonal antibody, a polyclonal antibody, a human antibody, a humanized antibody, a chimeric antibody, a bispecific antibody, a minibody, a diabody, or an antibody fragment.

Embodiments of the invention include compounds as described herein wherein the cytotoxic agent D is selected from the group consisting of: an anthracycline, an auristatin, a spliceostatin, a CBI/CPI dimer (including "mixed" dimers comprising both CBI and CPI components, as described in U.S. Provisional patent application 61/932,118), a calicheamicin, a duocarmycin, an enediyne, a geldanamycin, a maytansine, a puromycin, a taxane, a vinca alkaloid, SN-38, a tubulysin, a hemiasterlin, a camptothecin, a combretastatin, a dolastatin, an indolino-benzodiazepine dimer, a pyrrolobenzodiazepine dimer and a pladienolide, and stereoisomers, isosteres, analogs, or derivatives thereof. For instance, embodiments wherein the cytotoxic agent D is an auristatin selected from the group consisting of dolestatin, MMAD, MMAE, MMAF, PF-06380101, PF-06463377 and PF-06456780.

Additional embodiments of the invention include those wherein D is something other than a cytotoxic agent, for instance where D is a moiety having therapeutic properties (i.e., a therapeutic agent) and includes peptide(s), protein(s), nucleic acid(s), growth factor(s), anti-viral agent(s), or (an) immunological agent(s), or D is a fluorophore(s) or other imaging agent(s). As is the case where D is a cytotoxic agent, the invention includes the stability modulation of compounds wherein D is other than a cytotoxic agent.

Additional embodiments of the invention include compounds wherein P is a peptide comprising an amino acid sequence selected from the group consisting of: Q, LQG, LLQGG (SEQ ID NO:1), LLQG (SEQ ID NO:2), LSLSQG (SEQ ID NO:3), GGGLLQGG (SEQ ID NO:4), GLLQG (SEQ ID NO:5), LLQ, GSPLAQSHGG (SEQ ID NO:6), GLLQGGG (SEQ ID NO:7), GLLQGG (SEQ ID NO:8), GLLQ (SEQ ID NO:9), LLQLLQGA (SEQ ID NO:10), LLQGA (SEQ ID NO:11), LLQYQGA (SEQ ID NO:12), LLQGSG (SEQ ID NO:13), LLQYQG (SEQ ID NO:14), LLQLLQG (SEQ ID NO:15), SLLQG (SEQ ID NO:16), LLQLQ (SEQ ID NO:17), LLQLLQ (SEQ ID NO:18), LLQGR (SEQ ID NO:19), LLQGPP (SEQ ID NO:20), LLQGPA (SEQ ID NO:21), GGLLQGPP (SEQ ID NO:22), GGLLQGA (SEQ ID NO:23), LLQGA (SEQ ID NO:24), LLQGPGK (SEQ ID NO:25), LLQGPG (SEQ ID NO:26), LLQGP (SEQ ID NO:27), LLQP (SEQ ID NO:28), LLQPGK (SEQ ID NO:29), LLQAPGK (SEQ ID NO:30), LLQGAPG (SEQ ID NO:31), LLQGAP (SEQ ID NO:32), LLQGPA (SEQ ID NO:33), LLQGPP (SEQ ID NO:34), GGLLQGPP (SEQ ID NO:35), and LLQLQG (SEQ ID NO:36).

Embodiments of the invention also include compounds as described herein wherein P is a peptide comprising the amino acid sequence XXQX (SEQ ID NO: 37), wherein X is any amino acid.

Embodiments of the invention include compounds as described herein wherein the stability of said compound decreases by at least 1-, 5-, 10-, 25-, 50-, 75-, or 100-fold, relative to the corresponding compound lacking said modulator M.

Embodiments of the invention include compounds as described herein wherein the stability of said compound increases at least 1-, 5-, 10-, 25-, 50-, 75-, or 100-fold, relative to the corresponding compound lacking said modulator M.

Embodiments of the invention include compounds as described herein wherein X-Y is selected from the group consisting of Gly, β-Ala, Val-Cit, Phe-Lys, Val-Lys, Phe-Phe-Lys, Ala-Lys, Phe-Cit, Leu-Cit, Ala-Cit, Trp-Cit, Phe-Ala, Gly-Phe-Leu-Gly (SEQ ID NO: 38), Ala-Leu-Ala-Leu (SEQ ID NO: 39), Phe-N9-tosyl-Arg, Phe-N9-Nitro-Arg, Val-Ala, and Ala-Ala-Asn.

Embodiments of the invention include compounds as described herein wherein P is selected from the group consisting of: a monoclonal antibody, a polyclonal antibody, a human antibody, a humanized antibody, a chimeric antibody, a bispecific antibody, a minibody and an antibody fragment.

Embodiments of the invention include compounds as described herein wherein the antibody is selected from: trastuzumab, trastuzumab mutants (for instance the trastuzumab mutants disclosed herein or in international patent application PCT/IB2012/056234), oregovomab, edrecolomab, cetuximab, a humanized monoclonal antibody to the vitronectin receptor ($\alpha v \beta 3$), alemtuzumab, anti-HLA-DR antibodies including a humanized anti-HLA-DR antibody for the treatment of non-Hodgkin's lymphoma, 131I Lym-1, anti-HLA-Dr10 antibodies including a murine anti-HLA-Dr10 antibody for the treatment of non-Hodgkin's lymphoma, anti-cd33 antibodies, anti-cd22 antibodies including a humanized anti-CD22 mAb for the treatment of Hodgkin's Disease or non-Hodgkin's lymphoma, labetuzumab, bevacizumab, ibritumomab tiuxetan, ofatumumab, panitumumab, rituximab, tositumomab, ipilimumab, and gemtuzumab.

Additional embodiments of the invention include compounds as described herein wherein each Q is independently a residue of a glutamine endogenous to a peptide sequence P, or a residue of a glutamine provided in an engineered tag sequence on said peptide sequence P (where the tag may be a multiple amino acid sequence containing glutamine, or simply glutamine).

In yet another aspect of the invention the antibody serves as a macromolecular carrier, with or without a targeted delivery feature, facilitating controlled release of the payload D through a stability-modulated cleavable linker.

Embodiments of the invention include compounds as described herein wherein each Q is a residue of a glutamine endogenous to said peptide sequence P.

Embodiments of the invention include compounds as described herein each Q is a residue of a glutamine provided in an engineered tag sequence on said peptide sequence P (again, where the tag may be a multiple amino acid sequence containing glutamine, or simply glutamine).

Further embodiments of the invention include methods of modulating the in vivo stability of an antibody drug conjugate of Formula (II):

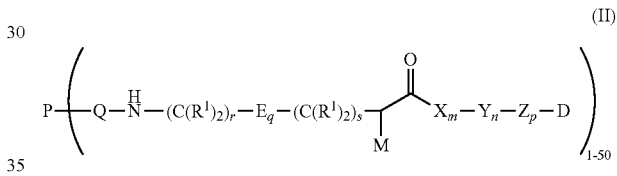

wherein:

M is a stability modulator;

P is a peptide sequence which includes one or more glutamine residues;

Q is one of said glutamine residues present in P;

each E is independently selected from the group consisting of: $-C(R^1)_2-$, $-O-C(R^1)_2-C(R^1)_2-$ where r is at least 2, and $-C(R^1)_2-C(R^1)_2-O-$ where s is at least 1;

each $R^1$ is independently selected from the group consisting of: H, $C_1$-$C_6$ straight or branched alkyl, $C_2$-$C_6$ straight or branched alkenyl, and $C_2$-$C_6$ straight or branched alkynyl;

each X is independently an amino acid, where each amino acid X is the same or is different;

each Y is independently an amino acid, where each amino acid Y is the same or is different;

each Z is independently a spacer element, where each spacer element is the same or is different;

m is 0-5, n is 1-5, p is 0-2, q is 0-10, r is 0-2, and s is 0-2, where q+r+s=2 or more; and D is a cytotoxic agent;

said method comprising the steps of:

selecting modulator M capable of modulating the extracellular stability of said compound;

incorporating said modulator M into said conjugate; and administering said conjugate to a patient.

Embodiments of the invention include methods of treatment as described herein wherein the ratio of cytotoxic agent released outside of target cells compared to cytotoxic agent released within target cells is increased.

Embodiments of the invention include methods of treatment as described wherein the ratio of cytotoxic agent released outside of target cells compared to cytotoxic agent released within target cells is decreased.

Embodiments of the invention include methods of treatment as described herein wherein the ratio of cytotoxic agent released inside of target cells compared to cytotoxic agent released outside of target cells is increased.

Embodiments of the invention include methods as described herein wherein the ratio of cytotoxic agent released inside of target cells compared to cytotoxic agent released outside of target cells is decreased.

Further embodiments of the invention include methods of synthesizing a compound of Formula (II):

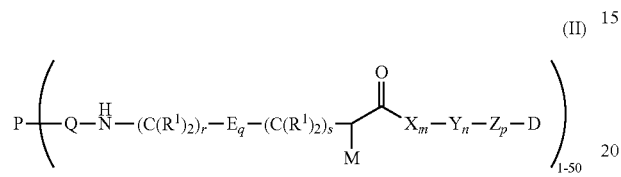

wherein:
M is a stability modulator;
P is a peptide sequence which includes one or more glutamine residues;
Q is one of said glutamine residues present in P;
each E is independently selected from the group consisting of: —C(R$^1$)$_2$—, —O—C(R$^1$)$_2$—C(R$^1$)$_2$— where r is at least 2, and —C(R$^1$)$_2$—C(R$^1$)$_2$—O— where s is at least 1;
each R$^1$ is independently selected from the group consisting of: H, C$_1$-C$_6$ straight or branched alkyl, C$_2$-C$_6$ straight or branched alkenyl, and C$_2$-C$_6$ straight or branched alkynyl;
each X is independently an amino acid, where each amino acid X is the same or is different;
each Y is independently an amino acid, where each amino acid Y is the same or is different;
each Z is independently a spacer element, where each spacer element is the same or is different;
m is 0-5, n is 1-5, p is 0-2, q is 0-10, r is 0-2, and s is 0-2, where q+r+s=2 or more; and
D is a cytotoxic agent;
comprising the steps of:
providing an amount of a first compound of the structure

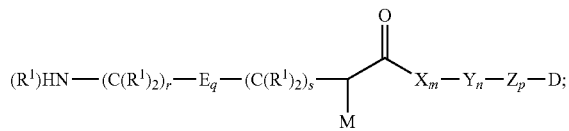

providing an amount of a second compound which comprises a peptide sequence incorporating a glutamine; and,
reacting said amounts of first and second compounds in the presence of transglutaminase.

Embodiments of the invention include compounds as described herein wherein Z is selected from the group consisting of PABC (p-aminobenzl-carbamoyl), PAB-OH (p-aminocarbamoyloxy),

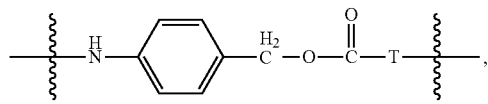

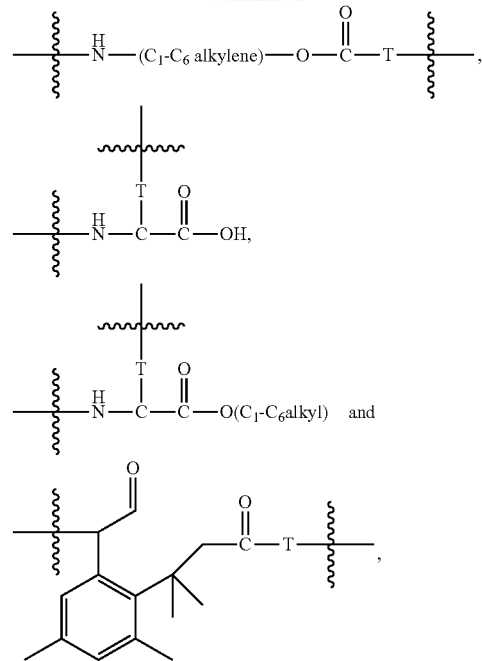

where T is O, NH or S.

Embodiments of the invention include compounds as described herein wherein Z is Z$^1$-Z$^2$, where: Z$^1$ is selected from the group consisting of p-aminobenzyl-carbamoyl (PABC), p-aminobenzyloxy, o-aminobenzyl-carbamoyl, o-aminobenzyloxy, —NH—U—C(R$^1$)$_2$OCO— and —NH—U—C(R$^1$)$_2$O—; Z$^2$ is absent or is selected from the group consisting of —N(R$^1$)$_2$—(C$_1$-C$_6$-alkylene)-OCO—, —N(R$^1$)$_2$—(C$_1$-C$_6$-alkylene)-N(R$^1$)$_2$CO—, —N(R$^1$)$_2$—(C$_1$-C$_6$-alkylene)-SCO—, —N(R$^1$)$_2$—(C$_3$-C$_9$-cycloalkylene)-OCO—, —N(R$^1$)$_2$—(C$_3$-C$_9$-cycloalkylene)-N(R$^1$)$_2$CO— and —N(R$^1$)$_2$—(C$_3$-C$_9$-alkylene)-SCO—; wherein U is a C$_5$-C$_{20}$ aromatic or heteroaromatic ring optionally substituted with up to five additional substituents selected from the group consisting of: —C$_1$-C$_6$ alkyl, —C$_1$-C$_6$ alkenyl, —C$_1$-C$_6$ alkynyl, halo, C$_1$-C$_6$ alkoxy, hydroxyl, —N(R$^1$)$_2$, —C(O)N(R$^1$)$_2$, —NO$_2$, —C$_6$-C$_{14}$ aryl, —C$_6$-C$_{14}$ heteroaryl, —C$_1$-C$_{10}$ heterocyclyl, —C$_3$-C$_{10}$ carbocyclyl, carboxy, —SH, —S(C$_1$-C$_6$ alkyl), —S(C$_6$-C$_{14}$ aryl), —S(C$_6$-C$_{14}$ heteroaryl), —S(C$_1$-C$_{10}$ heterocyclyl), —S(C$_3$-C$_{10}$ carbocyclyl), —C$_1$-C$_8$ alkyl-C(O)—C$_1$-C$_8$ alkyl, —C$_1$-C$_8$ alkyl-C(O)—H, —C$_1$-C$_8$ alkyl-C(O)—O—C$_1$-C$_8$ alkyl, —NR$^1$—C(O)—N(R$^1$)$_2$, —C$_1$-C$_8$ alkyl-O—C(O)—N(R$^1$)$_2$, —C$_1$-C$_8$ alkyl-S(O)$_2$—N(R$^1$)$_2$, —C$_1$-C$_8$ alkyl-S(O)$_2$—OH, —C$_1$-C$_8$ alkyl-S(O)$_2$—C$_1$-C$_8$ alkyl, and —C$_1$-C$_8$ alkyl-S(O)—C$_1$-C$_8$ alkyl. The substitution pattern of —NH— and —C(R$^1$)$_2$OCO— or —C(R$^1$)$_2$O— on U should be arranged so as to permit efficient elimination of Z$^2$-D upon cleavage of a Y—Z bond. For instance, see U.S. Pat. No. 7,754,681 B2 and U.S. Pat. No. 6,214,345 B2.

The term "alkyl" by itself or as part of another term refers to a straight chain or branched, saturated hydrocarbon having the indicated number of carbon atoms (e.g., "C$_1$-C$_8$" alkyl refer to an alkyl group having from 1 to 8 carbon atoms). When the number of carbon atoms is not indicated, the alkyl group has from 1 to 8 carbon atoms. Representative straight chain C$_1$-C$_8$ alkyls include, but are not limited to, methyl, ethyl, n-propyl, n-butyl, n-pentyl, n-hexyl, n-heptyl and n-octyl; while branched C$_1$-C$_8$ alkyls include, but are not limited to, -isopropyl, -sec-butyl, -isobutyl, -tent-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl.

The term "heteroalkyl" by itself or in combination with another term means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive.

The term "aryl," by itself or an part of another term, means, unless otherwise indicated, a substituted or unsubstituted monovalent carbocyclic aromatic hydrocarbon radical of 6-20, preferably 6-14, carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. An aryl group can be substituted with one or more, preferably 1 to 5, of the following groups: $C_1$-$C_8$ alkyl, —O—($C_1$-$C_8$ alkyl), —C(O)R', —OC(O)R', —C(O)OR', —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R'), —N(R')$_2$ and —CN; wherein each R' is independently selected from —H, $C_1$-$C_8$ alkyl and unsubstituted aryl. The term "heterocyclyl" by itself or as part of another term, unless otherwise indicated, refers to a monovalent substituted or unsubstituted aromatic or non-aromatic monocyclic, bicyclic or tricyclic ring system having from 1 to 10, preferably 3 to 8, carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. The ring that includes the heteroatom can be aromatic or nonaromatic. Unless otherwise noted, the heterocyclyl is attached to its pendant group at any heteroatom or carbon atom that results in a stable structure. Representative examples of a $C_1$-$C_{10}$ heterocyclyl include, but are not limited to, tetrahydrofuranyl, oxetanyl, pyranyl, pyrrolidinyl, piperidinyl, piperazinyl, benzofuranyl, benzothiophene, benzothiazolyl, indolyl, benzopyrazolyl, pyrrolyl, thiophenyl (thiopene), furanyl, thiazolyl, imidazolyl, pyrazolyl, triazolyl, quinolinyl including moieties such as 1,2,3,4-tetrshyhro-quinolinyl, pyrimidinyl, pyridinyl, pyridonyl, pyrazinyl, pyridazinyl, isothiazolyl, isoxazolyl, tetrazolyl, epoxide, oxetane and BODIPY (substituted or unsubstituted). A $C_1$-$C_{10}$ heterocyclyl can be substituted with up to seven groups including, but not limited to, $C_1$-$C_8$ alkyl, $C_1$-$C_8$ heteroalkyl, —OR', aryl, —C(O)R', —OC(O) R', —C(O)OR', —C(O)NH$_2$, —C(O)NHR', —C(O)N(R')$_2$, —NHC(O)R', —S(=O)$_2$R', —S(O)R', halogen, —N$_3$, —NH$_2$, —NH(R'), —N(R')$_2$ and —CN; wherein each R' is independently selected from —H, $C_1$-$C_8$ alkyl, $C_1$-$C_8$ heteroalkyl and aryl. In some embodiments, a substituted heterocyclyl can also include one or more of: —NHC(=NH)NH$_2$, —NHCONH$_2$, —S(=O)$_2$R' and —SR'.

The term "carbocyclyl" by itself or as part of another term, unless otherwise indicated, refers to a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(1.1.1.) pentane, and bicyclo(2.2.2.)octane. A carbocyclyl group can be unsubstituted or substituted with up to seven groups including, but not limited to, $C_1$-$C_8$ alkyl, $C_1$-$C_8$ heteroalkyl, —OR', aryl, —C(O)R', —OC(O)R', —C(O)OR', —C(O) NH$_2$, —C(O)NHR', —C(O)N(R')$_2$, —NHC(O)R', —S(=O)$_2$ R', —S(=O)R', —OH, -halogen, —N$_3$, —NH$_2$, —NH(R'), —N(R')$_2$ and —CN; where each R' is as indicated above.

The term "alkenyl-", unless otherwise indicated, refers to a straight or branched chain unsaturated hydrocarbon containing at least one double bond and preferably from 2 to 10 carbon atoms. Examples of a alkenyl-group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, 1-octene, 2-octene, 3-octene, 4-octene, 1-nonene, 2-nonene, 3-nonene, 4-nonene, 1-decene, 2-decene, 3-decene, 4-decene and 5-decene. An alkenyl-group can be unsubstituted or substituted.

The term "alkoxy-" refers to the group alkyl-O— where alkyl is defined herein. Exemplary alkoxy-groups include but are not limited to methoxy, ethoxy, n-propoxy, 1-propoxy, n-butoxy and t-butoxy. An alkoxy group can be unsubstituted or substituted.

The term "alkynyl-" refers to a straight or branched chain unsaturated hydrocarbon containing at least one triple bond and preferably from 2 to 10 carbon atoms. Examples of a alkynyl-group include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne, isohexyne, 1-heptyne, 2-heptyne, 3-heptyne, 1-octyne, 2-octyne, 3-octyne, 4-octyne, 1-nonyne, 2-nonyne, 3-nonyne, 4-nonyne, 1-decyne, 2-decyne, 3-decyne, 4-decyne and 5-decyne. An alkynyl group can be unsubstituted or substituted.

The term "heteroaryl-" refers to 5-10-membered mono and bicyclic aromatic groups containing at least one heteroatom selected from oxygen, sulfur and nitrogen and typically from 1 to 9 carbon atoms. Examples of monocyclic heteroaryl-radicals include, but are not limited to, oxazinyl, thiazinyl, diazinyl, triazinyl, thiadiazoyl, tetrazinyl, imidazolyl, tetrazolyl, isoxazolyl, furanyl, furazanyl, oxazolyl, thiazolyl, thiophenyl, pyrazolyl, triazolyl, pyrimidinyl, N-pyridyl, 2-pyridyl, 3-pyridyl and 4-pyridyl. Examples of bicyclic heteroaryl-radicals include but are not limited to, benzimidazolyl, indolyl, isoquinolinyl, benzofuranyl, benzothiophenyl, indazolyl, quinolinyl, quinazolinyl, purinyl, benzisoxazolyl, benzoxazolyl, benzthiazolyl, benzodiazolyl, benzotriazolyl, isoindolyl, and indazolyl. A heteroaryl group can be unsubstituted or substituted. The term "carboxyl-" refers to a group, typically an alkyl group as defined herein, that is attached to the parent structure through the oxygen atom of a carboxyl (C(O)—O—) functionality. Examples of carboxyl-groups include acetoxy, propionoxy, propylcarboxyl, and isopentylcarboxyl.

"Substituted", for instance in connection with a chemical moiety such as "substituted alkyl", unless otherwise specified, means a moiety in which one or more hydrogen atoms are each independently replaced with a substituent. Typical substituents include, but are not limited to, —X, —R, —O—, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)NR$_2$, —SO$_3$⁻, —SO$_3$H, —S(=O)$_2$R, —OS(=O)$_2$OR, —S(=O)$_2$ NR, —S(=O)R, —OP(=O)(OR)$_2$, —P(=O)(OR)$_2$, —PO$_3$²⁻, PO$_3$H$_2$, —AsO$_2$H$_2$, —C(=O)R, —C(=O)X, —C(=S)R, —CO$_2$R, —CO$_2$⁻, —C(=S)OR, —C(=O)SR, —C(=S)SR, —C(=O)NR$_2$, —C(=S)NR$_2$, or —C(=NR)NR$_2$, where each X is independently a halogen: —F, —Cl, —Br, or —I; and each R is independently —H, $C_1$-$C_{20}$ alkyl, $C_1$-$C_{20}$ heteroalkyl, $C_6$-$C_{20}$ aryl, $C_1$-$C_{10}$ heterocyclyl, a protecting group or a prodrug moiety.

Also provided are methods of treating a cancer, inhibiting tumor growth or progression, inhibiting metastasis of cancer cells or tumors, or inducing tumor regression in a subject in need thereof, comprising administering to the subject an effective amount of the pharmaceutical composition comprising the ADCs as described herein.

General Techniques and Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, molecular biology, biochemistry, immunology, analytical chemistry, synthetic organic chemistry, and medicinal and pharmaceutical chemistry described herein are those well known and commonly used in the art. Throughout this specification and claims, the word "comprise," or variations such as "comprises" or "comprising," will be understood to imply the inclusion of a stated integer or group of integers but not the exclusion of any other integer or group of integers.

The term "glutamine-containing tag", "glutamine tag," "Q-containing tag", "Q-tag", or "transglutaminase tag," as used herein refers to a polypeptide or a protein containing one or more Gln residue(s), or can refer to a single glutamine or glutamine residue.

As used herein, the term "site specificity," "site-specifically conjugated," or "site-specifically crosslinked" refers to the specific conjugation or crosslinking of the amine-containing moiety to the antibody at a specific site (e.g., at various positions listed in Table 1) via a glutamine-containing tag, endogenous glutamine, and/or an endogenous glutamine made reactive by the antibody engineering or an engineered transglutaminase. Site specificity can be measured by various techniques, including, but not limited to, mass spectrometry (e.g., matrix-assisted laser-desorption ionization mass spectrometry (MALDI-MS), electrospray ionization mass spectrometry (ESI-MS), tandem mass spectrometry (MS-MS), and time-of-flight mass spectrometry (TOF-MS), hydrophobic interaction chromatography, ion exchange chromatography, site-directed mutagenesis, fluorescence-labeling, size exclusion chromatography, and X-ray crystallography.

The terms "loading" or "drug loading" or "payload loading" represent or refer to the average number of payloads ("payload" and "payloads" are used interchangeable herein with "drug" and "drugs") per antibody in an ADC molecule. Drug loading may range from 1 to 20 drugs per antibody. This is sometimes referred to as the DAR, or drug to antibody ratio. The drug-antibody ratio (DAR) of the ADC of the present invention is about 1 to about 60. In some embodiments, the DAR is at least about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 and 60. The average number of drugs per antibody, or DAR value, may be characterized by conventional means such as UV/visible spectroscopy, mass spectrometry, ELISA assay, and HPLC. The quantitative DAR value may also be determined. In some instances, separation, purification, and characterization of homogeneous ADCs having a particular DAR value may be achieved by means such as reverse phase HPLC or electrophoresis. DAR may be limited by the number of attachment sites on the antibody. For example, where the attachment is a glutamine as in the present invention an antibody may have only one or several suitable glutamine residues through which a linker unit may be attached. Typically, fewer than the theoretical maximum of drug moieties are conjugated to an antibody during a conjugation reaction.

As used herein, the term "an endogenous glutamine (Q) made reactive" refers to an endogenous glutamine that has been made accessible, exposed, or reactive to the amine-containing moiety in the presence of a transglutaminase by antibody engineering (e.g., enzymatic deglycosylation and/or amino acid modification) or by an engineered transglutaminase.

As used herein, the term "biocompatible polymer" refers to a polymer (e.g., repeating monomeric or structural units) that is suitable for therapeutic or medical treatment in a recipient (e.g., human) without eliciting any undesirable local or systemic effects in the recipient. A biocompatible polymer (synthetic, recombinant, or native) can be a water soluble or water insoluble polymer. A biocompatible polymer can also be a linear or a branched polymer.

As used herein, the term "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also fragments thereof (such as Fab, Fab', F(ab')$_2$, Fv), single chain (ScFv) and domain antibodies, including shark and camelid antibodies), and fusion proteins comprising an antibody portion, multivalent antibodies (e.g., COVX-BODY™), multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. On one aspect, the immunoglobulin is a human, murine, monkey, or rabbit immunoglobulin.

The term "Fab containing polypeptide" as used herein refers to a polypeptide comprising a Fab fragment, Fab' fragment, or "(Fab')2 fragment." A Fab-containing polypeptide may comprise part or all of a wild-type hinge sequence (generally at the carboxyl terminus of the Fab portion of the polypeptide). A Fab-containing polypeptide may be obtained or derived from any suitable immunoglobulin, such as from at least one of the various IgG1, IgG2, IgG3, or IgG4 subtypes, or from IgA, IgE, IgD or IgM. A Fab-containing polypeptide may be a Fab-containing fusion polypeptide, wherein one or more polypeptides are linked to a Fab-containing polypeptide. A Fab fusion combines the Fab polypeptide of an immunoglobulin with a fusion partner, which in general may be any protein, polypeptide, or small molecule. Virtually any protein or small molecule may be linked to the Fab polypeptide to generate a Fab-containing fusion polypeptide. Fab-containing fusion partners may include, but are not limited to, the target-binding region of a receptor, an adhesion molecule, a ligand, an enzyme, a cytokine, a chemokine, or some other protein or protein domain.

A "Fab fragment" is comprised of one light chain and the CH1 and variable regions of one heavy chain. The heavy chain of a Fab molecule cannot form a disulfide bond with another heavy chain molecule.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a F(ab')2 molecule.

A "F(ab')2 fragment" contains two light chains and two heavy chains containing a portion of the constant region between the CH1 and CH2 domains, such that an interchain disulfide bond is formed between the two heavy chains. A F(ab')2 fragment thus is composed of two Fab' fragments that are held together by a disulfide bond between the two heavy chains.

"Antibody fragments" as used herein comprise only a portion of an intact antibody, wherein the portion preferably retains at least one, preferably most or all, of the functions normally associated with that portion when present in an intact antibody.

A "multispecific antibody" is one that targets more than one antigen or epitope. A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas, linking of Fab' fragments, or mutations at the antibody hinge and CH3 domains. See, e.g., Songsivilai & Lachmann, *Clin. Exp. Immunol.* 79:315-321 (1990); Kostelny et al., *J. Immunol.* 148:1547-1553 (1992); and Strop et al., *J. Mol. Biol.* 420(3):204-219 (2012). The two binding sites of a bispecific antibody will bind to two different epitopes, which may reside on the same or different protein targets.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Further, in contrast to polyclonal antibody preparations that typically include different antibodies directed against different determinants (epitopes), each monoclonal antibody is directed against a single determinant on the antigen.

The monoclonal antibodies herein may, in certain embodiments, specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Humanized antibodies may, moreover, comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

The "hinge region," "hinge sequence," and variation thereof, as used herein, includes the meaning known in the art, which is illustrated, for example, Janeway et al., Immu-noBiology: the immune system in health and disease, (Elsevier Science Ltd., NY) (4$^{th}$ ed., 1999); Bloom et al., Protein Science (1997), 6:407-415; Humphreys et al., *J. Immunol. Methods* (1997), 209:193-202.

The term "Fc-containing polypeptide" as used herein refers to a polypeptide (e.g., an antibody or an immunoadhesin) comprising the carboxyl terminal polypeptide sequences of an immunoglobulin heavy chain. The Fc-containing polypeptide may comprise native or variant Fc regions (i.e., sequences). The Fc region of an immunoglobulin generally comprises two constant domains, a CH2 domain and a CH3 domain, and optionally comprises a CH4 domain. An Fc-containing polypeptide may comprise part or all of a wild-type hinge sequence (generally at amino terminus of the Fc-containing polypeptide). An Fc-containing polypeptide may also be a dimer. An Fc-containing polypeptide may be obtained or derived from any suitable immunoglobulin, such as from at least one of the various IgG1, IgG2, IgG3, or IgG4 subtypes, or from IgA, IgE, IgD or IgM. Although the boundaries of the Fc region of an immunoglobulin heavy chain might vary, for example, the human IgG heavy chain Fc region is usually defined to stretch from an amino acid residue at position Glu216, or from Ala231, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991.

An Fc-containing polypeptide may be an Fc-containing fusion polypeptide, wherein one or more polypeptides are linked to an Fc-containing polypeptide. An Fc fusion combines the Fc polypeptide of an immunoglobulin with a fusion partner, which in general may be any protein, polypeptide, or small molecule. Virtually any protein or small molecule may be linked to the Fc region to generate an Fc-containing fusion polypeptide. Fc-containing fusion partners may include, but are not limited to, the target-binding region of a receptor, an adhesion molecule, a ligand, an enzyme, a cytokine, a chemokine, or some other protein or protein domain.

As used herein, the term "immunoadhesin" designates antibody-like or immunoglobulin-like molecules which combine the "binding domain" of a heterologous protein (an "adhesin", e.g. a receptor, ligand or enzyme) with the effector component of immunoglobulin constant domains (i.e., Fc domain). Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As used herein, the term "wild-type amino acid," "wild-type IgG," or "wild-type mAb" refers to a sequence of amino acids or nucleic acids that occurs naturally within a certain population (e.g., human, mice, rats, cells, etc.).

As used herein, the term "conjugation efficiency" or "crosslinking efficiency" is the ratio between the experimentally measured amounts of the ADC as described herein divided by the maximum expected ADC amount. Conjugation efficiency or crosslinking efficiency can be measured by various techniques well known to persons skilled in the art, such as hydrophobic interaction chromatography. Conjugation efficiency can also be measured at different temperature, such as room temperature or 37° C.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. Nos. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, *PNAS (USA)*, 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods,* 202: 163 (1996), may be performed.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, *Ann. Rev. Immunol.*, 9:457-92; Capel et al., 1994, *Immunomethods*, 4:25-34; de Haas et al., 1995, *J. Lab. Clin. Med.*, 126:330-41; Nimmerjahn et al., 2005, *Immunity* 23:2-4. "FcR" also includes the neonatal receptor, FcRn, which is responsible for the transfer of maternal IgGs to the fetus (Guyer et al., 1976, *J. Immunol.*, 117:587; and Kim et al., 1994, *J. Immunol.*, 24:249).

The term "purify," and grammatical variations thereof, is used to mean the removal, whether completely or partially, of at least one impurity from a mixture containing the ADC and one or more impurities, which thereby improves the level of purity of the ADC in the composition (i.e., by decreasing the amount (ppm) of impurity(ies) in the composition).

Reference to "about" a value or parameter herein includes (and describes) embodiments that are directed to that value or parameter per se. For example, description referring to "about X" includes description of "X." Numeric ranges are inclusive of the numbers defining the range.

An "individual" or a "subject" is a mammal, more preferably, a human. Mammals also include, but are not limited to, farm animals, sport animals, pets, primates, horses, dogs, cats, mice, and rats.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

The residue designations in this application are based on the EU numbering scheme of the constant domain (Edelman et al., *Proc. Natl. Acad. Sci. USA*, 63(1):78-85 (1969).

Unless otherwise defined, all technical and scientific terms used herein have the same meaning as commonly understood by one of ordinary skill in the art to which this invention belongs. Exemplary methods and materials are described herein, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. The materials, methods, and examples are illustrative only and not intended to be limiting Transglutaminases are protein-glutamine γ-glutamyltransferases, which typically catalyze pH-dependent transamidation of glutamine residues with lysine residues. The transglutaminase used in the invention described herein can be obtained or made from a variety of sources, or engineered to catalyze transamidation of one or more endogenous glutamine residues with one or more lysine residues or other amine-containing moiety. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, Mo.) and MP Biomedicals (Irvine, Calif.)). In some embodiments, the transglutaminase is a calcium independent transglutaminase which does not require calcium to induce enzyme conformational changes and to allow enzyme activity. In some embodiments, the transglutaminase is a microbial transglutaminase derived from a microbial genome, such as transglutaminase from *Streptoverticillium* or *Streptomices* (e.g., *Streptomyces mobarensis* or *Streptoverticillium mobarensis*). Commercially available calcium independent transglutaminase such as ACTIVA™ (Ajinomoto, Japan) is suitable for the present invention. In some embodiments, the transglutaminase is a mammalian protein (e.g., human transglutaminase), a bacterial protein, a plant protein, a fungi protein (e.g., *Oomycetes* and *Actinomicetes* transglutaminases), or a prokaryotic protein. In some embodiments, the transglutaminase is from *Micrococcus, Clostridium, Turolpsis, Rhizopus, Monascus*, or *Bacillus*.

In some embodiments, the transglutaminase used in the invention described herein is an engineered transglutaminase which catalyzes transamidation of one or more endogenous glutamine residues in the antibody with one or more lysine residues or other amines-containing moiety. For example, one or more wild-type amino acid residues in the naturally occurring transglutaminase can be deleted, or replaced or substituted with another amino acid residue(s) to make the engineered transglutaminase.

In some embodiments, the transglutaminase used in the invention described herein can also be a recombinant protein produced using recombinant techniques known to persons skilled in the art. In some embodiments, the transglutaminase used in the invention described herein can be a purified protein. For example, the purified transglutaminase is least about 50% pure. As used herein, "pure" or "purified" protein refers to a protein (e.g., transglutaminase) free from other protein contaminants. In some embodiments, the purified transglutaminase is at least about any of 55%-60%, 60%-65%, 65%-70%, 70%-75%, 75%-80%, 80%-85%, 85%-90%, 90%-95%, 95%-98%, or 99% pure. In some embodiments, the purified transglutaminase is about any of 50%, 55%, 60%, 65%, 70%, 75%, 80%, 85%, 90%, 95%, 96%, 97%, 98%, 99%, or 100% pure.

In some embodiments, the ADC of the present invention comprises at least 1 endogenous glutamine made reactive in a transamidation reaction by antibody engineering or by an engineered transglutaminase. In some embodiments, the antibody engineering is antibody deglycosylation (e.g., enzymatic deglycosylation); or amino acid modification including amino acid deletion, insertion, substitution, mutation, or any combination thereof on the antibody. For example, the wild-type amino acid Asn (N) at position 297 in an antibody is substituted or replaced with amino acid Ala (A), resulting in aglycosylation at position 297 and reactive endogenous glutamine (Q) at position 295. In another example, the amino acid modification in the antibody is an amino acid substitution from N to Q at position 297, resulting in aglycosylation at position 297, reactive endogenous Q at position 295, and site-specific conjugation between the N297Q and Q295 and one or more amine-containing moieties at these two sites in the presence of a transglutaminase.

In some embodiments, the ADC of the present invention comprises a glutamine-containing tag engineered at at least one or more positions including, but not limited to, 1) carboxyl terminus of a light chain, a heavy chain, or both the light chain and the heavy chain; 2) amino terminus of a light chain, a heavy chain, or both the light chain and the heavy chain; and 3) S60-R61, R108, T135, S160, S168, S190-S192, P189-S192, G200-S202, K222-T225, K222-T223, T223, L251-S254, M252-I253, E294-N297, E293-N297, N297, and/or G385, wherein the glutamine-containing tag is inserted in the antibody or replaces one or more endogenous amino acid in the antibody.

Examples of the specific glutamine containing tag and their corresponding engineered position are provided in Table 1, and are described in WO2012/059882 and WO2015/015448, which are incorporated herein by reference.

TABLE 1

| Glutamine-Containing Tag Name | Tag Sequence | Amino Acid Positions |
| --- | --- | --- |
| TG6 | LLQGA (SEQ ID NO: 11) | C-terminus of the antibody heavy chain (e.g., K447) |
| LCQ04 | GGLLQGA (SEQ ID NO: 23) | C-terminus of the antibody light chain |
| H7c | LLQG (SEQ ID NO: 2) | Insertion after residue T135 in the antibody heavy chain |
| L11b | LLQG (SEQ ID NO: 2) | Replacement of residues G200-S202 with the glutamine-containing tag in the antibody light chain |
| H1 | LLQGSG (SEQ ID NO: 13) | N-terminus |
| H8a | LLQG (SEQ ID NO: 2) | Insertion after residue S160 in the antibody heavy chain |
| H10 | LLQG (SEQ ID NO: 2) | Replacement of residues S190-S192 with the glutamine-containing tag in the antibody heavy chain |
| H10a | LLQYQG (SEQ ID NO: 14) | Replacement of residues P189-S192 with the glutamine-containing tag in the antibody heavy chain |
| H10b | LLQLLQG (SEQ ID NO: 15) | Replacement of residues P189-S192 with the glutamine-containing tag in the antibody heavy chain |
| H12 | LLQG (SEQ ID NO: 2) | Replacement of residues K222-T225 with the glutamine-containing tag in the antibody heavy chain |
| H12c | LLQG (SEQ ID NO: 2) | Replacement of residues K222-T223 with the glutamine-containing tag in the antibody heavy chain |
| H12d | LLQG (SEQ ID NO: 2) | Insertion after residue T223 in the antibody heavy chain |
| H13a | SLLQG (SEQ ID NO: 16) | Replacement of residues L251-S254 with the glutamine-containing tag in the antibody heavy chain |
| 13b | LQG | Replacement of residues M252-I253 with the glutamine-containing tag in the antibody heavy chain |

TABLE 1-continued

| Glutamine-Containing Tag Name | Tag Sequence | Amino Acid Positions |
|---|---|---|
| H16 | LLQG (SEQ ID NO: 2) | Replacement of residues E294-N297 with the glutamine-containing tag in the antibody heavy chain |
| H16a | LLQLQG (SEQ ID NO: 36) | Replacement of residues E293-N297 with the glutamine-containing tag in the antibody heavy chain |
| H16b | LLQLLQG (SEQ ID NO: 15) | Replacement of residues E293-N297 with the glutamine-containing tag in the antibody heavy chain |
| H16c | LLQLQ (SEQ ID NO: 17) | Replacement of residues E294-N297 with the glutamine-containing tag in the antibody heavy chain |
| H16d | LLQLLQ (SEQ ID NO: 18) | Replacement of residues E294-N297 with the glutamine-containing tag in the antibody heavy chain |
| N297Q | Q | Replacement of residue N297 with the glutamine-containing tag in the antibody |
| N297A | Q | Deglycosylation at A297 residue, which makes 295Q available for conjugation. |
| H21a | LLQG (SEQ ID NO: 2) | Insertion after residue G385 in the antibody heavy chain |
| L2 | LLQG (SEQ ID NO: 2) | Replacement of residues S60-R61 with the glutamine-containing tag in the antibody light chain |
| L4b | LLQG (SEQ ID NO: 2) | Insertion after residue R108 in the antibody light chain |
| L8a | LLQG (SEQ ID NO: 2) | Insertion after residue S168 in the antibody light chain |
| L11c | LLQGR (SEQ ID NO: 19) | Replacement of residues G200-S202 with the glutamine-containing tag in the antibody light chain |
| TG4 | LLQYQGA (SEQ ID NO: 12) | C-terminus of the antibody heavy chain (e.g., K447) |
| TG5 | LLQLLQGA (SEQ ID NO: 10) | C-terminus of the antibody heavy chain (e.g., K447) |

In some embodiments, the antibody of the ADC comprises an amino acid modification at position 222, 340, or 370 (EU numbering) relative to the wild-type antibody at the same position. In some embodiments, the modification is an amino acid deletion, insertion, substitution, mutation, or any combination thereof. In some embodiments, the substitution comprises replacing a wild type amino acid with another (e.g., a non-wild type amino acid). In some embodiments, the other (e.g., non-wild type) or inserted amino acid is Arg (e.g., K222R, K340R, or K370R). In some embodiments, the insertion comprises inserting one or more amino acid(s) (e.g., inserting one, two, three or more amino acids). In some embodiments, the other (e.g., non-wild type) amino acid is Ala, Asn, Asp, Cys, Glu, Gln, Gly, His, Ile, Leu, Met, Phe, Pro, Ser, Thr, Trp, Tyr, or Val.

Accordingly, in some embodiments, the ADC of the present invention comprises a) an amino acid substitutions at positions N297Q and K222R, wherein the amine-containing moiety is site-specifically conjugated to the endogenous glutamine at position 295 and the substituted glutamine at position 297; and/or b) one or more glutamine-containing tag(s), wherein the amine-containing moiety is site-specifically conjugated to the glutamine-containing tag(s) at a carboxyl terminus of a light chain of the antibody. In some embodiments the drug-antibody ratio (DAR) is about 3-9. In some embodiments, the glutamine-containing tag at the carboxyl terminus of the light chain of the antibody is GGLLQGA (SEQ ID NO: 23).

In some embodiments, the ADC of the present invention comprises a) an amino acid substitutions at positions N297Q and K222R, wherein the amine-containing moiety is site-specifically conjugated to the endogenous glutamine at position 295 and the substituted glutamine at position 297; b) one or more glutamine-containing tag(s), wherein the amine-containing moiety is site-specifically conjugated to the glutamine-containing tag(s) at a carboxyl terminus of a light chain of the antibody; and/or c) one or more glutamine-containing tag(s), wherein the amine-containing moiety is further site-specifically conjugated to the glutamine-containing tag at one or more positions selected from the group consisting of S60-R61, R108, T135, S160, S168, S190-S192, P189-S192, G200-S202, K222-T225, K222-T223, T223, L251-S254, M252-I253, E294-N297, E293-N297, N297, and G385 in the antibody, wherein the glutamine-containing tag is inserted in the antibody or replaces one or more endogenous amino acid in the antibody. In some embodiments the drug-antibody ratio is at least about 6. For example, in some embodiments, the ADC of the present invention also comprises a) an amino acid substitutions at positions N297Q and K222R, wherein the amine-containing moiety is site-specifically conjugated to the endogenous glutamine at position 295 and the substituted glutamine at position 297; b) one or more glutamine-containing tag(s), wherein the amine-containing moiety is site-specifically conjugated to the glutamine-containing tag(s) at a carboxyl terminus of a light chain of the antibody; c) one or more glutamine tag(s), wherein the amine-containing moiety is further site-specifically conjugated to the glutamine-containing tag at a carboxyl terminus of a heavy chain of the antibody; and wherein the drug-antibody ratio (DAR) is about 6-9. In some embodiments, the glutamine-containing tag at the carboxyl terminus of the light chain of the antibody is GGLLQGA (SEQ ID NO: 23); and the glutamine-containing tag at the carboxyl terminus of the heavy chain of the antibody is LLQGA (SEQ ID NO: 11).

In one variation, the ADC of the present invention comprises a) an amino acid substitutions at positions N297Q and K222R, wherein the amine-containing moiety is site-specifically conjugated to the endogenous glutamine at position 295 and the substituted glutamine at position 297; b) one or more glutamine-containing tag(s), wherein the amine-containing moiety is site-specifically conjugated to the glutamine-containing tag(s) at a carboxyl terminus of a light chain of the antibody; c) one or more glutamine-containing tag(s), wherein the amine-containing moiety is further site-specifically conjugated to the glutamine-containing tag inserted after amino acid position T135 in a heavy chain of the antibody; and wherein the drug-antibody ratio (DAR) is about 6-9. In some embodiments, the glutamine-containing tag at the carboxyl terminus of the light chain of the antibody is GGLLQGA (SEQ ID NO: 23); and the glutamine-containing tag inserted after T135 in the heavy chain of the antibody is LLQG (SEQ ID NO: 2).

In another variation, the ADC of the present invention comprises a) an amino acid substitutions at positions N297Q and K222R, wherein the amine-containing moiety is site-specifically conjugated to the endogenous glutamine at position 295 and the substituted glutamine at position 297; b) one or more glutamine-containing tag(s), wherein the amine-containing moiety is site-specifically conjugated to the glutamine-containing tag(s) at a carboxyl terminus of a light chain of the antibody; c) one or more glutamine-containing tag(s), wherein the amine-containing moiety is further site-specifically conjugated to the glutamine-containing tag at amino acid positions G200-S202 in a heavy chain of the antibody; and wherein the drug-antibody ratio (DAR) is about 6-9. In some embodiments, the glutamine-containing tag at the carboxyl terminus of the light chain of the antibody is GGLLQGA (SEQ ID NO: 23); and the glutamine-containing tag inserted after T135 in the heavy chain of the antibody is LLQG (SEQ ID NO: 2).

In some embodiments, the glutamine-containing tag for the ADC described herein comprises an amino acid sequence XXQX (SEQ ID NO:37), wherein X can be a conventional or nonconventional amino acid, as described herein. For example, in some embodiments, X is L (Leu), A (Ala), G (Gly), S (Ser), V (Val), F (Phe), Y (Tyr), H (His), R (Arg), N (Asn), E (Glu), D (Asp), C (Cys), Q (Gln), I (Ile), M (Met), P (Pro), T (Thr), K (Lys), or W (Trp).

In some embodiments, the glutamine-containing tag comprises an amino acid sequence selected from the group consisting of Q, LQG, LLQGG (SEQ ID NO:1), LLQG (SEQ ID NO:2), LSLSQG (SEQ ID NO:3), GGGLLQGG (SEQ ID NO:4), GLLQG (SEQ ID NO:5), LLQ, GSPLAQSHGG (SEQ ID NO:6), GLLQGGG (SEQ ID NO:7), GLLQGG (SEQ ID NO:8), GLLQ (SEQ ID NO:9), LLQLLQGA (SEQ ID NO:10), LLQGA (SEQ ID NO:11), LLQYQGA (SEQ ID NO:12), LLQGSG (SEQ ID NO:13), LLQYQG (SEQ ID NO:14), LLQLLQG (SEQ ID NO:15), SLLQG (SEQ ID NO:16), LLQLQ (SEQ ID NO:17), LLQLLQ (SEQ ID NO:18), LLQGR (SEQ ID NO:19), LLQGPP (SEQ ID NO:20), LLQGPA (SEQ ID NO:21), GGLLQGPP (SEQ ID NO:22), GGLLQGA (SEQ ID NO:23), LLQGA (SEQ ID NO:24), LLQGPGK (SEQ ID NO:25), LLQGPG (SEQ ID NO:26), LLQGP (SEQ ID NO:27), LLQP (SEQ ID NO:28), LLQPGK (SEQ ID NO:29), LLQAPGK (SEQ ID NO:30), LLQGAPG (SEQ ID NO:31), LLQGAP (SEQ ID NO:32), LLQGPA (SEQ ID NO:33), LLQGPP (SEQ ID NO:34), GGLLQGPP (SEQ ID NO:35), and LLQLQG (SEQ ID NO:36).

In some embodiments, the glutamine-containing tag comprises an amino acid sequence LLQGA (SEQ ID NO: 24), LQG, GGLLQGA (SEQ ID NO:23), LLQGPA (SEQ ID NO:33), LLQGPP (SEQ ID NO:34), GGLLQGPP (SEQ ID NO:35), LLQGSG (SEQ ID NO:13), LLQG (SEQ ID NO:2), LLQYQG (SEQ ID NO:14), LLQLLQG (SEQ ID NO:15), LLQLQG (SEQ ID NO:36), LLQLLQ (SEQ ID NO:18), LLQLQ (SEQ ID NO:17), LLQGR (SEQ ID NO:19), LLQYQGA (SEQ ID NO:12), SLLQG (SEQ ID NO:16), or LLQLLQGA (SEQ ID NO:10).

In some embodiments, the glutamine-containing tag does not comprise an amino acid sequence selected from the group consisting of LGGQGGG (SEQ ID NO:41), GGGQGGL (SEQ ID NO:42), GXGQGGG (SEQ ID NO:43), GGXQGGG (SEQ ID NO:44), GGGQXGG (SEQ ID NO:45), and GGGQGXG (SEQ ID NO:46), wherein X is G, A, S, L, V, F, Y, R, N, or E). Other exemplary tags are also described, for example, in US2013/0230543 and US2013/0122020.

In some embodiments, the antibody of the ADCs as described herein comprises an amino acid modification at the last amino acid position in the carboxyl terminus relative to a wild-type antibody at the same position. In some embodiments, the modification is an amino acid deletion, insertion, substitution, mutation, or any combination thereof. In some embodiments, the substitution comprises replacing a wild type amino acid with another (e.g., a non-wild type amino acid). In some embodiments, the insertion comprises inserting one or more amino acid(s) (e.g., inserting one, two, three or more amino acids). In some embodiments, the other (e.g., non-wild type) or inserted amino acid is Arg. In some embodiments, the other (e.g., non-wild type) amino acid is Ala, Asn, Asp, Cys, Glu, Gln, Gly, His, Ile, Leu, Met, Phe, Pro, Ser, Thr, Trp, Tyr, or Val. For example, in some embodiments, the last amino acid in the carboxyl terminus of the antibody (e.g., the heavy chain of an antibody) can be deleted, and the glutamine-containing tag engineered to the C-terminus of the polypeptide comprises the amino acid sequence LLQGA (SEQ ID NO:11) or GGLLQGA (SEQ ID NO:23).

In some embodiments, the antibody comprises an amino acid modification at the first amino acid position in the amino terminus relative to a wild-type antibody at the same position. In some embodiments, the modification is an amino acid deletion, insertion, substitution, mutation, or any combination thereof. In some embodiments, the substitution comprises replacing a wild type amino acid with another (e.g., non-wild type) amino acid. In some embodiments, the insertion comprises inserting an amino acid. In some embodiments, the non-wild type or inserted amino acid is Arg. In some embodiments, the other (non-wild type or inserted) amino acid is Ala, Asn, Asp, Cys, Glu, Gln, Gly, His, Ile, Leu, Met, Phe, Pro, Ser, Thr, Trp, Tyr, or Val.

In some embodiments, the ADC described herein comprises a full length antibody heavy chain and an antibody light chain. In some embodiments, the antibody described herein is a monoclonal antibody, a polyclonal antibody, a human antibody, a humanized antibody, a chimeric antibody, a bispecific antibody, a minibody, a diabody, or an antibody fragment. In some embodiments, the antibody is an IgG. In some embodiments, the IgG is selected from the group consisting of IgG1, IgG2, IgG3, and IgG4. In some embodiments, the antibody is an IgA, IgE, IgD, or IgM. In some embodiments, the effector function (e.g., as measured by Fcγ3 and/or C1q binding) of the ADCs described herein decreases no greater than about any of 1-fold, 2-fold, 3-fold, 4-fold, or 5-fold relative to a wild type antibody. In some embodiments, the antibody of the ADC is an IgG, wherein the effector function of the IgG decreases no greater than about 2-fold relative to a wild type IgG. In other embodiments, the effector function of the IgG decreases about 2-fold relative to a wild type IgG. In other embodiments, the effector function of the IgG decreases more than about 2-fold relative to a wild type IgG. In some embodiments, the antibody of the ADC is an IgG, wherein the effector function of the IgG decreases no greater than about 1-fold relative to a wild type IgG. In other embodiments, the effector function of the IgG decreases about 1-fold relative to a wild type IgG. In some embodiments, the effector function of the IgG decreases more than about any of 1-fold, 3-fold, 4-fold, or 5-fold relative to a wild type IgG.

The number of amine-containing moieties agents which may be conjugated to the antibody is dependent on 1) the number of glutamine-containing tags which are linked/inserted to the antibody as well as the number of glutamines on the glutamine-containing tag; and/or 2) the number of endogenous glutamines on the antibody (i.e., native glutamines without engineering, such as glutamines in the variable domains, CDRs, etc.) and/or 3) the number of endogenous glutamines made reactive by the antibody engineering as described herein or an engineered transglutaminase. For example, two amine-containing moieties may be site-specifically conjugated to an antibody at the carboxyl termini of the two light chains, and four amine-containing moieties may be site-specifically conjugated to the antibody at positions Q295 and N297Q. In some embodiments, the amine-containing moiety can be the same or different at each conjugation position.

Examples of a cytotoxic agent include, but are not limited to, an anthracycline, an auristatin (e.g., dolestatin, MMAD, MMAE, MMAF, PF-06380101, PF-06463377 and PF-06456780), a spliceostatin, a CBI/CPI dimer (including "mixed" dimers comprising both CBI and CPI components, as described in U.S. Provisional patent application 61/932, 118), a calicheamicin, a duocarmycin, an enediyne, a geldanamycin, a maytansine, a puromycin, a taxane, a vinca alkaloid, SN-38, a tubulysin, a hemiasterlin, a camptothecin, a combretastatin, a dolastatin, an indolino-benzodiazepine dimer, a pyrrolobenzodiazepine dimer and a pladienolide, and stereoisomers, isosteres, analogs, or derivatives thereof.

The anthracyclines are derived from bacteria *Streptomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965, 1998. Exemplary dolastatins and auristatins include, but are not limited to, dolastatin 10, auristatin E, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other novel auristatins (such as the ones described in U.S. Publication No. 2013/0129753). In some embodiments, the auristatin is 0101 (2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide) having the following structure:

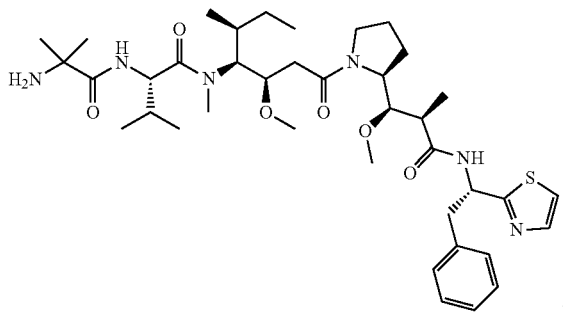

In some embodiments, the auristatin is 3377 (N,2-dimethylalanyl-N-{(1S,2R)-4-{(2S)-2-[(1R,2R)-3-{[(1S)-1-carboxyl-2-phenylethyl]amino}-1-methoxy-2-methyl-3-oxopropyl]pyrrolidin-1-yl}-2-methoxy-1-[(1S)-1-methylpropyl]-4-oxobutyl}-N-methyl-L-valinamide) having the following structure:

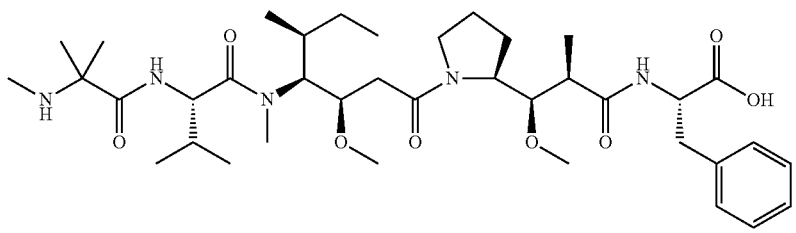 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)C(C)(C)NC)C(C)C]

In other embodiments, the auristatin is 0131 (2-methyl-L-proly-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

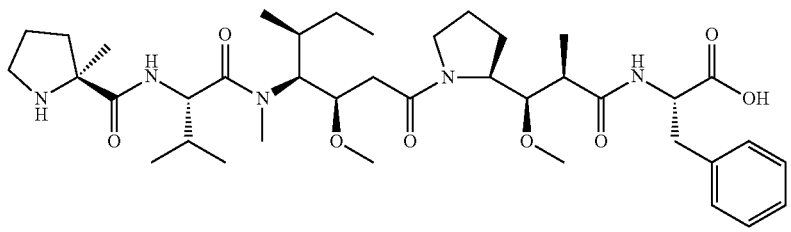 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@]1(C)CCCN1)C(C)C]

In other embodiments, the auristatin is 0121 (2-methyl-L-proly-N-[(3R,4S,5S)-1-{(2S)-2-[(1R,2R)-3-{[(2S)-1-methoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide) having the following structure:

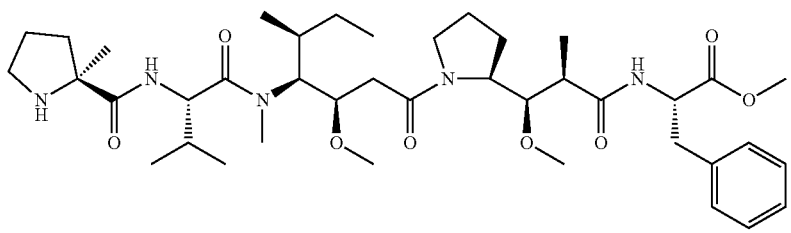 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@]1(C)CCCN1)C(C)C]

Camptothecin is a cytotoxic quinoline alkaloid which inhibits the enzyme topoisomerase I. Examples of camptothecin and its derivatives include, but are not limited to, topotecan and irinotecan, and their metabolites, such as SN-38.

Combretastatins are natural phenols with vascular disruption properties in tumors. Exemplary combretastatins and their derivatives include, but are not limited to, combretastatin A-4 (CA-4) and ombrabulin.

Duocarmycin and CC-1065 are DNA alkylating agents with cytotoxic potency. See Boger and Johnson, *PNAS* 92:3642-3649 (1995). Exemplary dolastatins and auristatins include, but are not limited to, (+)-docarmycin A and (+)-duocarmycin SA, and (+)-CC-1065.

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, uncialamicin, dynemicin, and their derivatives.

Hemiasterlin and its analogues (e.g., HTI-286) bind to the tubulin, disrupt normal microtubule dynamics, and, at stoichiometric amounts, depolymerize microtubules.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethylaminoethylamino-17-demethoxygeldanamycin).

Maytansines or their derivatives maytansinoids inhibit cell proliferation by inhibiting the microtubules formation during mitosis through inhibition of polymerization of tubulin. See Remillard et al., *Science* 189:1002-1005 (1975). Exemplary maytansines and maytansinoids include, but are not limited to, mertansine (DM1) and its derivatives as well as ansamitocin.

Pyrrolobenzodiazepine dimers (PBDs) and indolino-benzodiazepine dimers (IGNs) are anti-tumor agents that contain one or more immine functional groups, or their equivalents, that bind to duplex DNA. PBD and IGN molecules are based on the natural product athramycin, and interact with DNA in a sequence-selective manner, with a preference for purine-guanine-purine sequences. Exemplary PBDs and their analogs include, but are not limited to, SJG-136.

Spliceostatins and pladienolides are anti-tumor compounds which inhibit splicing and interacts with spliceosome, SF3b. Examples of spliceostatins include, but are not limited to, spliceostatin A, FR901464. Examples of pladienolides include, but are not limited to, Pladienolide B, Pladienolide D, and E7107.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Vinca alkyloids are also anti-tubulin agents. Exemplary vinca alkyloids include, but are not limited to, vincristine, vinblastine, vindesine, and vinorelbine.

In some embodiments, the agent moiety is a toxin polypeptide (or a toxin protein). Examples of a toxin polypeptide include, but are not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, tricothecenes, inhibitor cystine knot (ICK) peptides (e.g., ceratotoxins), and conotoxin (e.g., KIIIA or SmIIIa).

Methods for Conjugating ADCs

Conjugation of anti-Trop2 antibodies with the linker-payloads of the present invention is accomplished whereby an amount of antibody is adjusted to 5 mg/mL in buffer containing 25 mM Tris-HCl, pH 8.0-8.5. An amount of linker-payload is added in a 5-50 fold, or 5-500 fold, molar excess over antibody and the enzymatic reaction initiated by addition of 2% (w/v) bacterial transglutaminase (Ajinomoto Activa TI, Japan), and incubated with gentle shaking at 37° C. for 16-24 hours. The ADC is purified using Butyl Sepharose™ High Performance (Butyl HP, GE Healthcare Biosciences) by adjusting the reaction mixture to obtain a buffer composition of 0.75 M ammonium sulfate, 25 mM potassium phosphate, pH 7 (Buffer A). The material is applied to a Butyl HP, washed with 5 CV Buffer A, and eluted with a 20 CV linear gradient into 25 mM potassium phosphate, pH 7. Fractions containing the ADC are pooled, dialyzed against PBS, concentrated using a 10 kDa Amicon Ultra centrifugal filter unit (Millipore Corporation), and sterile filtered through a 0.2 µm filter. Alternatively, the ADC is purified using MabSelect Protein A resin (GE Healthcare Biosciences) following standard protocols, and buffer exchanged into PBS. Other methods of conjugating ADCs are knows, including those methods described in WO2012/059882.

Method of Using Antibody-Drug Conjugates of the Invention

The ADCs of the present invention are useful in various applications including, but not limited to, therapeutic treatment methods and diagnostic treatment methods.

In one aspect, the invention provides a method for treating a cancer in a subject. Accordingly, in some embodiments, provided is a method of treating a cancer in a subject in need thereof comprising administering to the subject an effective amount of a composition (e.g., pharmaceutical composition) comprising the ADC as described herein. As used herein, cancers include, but are not limited to, a solid cancer (such as bladder, breast, cervical, choriocarcinoma, colon, esophageal, gastric, glioblastoma, head and neck, kidney, liver, lung (e.g., Non Small Cell Lung Cancer (NSCLC)), oral, ovarian, pancreatic, prostate, and skin cancer); and a liquid cancer (such as acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, adult T-cell leukemia and multiple myeloma.)

In some embodiments, provided is a method of inhibiting tumor growth or progression in a subject in need thereof, comprising administering to the subject an effective amount of a composition comprising the ADCs as described herein. In other embodiments, provided is a method of inhibiting metastasis of cancer cells or tumors (e.g., solid or liquid tumors) in a subject in need thereof, comprising administering to the subject an effective amount of a composition comprising the ADCs as described herein. In other embodiments, provided is a method of inducing tumor regression in a subject in need thereof, comprising administering to the subject an effective amount of a composition comprising the ADCs as described herein.

The agent moiety in the ADCs as described herein can be a detectable moiety such as an imaging agent and an enzyme-substrate label. The ADCs as described herein can also be used for in vivo diagnostic assays, such as in vivo imaging (e.g., PET or SPECT), or a staining reagent.

In some embodiments, the methods described herein further comprise a step of treating a subject with an additional form of therapy. In some embodiments, the additional form of therapy is an additional anti-cancer therapy including, but not limited to, chemotherapy, radiation, surgery, hormone therapy, and/or additional immunotherapy.

In some embodiments, the additional form of therapy comprises administering one or more therapeutic agent in addition to the ADCs as described herein. The therapeutic agents include, but are not limited to, a second ADC (e.g., conventional ADC such as brentuximab vedotin (ADCETRIS®) and ado-trastuzumab emtansine)) (KADCYLA®)), an antibody (e.g., an anti-VEGF antibody, an anti-HER2 antibody, anti-CD25 antibody, and/or an anti-CD20 antibody), an angiogenesis inhibitor, a cytotoxic agent (e.g., docetaxel, cisplatin, doxorubicin, mitomycin, tamoxifen, or fluorouracil), and an anti-inflammatory agent (e.g., prednisone, and progesterone).

Pharmaceutical Compositions

The present invention also provides a pharmaceutical composition comprising the ADCs as described herein in a pharmaceutically acceptable excipient or carrier. The ADCs can be administered alone or in combination with one or more other ADCs of the invention or in combination with one or more other drugs (or as any combination thereof). For example, the ADCs of the present invention can be administered in combination with the conventional ADCs (i.e., not designed with stability modulation features). The methods and uses of the invention thus also encompass embodiments of combinations (co-administration) with other active agents, as detailed below.

As used herein, the term "co-administration," "co-administered," or "in combination with" is intended to mean and does refer to the following: (i) simultaneous administration of a combination of an ADC disclosed herein and therapeutic agent(s) to a patient in need of treatment, when such components are formulated together into a single dosage form which releases said components at substantially the same time to said patient; (ii) substantially simultaneous administration of such combination of an ADC disclosed herein and therapeutic agent(s) to a patient in need of treatment, when such components are formulated apart from each other into separate dosage forms which are taken at substantially the same time by said patient, whereupon said components are released at substantially the same time to said patient; (iii) sequential administration of such combination of an ADC disclosed herein and therapeutic agent(s)

to a patient in need of treatment, when such components are formulated apart from each other into separate dosage forms which are taken at consecutive times by said patient with a significant time interval between each administration, whereupon said components are released at substantially different times to said patient; and (iv) sequential administration of such combination of an ADC disclosed herein and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

Generally, the ADCs disclosed herein are suitable to be administered as a formulation in association with one or more pharmaceutically acceptable excipient(s). The term 'excipient' is used herein to describe any ingredient other than the compound(s) of the invention. The choice of excipient(s) to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In some embodiments, isotonic agents, including, but not limited to, sugars, polyalcohols (e.g., mannitol, sorbitol) or sodium chloride are included in the pharmaceutical composition. Additional examples of pharmaceutically acceptable substances include, but are not limited to, wetting agents or minor amounts of auxiliary substances such as wetting or emulsifying agents, preservatives or buffers, which enhance the shelf life or effectiveness of the antibody.

In some embodiments, the ADCs described herein can be deimmunized to reduce immunogenicity upon administration to a subject suing known techniques such as those described, e.g., in PCT Publication WO98/52976 and WO00/34317.

Pharmaceutical compositions of the present invention and methods for their preparation are readily apparent to those skilled in the art. Such compositions and methods for their preparation may be found, for example, in Remington's Pharmaceutical Sciences, 22nd Edition (Mack Publishing Company, 2012). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the engineered polypeptide conjugates disclosed herein.

The pharmaceutical compositions of the invention are typically suitable for parenteral administration. Parenteral administration of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. For example, parenteral administration includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. In some embodiments, parenteral administration is the intravenous or the subcutaneous route.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include controlled, delayed, sustained, pulsed, targeted and programmed release formulations. For example, in one aspect, sterile injectable solutions can be prepared by incorporating the engineered Fc-containing polypeptide, e.g., antibody-drug conjugate or bispecific antibody, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the agent moiety (e.g., small molecules such as cytotoxic agent) and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of an ADC disclosed herein is typically in the range of about 0.01 mg to about 1200 mg per patient, depending, of course, on the mode of administration. For example, an intravenous monthly dose may require about 1 to about 1000 mg/patient. The total monthly dose may be administered in single or divided doses and may, at the physician's discretion, fall outside of the typical range given herein.

An exemplary, non-limiting range for a therapeutically or prophylactically effective amount of an ADC as disclosed herein is about 0.01 to about 1000 mg/patient/month. In certain embodiments, the ADC may be administered at about 1 to about 200 or about 1 to about 150 mg/patient/month. In some embodiments, the patient is human.

Kits

The invention also provides kits (or articles of manufacture) for use in the treatment of the disorders described above. Kits of the invention include one or more containers comprising a purified ADC and instructions for using the conjugate for treating a disease. For example, the instructions comprise a description of administration of the ADC to treat a disease, such as cancer (e.g., a solid or liquid cancer). The kit may further comprise a description of selecting an individual suitable for treatment based on identifying whether that individual has the disease and the stage of the disease.

The instructions relating to the use of the ADC generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is the higher loaded ADC as described herein. The container may further comprise a second pharmaceutically active agent.

Kits may optionally provide additional components such as buffers and interpretive information. Normally, the kit comprises a container and a label or package insert(s) on or associated with the container.

EXAMPLES

It is understood that the examples and embodiments described herein are for illustrative purposes only and that various modifications or changes in light thereof will be suggested to persons skilled in the art and are to be included within the spirit and purview of this application.

HPLC and LC-MS Conditions Used for Analyses:

Analytical HPLC conditions: Phenomenex Luna C18 (2), 150×3.0 mm, 5 μm column; Mobile phase A: 0.02% trifluoroacetic acid in water (v/v); Mobile phase B: 0.02% trifluoroacetic acid in acetonitrile (v/v); Gradient: 0% to 100% B over 8.5 minutes, then 100% B for 1.5 minutes; Flow rate: 1.5 mL/minute. Temperature: not controlled; Detection: DAD 210, 254 nm; Injection volume: 10 μL; Instrument: Agilent 1100 HPLC. Analytical LC-MS conditions: Waters Acquity UPLC HSS T3, C18, 2.1×50 mm, 1.7 µm; Mobile phase A: 0.1% formic acid in water (v/v); Mobile phase B: 0.1% formic acid in acetonitrile (v/v); Gradient: 5% B over 0.1 minute, 5% to 95% B over 2.5 minutes, 95% B over 0.35 minute; Flow rate: 1.25 mL/minute. Temperature: 60° C.; Detection: 200-450 nm; MS (+) range 100-2000 daltons; Injection volume: 5 µL; Instrument: Waters Acquity.

Preparative HPLC Conditions Used for Purifications:

Method A: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 5% to 50% B over 20 minutes; Flow rate: 20 mL/minute. Temperature: not controlled; Detection: DAD 210, 254 nm; Injection volume: up to 5 mL. Instrument: Gilson 215.

Method B: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 20% to 80% B over 20 minutes; Flow rate: 20 mL/minute. Temperature: not controlled; Detection: DAD 210, 254 nm; Injection volume: up to 5 mL. Instrument: Gilson 215.

Method C: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 5% to 70% B over 20 minutes; Flow rate: 20 mL/minute. Temperature: not controlled; Detection: DAD 210, 254 nm; Injection volume: up to 5 mL. Instrument: Gilson 215.

Method D: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 10% to 70% B over 20 minutes; Flow rate: 20 mL/minute. Temperature: not controlled; Detection: DAD 210, 254 nm; Injection volume: up to 5 mL. Instrument: Gilson 215.

Method E: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 30% to 85% B over 20 minutes; Flow rate: 20 mL/minute. Temperature: not controlled; Detection: DAD 210, 254 nm; Injection volume: up to 5 mL. Instrument: Gilson 215.

Method F: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 10% to 90% B over 20 minutes; Flow rate: 20 mL/minute. Temperature: not controlled; Detection: DAD 210, 254 nm; Injection volume: up to 5 mL. Instrument: Gilson 215.

Method G: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 10% to 95% B over 20 minutes; Flow rate: 20 mL/minute. Temperature: not controlled; Detection: DAD 210, 254 nm; Injection volume: up to 5 mL. Instrument: Gilson 215.

Method H: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 25% to 65% B over 20 minutes; Flow rate: 20 mL/minute. Temperature: not controlled; Detection: DAD 210, 254 nm; Injection volume: up to 5 mL. Instrument: Gilson 215.

Method I: Phenomenex Synergi Max C18, 250×50 mm, 10 um column; Mobile phase A: 0.2% formic acid in water (v/v); Mobile phase B: acetonitrile; Gradient: 33.0% to 58% B in 25 minutes, then rising to 100% B in 2 minutes, hold for 5 minutes; Flow rate: 80 mL/minute. Temperature: not controlled; Detection: DAD 220 nm.

Method J: DIKMA Diamonsil(2) C18, 200×20 mm, 5 um column; Mobile phase A: 0.225% formic acid in water (v/v); Mobile phase B: acetonitrile; Gradient: 53% to 73% B over 11 minutes, then rising to 100% B in 0.5 minutes, hold for 2 minutes; Flow rate: 35 mL/minute. Temperature: not controlled; Detection: DAD 220 nm.

Method K: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 20% to 90% B over 20 minutes; Flow rate: 20 mL/minute. Temperature: not controlled; Detection: DAD 210, 254 nm; Injection volume: up to 5 mL. Instrument: Gilson 215.

Method L: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 10% to 80% B over 20 minutes; Flow rate: 20 mL/minute. Temperature: not controlled; Detection: DAD 210, 254 nm; Injection volume: up to 5 mL. Instrument: Gilson 215.

Method M: Phenomenex Luna C18, 150×21.2 mm, 5 µm column; Mobile phase A: 0.02% acetic acid in water (v/v); Mobile phase B: 0.02% acetic acid in acetonitrile (v/v); Gradient: 1% to 100% B over 8.5 minutes then hold at 100% B over 2 minutes; Flow rate: 27 mL/minute. Temperature: 25° C.; Detection: DAD 215 nm, 254 nm; MS (+) range 150-2000 daltons; Injection volume: up to 5 mL. Instrument: 305 RP Waters FractionLynx LCMS.

Method N: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 50% to 100% B over 20 minutes; Flow rate: 20 mL/minute. Temperature: not controlled; Detection: DAD 210, 254 nm; Injection volume: up to 5 mL. Instrument: Gilson 215.

Method O: Phenomenex Luna C18, 150×21.2 mm, 5 µm column; Mobile phase A: 0.02% acetic acid in water (v/v); Mobile phase B: 0.02% acetic acid in acetonitrile (v/v); Gradient: 35% to 50% B over 8.5 minutes then hold at 100% B over 2 minutes; Flow rate: 27 mL/minute. Temperature: 25° C.; Detection: DAD 215 nm, 254 nm; MS (+) range 150-2000 daltons; Injection volume: up to 5 mL. Instrument: 305 RP Waters FractionLynx LCMS.

Method P: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 25% to 100% B over 20 minutes; Flow rate: 20 mL/minute. Temperature: not controlled; Detection: DAD 210, 254 nm; Injection volume: up to 5 mL. Instrument: Gilson 215.

Method Q: Phenomenex Luna C18, 100×30 mm, 5 µm column; Mobile phase A: 0.02% trifluoroacetic acid in water (v/v); Mobile phase B: 0.02% trifluoroacetic acid in acetonitrile (v/v); Gradient: 20% to 100% B over 20 minutes; Flow rate: 20 mL/minute. Temperature: not controlled; Detection: DAD 210, 254 nm; Injection volume: up to 5 mL. Instrument: Gilson 215.

Method R: Phenomenex Luna C18, 150×21.2 mm, 5 µm column; Mobile phase A: 0.02% acetic acid in water (v/v); Mobile phase B: 0.02% acetic acid in acetonitrile (v/v); Gradient: 35% to 50% B over 8.5 minutes then hold at 100% B over 2 minutes; Flow rate: 27 mL/minute. Temperature: 25° C.; Detection: DAD 215 nm, 254 nm; MS (+) range 150-2000 daltons; Injection volume: up to 5 mL. Instrument: 305 RP Waters FractionLynx LCMS.

Method S: Phenomenex Luna C18, 100×30 mm, 5 μm column; Mobile phase A: 0.02% trifluoroacetic acid in water (v/v); Mobile phase B: 0.02% trifluoroacetic acid in acetonitrile (v/v); Gradient: 20% to 90% B over 20 minutes; Flow rate: 20 mL/minute. Temperature: not controlled; Detection: DAD 210, 254 nm; Injection volume: up to 5 mL. Instrument: Gilson 215.

Method T: Phenomenex Synergi Max C18, 250×50 mm, 10 um column; Mobile phase A: 0.2% formic acid in water (v/v); Mobile phase B: acetonitrile; Gradient: 35.0% to 65% B in 30 minutes, then rising to 100% B in 2 minutes, hold for 5 minutes; Flow rate: 30 mL/minute. Temperature: not controlled; Detection: DAD 220 nm.

Method U: Isco MPLC, RediSep 43 g C18 column Gold; Mobile phase A: 0.02% trifluoroacetic acid in water (v/v); Mobile phase B: 0.02% trifluoroacetic acid in acetonitrile (v/v); Gradient: 20-100% B in 20 minutes; Flow rate: 40 ml/min; Temperature: not controlled; DAD 214, 254 nm.

Method V: Isco MPLC, RediSep 43 g C18 column Gold; Mobile phase A: 0.02% trifluoroacetic acid in water (v/v); Mobile phase B: 0.02% trifluoroacetic acid in acetonitrile (v/v); Gradient 10-80% B in 20 minutes; Flow rate: 40 ml/min; Temperature: not controlled; DAD 214, 254 nm.

Method W: Phenomenex Synergi Max-RP 250×50 mm, 10 μm column; Mobile phase A: 0.1% trifluoroacetic acid in water (v/v); Mobile phase B: 0.1% trifluoroacetic acid in acetonitrile (v/v); Gradient: 24% to 54% B over 30 minutes; Flow rate: 30 mL/minute. Temperature: not controlled; Detection: DAD 210, 254 nm; Injection volume: up to 5 mL.

Method X: Luna C18 150×25, 5 μm column; Mobile phase A: 0.2% trifluoroacetic acid in water (v/v); Mobile phase B: 0.2% trifluoroacetic acid in acetonitrile (v/v); Gradient: 30% to 50% B over 11 minutes; Flow rate: 35 mL/minute. Temperature: not controlled; Detection: DAD 210, 254 nm; Injection volume: up to 5 mL.

Method Y: Phenomenex Synergi Max-RP 250×50 mm, 100×30 mm, 10 μm column; Mobile phase A: 0.1% trifluoroacetic acid in water (v/v); Mobile phase B: 0.1% trifluoroacetic acid in acetonitrile (v/v); Gradient: 30% to 60% B over 22 minutes; Flow rate: 80 mL/minute. Temperature: not controlled; Detection: DAD 210, 254 nm; Injection volume: up to 5 mL.

Method Z: Phenomenex Synergi Max-RP 250×50 mm, 10 μm column; Mobile phase A: 0.1% trifluoroacetic acid in water (v/v); Mobile phase B: 0.1% trifluoroacetic acid in acetonitrile (v/v); Gradient: 30% to 60% B over 21.5 minutes; Flow rate: 80 mL/minute. Temperature: not controlled; Detection: DAD 210, 254 nm; Injection volume: up to 5 mL.

Method AA: Phenomenex Synergi Max-RP 250×80, 10 μm column; Mobile phase A: 0.1% trifluoroacetic acid in water (v/v); Mobile phase B: 0.1% trifluoroacetic acid in acetonitrile (v/v); Gradient: 40% to 70% B over 30 minutes; Flow rate: 30 mL/minute. Temperature: not controlled; Detection: DAD 220 nm; Injection volume: up to 5 m L.

Example 1

Preparation of N~2~-Benzoyl-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (6)

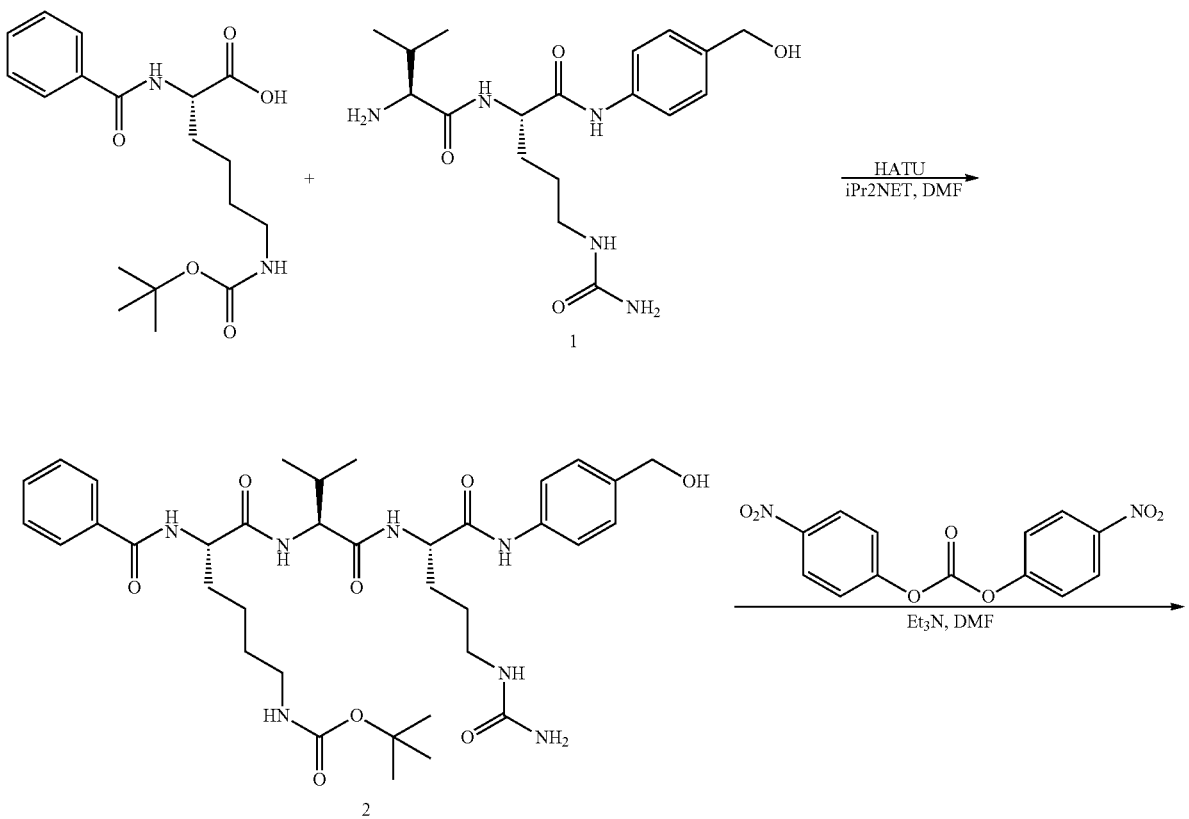

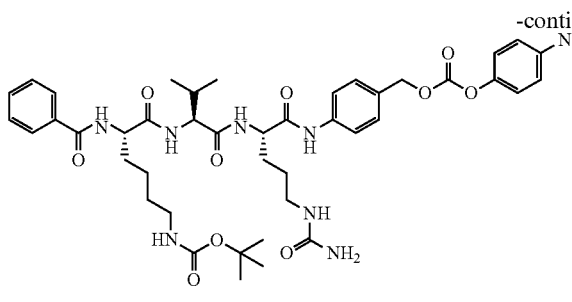
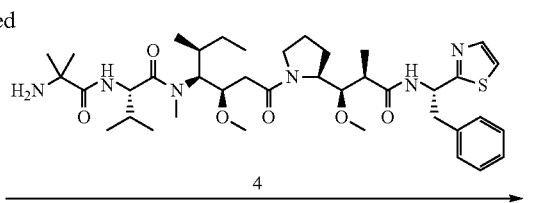
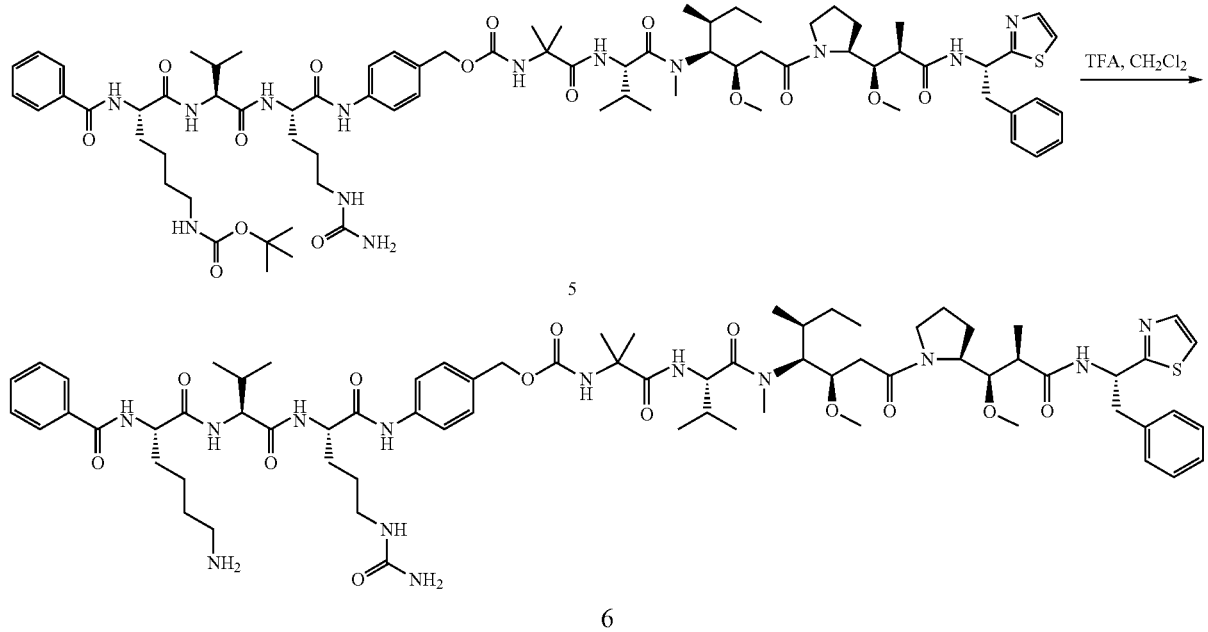

Step 1: Synthesis of N~2~-benzoyl-N~6~-(tert-butoxycarbonyl)-L-lysyl-L-valyl-N~5~-carbamoyl-N-[4-(hydroxymethyl)phenyl]-L-ornithinamide (2). To a solution of N~2~-benzoyl-N~6~-(tert-butoxycarbonyl)-L-lysine (100 mg, 0.285 mmol) and L-valyl-N~5~-carbamoyl-N-[4-(hydroxymethyl)phenyl]-L-ornithinamide (1, 108 mg, 0.285 mmol) in 1 mL of N,N-dimethylformamide were added O-(7-azabenzotriazol-1-yl)-N,N,N',N'-tetramethyluronium hexafluorophosphate (HATU, 111 mg, 0.285 mmol) followed by N,N-diisopropylethylamine (201 ul, 149 mg, 1.14 mmol). The mixture was monitored by LC-MS and allowed to stir for 16 hours at room temperature. The reaction was then concentrated and purified by reverse phase HPLC (Method A). Product containing fractions were lyophilized to provide 127 mg (63%) of the desired product. LC-MS m/z 712.4 [M+H$^+$]; 710.4 [M−H$^+$]; retention time=1.30 minutes.

Step 2: Synthesis of N~2~-benzoyl-N~6~-(tert-butoxycarbonyl)-L-lysyl-L-valyl-N~5~-carbamoyl-N-[4-({[(4-nitrophenoxy)carbonyl]oxy}methyl)phenyl]-L-ornithinamide (3). A solution of N~2~-benzoyl-N~6~-(tert-butoxycarbonyl)-L-lysyl-L-valyl-N~5~-carbamoyl-N-[4-(hydroxymethyl)phenyl]-L-ornithinamide (2, 125 mg, 0.352 mmol) in 1 mL of N,N-dimethylformamide was treated with p-nitrophenyl carbonate (107 mg, 0.352 mmol) and triethylamine (101 ul, 73.4 mg, 0.704 mmol). The mixture was stirred for two hours at room temperature and was then concentrated to near dryness and purified by silica gel chromatography using a gradient elution of 5% to 20% methanol in dichloromethane to give 129 mg (83.6%) of the desired product. LC-MS m/z 877.4 [M+H$^+$]; 899.3 [M+Na$^+$]; retention time=1.73 minutes.

Step 3: Synthesis of N~2~-benzoyl-N~6~-(tert-butoxycarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (5). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (4, 20 mg, 0.027 mmol) N~2~-benzoyl-N~6~-(tert-butoxycarbonyl)-L-lysyl-L-valyl-N~5~-carbamoyl-N-[4-({[(4-nitrophenoxy)carbonyl]oxy}methyl)phenyl]-L-ornithinamide (3, 28 mg, 0.032 mmol) in 0.2 mL of N,N-dimethylformamide were added 2,6-lutidine (5.8 mg, 0.032 mmol), N,N-diisopropylethylamine (9 ul, 7 mg, 0.054 mmol) and 3H-[1,2,3]triazolo[4,5-b]pyridin-3-ol (HOAt, 4.4 mg, 0.032 mmol). The mixture was monitored by LC-MS and allowed to stir for 16 hours at room temperature. The reaction was then concentrated and purified by reverse phase HPLC (Method B). Product containing fractions were lyophilized to provide 30 mg (75%) of the desired product. LC-MS m/z 1481.8 [M+H$^+$]; 1478.8 [M−H+]; retention time=1.91 minutes.

Step 4: Synthesis of N~2~-benzoyl-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (6). To a solution of N~2~-benzoyl-N~6~-(tert-butoxycarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (5, 30 mg, 0.02 mmol) in 2.5 mL of dichloromethane was added 2.5 mL of a 10% solution of trifluoroacetic acid in dichloromethane. The mixture was monitored by LC-MS and allowed to stir for 2.25 hours at room temperature. The reaction was then concentrated and purified by reverse phase HPLC (Method C). Product containing fractions were lyophilized to provide 22 mg (74%) of the desired product. LC-MS m/z 1381.7 [M+H$^+$]; retention time=1.54 minutes. Analytical HPLC retention time=6.00 minutes.

Example 2

Preparation of N~2~-(2,2-Dimethylpropanoyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (12)

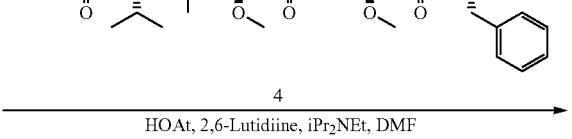

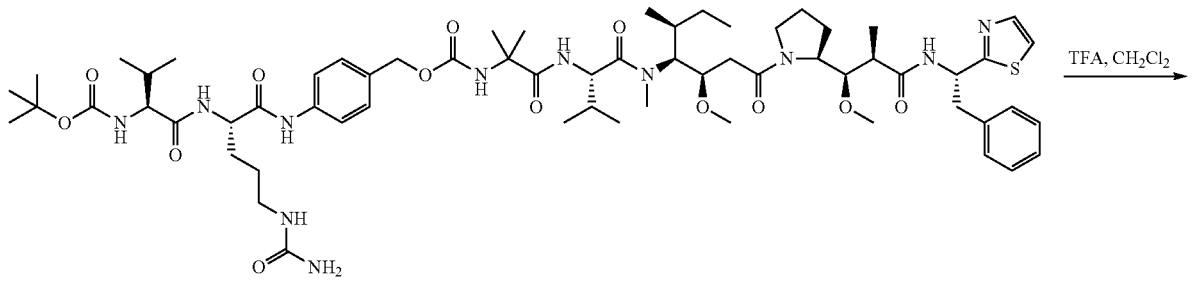

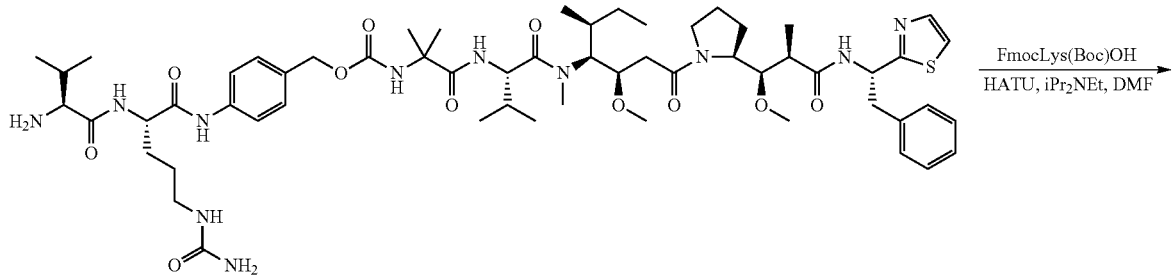

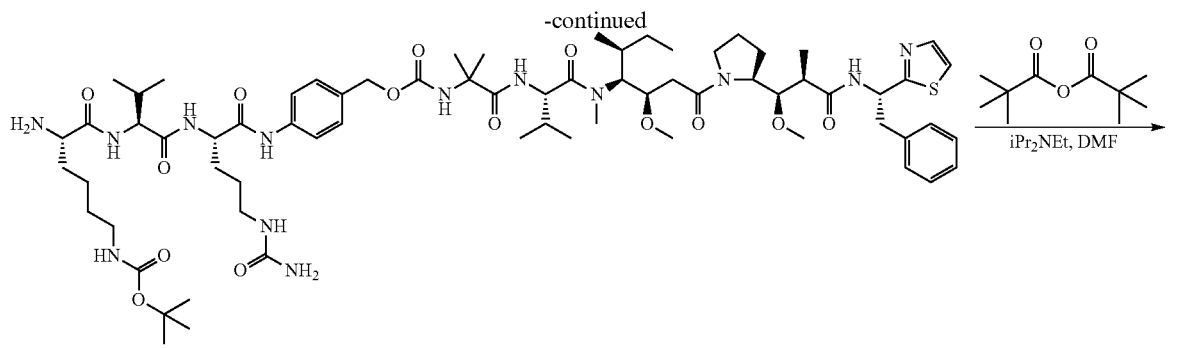

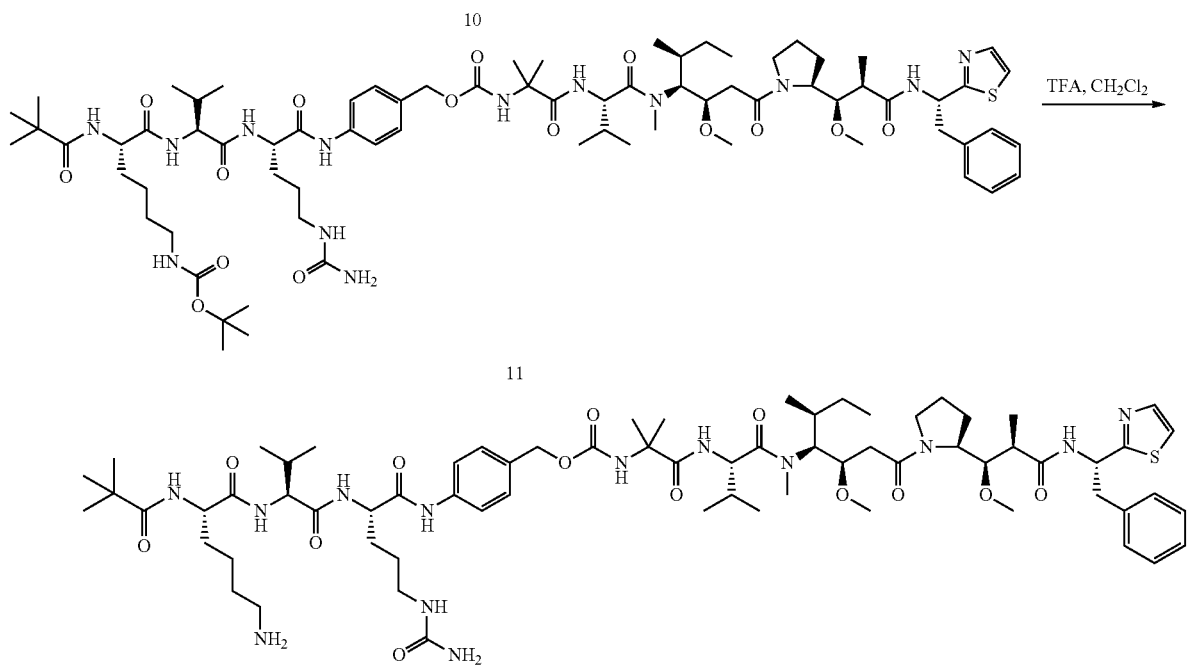

Step 1: Synthesis of N-(tert-butoxycarbonyl)-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (8). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (4, 80 mg, 0.11 mmol) and N-(tert-butoxycarbonyl)-L-valyl-N~5~-carbamoyl-N-[4-({[(4-nitrophenoxy)carbonyl]oxy}methyl)phenyl]-L-ornithinamide (7, 76.7 mg, 0.119 mmol) in 0.5 mL of N,N-dimethylformamide were added 2,6-lutidine (46.3 mg, 0.432 mmol), N,N-diisopropylethylamine (67.7 ul, 56.4 mg, 0.432 mmol) and 3H-[1,2,3]triazolo[4,5-b]pyridin-3-ol (HOAt, 17.7 mg, 0.130 mmol). The mixture was monitored by LC-MS and allowed to stir for 16 hours at 45° C. The reaction was then concentrated and purified by silica gel chromatography using a gradient elution of 5% to 20% methanol in dichloromethane to provide 90 mg (67%) of the desired product. LC-MS m/z 1248.7 [M+H+]; retention time=1.84 minutes.

Step 2: Synthesis of L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (9). To a solution of N-(tert-butoxycarbonyl)-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (8, 91 mg, 0.072 mmol) in 5 mL of dichloromethane was added 2 mL of a 20% solution trifluoroacetic acid in dichloromethane. The mixture was monitored by LC-MS and allowed to stir for 2.75 hours at room temperature. The reaction was then concentrated to provide 91 mg (100%) of the desired product that was used directly in the next step without purification. LC-MS m/z 1148.7 [M+H+]; retention time=1.43 minutes.

Step 3: Synthesis of N~6~-(tert-butoxycarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (10). To a solution of N~6~-

(tert-butoxycarbonyl)-N~2~-[(9H-fluoren-9-ylmethoxy)carbonyl]-L-lysine (50.6 mg, 0.108 mmol) in 0.5 mL of N,N-dimethylformamide were added O-(7-azabenzotriazol-1-yl)-N,N,N',N'-tetramethyluronium hexafluorophosphate (HATU, 41.6 mg, 0.108 mmol) followed by N,N-diisopropylethylamine (51 ul, 37.6 mg, 0.288 mmol) and the mixture was stirred for 15 minutes at room temperature. A solution of L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (9, 91 mg, 0.072 mmol) in 1 mL of N,N-dimethylformamide was then added. The mixture was monitored by LC-MS and allowed to stir for 2 hours at room temperature before diethylamine (2 ml, 1.41 g, 19.3 mmol) was slowly added. The reaction was allowed to stir for 16 hours, and was then acidified by addition of trifluoroacetic acid, concentrated and purified by reverse phase HPLC (Method D). Product containing fractions were lyophilized to provide 99 mg (92%) of the desired product. LC-MS m/z 1376.8 [M+H$^+$]; 1374.8 [M–H$^+$]; retention time=1.40 minutes.

Step 4: Synthesis of N~6~-(tert-butoxycarbonyl)-N~2~-(2,2-dimethylpropanoyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (11). To a solution of N~6~-(tert-butoxycarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide trifluoracetate (10, 21.5 mg, 0.015 mmol) and pivalic anhydride (5.6 mg, 0.030 mmol) in 0.2 mL of N,N-dimethylformamide was added N,N-diisopropylethylamine (26 ul, 19.4 mg, 0.15 mmol) and the mixture was stirred at room temperature for 45 minutes. The solution was then concentrated and purified by reverse phase HPLC (Method E). Product containing fractions were lyophilized to provide 21.9 mg (100%) of the desired product. LC-MS m/z 1460.7 [M+H$^+$]; 1458.5 [M–H$^+$]; retention time=1.93 minutes.

Step 5: Synthesis of N~2~-(2,2-dimethylpropanoyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (12). To a solution of N~6~-(tert-butoxycarbonyl)-N~2~-(2,2-dimethylpropanoyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (11, 21.9 mg, 0.015 mmol) in 1 mL of dichloromethane was added 0.33 mL of trifluoroacetic acid. The mixture was monitored by LC-MS and allowed to stir for 1 hour at room temperature. The reaction was then concentrated and purified by reverse phase HPLC (Method F). Product containing fractions were lyophilized to provide 8 mg (36%) of the desired product. LC-MS m/z 1360.7 [M+H$^+$]; retention time=1.45 minutes. Analytical HPLC retention time=6.01 minutes.

Example 3

Preparation of N~2~-(Phenylacetyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (14)

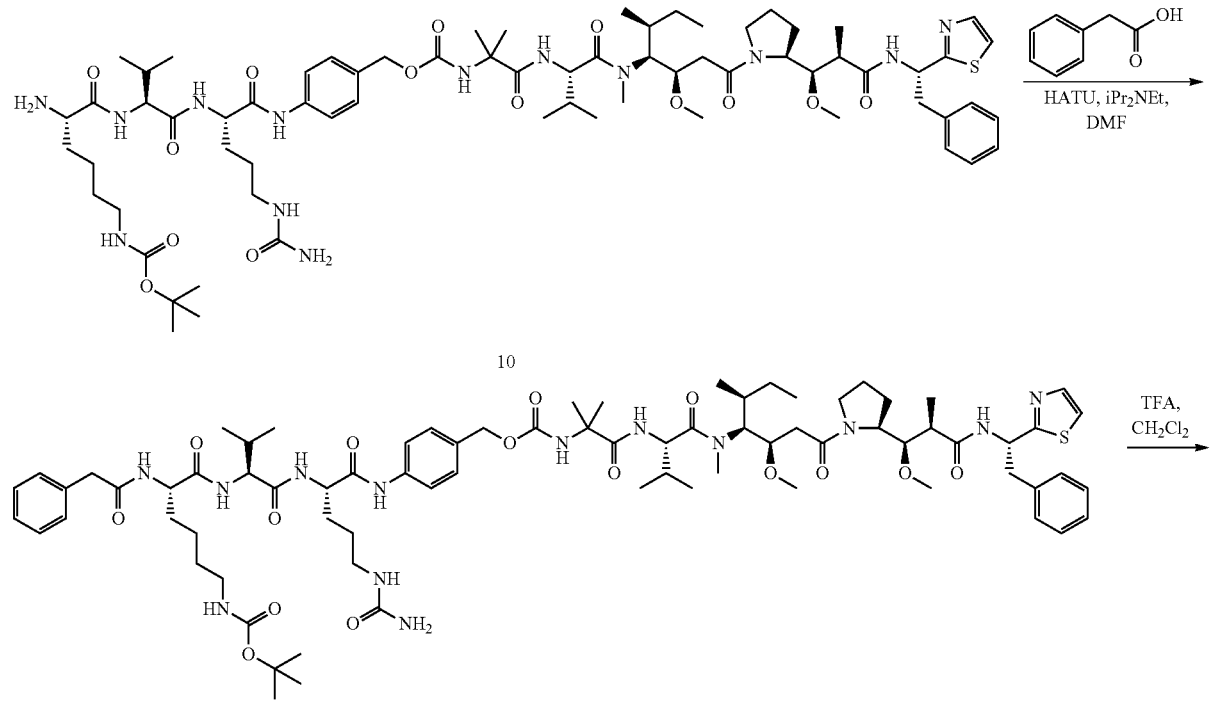

-continued

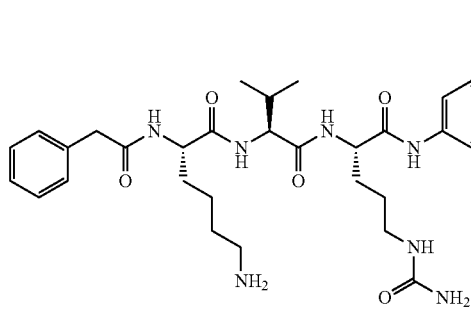
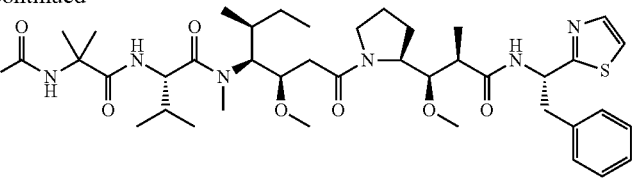

14

Step 1: Synthesis of N~6~-(tert-butoxycarbonyl)-N~2~-(phenylacetyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (13). To a solution of phenylacetic acid (15 mg, 0.11 mmol) in 0.2 mL of N,N-dimethylformamide was added O-(7-azabenzotriazol-1-yl)-N,N,N',N'-tetramethyl-uronium hexafluorophosphate (HATU, 43.1 mg, 0.11 mmol) followed by N,N-diisopropylethylamine (20 ul, 14.5 mg, 0.11 mmol) and the mixture was stirred at room temperature for 45 minutes. A solution of N~6~-(tert-butoxycarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide trifluroacetate (10, 20 mg, 0.013 mmol) in 0.2 mL of N,N-dimethylformamide was added and the mixture was stirred at room temperature for 16 hours. The solution was then concentrated and purified by reverse phase HPLC (Method G). Product containing fractions were lyophilized to provide 10 mg (52%) of the desired product. LC-MS m/z 1495.3 [M+H$^+$]; 1493.1 [M−H$^+$]; retention time=1.93 minutes.

Step 2: Synthesis of N~2~-(phenylacetyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (14). To a solution of N~6~-(tert-butoxycarbonyl)-N~2~-(phenylacetyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (13, 10 mg, 0.007 mmol) in 1 mL of dichloromethane was added 1 mL of a 20% solution of trifluoroacetic acid in dichloromethane. The mixture was monitored by LC-MS and allowed to stir for 2 hours at room temperature. The reaction was then concentrated and purified by reverse phase HPLC (Method G). Product containing fractions were lyophilized to provide 10 mg (100%) of the desired product. LC-MS m/z 1394.7 [M+H$^+$]; retention time=1.52 minutes. Analytical HPLC retention time=5.39 minutes.

Example 4

Preparation of N~2~-(1H-Imidazol-5-ylcarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (16)

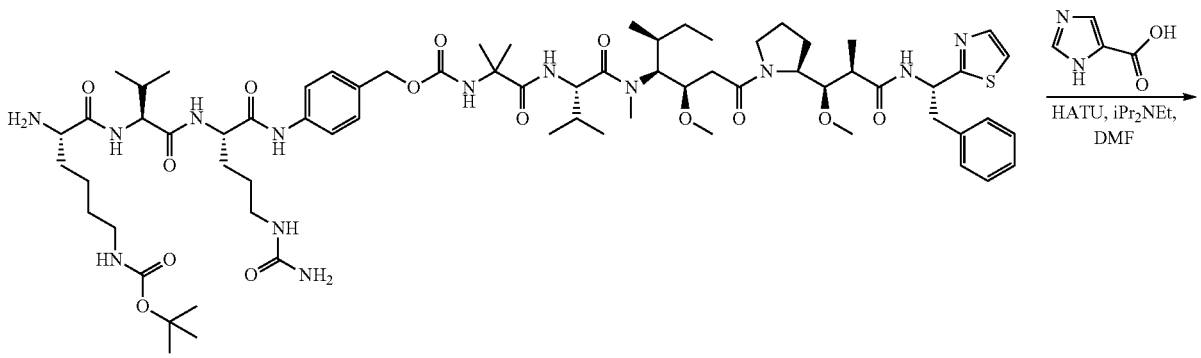

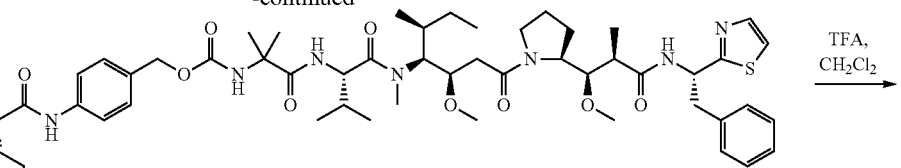
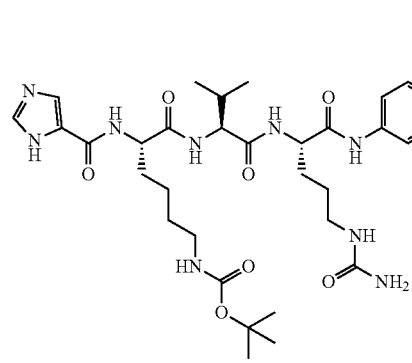

15

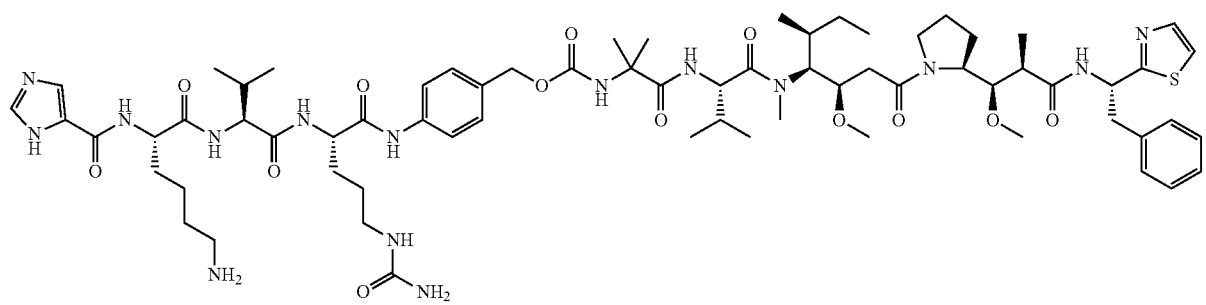

16

Step1: Synthesis of N~6~-(tert-butoxycarbonyl)-N~2~-(1H-imidazol-5-ylcarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (15). To a solution of N~6~-(tert-butoxycarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide trifluroacetate (10, 20.5 mg, 0.014 mmol) and 1H-imidazole-5-carboxylic acid (15.7 mg, 0.14 mmol) in 0.2 mL of N,N-dimethylformamide was added N,N-diisopropylethylamine (25 ul, 18.3 mg, 0.14 mmol) and the mixture was stirred at room temperature for 5 minutes. O-(7-Azabenzotriazol-1-yl)-N,N,N',N'-tetramethyluronium hexafluorophosphate (HATU, 54.3 mg, 0.14 mmol) was added and the mixture was stirred for an additional hour at room temperature. The solution was then concentrated and purified by reverse phase HPLC (Method G). Product containing fractions were lyophilized to provide 13 mg (59%) of the desired product. LC-MS m/z 1471.6 [M+H$^+$]; 1469.0 [M−H$^+$]; retention time=1.70 minutes.

Step 2: Synthesis of N~2~-(1H-imidazol-5-ylcarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (16). To a solution of N~6~-(tert-butoxycarbonyl)-N~2~-(1H-imidazol-5-ylcarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (15, 13 mg, 0.008 mmol) in 5 mL of dichloromethane was added 2 mL of a 20% solution of trifluoroacetic acid in dichloromethane. The mixture was monitored by LC-MS and allowed to stir for 15 minutes at room temperature. The reaction was then concentrated and purified by reverse phase HPLC (Method D). Product containing fractions were lyophilized to provide 6 mg (50%) of the desired product. LC-MS m/z 1370.7 [M+H$^+$]; 1368.6 [M−H$^+$]; retention time=1.39 minutes. Analytical HPLC retention time=5.30 minutes.

Example 5

Preparation of N~2~-(1H-Imidazol-5-ylacetyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (18)

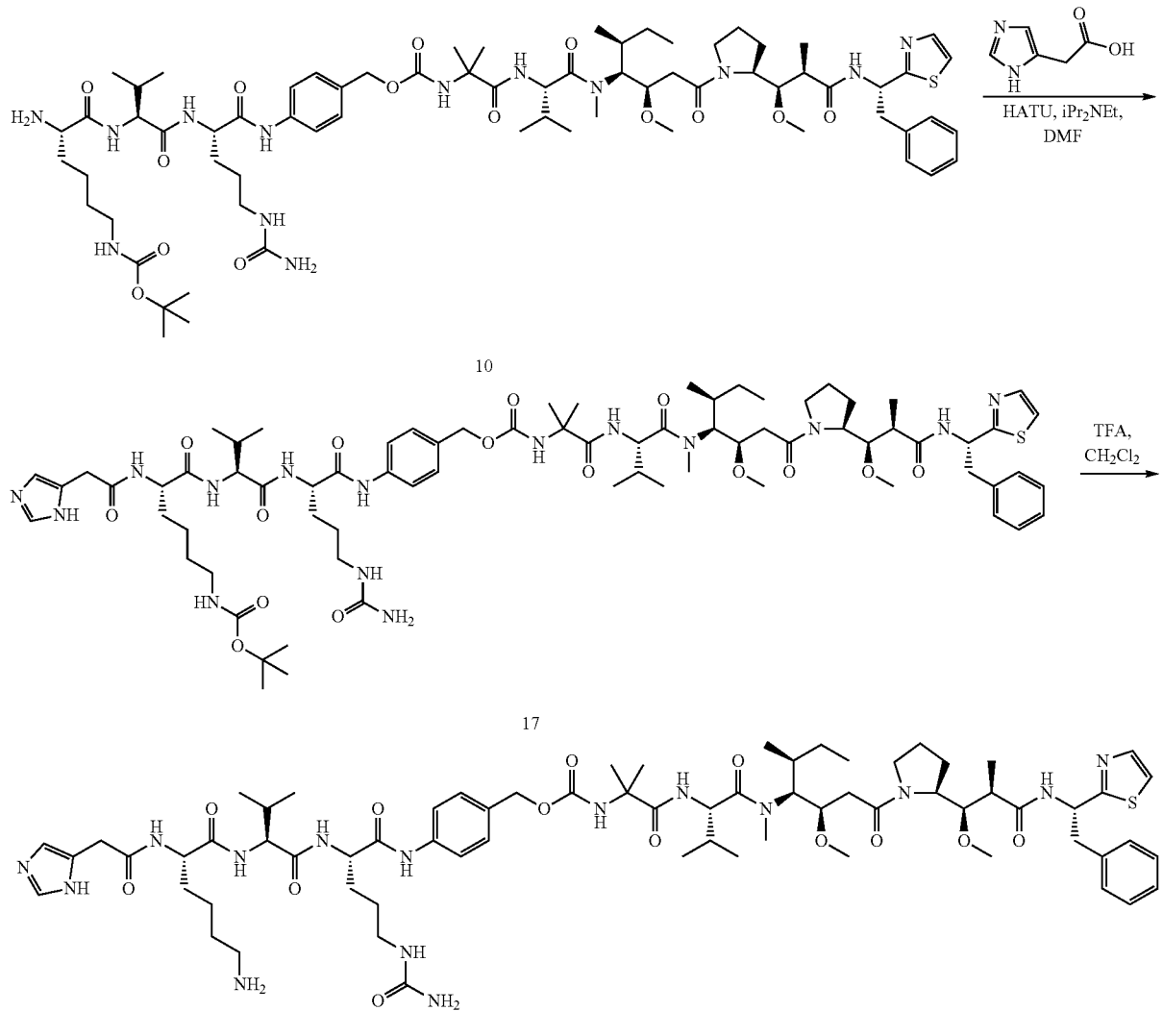

Step1: Synthesis of N~6~-(tert-butoxycarbonyl)-N~2~-(1H-imidazol-5-ylacetyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (17). To a solution of N~6~-(tert-butoxycarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide trifluroacetate (10, 20 mg, 0.013 mmol) and 2-(1H-imidazol-5-yl)acetic acid (30.0 mg, 0.20 mmol) in 0.2 mL of N,N-dimethylformamide was added N,N-diisopropylethylamine (23 ul, 17 mg, 0.13 mmol) and the mixture was stirred at room temperature for 5 minutes. O-(7-Azabenzotriazol-1-yl)-N,N,N',N'-tetramethyluronium hexafluorophosphate (HATU, 50.4 mg, 0.13 mmol) was added and the mixture was stirred for an additional hour at room temperature. The solution was then concentrated and purified by reverse phase HPLC (Method G). Product containing fractions were lyophilized to provide 13.6 mg (65%) of the desired product. LC-MS m/z 1485.6 [M+H$^+$]; 1483.5 [M−H$^+$]; retention time=1.44 minutes.

Step 2: Synthesis of N~2~-(1H-imidazol-5-ylacetyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (18). To a solution of N~6~-(tert-butoxycarbonyl)-N~2~-(1H-imidazol-5-ylacetyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (17, 13.6 mg, 0.009 mmol) in 5 mL of dichloromethane was added 2 mL of a 20% solution of trifluoroacetic acid in dichloromethane. The mixture was monitored by LC-MS and allowed to stir for 15 minutes at room temperature. The reaction was then concentrated and purified by reverse phase HPLC (Method D). Product containing fractions were lyophilized to provide 13 mg (96%) of the desired product. LC-MS m/z 1384.9 [M+H$^+$]; 1382.8 [M–H$^+$]; retention time=1.26 minutes. Analytical HPLC retention time=5.21 minutes.

Example 6

Preparation of N~2~-(3-Methylbutanoyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (19)

A solution of 3-methylbutanoic acid (10.2 mg, 0.100 mmol) in 0.4 mL of N,N-dimethylformamide was treated with N,N-diisopropylethylamine (35 ul, 26.1 mg, 0.200 mmol) and O-(7-azabenzotriazol-1-yl)-N,N,N',N'-tetramethyluronium hexafluorophosphate (HATU, 77.6 mg, 0.200 mmol) and the mixture was stirred at room temperature for five minutes. A solution of N~6~-(tert-butoxycarbonyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide trifluroacetate (10, 30 mg, 0.020 mmol) in 0.4 mL of N,N-dimethylformamide was added and the mixture was allowed to stir at room temperature for 1 hour. The solution was then concentrated to near dryness, then dissolved in 2 mL of dichloromethane and treated with 0.5 mL of trifluoroacetic acid. After stirring at room temperature of an additional 30 minutes, the reaction was concentrated and purified by reverse phase HPLC (Method H). Product containing fractions were lyophilized to provide 13 mg (44%) of the desired product. LC-MS m/z 1360.8 [M+H$^+$]; 1358.4 [M–H$^+$]; retention time=1.49 minutes. Analytical HPLC retention time=5.98 minutes.

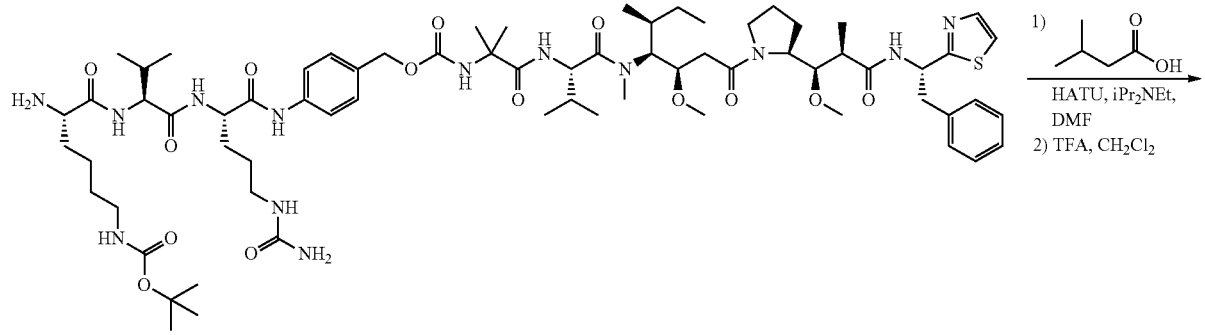

10

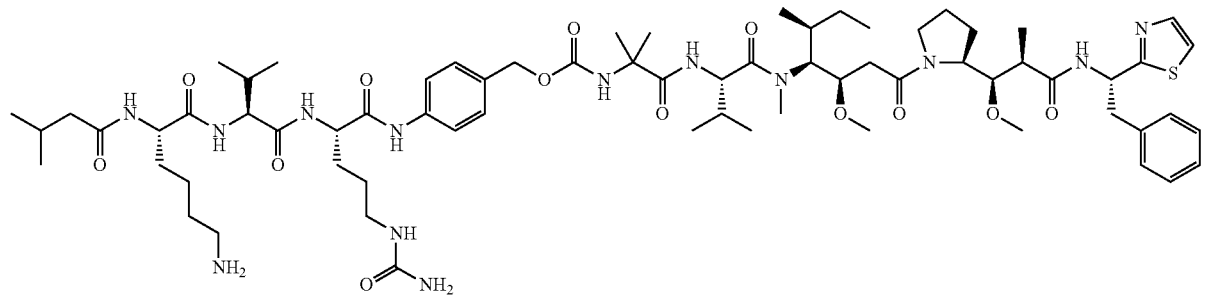

19

Example 7
Preparation of N~2~-(2-Methylpropanoyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (25)
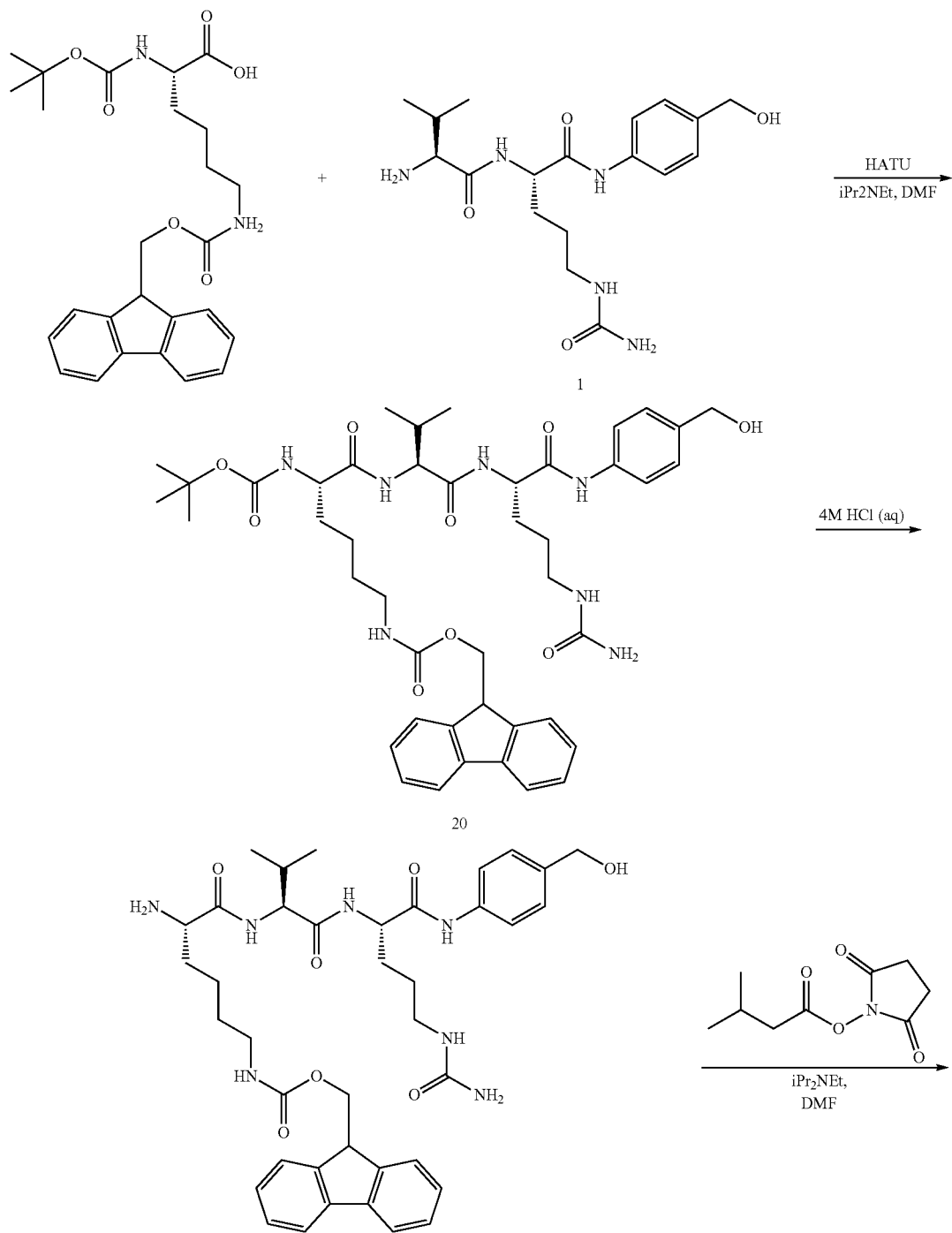

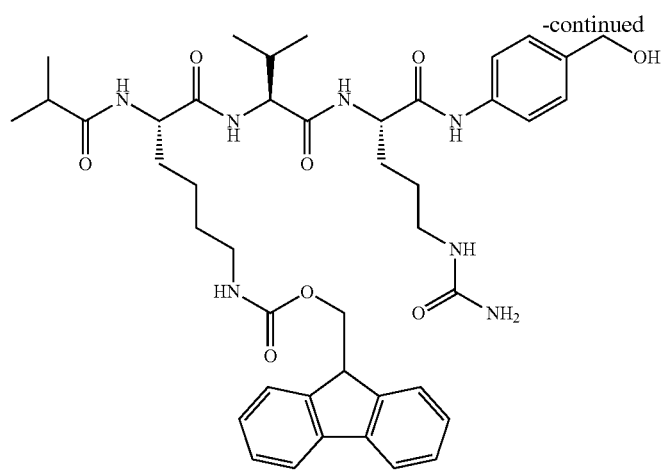
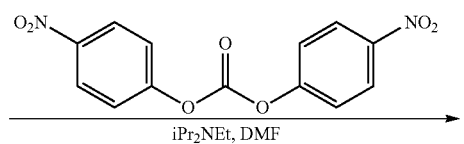
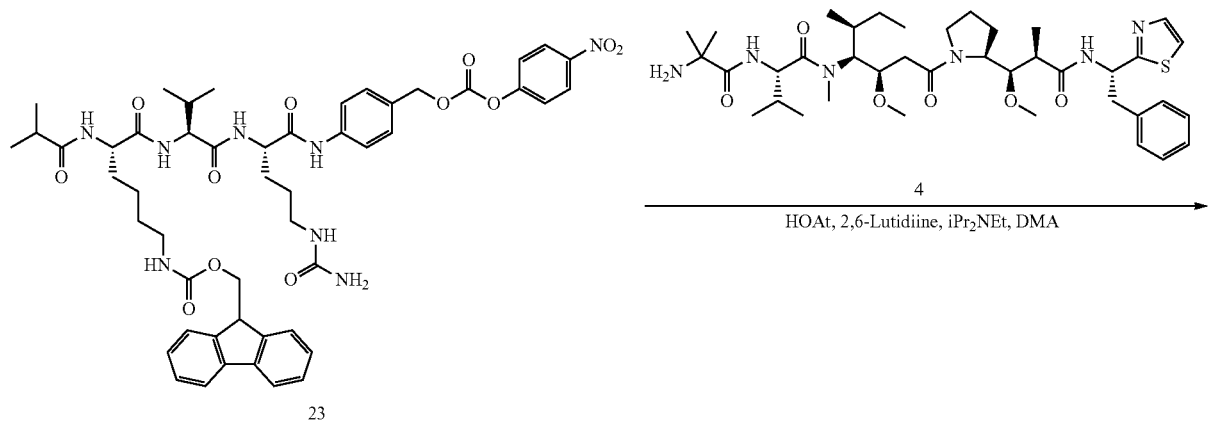
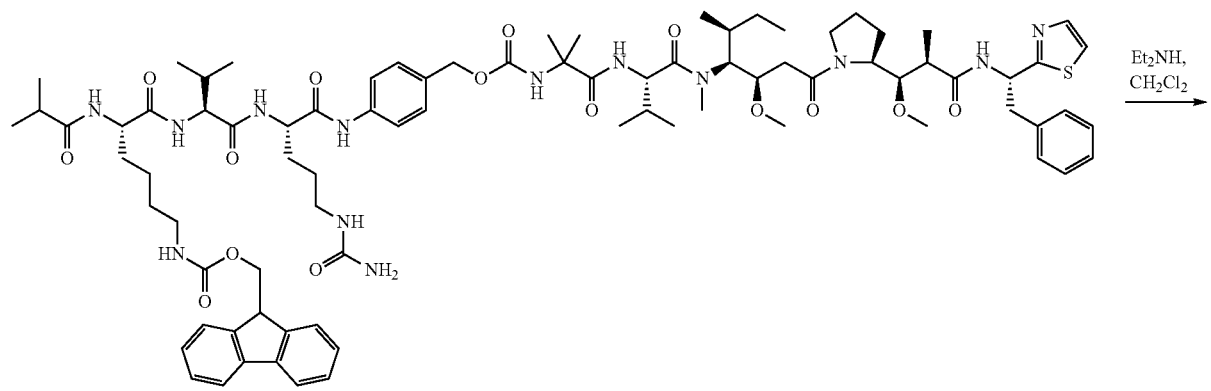
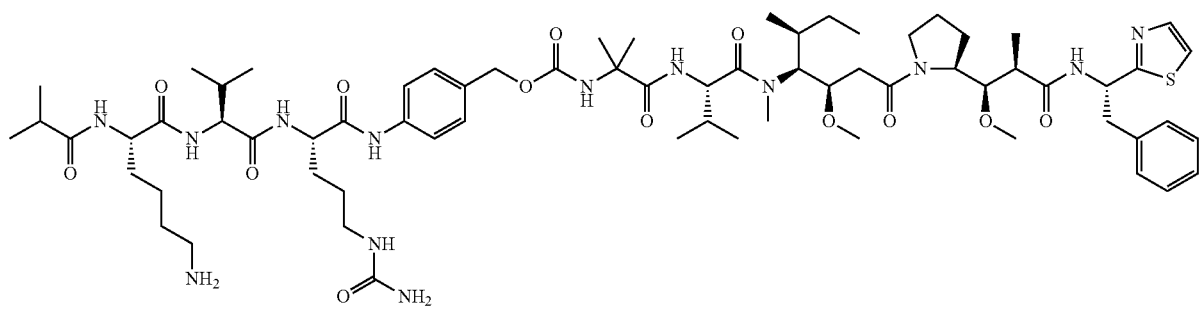

Step 1: Synthesis of N~2~-(tert-butoxycarbonyl)-N~6~-[(9H-fluoren-9-ylmethoxy)carbonyl]-L-lysyl-L-valyl-N~5~-carbamoyl-N-[4-(hydroxymethyl)phenyl]-L-ornithinamide (20). To a solution of L-valyl-N~5~-carbamoyl-N-[4-(hydroxymethyl)phenyl]-L-ornithinamide (1, 6.5 g, 17.1 mmol) and N~2~-(tert-butoxycarbonyl)-N~6~-[(9H-fluoren-9-ylmethoxy)carbonyl]-L-lysine (8.03 g, 17.1 mmol) in 200 mL of N,N-dimethylformamide were added N,N-diisopropylethylamine (3.32 g, 25.7 mmol) and O-(7-Azabenzotriazol-1-yl)-N,N,N',N'-tetramethyluronium hexafluorophosphate (HATU, 7.8 g, 20.56 mmol). The reaction mixture was stirred at room temperature for 12 hours and was then concentrated and purified by silica chromatography using a gradient elution of 5% to 17% methanol in dichloromethane to give 4.00 g (28.2%) of the desired product as a white solid.

Step 2: Synthesis of N~6~-[(9H-fluoren-9-ylmethoxy)carbonyl]-L-lysyl-L-valyl-N~5~-carbamoyl-N-[4-(hydroxymethyl)phenyl]-L-ornithinamide (21). A mixture of N~2~-(tert-butoxycarbonyl)-N~6~-[(9H-fluoren-9-ylmethoxy)carbonyl]-L-lysyl-L-valyl-N~5~-carbamoyl-N-[4-(hydroxymethyl)phenyl]-L-ornithinamide (20, 4.8 g, 5.78 mmol) in 96 mL of 4M aqueous hydrochloric acid was stirred at room temperature for 12 hours. The reaction mixture was adjusted to pH 7.5 by slow addition of saturated aqueous $K_2CO_3$ and then the resulting suspension was filtered. The solid was collected and dried in vacuum to give 4.00 g (94.9%) of the desired product as a yellow solid.

Step 3: Synthesis of N~6~-[(9H-fluoren-9-ylmethoxy)carbonyl]-N~2~-(2-methylpropanoyl)-L-lysyl-L-valyl-N~5~-carbamoyl-N-[4-(hydroxymethyl)phenyl]-L-ornithinamide (22). To a solution of N~6~-[(9H-fluoren-9-ylmethoxy)carbonyl]-L-lysyl-L-valyl-N~5~-carbamoyl-N-[4-(hydroxymethyl)phenyl]-L-ornithinamide (21, 500 mg, 0.685 mmol) and 1-[(2-methylpropanoyl)oxy]pyrrolidine-2,5-dione (190 mg, 1.03 mmol) in 20 mL of N,N-dimethylformamide was added N—N-diisopropylethylamine (221 mg, 1.7 mmol). After stirring for 2 hours at room temperature, the mixture was concentrated and purified by reverse phase HPLC (Method I) to give 100 mg (18.2%) of the desired product as a white solid.

Step 4: Synthesis of N~6~-[(9H-fluoren-9-ylmethoxy)carbonyl]-N~2~-(2-methylpropanoyl)-L-lysyl-L-valyl-N~5~-carbamoyl-N-[4-({[(4-nitrophenoxy)carbonyl]oxy}methyl)phenyl]-L-ornithinamide (23). To a solution of N~6~-[(9H-fluoren-9-ylmethoxy)carbonyl]-N~2~-(2-methylpropanoyl)-L-lysyl-L-valyl-N~5~-carbamoyl-N-[4-(hydroxymethyl)phenyl]-L-ornithinamide (22, 100 mg, 0.125 mmol) and p-nitrophenyl carbonate (42 mg, 0.138 mmol) in 5 mL of N,N-dimethylformamide was added N,N-diisopropylethylamine (32 mg, 0.25 mmol) and the mixture was stirred at room temperature for 12 hours. The solution was then concentrated and purified by reverse phase HPLC (Method J) to give 110 mg (91.7%) of the desired product as a white solid. HRMS m/z for $C_{50}H_{60}N_8O_{12}$: 987.4036 (M+Na)+. 1H NMR (400 MHz, DMSO): □ 10.12 (s, 1H), 8.30 (m, 2H), 8.18 (m, 1H), 7.88 (m, 3H), 7.64 (m, 6H), 7.27 (m, 6H), 6.00 (s, 1H), 5.44 (s, 2H), 5.23 (s, 2H), 4.21 (m, 6H), 2.95 (m, 5H), 1.99 (m, 1H), 1.24 (m, 12H), 0.99 (d, 6H), 0.85 (d, 6H);

Step 4: Synthesis of N~6~-[(9H-fluoren-9-ylmethoxy)carbonyl]-N~2~-(2-methylpropanoyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (24). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (4, 27.5 mg, 0.032 mmol) and N~6~-[(9H-fluoren-9-ylmethoxy)carbonyl]-N~2~-(2-methylpropanoyl)-L-lysyl-L-valyl-N~5~-carbamoyl-N-[4-({[(4-nitrophenoxy)carbonyl]oxy}methyl)phenyl]-L-ornithinamide (23, 36.7 mg, 0.038 mmol) in 1 mL of N,N-dimethylacetamide were added 2,6-lutidine (13.7 mg, 0.128 mmol), N,N-diisopropylethylamine (23 ul, 16.7 mg, 0.128 mmol) and 3H-[1,2,3]triazolo[4,5-b]pyridin-3-ol (HOAt, 5.2 mg, 0.038 mmol). The mixture was monitored by LC-MS and allowed to stir for 16 hours at room temperature. The solution was then concentrated and purified by reverse phase HPLC (Method K). Product containing fractions were lyophilized to provide 30 mg (60%) of the desired product.

Step 5: Synthesis of N~2~-(2-methylpropanoyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (25). A solution of N~6~-[(9H-fluoren-9-ylmethoxy)carbonyl]-N~2~-(2-methylpropanoyl)-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (24, 30 mg, 0.019 mmol) in 1 mL of dichloromethane was treated with 1 mL of diethylamine. The solution was stirred at room temperature for five hours, and then concentrated and purified by reverse phase HPLC (Method K). Product containing fractions were lyophilized to provide 6.0 mg (21%) of the desired product. LC-MS m/z 1346.9 [M+H$^+$]; retention time=1.47 minutes. Analytical HPLC retention time=5.87 minutes.

Procedure for Examples 8-18 and 49-71

Conjugation, Purification of Site-Specific Anti-Trop2 ADCs

For the conjugation of anti-Trop2 antibodies with the linker-payloads (LPs) of Examples 1 through 7, the indicated amount of antibody was adjusted to 5 mg/mL in buffer containing 25 mM Tris-HCl, pH 8.0-8.5. The indicated amount of LP was added in a 5-50 fold molar excess over antibody and the enzymatic reaction initiated by addition of 2% (w/v) bacterial transglutaminase (Ajinomoto Activa TI, Japan), and incubated with gentle shaking at 37° C. for 16-24 hours. The ADC was purified using Butyl Sepharose™ High Performance (Butyl HP, GE Healthcare Biosciences) by adjusting the reaction mixture to obtain a buffer composition of 0.75 M ammonium sulfate, 25 mM potassium phosphate, pH 7 (Buffer A). The material was applied to a Butyl HP, washed with 5 CV Buffer A, and eluted with a 20 CV linear gradient into 25 mM potassium phosphate, pH 7. Fractions containing the ADC were pooled, dialyzed against PBS, concentrated using a 10 kDa Amicon Ultra centrifugal filter unit (Millipore Corporation), and sterile filtered through a 0.2 μm filter. Alternatively, the ADC was purified using MabSelect Protein A resin (GE Healthcare Biosciences) following standard protocols, and buffer exchanged into PBS.

The following ADCs (attached at various positions and on various tags on the Trop2 antibody, as indicated on Tables 2 through 7) were made using the above described technique (bracketed portion indicates a glutamine residue, with wavy lines showing attachments points to the remainder of the Anti-Trop2 antibody):

Comparative Example 8

C6vcMMAD

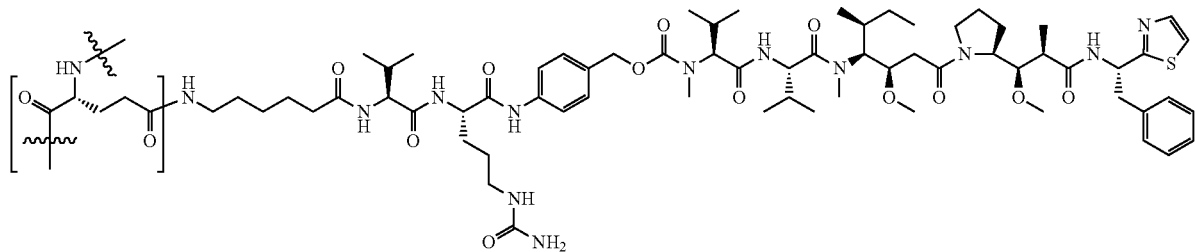

Comparative Example 9

AcLys-vcMMAD

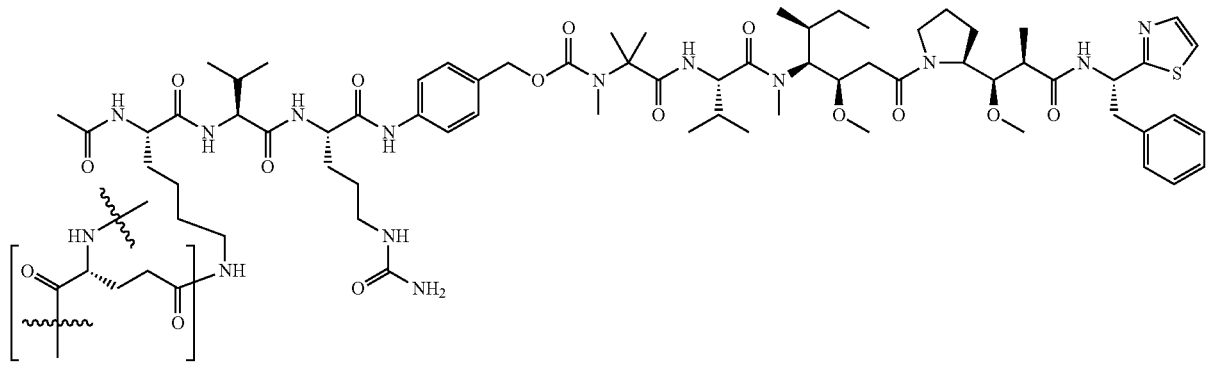

Comparative Example 10

C6vc0101

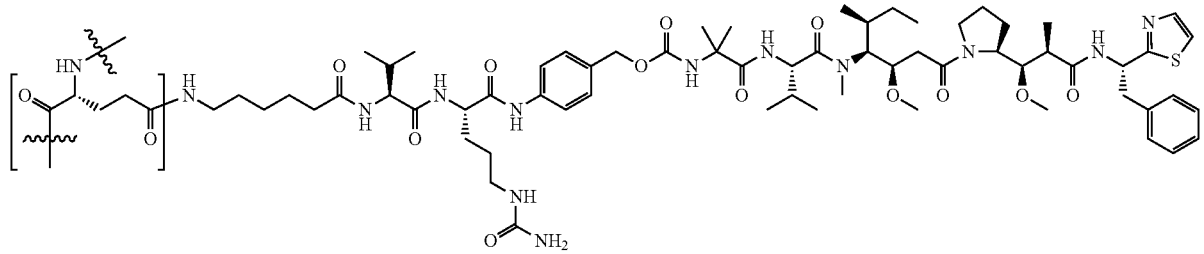

Comparative Example 11
AcLys-vc0101
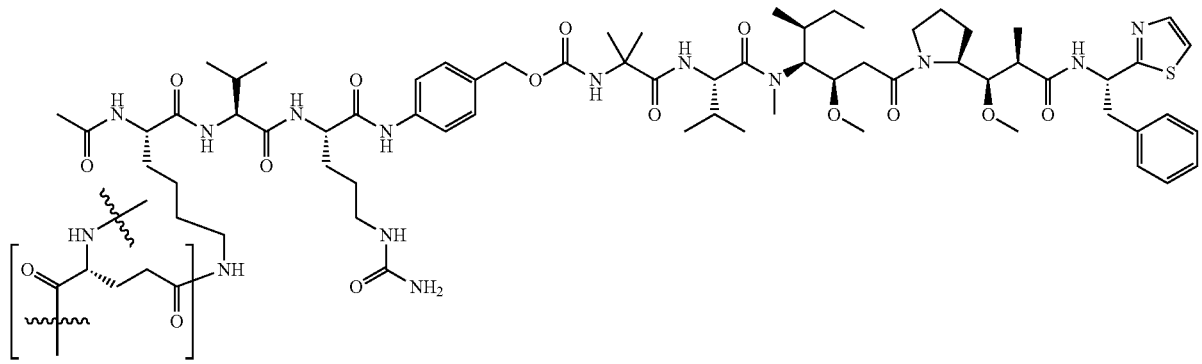
Example 12
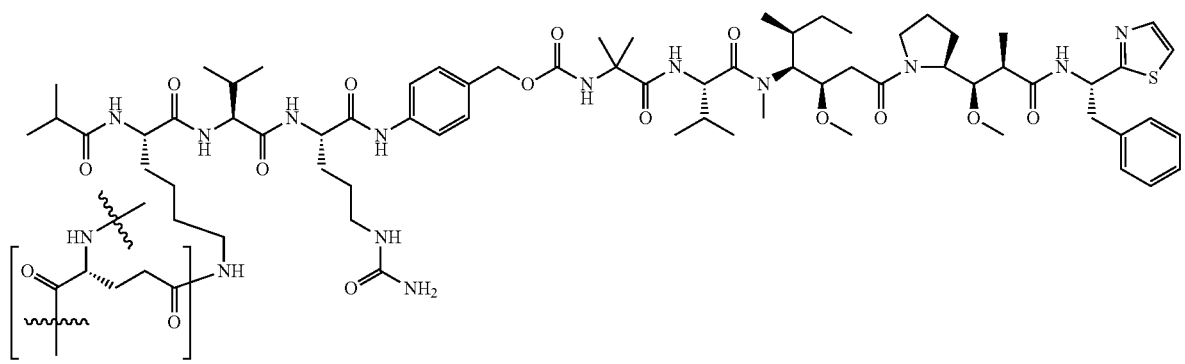
Example 13
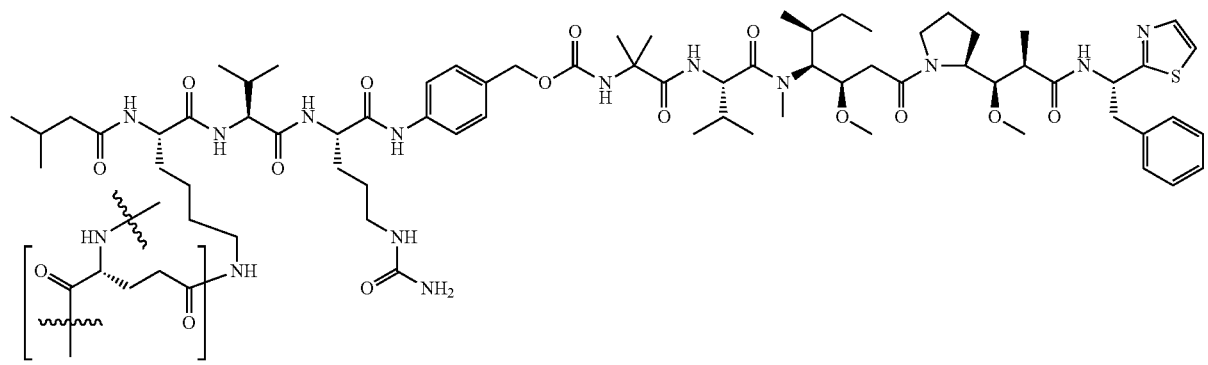

Example 14
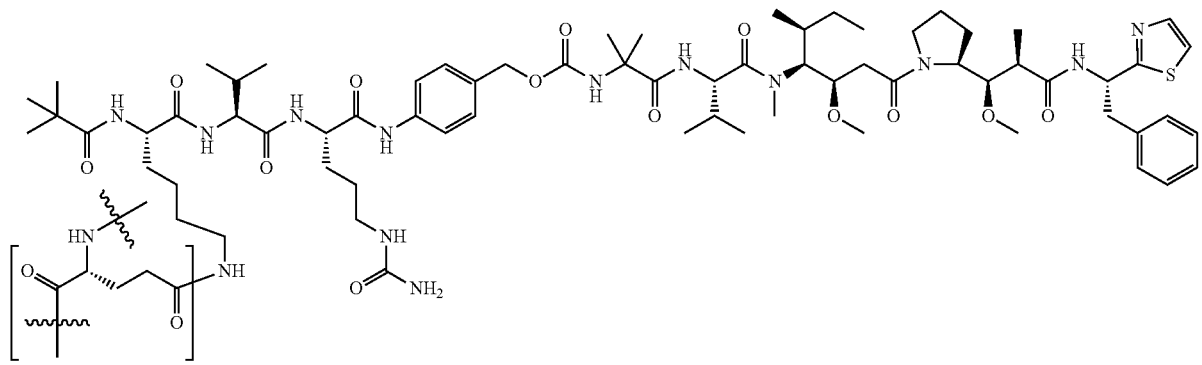
Example 15
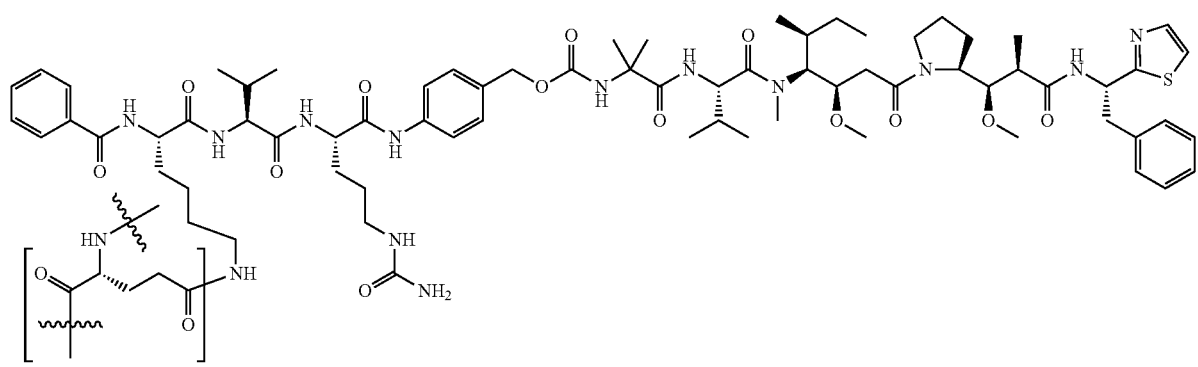
Example 16
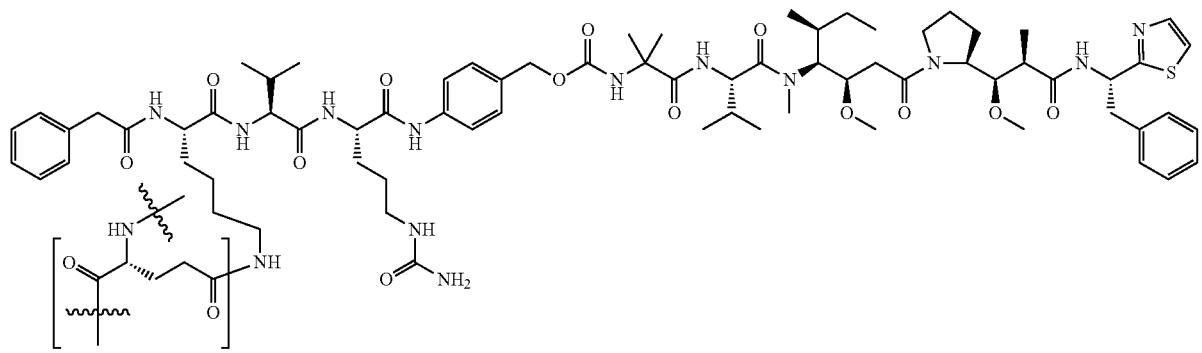

Example 17

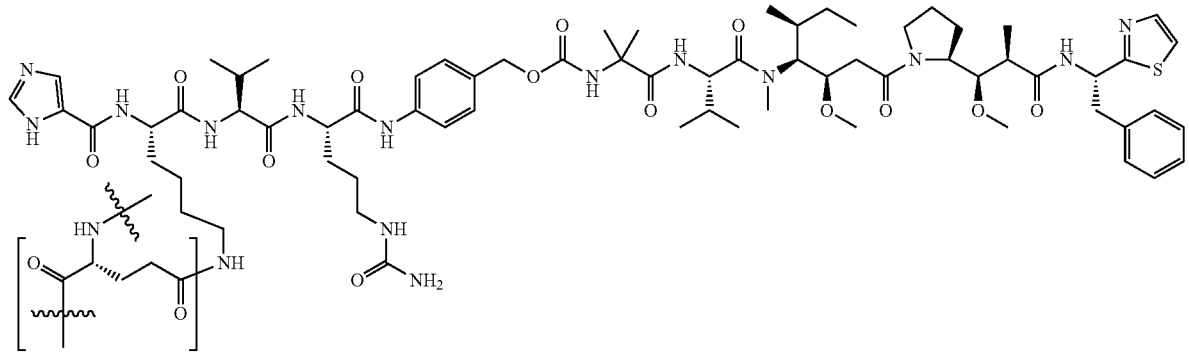

Example 18

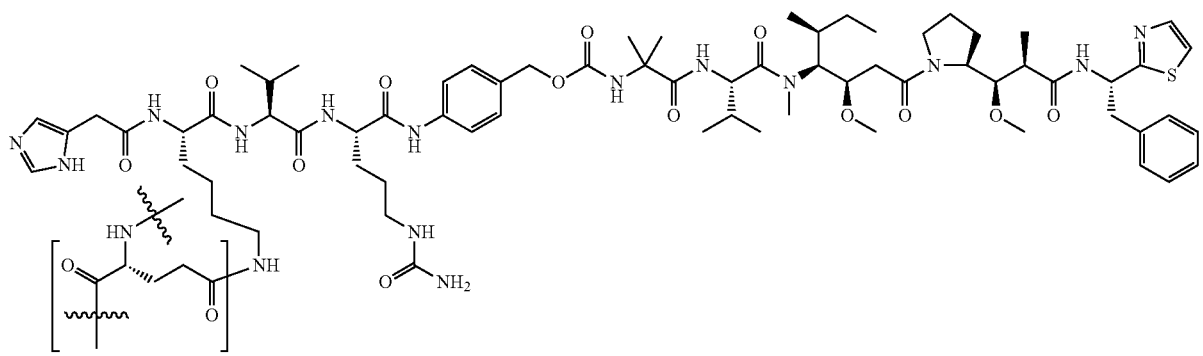

Example 19

In Vivo Stability Assay—Mouse

Plasma samples were obtained from mice at time points ranging from 1 to 10 days after a single 9 mg/kg dose of ADC. Samples were diluted with an equal volume of 1×PBS, and ADCs were isolated using MabSelect beads or Trop2 antigen coupled to CNBr-activated Sepharose (GE Healthcare) using standard protocols. Drug-antibody ratios were assessed before and after in vivo exposure using HIC methods and mass spectrometry.

Example 20

In Vivo Stability Assay—Rat

Plasma samples were obtained from rats at time points ranging from 1 to 10 days after a single 9 mg/kg dose of ADC. Samples were diluted with an equal volume of 1×PBS, and ADCs were isolated using Trop2 antigen coupled to CNBr-activated Sepharose (GE Healthcare) using standard protocols. Drug-antibody ratios were assessed before and after in vivo exposure using HIC methods and mass spectrometry.

Example 21A

In Vitro Stability Assay—Mouse Plasma 100-200 ug of ADC were incubated in mouse plasma (provided by Bioreclamation) supplemented with 1×PBS to the final ADC concentration of 0.125 mg/mL. Following incubation for 3-7 days, samples were diluted with an equal volume of 1×PBS, and ADCs were isolated using Trop2 antigen coupled to CNBr-activated Sepharose (GE Healthcare) using standard protocols. Drug-antibody ratios were assessed before and after in vitro exposure using HIC methods and mass spectrometry.

Example 21B

Identification of the Mouse Plasma Enzyme Responsible for Linker Cleavage

To classify the mouse plasma enzyme, in vitro stability assays were carried out in the presence of various protease inhibitors using anti-Trop2 L11B C6 vc0101 conjugate as a substrate. The results showed that the mouse plasma enzyme is likely a serine hydrolase inhibited by 1 mM Pefabloc (Roche) and 100 uM BNPP (Sigma). To identify the enzyme, we enriched the anti-Trop2 L11B C6 vc0101 linker hydrolysis activity by fractionating the Balb/c mouse serum using a sequence of steps. First, Balb/c serum (Bioreclamation-IVT) was depleted of IgG and albumin using commercially available MabSelect Protein A and Protein G resins (GE Healthcare), followed by Qproteome Murine Albumin Depletion Kit (Qiagen). The depleted serum was then subjected to sequential precipitation with ammonium sulfate. Fractions with the highest linker hydrolase activity were then applied to cation exchange HiTrap SP column (GE Healthcare) using step gradient elutions with sodium chloride. After that, SP fractions with the highest activity were applied to anion exchange HiTrap Q column (GE Healthcare) using step gradient elutions with sodium chloride. Fractions with the highest hydrolase activity were then combined and size fractionated using Superdex 200 column (GE Healthcare). Proteomics analysis of the pooled Superdex 200 fractions with the highest activity revealed Carboxylesterase 1C which is capable of hydrolyzing amide bonds, and can be inhibited with Pefabloc and BNPP. To verify the correct identification of mouse Carboxylesterase 1C as the plasma enzyme responsible for linker cleavage, the recombinant protein was expressed in Expi 293 cells, and purified using a HIS tag following standard protocols. The purified protein was confirmed to cleave multiple conjugates with VC-based linkers with the same relative activity as shown for the mouse plasma.

Example 22

In Vitro Stability Assay—Rat Plasma 100-200 ug of ADC were incubated in rat plasma (provided by Bioreclamation) supplemented with 1×PBS to the final ADC concentration of 0.125 mg/mL. Following incubation for 3-7 days, samples were diluted with an equal volume of 1×PBS, and ADCs were isolated using Trop2 antigen coupled to CNBr-activated Sepharose (GE Healthcare) using standard protocols. Drug-antibody ratios were assessed before and after in vitro exposure using HIC methods and mass spectrometry.

Example 23

In Vitro Stability Assay—Cynomolgus Plasma 100-200 ug of ADC were incubated in cynomolgus plasma (provided by Bioreclamation) supplemented with 1×PBS to the final ADC concentration of 0.125 mg/mL. Following incubation for 3-7 days, samples were diluted with an equal volume of 1×PBS, and ADCs were isolated using Trop2 antigen coupled to CNBr-activated Sepharose (GE Healthcare) using standard protocols. Drug-antibody ratios were assessed before and after in vitro exposure using HIC methods and mass spectrometry.

Example 24

In Vitro Cytotoxicity Assay

As shown in FIG. 1(A through I), in vitro cytotoxicity studies of chimeric anti-Trop2 antibodies conjugated at a range of sites with the aminocaproyl (C6) vc Aur0101 cytotoxic payload were performed with target-expressing BxPC3 cells. Untreated compounds (solid line) and their metabolites isolated after a 4.5 days of treatment in mouse plasma (broken line) were tested side-by-side to determine any changes in cytotoxicity. BxPc3 is a cancer cell line with high target expression levels (Trop-2 +++). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control.

Also as shown in FIG. 1(J through O), in vitro cytotoxicity studies of chimeric anti-Trop2 antibodies conjugated at the LCQ04 or L11B sites with one of the three linker-payloads (linker payloads of Examples 2, 3 and 5) were performed with target-expressing BxPC3 cells. Untreated compounds (solid line) and their metabolites isolated after a 4.5 days of treatment in mouse plasma (broken line) were tested side-by-side to determine any changes in cytotoxicity. BxPc3 is a cancer cell line with high target expression levels (Trop-2 +++). Cells were seeded on white walled clear bottom plates at 2000 cells per well for 24 hours before treatment. Cells were treated with 4 fold serially diluted antibody-drug conjugates in triplicates. Cell viability was determined by CellTiter-Glo® Luminescent Cell Viability Assay 96 (Promega, Madison, Wis.) 96 hours after treatment. Relative cell viability was determined as percentage of untreated control.

Example 25

Preparation of N~2~-(hydroxyacetyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (30)

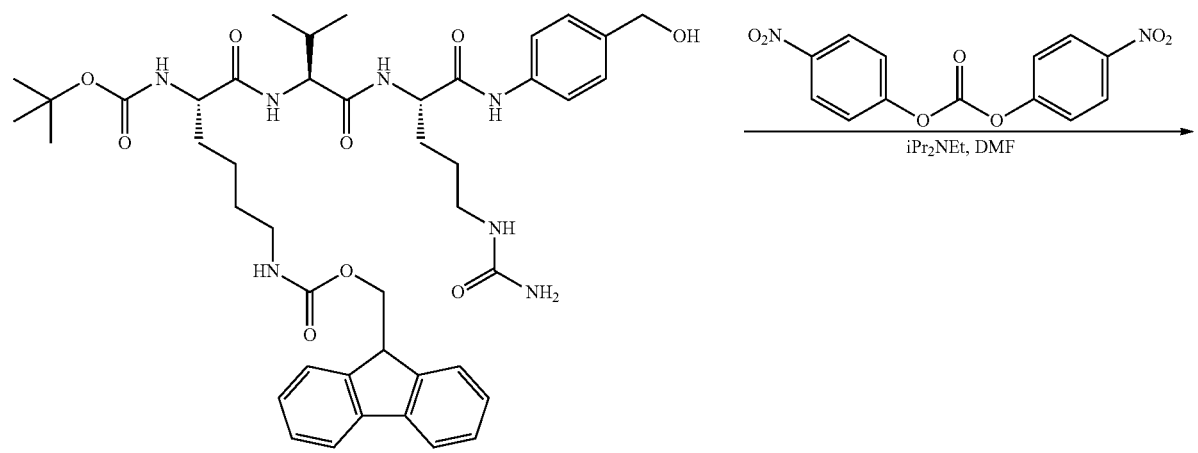

20

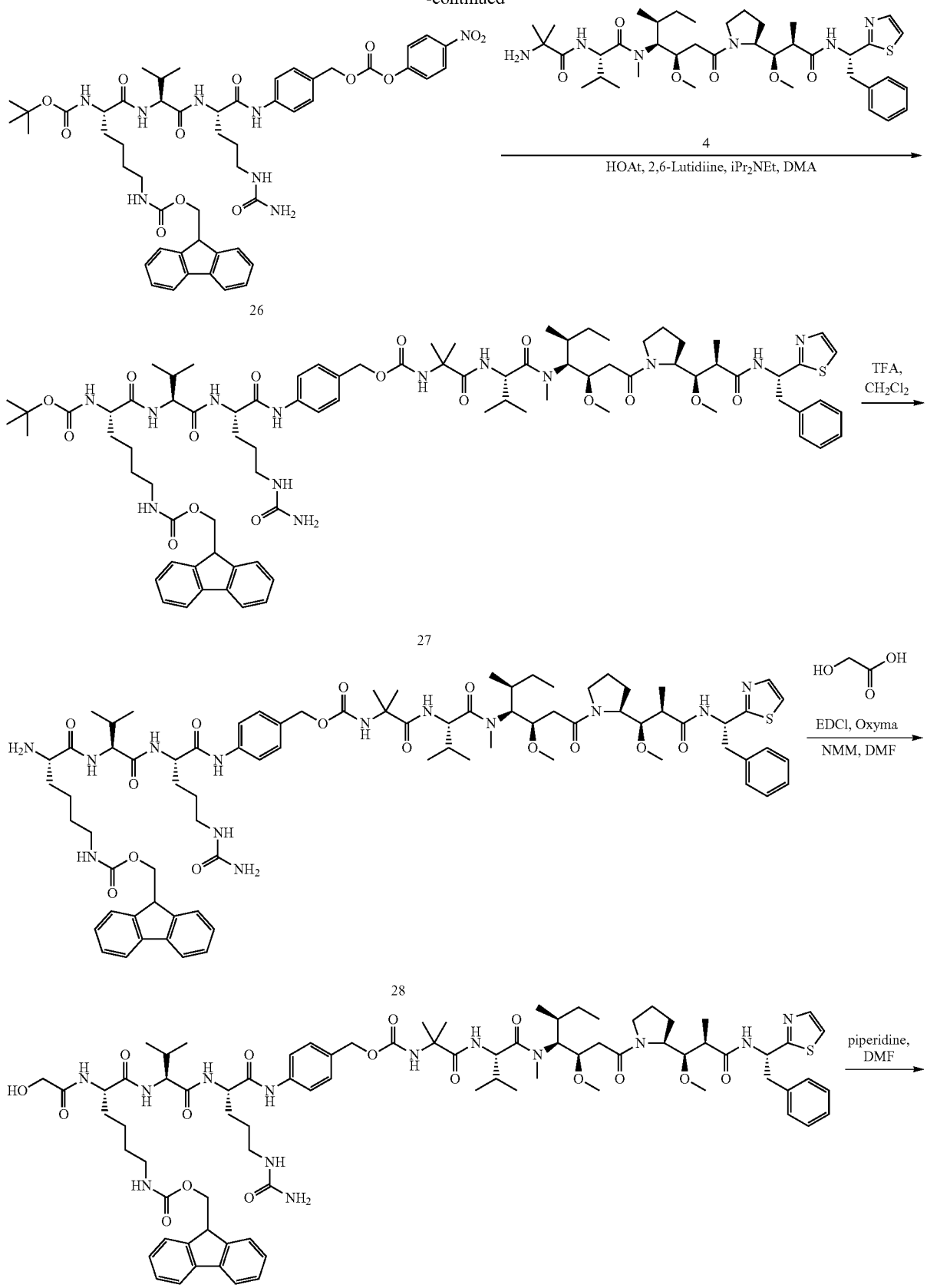

-continued

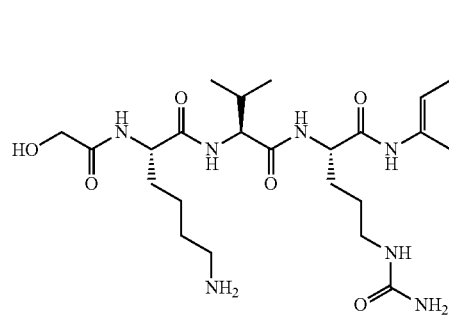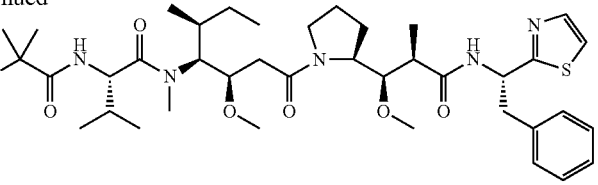

Step 1: Synthesis of N~2~-(tert-butoxycarbonyl)-N~6~-[(9H-fluoren-9-ylmethoxy)carbonyl]-L-lysyl-L-valyl-N~5~-carbamoyl-N-[4-({[(4-nitrophenoxy)carbonyl]oxy}methyl)phenyl]-L-ornithinamide (26). To a solution of N~2~-(tert-butoxycarbonyl)-N~6~-[(9H-fluoren-9-ylmethoxy)carbonyl]-L-lysyl-L-valyl-N~5~-carbamoyl-N-[4-(hydroxymethyl)phenyl]-L-ornithinamide (20, 998 mg, 1.20 mmol) and p-nitrophenyl carbonate (748 mg, 2.41 mmol)) in 7 mL of N,N-dimethylformamide and in 7 mL of dichloromethane was added N,N-diisopropylethylamine (452 uL 0.328 g, 2.41 mmol,) and the mixture was stirred at room temperature for 3 hours. The residue was diluted with ethyl acetate and diethyl ether and the resulting slurry was stirred for 30 minutes. The solid were isolated by filtration and washed with ether several times and to give after air drying the desired product as a yellow solid (1319 mg) which was used as is without further purification. LC-MS m/z 995.5 [M+H$^+$]; retention time=1.02 minutes. Analytical HPLC retention time=8.181 minutes.

Step 2: Synthesis of N~2~-(tert-butoxycarbonyl)-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (27). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (4, 371 mg, 0.499 mmol) and N~2~-(tert-butoxycarbonyl)-N~6~-[(9H-fluoren-9-ylmethoxy)carbonyl]-L-lysyl-L-valyl-N~5~-carbamoyl-N-[4-({[(4-nitrophenoxy)carbonyl]oxy}methyl)phenyl]-L-ornithinamide (26, 802 mg, 0.64 mmol) in 2.5 mL of N,N-dimethylacetamide were added 2,6-lutidine (216 uL, 200 mg, 1.9 mmol,) N,N-diisopropylethylamine (326 uL, 240 mg, 1.9 mmol) and 3H-[1,2,3]triazolo[4,5-b]pyridin-3-ol (HOAt, 17.7 mg, 0.130 mmol). The mixture was monitored by LC-MS and allowed to stir for 90 minutes at 50° C. and then at room temperature for 16 hours. The reaction was then purified by reverse phase chromatography (Method U) to provide after lyophilization 339 mg (42%, 2 steps) of the desired product as a white solid. LC-MS m/z 1599.9 [M+H$^+$]; retention time=1.09 minutes. Analytical HPLC retention time=8.163 minutes.

Step 3: Synthesis of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28). To a suspension of N~2~-(tert-butoxycarbonyl)-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (27, 439 mg, 0.275 mmol) in 2 mL of dichloromethane was added 1 mL of trifluoroacetic acid. The mixture was monitored by LC-MS and allowed to stir for 20 minutes at room temperature. The reaction was then concentrated and purified by reverse phase chromatography (Method V) to provide after lyophilization 410 mg (96%). LC-MS m/z 1499.8 [M+H$^+$]; retention time=0.86 minutes. Analytical HPLC retention time=6.778 minutes.

Step 4: Synthesis of N~6~-[(9H-fluoren-9-ylmethoxy)carbonyl]-N~2~-(hydroxyacetyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (29). To a solution of hydroxyacetic acid (14.7 mg, 0.193 mmol) in 0.3 mL of N,N-dimethylformamide was added N-(3-Dimethylaminopropyl)-N'-ethylcarbodiimide hydrochloride (EDCI, 7.99 mg, 0.0417 mmol), Ethyl (hydroxyimino)cyanoacetate (Oxyma, 20 mg, 0.14 mmol) and N-methyl morpholine (40 uL, 37 mg, 0.36 mmol). The resulting yellow solution was stirred for 20 minutes and then a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 50 mg, 0.032 mmol) in 0.5 mL of N,N-dimethylformamide was added. The mixture was monitored by LC-MS and allowed to stir for an hour at room temperature, and was then concentrated and purified by reverse phase HPLC (Method F). Product containing fractions were lyophilized to provide after lyophilization 12.2 mg (24%). LC-MS m/z 1557.8 [M+H$^+$]; retention time=0.98 minutes. Analytical HPLC retention time=7.371 minutes.

Step 5: Synthesis of N~2~-(hydroxyacetyl)-L-lysylvalyl-N-{4-[(8S,11S,12R)-11-[(2S)-butan-2-yl]-12-(2-{(2S)-2-

[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (30) To a solution of N~6~-[(9H-fluoren-9-ylmethoxy)carbonyl]-N~2~-(hydroxyacetyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (29, 12.2 mg, 0.00784 mmol) in 0.3 mL of N,N-dimethylformamide was added piperidine (0.1 mL, 90 mg, 1 mmol) and the mixture was stirred at room temperature for an hour. The solution was then concentrated and purified by reverse phase HPLC (Method E). Product containing fractions were lyophilized to provide 8 mg (70%) of the desired product. LC-MS m/z 1334.8 [M+H$^+$]; retention time=0.76 minutes. Analytical HPLC retention time=5.788 minutes.

Example 26

Preparation of N~2~-(methylcarbamoyl)-L-lysyl-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (33)

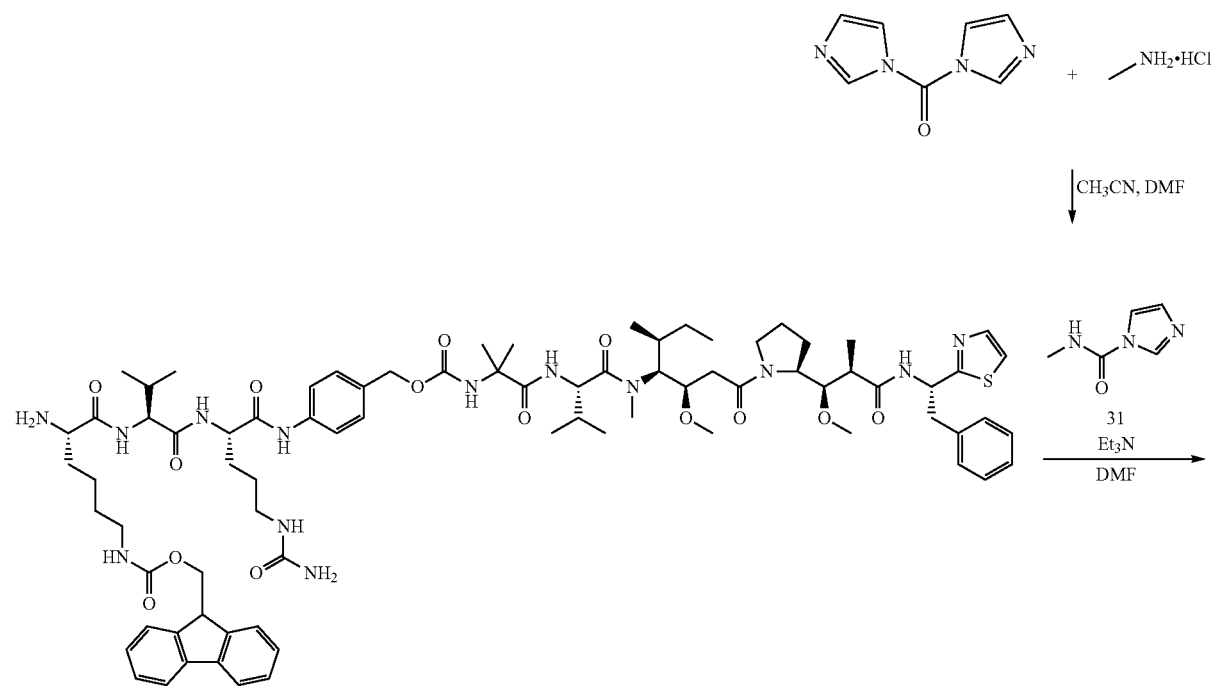

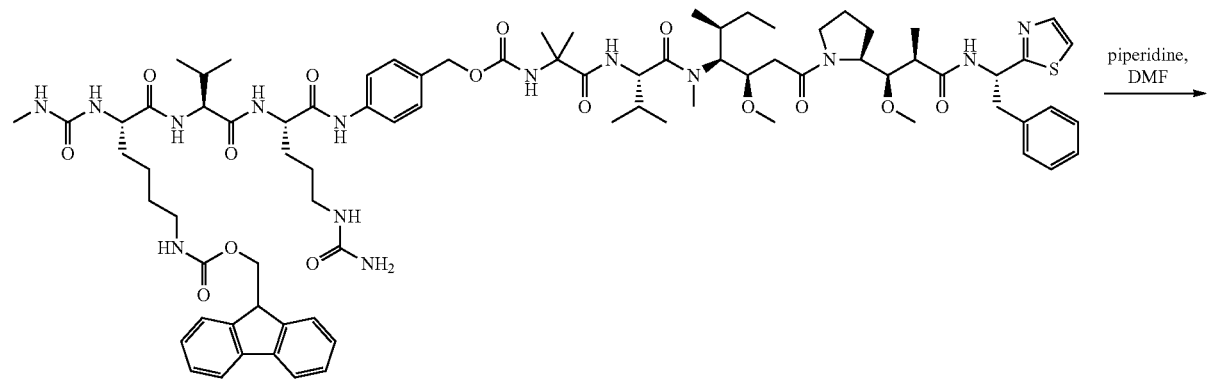

-continued

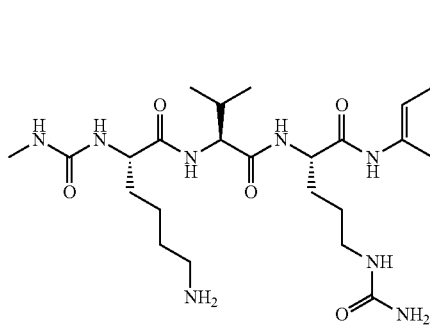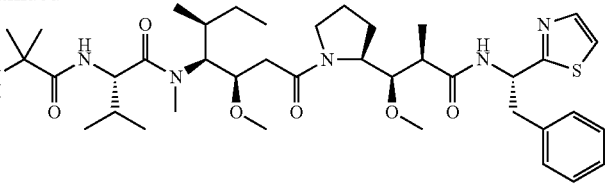

33

Step 1: Synthesis of N-methyl-1H-imidazole-1-carboxamide (31). A mixture of 1,1'-carbonyldiimidazole (1.76 g, 10.7 mmol) and methylamine hydrochloride (661 mg, 9.7 mmol) were dissolved in 1.8 mL of N,N-dimethylformamide and 5.5 mL of acetonitrile. The mixture was monitored by LC-MS and allowed to stir for 3.25 hours at room temperature. The reaction was then concentrated and purified by silica gel chromatography using a gradient elution of 0% to 10% methanol in dichloromethane to provide 696 mg (57%) of the desired product. LC-MS m/z 126.0 [M+H$^+$]; retention time=0.17 minutes. $^1$H NMR (400 MHz, DMSO-d$_6$) δ=8.22 (s, 1H), 7.65 (s, 1H), 7.03 (s, 1H), 2.83 (d, J=4.3 Hz, 3H).

Step 2: Synthesis of N~6~-[(9H-fluoren-9-ylmethoxy)carbonyl]-N~2~-(methylcarbamoyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (32). To a mixture of N-methyl-1H-imidazole-1-carboxamide (40.1 mg, 0.321 mmol) and N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 50 mg, 0.032 mmol) in 0.5 mL of N,N-dimethylformamide was added triethylamine (44.7 uL, 32.5 mg, 0.321 mmol). The mixture was monitored by LC-MS and allowed to stir for 1.5 at room temperature, and was then diluted with dimethylsulfoxide and purified by reverse phase HPLC (Method L) to provide after lyophilization 8.8 mg (18%) of the desired product. LC-MS m/z 1556.8 [M+H$^+$]; retention time=0.99 minutes. Analytical HPLC retention time=7.521 minutes.

Step 3: Synthesis of N~2~-(methylcarbamoyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (33) To a solution of N~6~-[(9H-fluoren-9-ylmethoxy)carbonyl]-N~2~-(methylcarbamoyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (32, 8.8 mg, 0.0057 mmol) in 0.3 mL of N,N-dimethylformamide was added piperidine (0.1 mL, 90 mg, 1 mmol) and the mixture was stirred at room temperature for 1.5 hour. The solution was then concentrated and purified by reverse phase HPLC (Method E then M). Product containing fractions were lyophilized to provide 4.6 mg (58%) of the desired product. LC-MS m/z 1333.7 [M+H$^+$]; retention time=0.76 minutes. Analytical HPLC retention time=5.825 minutes.

Example 27

Preparation of N-methylglycyl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (34)

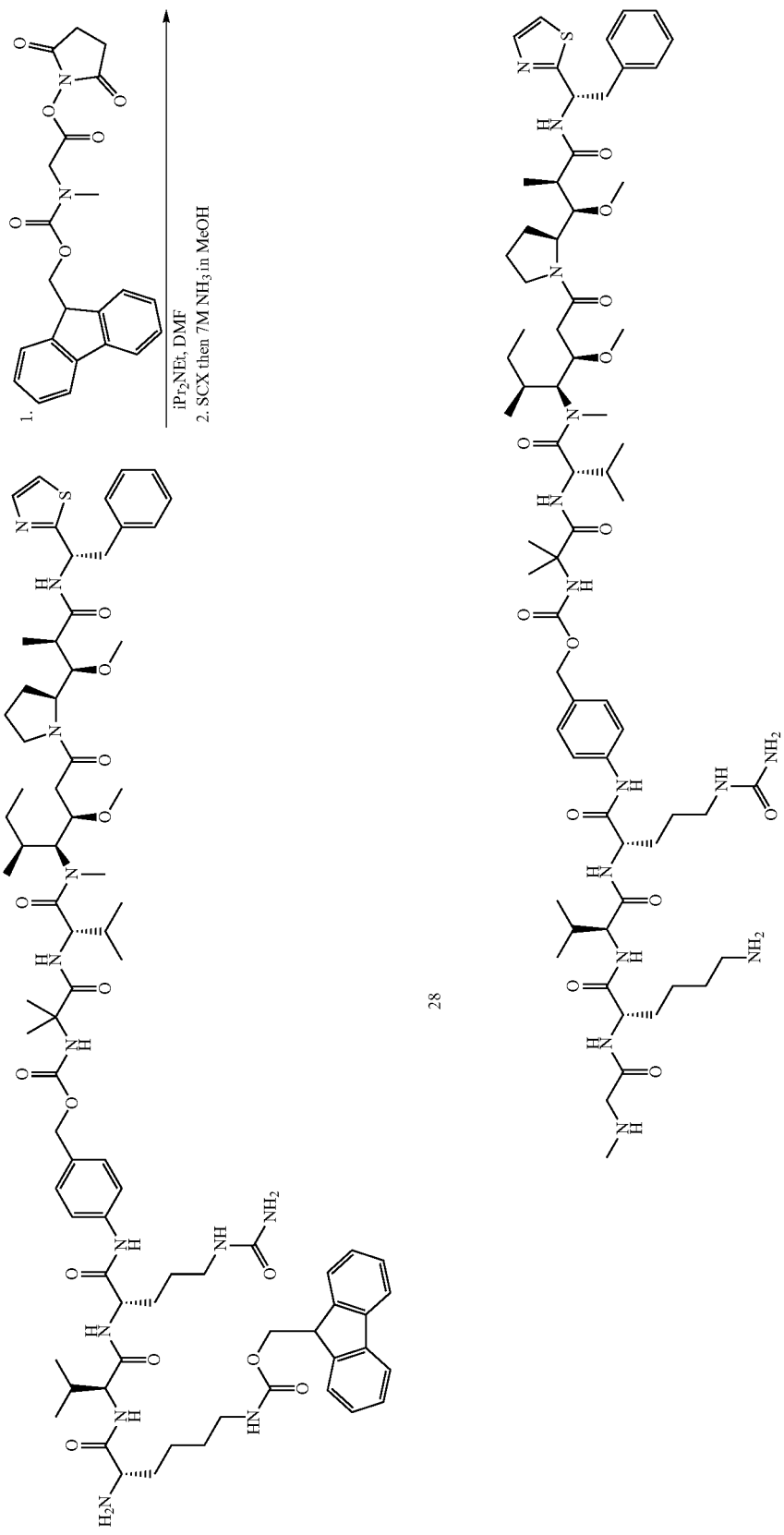

To a solution of 2,5-dioxopyrrolidin-1-yl N-[(9H-fluoren-9-ylmethoxy)carbonyl]-N-methylglycinate (11.9 mg, 0.0416 mmol) in 0.1 mL of N,N-dimethylformamide was added N~6~-[(9H-fluoren-9-ylmethoxy)carbonyl]-L-lysyl-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 50 mg, 0.032 mmol) and N,N-diisopropylethylamine (17 uL, 13 mg, 0.096 mmol). The mixture was monitored by LC-MS and allowed to stir for an hour at room temperature (LC-MS m/z 1670.7 1[M+H$^+$]; retention time=1.03 minutes). The mixture was concentrated under a strong flow of nitrogen and the residue was dissolved back in methanol and pass through an SCX column (prewashed with 2 column volumes of methanol). The cartridge was washed with column volume of methanol and the product was let sitting on column overnight. The column was flushed with a 7M solution of ammonia in methanol after concentration the residue was purified by reverse phase HPLC (Method L). Product containing fractions were lyophilized to provide 4.2 mg (8%) of the desired product. LC-MS m/z 1347.51 [M+H$^+$]; retention time=0.68 minutes. Analytical HPLC retention time=5.486 minutes.

Example 28

Preparation of N,N-dimethylglycyl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (35)

To a solution of N,N-dimethylglycine (4.5 mg, 0.044 mmol) in 0.1 mL of N,N-dimethylformamide was added 0.1 mL of a stock solution of N-(3-Dimethylaminopropyl)-N'-ethylcarbodiimide hydrochloride (EDCI, 79.9 mg, 0.417 mmol), Ethyl (hydroxyimino)cyanoacetate (Oxyma, 10 mg, 0.07 mmol) and N-methyl morpholine (10 uL, 9 mg, 0.09 mmol) in 1 mL of N,N-dimethylformamide. The resulting yellow solution was stirred for 15 minutes, then a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 50 mg, 0.032 mmol) in 0.5 mL of N,N-dimethylformamide was added. The mixture was monitored by LC-MS and allowed to stir for 40 minutes at room temperature and more N-methyl morpholine (50 uL, 45 mg, 0.45 mmol). The mixture was stirred for 16 hours, concentrated and purified by reverse phase HPLC (Method L). Product containing fractions were lyophilized to provide 5.4 mg (11%) of the desired product. LC-MS m/z 1361.8 [M+H$^+$]; retention time=0.71 minutes. Analytical HPLC retention time=5.481 minutes.

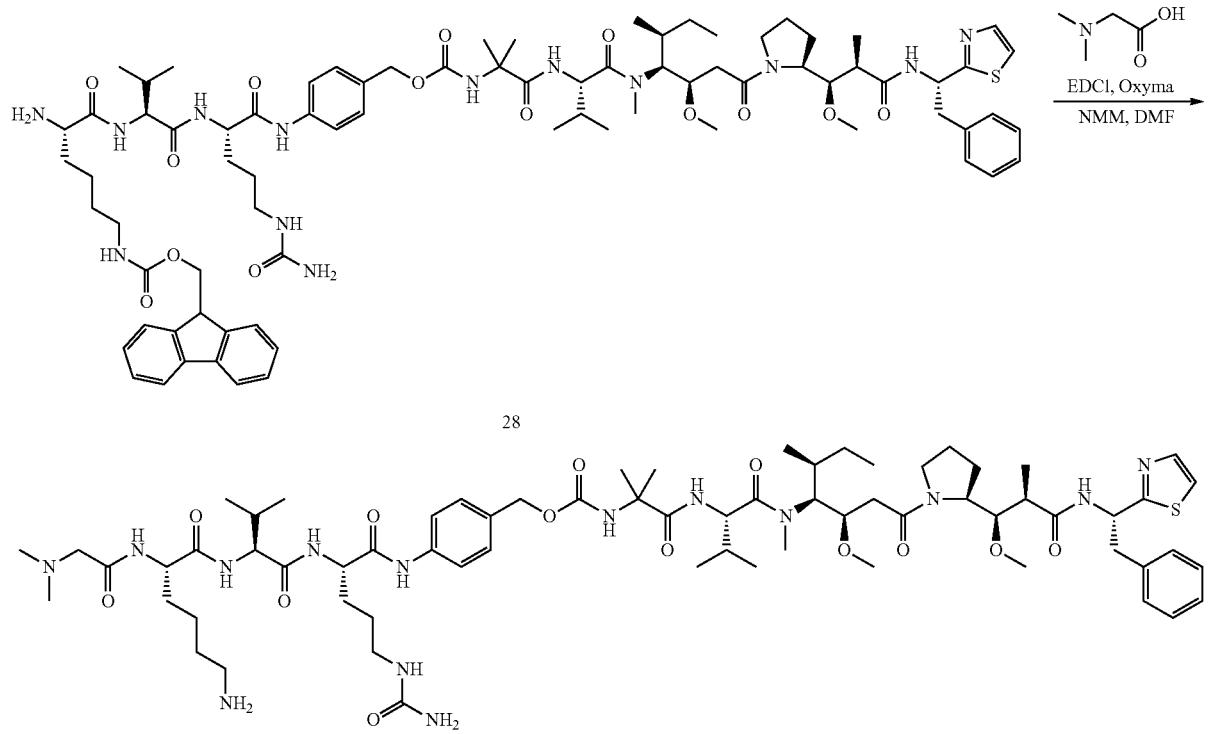

Example 29

Preparation of glycyl-L-lysylvalyl-N-{4-[(8S,11S, 12R)-11-[(2S)-butan-2-yl]-12-(2-{(2S)-2-[(1R,2R)-1-methoxy-2-methyl-3-oxo-3-{[(1S)-2-phenyl-1-(1, 3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (37)

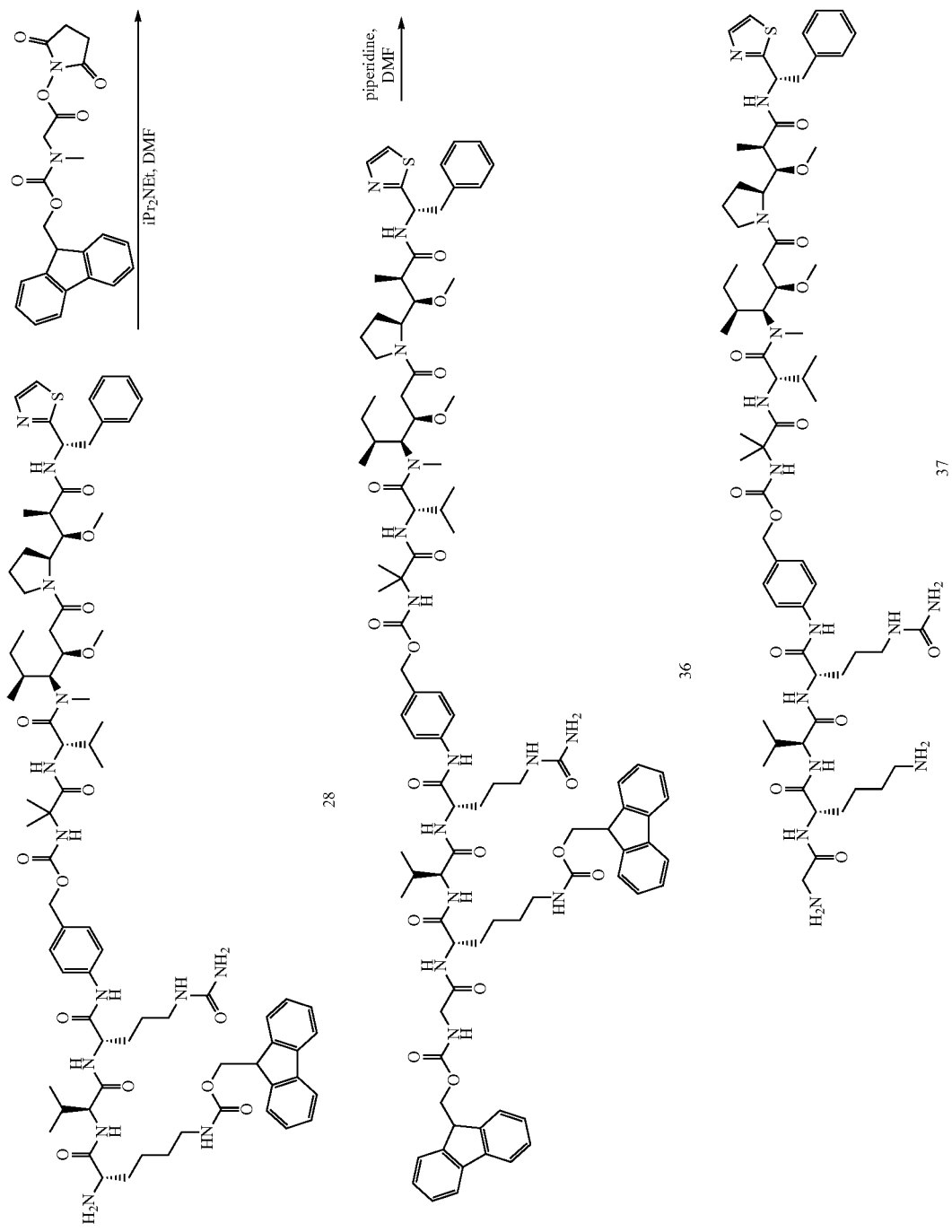

Step 1: Synthesis of N-[(9H-fluoren-9-ylmethoxy)carbonyl]glycyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (36) To a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 65.0 mg, 0.043 mmol)) in 0.650 mL of N,N-dimethylformamide was added 2,5-dioxopyrrolidin-1-yl N-[(9H-fluoren-9-ylmethoxy)carbonyl]glycinate (68.4 mg, 0.173 mmol) and N,N-diisopropylethylamine (23.1 mg, 0.173 mmol, 30.8 uL). The mixture was monitored by LC-MS and allowed to stir for 2 hours at room temperature and was directly purified by reverse phase HPLC (Method N). Product containing fractions were lyophilized to provide 22.3 mg (29%) of the desired product. LC-MS m/z 1777.2 [M+H$^+$]; retention time=1.10 minutes. Analytical HPLC retention time=8.544 minutes.

Step 2: Synthesis of glycyl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (37) To a solution of N-[(9H-fluoren-9-ylmethoxy)carbonyl]glycyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (36, 20 mg, 0.011 mmol) in 0.6 mL of N,N-dimethylacetamide was added piperidine (0.3 mL, 270 mg, 3 mmol) and the mixture was stirred at room temperature for 15 minutes. The solution was then concentrated and purified by reverse phase HPLC (Method L then M). Product containing fractions were lyophilized to provide 14.4 mg (90%) of the desired product. LC-MS m/z 1333.8 [M+H$^+$]; retention time=0.70 minutes. Analytical HPLC retention time=5.825 minutes.

Example 30

Preparation of N~2~-[(3-methyloxetan-3-yl)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (39)

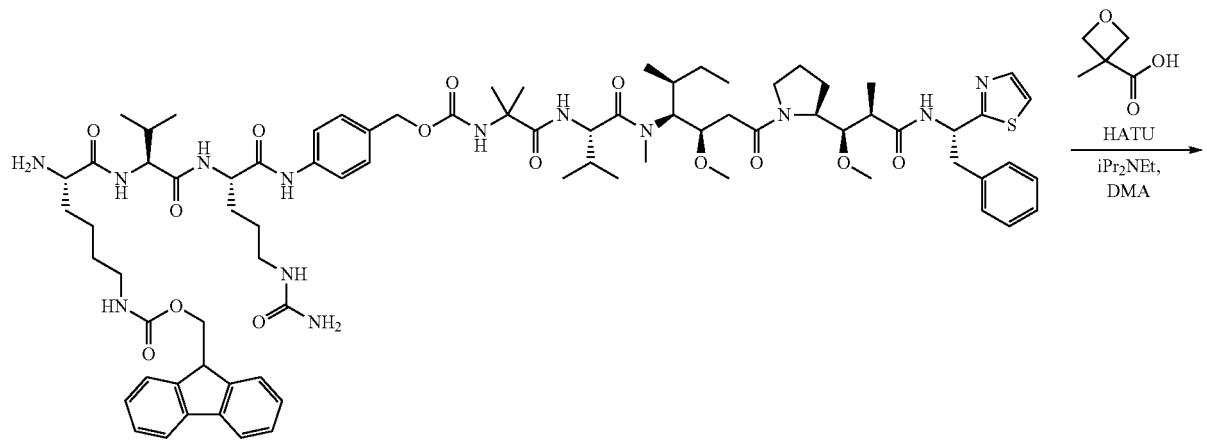

28

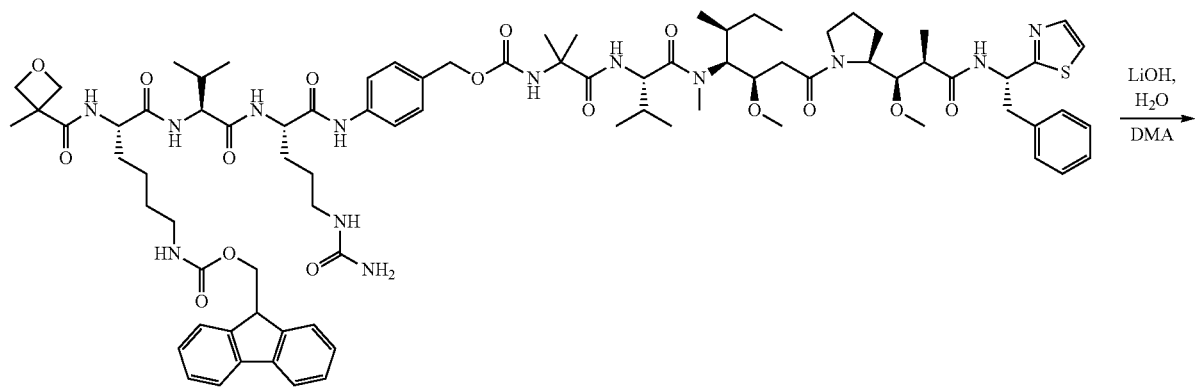

-continued

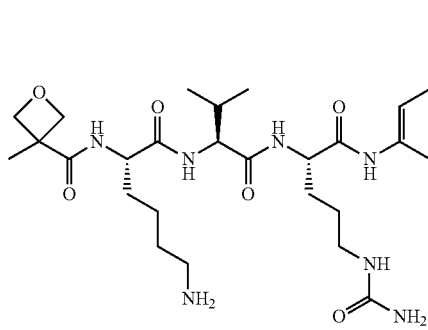

39

Step1: Synthesis of N~6~-[(9H-fluoren-9-ylmethoxy)carbonyl]-N~2~-[(3-methyloxetan-3-yl)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (38) In an iced water bath, to a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 50.0 mg, 0.031 mmol) in 0.5 mL of N,N-dimethylacetamide were added 3-methyloxetane-3-carboxylic acid (22 mg, 0.19 mmol), O-(7-Azabenzotriazol-1-yl)-N,N,N',N'-tetramethyluronium hexafluorophosphate (HATU, 65 mg, 0.17 mmol) and N,N-diisopropylethylamine (35 uL, 26 mg, 0.20 mmol). The mixture was stirred for an additional 40 minutes in the iced water bath. The solution was then directly purified by reverse phase HPLC (Method P). Product containing fractions were lyophilized to provide 37.4 mg (55%) of the desired product. LC-MS m/z 1597.8 [M+H⁺]; retention time=1.00 minutes. Analytical HPLC retention time=7.567 minutes.

Step 2: Synthesis of N~2~-[(3-methyloxetan-3-yl)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (39) To a solution of N~6~-[(9H-fluoren-9-ylmethoxy)carbonyl]-N~2~-[(3-methyloxetan-3-yl)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (38, 27.4 mg, 0.0172 mmol) in 0.5 mL of N,N-dimethylacetamide was added an aqueous solution of lithium hydroxide (411 uL, 41.1 mg, 0.0343 mmol) and the mixture was stirred at room temperature for an hour. The solution was then concentrated and purified by reverse phase HPLC (Method L). Product containing fractions were lyophilized to provide 9.3 mg (36%) of the desired product. LC-MS m/z 1374.4 [M+H⁺]; retention time=0.77 minutes. Analytical HPLC retention time=5.841 minutes.

Example 31

Preparation of 2-methylalanyl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (41)

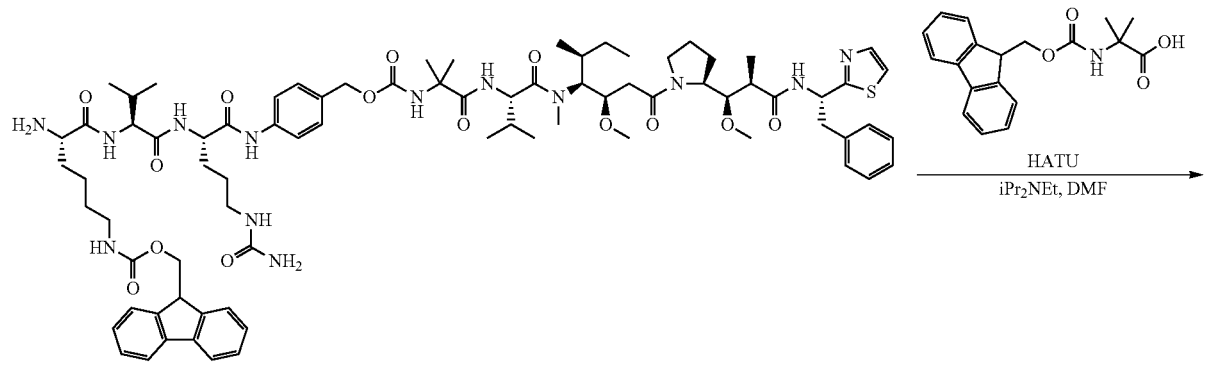

28

-continued

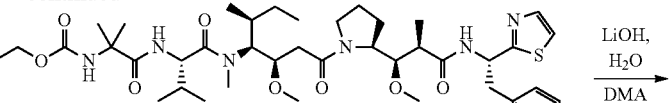
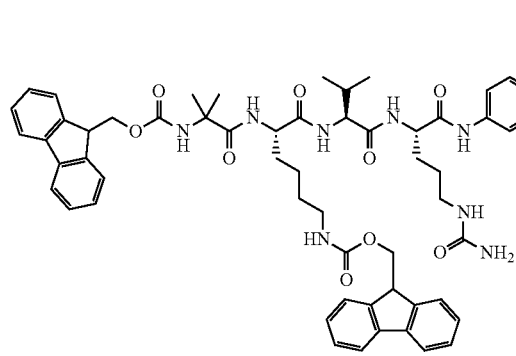

40

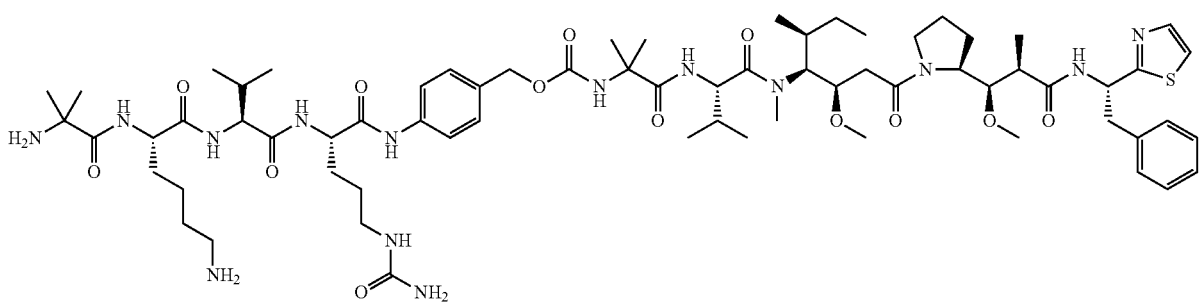

41

Step 1: Synthesis of N-[(9H-fluoren-9-ylmethoxy)carbonyl]-2-methylalanyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (40) In an iced water bath, to a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 50.0 mg, 0.031 mmol) in 0.5 mL of N,N-dimethylacetamide were added N-[(9H-fluoren-9-ylmethoxy)carbonyl]-2-methylalanine (17.5 mg, 0.0538 mmol), O-(7-Azabenzotriazol-1-yl)-N,N,N',N'-tetramethyluronium hexafluorophosphate (HATU, 25.9 mg, 0.0681 mmol) and N,N-diisopropylethylamine (25 uL, 19 mg, 0.14 mmol). The mixture was stirred for an additional 40 minutes in the iced water bath. The solution was then directly purified by reverse phase HPLC (Method Q). Product containing fractions were lyophilized to provide 56 mg (100%) of the desired product. LC-MS m/z 1806.9 [M+H$^+$]; retention time=1.12 minutes. Analytical HPLC retention time=8.817 minutes.

Step 2: Synthesis of 2-methylalanyl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (40) To a solution of N-[(9H-fluoren-9-ylmethoxy)carbonyl]-2-methylalanyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (40, 56 mg, 0.031 mmol) in 0.5 mL of N,N-dimethylacetamide was added an aqueous solution of lithium hydroxide (100 uL, 10 mg, 0.4 mmol) and the mixture was stirred at room temperature for an hour. The solution was then concentrated and purified by reverse phase HPLC (Method L). Product containing fractions were lyophilized to provide 7.6 mg (15%) of the desired product. LC-MS m/z 1384.2 [M+Na$^+$]; retention time=0.71 minutes. Analytical HPLC retention time=5.467 minutes.

Example 32

Preparation of N~2~-(methoxycarbonyl)-L-lysyl-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (43)

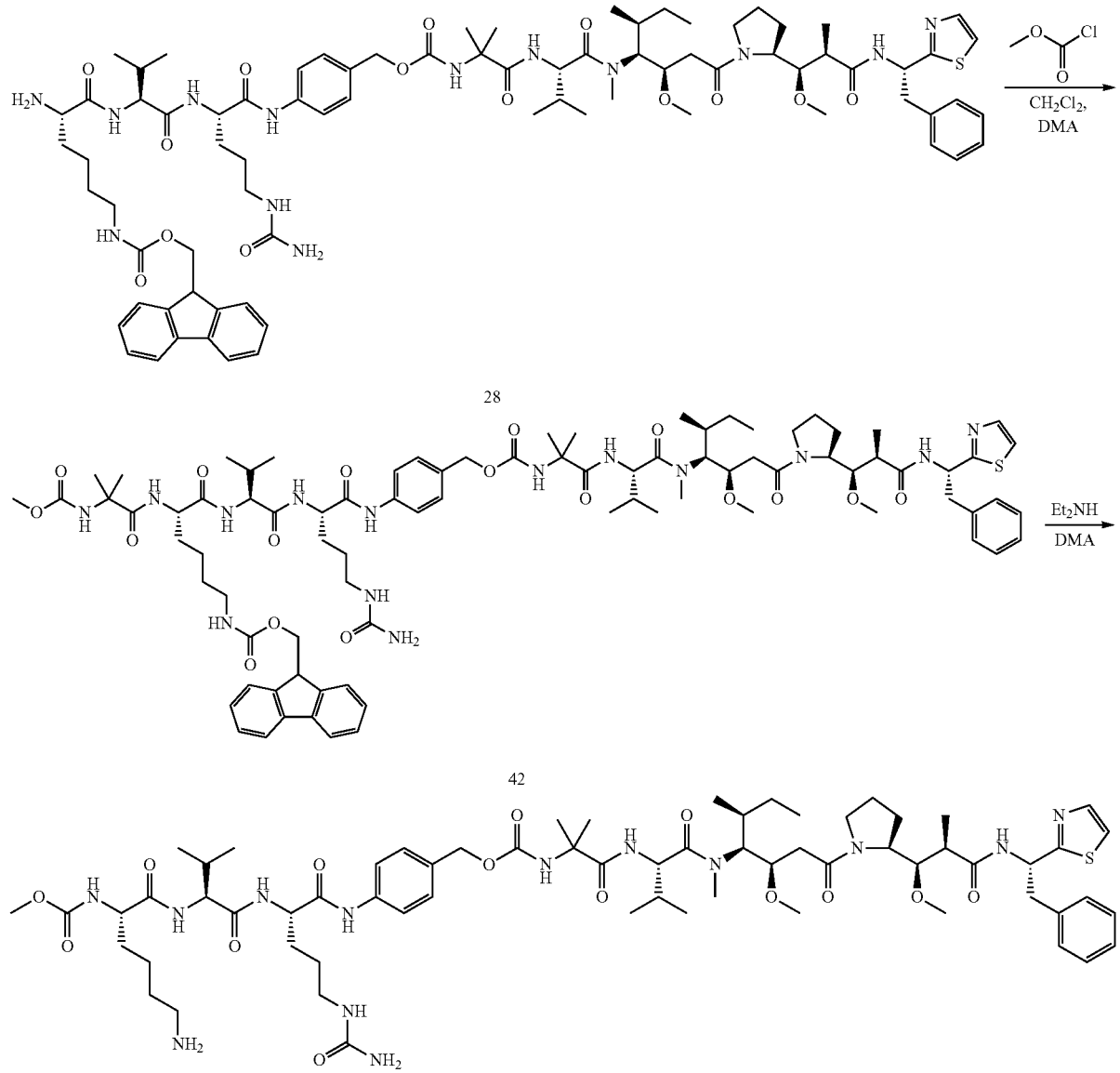

Step 1: Synthesis of N-(methoxycarbonyl)-2-methylalanyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (42) To a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 30.0 mg, 0.019 mmol)) in 0.3 mL of N,N-dimethylacetamide and 0.2 mL of dichloromethane was added methylchloroformate (29 uL, 35.2 mg, 0.372 mmol). The mixture was monitored by LC-MS and allowed to stir for 2 hours at room temperature After 2 h, N,N-diisopropylethylamine (10.0 uL, 7.5 mg, 0.056 mmol) was added and the mixture stirred for an extra 16 hours. LC-MS still showed reaction to be incomplete so methylchloroformate (60 uL, 73 mg, 0.78 mmol) was added followed by N,N-diisopropylethylamine (10 uL, 7.5 mg, 0.056 mmol). After stirring at room temperature for another 4 hours, the mixture was directly purified by reverse phase HPLC (Method Q). Product containing fractions were lyophilized to provide 6.4 mg (22%) of the desired product.

LC-MS m/z 1557.9 [M+H$^+$]; retention time=1.05 minutes. Analytical HPLC retention time=7.709 minutes.

Step 2: Synthesis of N~2~-(methoxycarbonyl)-L-lysyl-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (43) To a solution of N-(methoxycarbonyl)-2-methylalanyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (42, 6.4 mg, 0.0041 mmol) in 0.5 mL of N,N-dimethylacetamide was added diethylamine (0.3 mL, 200 mg, 3 mmol) and the mixture was stirred at room temperature for 3 hours. The solution was then concentrated and purified by reverse phase HPLC (Method L). Product containing fractions were lyophilized to provide 2.6 mg (44%) of the desired product. LC-MS m/z 1334.8 [M+H$^+$]; retention time=0.83 minutes. Analytical HPLC retention time=5.908 minutes.

Example 33

Preparation of L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (44)

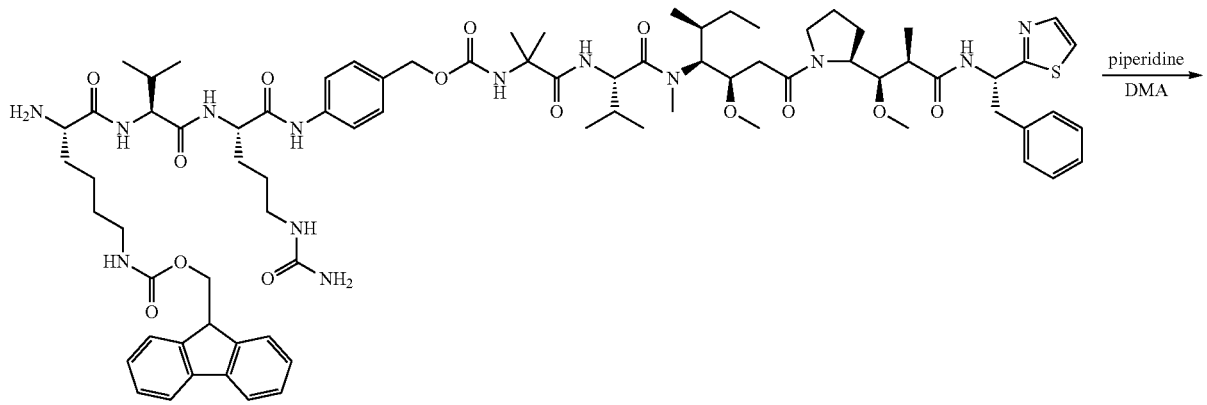

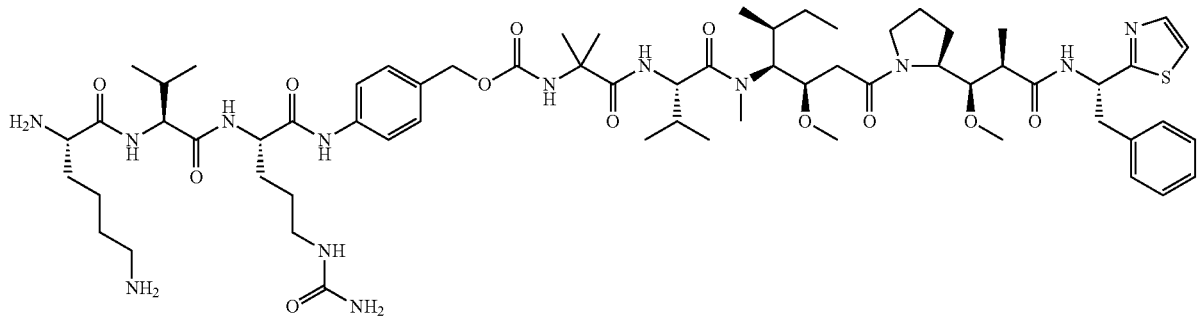

To a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 20.0 mg, 0.012 mmol)) in 0.2 mL of N,N-dimethylacetamide was added piperidine (0.1 mL, 90 mg, 1 mmol) and the mixture was stirred at room temperature for 4 hours. The solution was then directly purified by reverse phase HPLC (Method L then R). Product containing fractions were lyophilized to provide 7.6 mg (44%) of the desired product. LC-MS m/z 1276.7 [M+H$^+$]; retention time=0.70 minutes. Analytical HPLC retention time=5.516 minutes.

Example 34

Preparation of L-alanyl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (46)

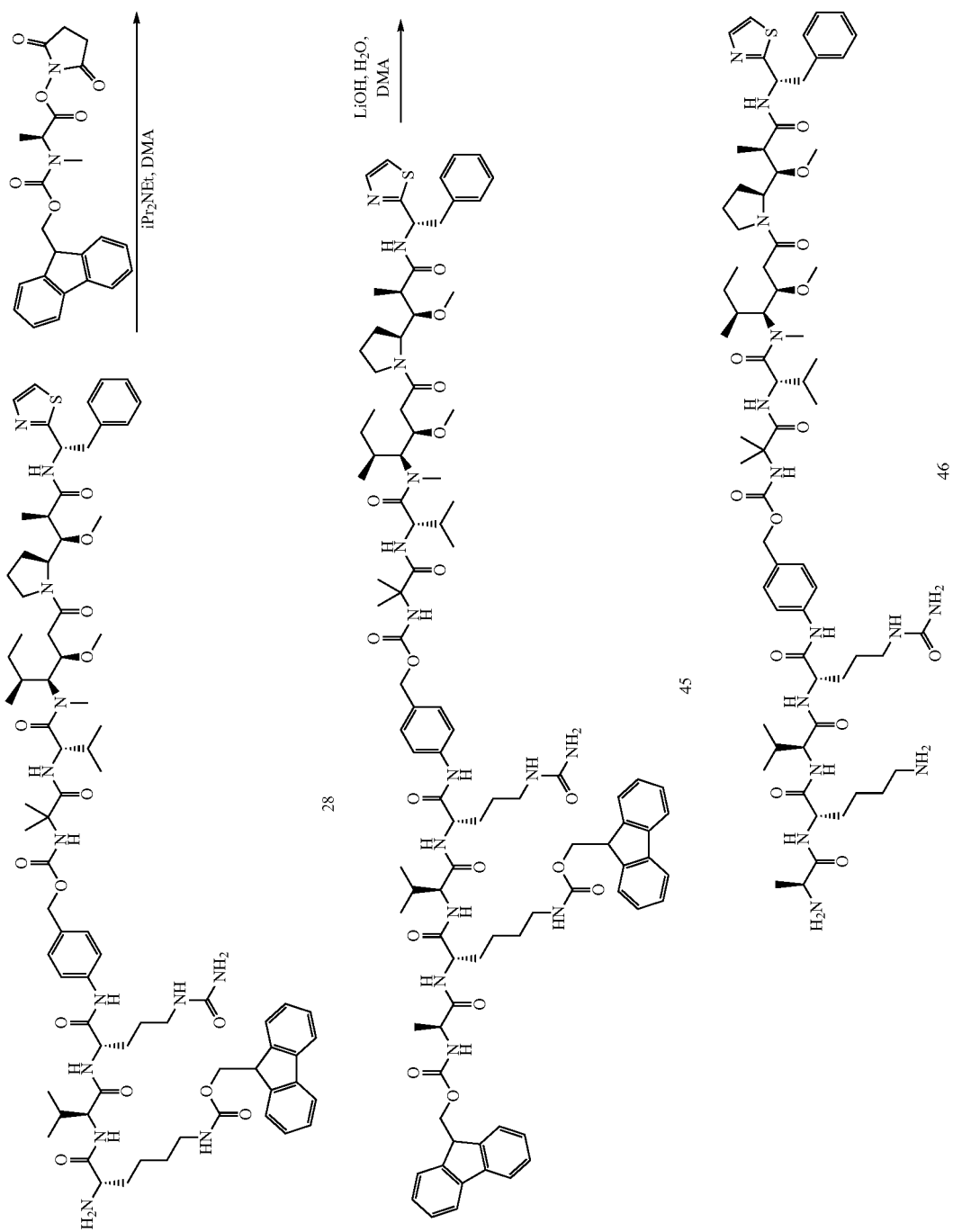

Step 1: Synthesis of N-[(9H-fluoren-9-ylmethoxy)carbonyl]-L-alanyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (45) In an iced water bath, to a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 8.7 mg, 0.0054 mmol) in 0.5 mL of N,N-dimethylacetamide was added 2,5-dioxopyrrolidin-1-yl N-[(9H-fluoren-9-ylmethoxy)carbonyl]-L-alaninate ((8.81 mg, 0.0216 mmol) and N,N-diisopropylethylamine (10.0 uL, 7.5 mg, 0.056 mmol). The mixture was monitored by LC-MS and allowed to stir for 16 hours at room temperature and was directly purified by reverse phase HPLC (Method S). Product containing fractions were lyophilized to provide 5.3 mg (55%) of the desired product. LC-MS m/z 1791.7 [M+H$^+$]; retention time=1.11 minutes. Analytical HPLC retention time=8.655 minutes.

Step 2: Synthesis of L-alanyl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl] pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (46) To a solution of N-[(9H-fluoren-9-ylmethoxy)carbonyl]-L-alanyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (45, 5.3 mg, 0.0030 mmol) in 0.5 mL of N,N-dimethylacetamide was added an aqueous solution of lithium hydroxide (210 uL, 20 mg, 0.9 mmol) and the mixture was stirred at room temperature for an hour. The solution was then concentrated and purified by reverse phase HPLC (Method L). Product containing fractions were lyophilized to provide 3.4 mg (73%) of the desired product. LC-MS m/z 1347.7 [M+H]+; retention time=0.69 minutes. Analytical HPLC retention time=5.487 minutes.

Example 35

Preparation of D-alanyl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (48)

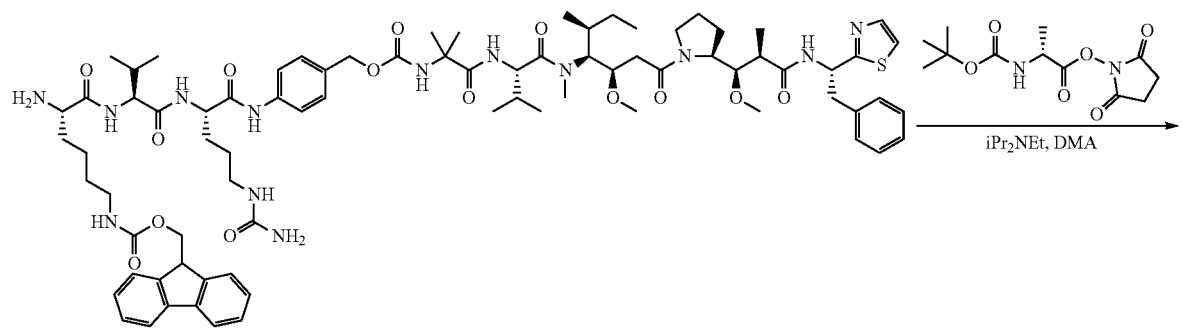

28

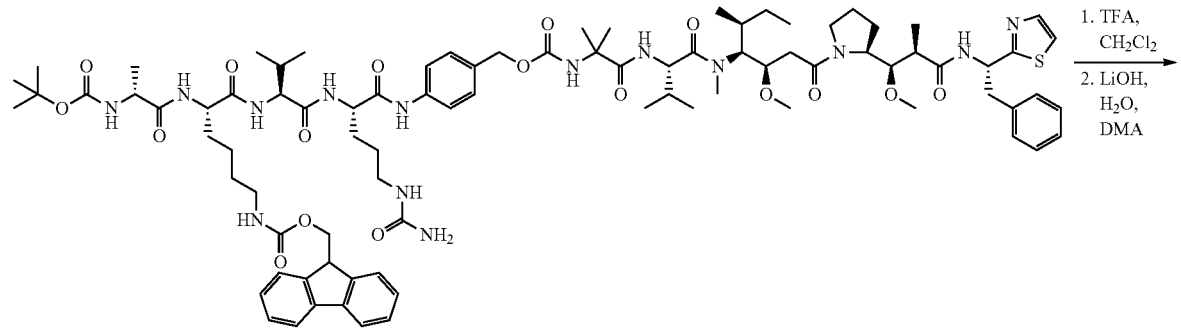

47

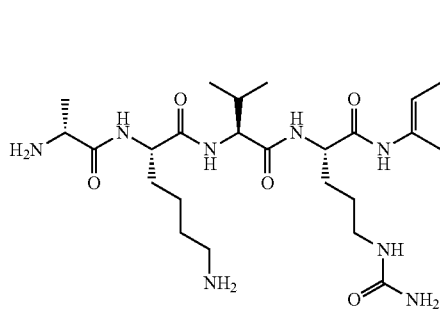
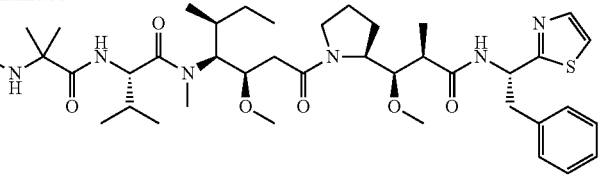

48

Step 1: Synthesis of N-(tert-butoxycarbonyl)-D-alanyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (47) In an iced water bath, to a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 50 mg, 0.03 mmol) in 0.5 mL of N,N-dimethylacetamide was added 2,5-dioxopyrrolidin-1-yl N-(tert-butoxycarbonyl)-D-alaninate (15.7 mg, 0.0548 mmol) and N,N-diisopropylethylamine (22.0 uL, 16 mg, 0.12 mmol). The mixture was monitored by LC-MS and allowed to stir for 16 hours at room temperature and was directly purified by reverse phase HPLC (Method S). Product containing fractions were lyophilized to provide 20.0 mg (40%) of the desired product. LC-MS m/z 1791.7 [M+H⁺]; retention time=1.08 minutes. Analytical HPLC retention time=8.024 minutes.

Step 2: Synthesis of D-alanyl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (48) To a solution of N-(tert-butoxycarbonyl)-D-alanyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (47, 20.0 mg, 0.012 mmol) in 1 mL of acetonitrile was added 0.5 mL of trifluoroacetic acid. The mixture was stirred at room temperature for 15 minutes then concentrated. The residue was dissolved in 0.5 mL of N,N-dimethylacetamide and cooled with an iced water bath. To this was added an aqueous solution of lithium hydroxide (50.3 uL, 5.3 mg, 0.12 mmol) and the mixture was stirred at room temperature for 30 minutes. The solution was then directly purified by reverse phase HPLC (Method L). Product containing fractions were lyophilized to provide 8.9 mg (47%) of the desired product. LC-MS m/z 1347.9 [M+H]+; retention time=0.77 minutes. Analytical HPLC retention time=5.429 minutes.

Example 36

Preparation of L-alpha-aspartyl-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (50)

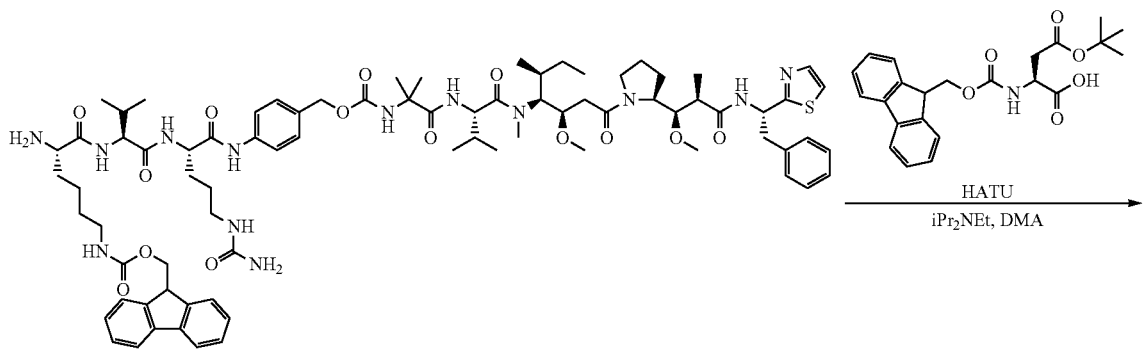

28

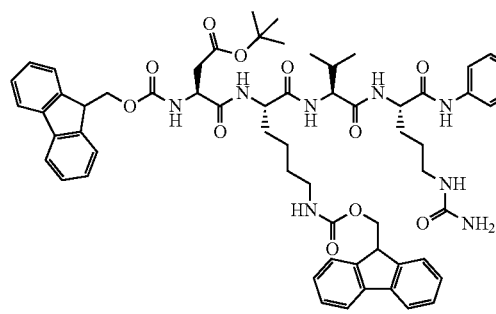
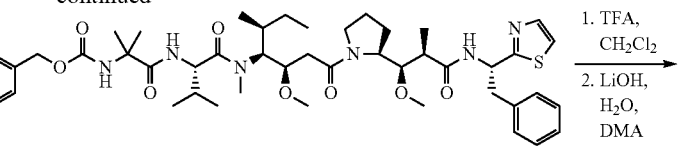

-continued

49

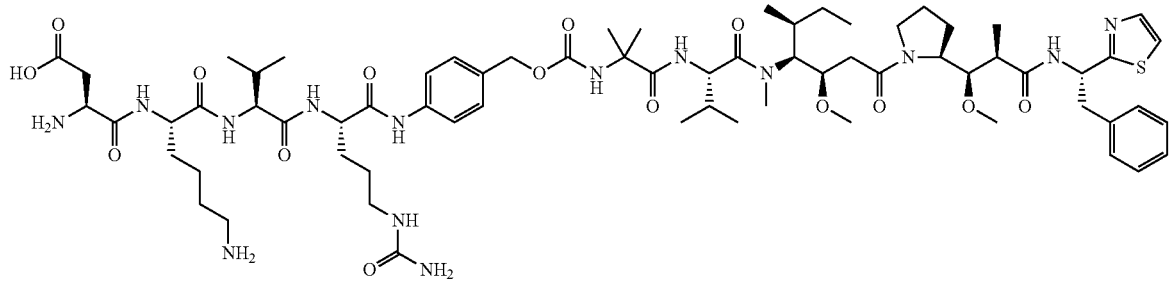

50

Step 1: Synthesis of tert-butyl (6S,9S,12S,15S)-1-amino-6-({4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino} propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}carbamoyl)-15-{[(9H-fluoren-9-ylmethoxy)carbonyl]amino}-12-(4-{[(9H-fluoren-9-ylmethoxy)carbonyl]amino}butyl)-1,8,11,14-tetraoxo-9-(propan-2-yl)-2,7,10,13-tetraazaheptadecan-17-oate (49) In an iced water bath, to a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 50 mg, 0.03 mmol) in 0.5 mL of N,N-dimethylacetamide was added (2S)-4-tert-butoxy-2-{[(9H-fluoren-9-ylmethoxy)carbonyl]amino}-4-oxobutanoic acid (20.9 mg, 0.0722 mmol), O-(7-Azabenzotriazol-1-yl)-N,N,N',N'-tetramethyluronium hexafluorophosphate (HATU, 28.0 mg, 0.074 mmol) and N,N-diisopropylethylamine (22.0 uL, 16 mg, 0.12 mmol). The mixture was monitored by LC-MS and allowed to stir for an hour and was directly purified by reverse phase HPLC (Method Q). Product containing fractions were lyophilized to provide 41 mg (70%) of the desired product. LC-MS m/z 1771.2 [M+H+]; retention time=1.16 minutes. Analytical HPLC retention time=8.591 minutes.

Step 2: Synthesis of L-alpha-aspartyl-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (50) To a solution of tert-butyl (6S,9S,12S,15S)-1-amino-6-({4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino} propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}carbamoyl)-15-{[(9H-fluoren-9-ylmethoxy)carbonyl]amino}-12-(4-{[(9H-fluoren-9-ylmethoxy)carbonyl]amino}butyl)-1,8,11,14-tetraoxo-9-(propan-2-yl)-2,7,10,13-tetraazaheptadecan-17-oate (49, 41.0 mg, 0.023 mmol) in 1 mL of acetonitrile was added 0.5 mL of trifluoroacetic acid. The mixture was stirred at room temperature for 25 minutes (LC-MS m/z 1671.0 [M+H]+; retention time=0.93 minutes) then concentrated. The residue was dissolved in 0.5 mL of N,N-dimethylacetamide and cooled with an iced water bath. To this was added an aqueous solution of lithium hydroxide (50.3 uL, 5.3 mg, 0.12 mmol) and the mixture was stirred at room temperature for 20 minutes. The solution was then directly purified by reverse phase HPLC (Method Q). Product containing fractions were lyophilized to provide 1.1 mg (3%) of the desired product. LC-MS m/z 1392.1 [M+H]+; retention time=0.80 minutes. Analytical HPLC retention time=5.309 minutes.

Example 37

Preparation of N-acetylglycyl-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (52)

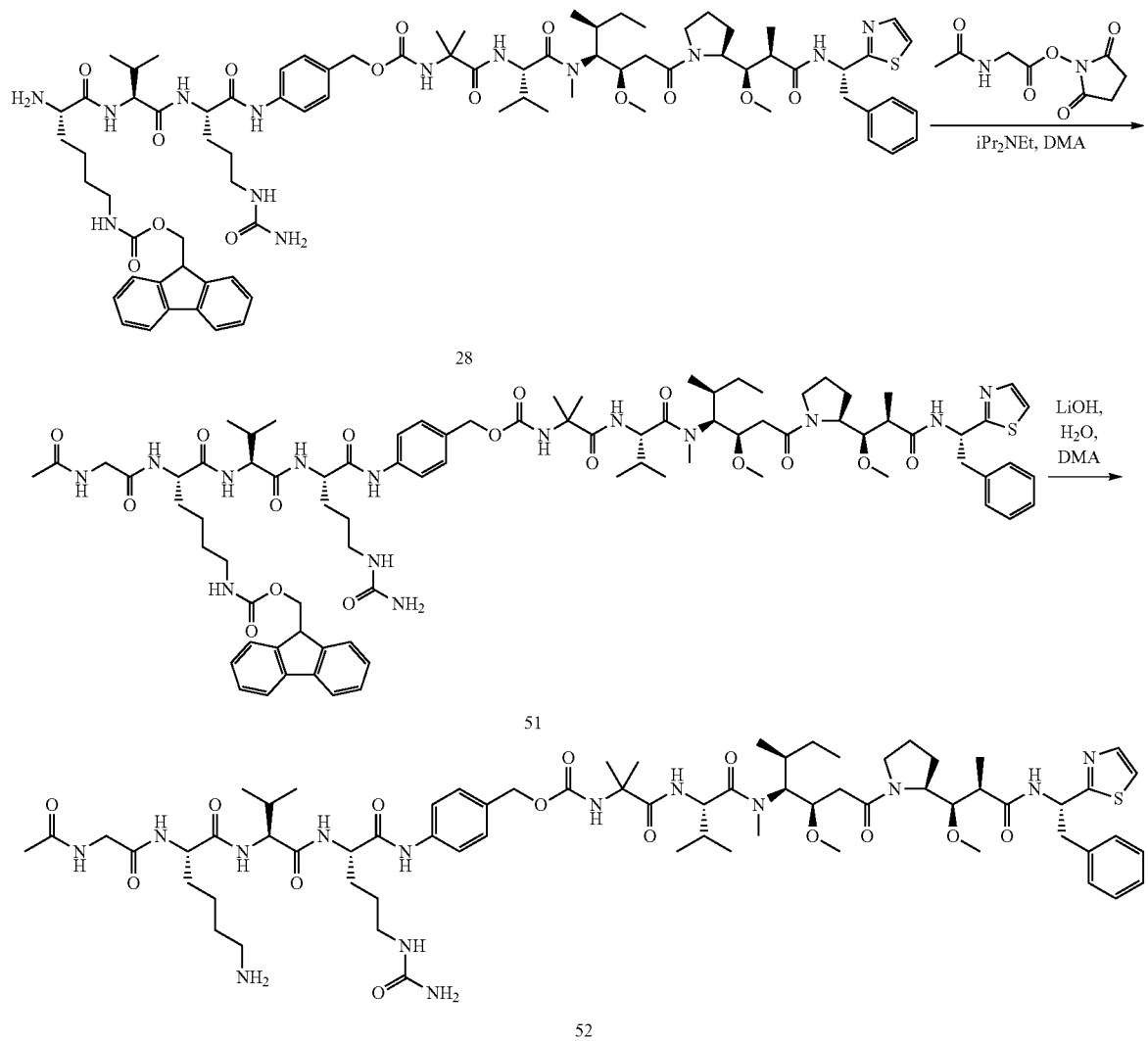

Step 1: Synthesis of N-acetylglycyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (51) In an iced water bath, to a solution of N~6~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (28, 30 mg, 0.02 mmol) in 0.3 mL of N,N-dimethylacetamide was added 2,5-dioxopyrrolidin-1-yl N-acetylglycinate (13.7 mg, 0.0640 mmol) and N,N-diisopropylethylamine (22 uL, 16 mg, 0.12 mmol). The mixture was monitored by LC-MS and allowed to stir for 16 hours at room temperature and was directly purified by reverse phase HPLC (Method Q). Product containing fractions were lyophilized to provide 17.4 mg (60%) of the desired product. LC-MS m/z 1598.9 [M+H$^+$]; retention time=1.04 minutes. Analytical HPLC retention time=7.326 minutes.

Step 2: Synthesis of N-acetylglycyl-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino} propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (52) To a solution of N-acetylglycyl-N~6~-[(9H-fluoren-9-ylmethoxy)carbonyl]-L-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{

[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (51, 17.4 mg, 0.0109 mmol) in 0.5 mL of N,N-dimethylacetamide was added an aqueous solution of lithium hydroxide (100 uL, 10 mg, 0.2 mmol) and the mixture was stirred at room temperature for 20 minutes. The solution was then directly purified by reverse phase HPLC (Method B). Product containing fractions were lyophilized to provide 9.4 mg (58%) of the desired product. LC-MS m/z 1398.1 [M+Na+]; retention time=0.84 minutes. Analytical HPLC retention time=5.715 minutes.

Example 38

Preparation of L-seryl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (57)

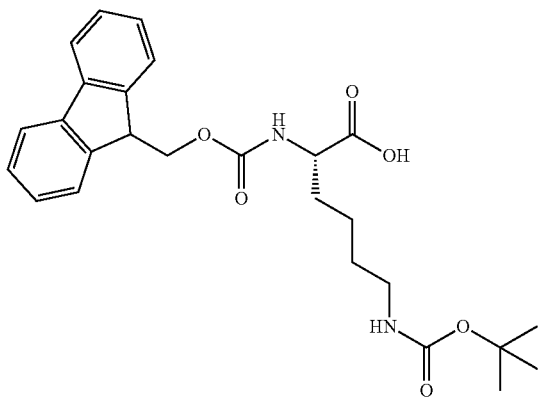

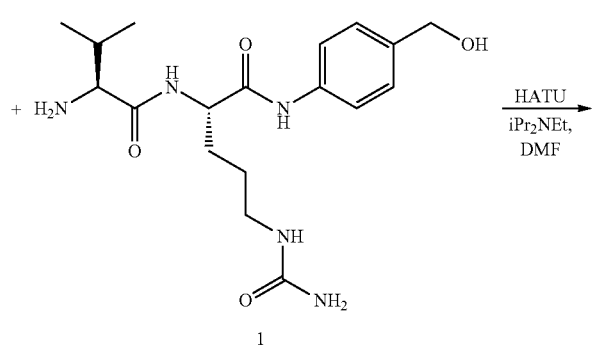

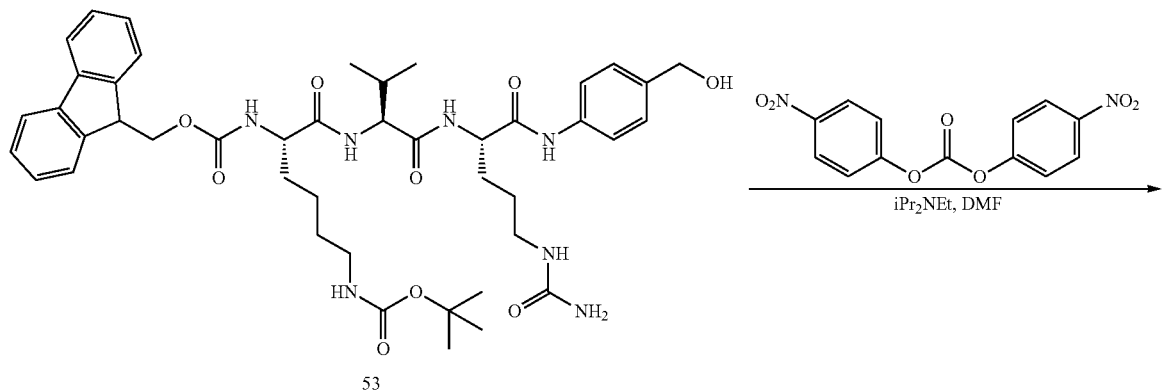

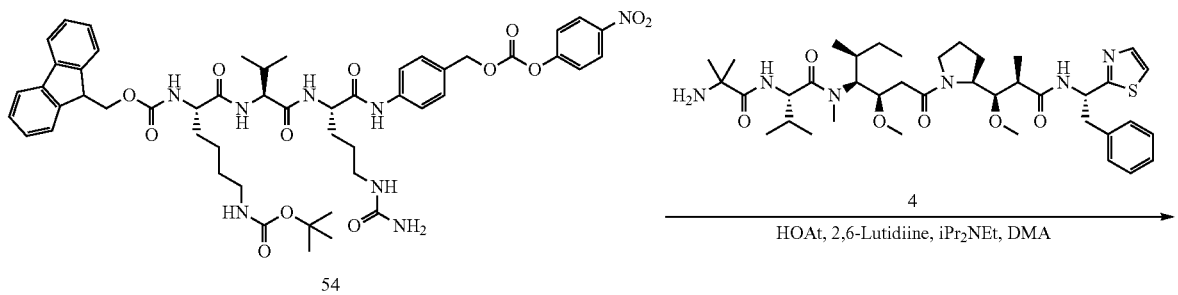

-continued

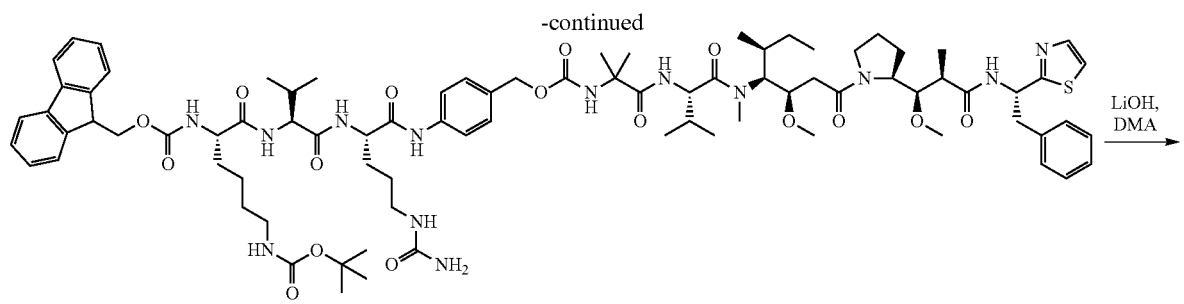

55

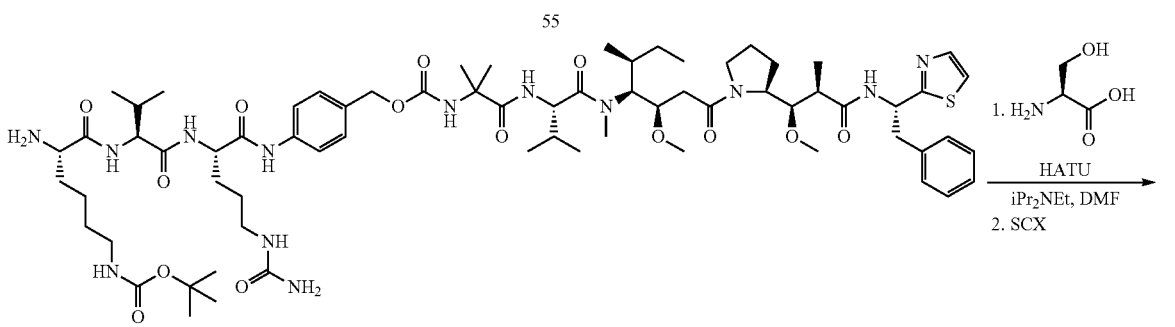

56

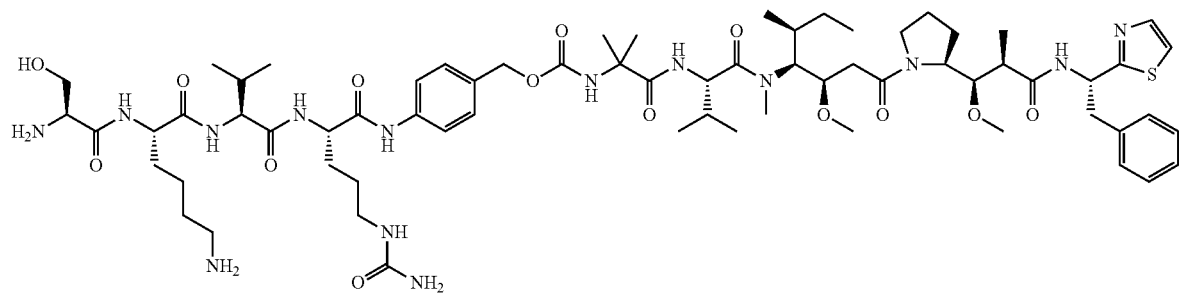

57

Step 1: Synthesis of N~6~-(tert-butoxycarbonyl)-N~2~-[(9H-fluoren-9-ylmethoxy)carbonyl]-L-lysylvalyl-N~5~-carbamoyl-N-[4-(hydroxymethyl)phenyl]-L-ornithinamide (53). In an iced water bath, to a solution of N~6~-(tert-butoxycarbonyl)-N~2~-[(9H-fluoren-9-ylmethoxy)carbonyl]-L-lysine (1090 mg, 2.32 mmol) in 15 mL of N,N-dimethylformamide was added O-(7-azabenzotriazol-1-yl)-N,N,N',N'-tetramethyluronium hexafluorophosphate (HATU, 882 mg, 2.32 mmol). After 40 minutes, L-valyl-N~5~-carbamoyl-N-[4-(hydroxymethyl) phenyl]-L-ornithinamide (1, 800 mg, 2.11 mmol) was added followed by N,N-diisopropylethylamine (1.114 ml, 817 mg, 6.32 mmol). The mixture was monitored by LC-MS and allowed to stir for 2 hours at room temperature. The reaction was then poured in methyl tert-butyl ether (150 mL), stirred for 15 minutes, then filtered. The resulting solid was washed with a dichloromethane:methyl tert-butyl ether:methanol (10:10:2) mixture to afford the crude product (1.3 g) as gray solid. This solid was purified by reverse phase HPLC (Method T). Product containing fractions were lyophilized to provide 570 mg (33%) of the desired product. Analytical HPLC retention time=4.55 minutes. $^1$H NMR (400 MHz, DMSO-$d_6$) δ=9.97 (br. s., 1H), 8.14 (d, J=6.5 Hz, 1H), 7.90 (d, J=7.5 Hz, 2H), 7.73 (br. s., 3H), 7.54 (d, J=8.5 Hz, 3H), 7.42 (t, J=7.3 Hz, 2H), 7.33 (t, J=7.3 Hz, 2H), 7.23 (d, J=8.0 Hz, 2H), 6.78 (br. s., 1H), 5.98 (br. s., 1H), 5.43 (br. s., 2H), 5.11 (br. s., 1H), 4.45-4.34 (m, 3H), 4.34-4.15 (m, 4H), 4.02 (br. s., 1H), 3.02 (d, J=5.5 Hz, 1H), 2.89 (br. s., 3H), 1.98 (d, J=6.5 Hz, 1H), 1.61 (br. s., 3H), 1.52 (br. s., 1H), 1.42-1.30 (m, 13H), 1.24 (br. s., 2H), 0.83 (d, J=12.0 Hz, 3H), 0.85 (d, J=11.5 Hz, 3H).

Step 2: Synthesis of N~6~-(tert-butoxycarbonyl)-N~2~-[(9H-fluoren-9-ylmethoxy)carbonyl]-L-lysylvalyl-N~5~-carbamoyl-N-[4-({[(4-nitrophenoxy)carbonyl]oxy}methyl)phenyl]-L-ornithinamide (54). In an iced water bath, to a solution of N~6~-(tert-butoxycarbonyl)-N~2~-[(9H-fluoren-9-ylmethoxy)carbonyl]-L-lysylvalyl-N~5~-carbamoyl-N-[4-(hydroxymethyl)phenyl]-L-ornithinamide (53, 570 mg, 0.687 mmol) and p-nitrophenyl carbonate (418 mg, 1.37 mmol) in 10 mL of N,N-dimethylformamide was added N,N-diisopropylethylamine (257 uL, 178 mg, 1.37 mmol,) and the mixture was stirred at room temperature for 6 hours. The reaction was then poured in methyl tert-butyl ether (150 mL), stirred for 15 minutes, then filtered. The resulting solid was dispersed in dichloromethane (20 mL) for 20 minutes then filtered to provide 400 mg (58%) of the desired product. LC-MS m/z 996.0 [M+H$^+$]; retention time=4.829 minutes. Analytical HPLC retention time=5.43 minutes. $^1$H NMR (400 MHz, DMSO-$d_6$) δ=10.14 (s, 1H), 8.36-8.29 (m, 2H), 8.18 (d, J=7.5 Hz, 1H), 7.90 (d, J=7.5 Hz, 2H), 7.74 (d, J=7.0 Hz, 2H), 7.66 (d, J=8.0 Hz, 2H), 7.62-7.50 (m, 2H), 7.42 (d, J=7.0 Hz, 3H), 7.38-7.11 (m, 3H), 6.78 (br. s., 1H), 6.00 (br. s., 1H), 5.44 (br. s., 2H), 5.26 (s, 2H), 4.39 (br. s., 1H), 4.35-4.16 (m, 4H), 4.04 (br. s., 1H), 3.05 (d, J=7.0 Hz, 1H), 2.90 (br. s., 3H), 2.74 (s, 1H), 2.34 (br. s., 1H), 2.10 (s, 1H), 1.99 (d, J=6.0 Hz, 1H), 1.68 (br. s., 1H), 1.62 (br. s., 2H), 1.53 (br. s., 2H), 1.38 (s, 11H), 1.42-1.20 (m, 1H), 1.42-1.20 (m, 1H), 0.85 (d, J=12.5 Hz, 3H), 0.86 (d, J=12.5 Hz, 3H).

Step 3: Synthesis of N~6~-(tert-butoxycarbonyl)-N~2~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl] pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (55). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (4, 440 mg, 0.59 mmol) and N~6~-(tert-butoxycarbonyl)-N~2~-[(9H-fluoren-9-ylmethoxy)carbonyl]-L-lysylvalyl-N~5~-carbamoyl-N-[4-({[(4-nitrophenoxy)carbonyl]oxy}methyl)phenyl]-L-ornithinamide (54, 658.0 mg, 0.661 mmol) in 1.3 mL of N,N-dimethylacetamide were added 2,6-lutidine (137 uL, 130 mg, 1.2 mmol) N,N-diisopropylethylamine (207.0 uL, 160 mg, 1.2 mmol) and 3H-[1,2,3]triazolo[4,5-b]pyridin-3-ol (HOAt, 92.1 mg, 0.677 mmol). The mixture was monitored by LC-MS and allowed to stir for 2.5 hours at 50° C. and then at room temperature for 16 hours. The reaction was then purified by reverse phase chromatography (Method U) to provide after lyophilization 630 mg (67%) of the desired product as a white solid. LC-MS m/z 1600.6 [M+H$^+$]; retention time=1.07 minutes. Analytical HPLC retention time=8.213 minutes.

Step 4: Synthesis N~6~-(tert-butoxycarbonyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (56) In an iced water bath, to a solution N~6~-(tert-butoxycarbonyl)-N~2~-[(9H-fluoren-9-ylmethoxy)carbonyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl] pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (55, 630 mg, 0.394 mmol) in 5 mL of N,N-dimethylacetamide was added a solution of lithium hydroxide (29.4 mg, 1.23 mmol) in 0.5 mL of water and the mixture was stirred at room temperature for 30 minutes upon which lithium hydroxide (40.4 mg, 1.69 mmol) was added. After a total of 3 hours, the solution was cooled in an iced bath water, then quench with acetic acid (0.2 mL) and purified by reverse phase HPLC (Method 2). Product containing fractions were lyophilized to provide 350 mg (60%) of the desired product. LC-MS m/z 1377.6 [M+H$^+$]; retention time=0.77 minutes. Analytical HPLC retention time=6.181 minutes.

Step 5: Synthesis of L-seryl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (57). In an iced water bath, to a solution of N~6~-(tert-butoxycarbonyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (56, 50.0 mg, 0.0335 mmol) in 0.5 mL of N,N-dimethylacetamide were added N-(tert-butoxycarbonyl)-L-serine (6.88 mg, 0.0335 mmol) in 0.1 mL of N,N-dimethylacetamide, O-(7-azabenzotriazol-1-yl)-N,N,N',N'-tetramethyluronium hexafluorophosphate (HATU, 15.3 mg, 0.0402 mmol mmol) in 0.1 mL of N,N-dimethylacetamide and N,N-diisopropylethylamine (17.9 uL, 13.4 mg, 0.101 mmol). The mixture was monitored by LC-MS and allowed to stir for 45 minutes at room temperature then concentrated under a strong flow of nitrogen to give the crude (LC-MS m/z 1565.6 [M+H$^+$], retention time=0.96 minutes). The yellow residue was dissolved in 1.2 mL of methanol and loaded equally on two SCX cartridges pre-eluted with 3 column volumes of methanol. The columns were washed with 3 column volumes of methanol (no traces of product in washes according to LC-MS). The product was let sitting on the column overnight. The desired product was eluted with 2 column volumes of 1 N triethylamine in methanol. After concentration under reduced pressure, the residue was then purified by reverse phase chromatography (Method V) to provide after lyophilization 8.3 mg (16%) of the desired product. LC-MS m/z 1364.5 [M+H$^+$], retention time=0.68 minutes. Analytical HPLC retention time=5.464 minutes.

Example 39

Preparation of D-seryl-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (58)

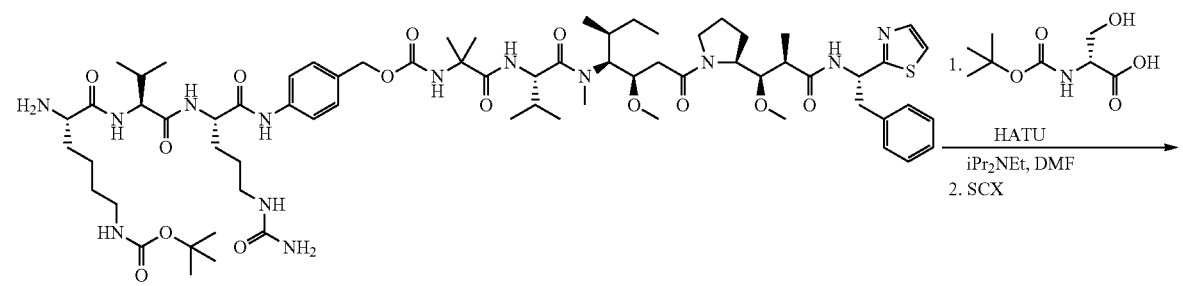

-continued

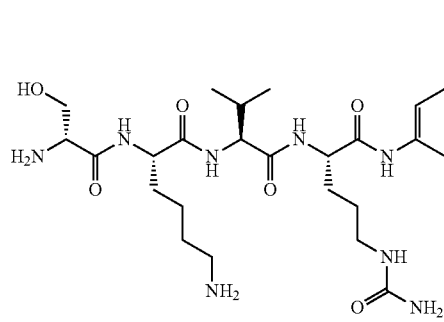

58

In an iced water bath, to a solution of N~6~-(tert-butoxycarbonyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (56, 50.0 mg, 0.0335 mmol) in 0.5 mL of N,N-dimethylacetamide were added N-(tert-butoxycarbonyl)-D-serine (6.88 mg, 0.0335 mmol) in 0.1 mL of N,N-dimethylacetamide, O-(7-azabenzotriazol-1-yl)-N,N,N',N'-tetramethyluronium hexafluorophosphate (HATU, 15.3 mg, 0.0402 mmol mmol) in 0.1 mL of N,N-dimethylacetamide and N,N-diisopropylethylamine (17.9 uL, 13.4 mg, 0.101 mmol). The mixture was monitored by LC-MS and allowed to stir for 45 minutes at room temperature then concentrated under a strong flow of nitrogen to give the crude (LC-MS m/z 1565.6 [M+H⁺], retention time=0.96 minutes). The yellow residue was dissolved in 1.2 mL of methanol and loaded equally on two SCX cartridges pre-eluted with 3 column volumes of methanol. The columns were washed with 3 column volumes of methanol (no traces of product in washes according to LC-MS). The product was let sitting on the column overnight. The desired product was eluted with 2 column volumes of 1 N triethylamine in methanol. After concentration under reduced pressure, the residue was then purified by reverse phase chromatography (Method V) to provide after lyophilization 10.4 mg (19%) of the desired product. LC-MS m/z 1364.5 [M+H⁺], retention time=0.67 minutes. Analytical HPLC retention time=5.424 minutes.

Example 40

Preparation of N~2~-[(2S)-2-hydroxypropanoyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (59)

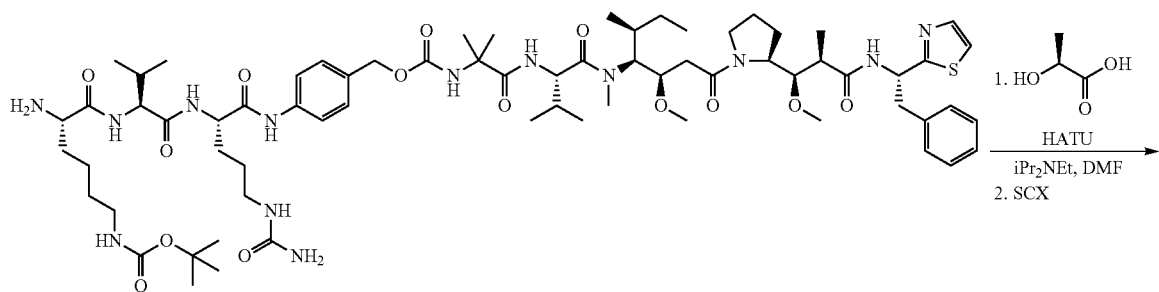

56

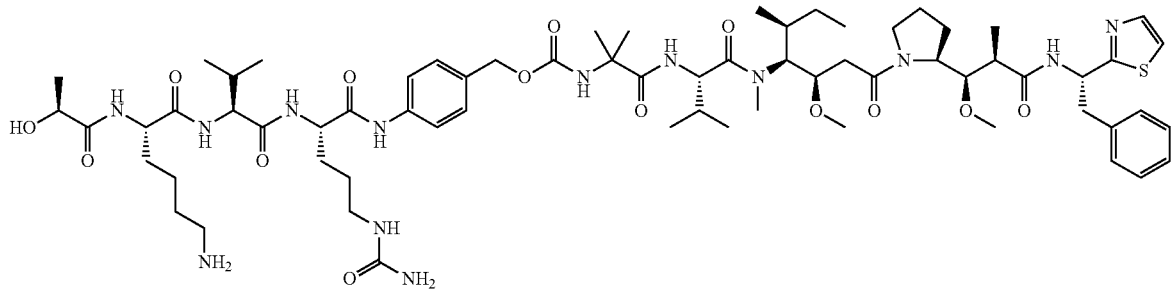

59

In an iced water bath, to a solution of N~6~-(tert-butoxycarbonyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (56, 50.0 mg, 0.0335 mmol) in 0.5 mL of N,N-dimethylacetamide were added (2S)-2-hydroxypropanoic acid (3.02 mg, 0.0335 mmol) in 0.1 mL of N,N-dimethylacetamide, O-(7-azabenzotriazol-1-yl)-N,N,N',N'-tetramethyluronium hexafluorophosphate (HATU, 15.3 mg, 0.0402 mmol mmol) in 0.1 mL of N,N-dimethylacetamide and N,N-diisopropylethylamine (17.9 uL, 13.4 mg, 0.101 mmol). The mixture was monitored by LC-MS and allowed to stir for 45 minutes at room temperature then concentrated under a strong flow of nitrogen to give the crude (LC-MS m/z 1449.5 [M+H⁺], retention time=0.91 minutes). The yellow residue was dissolved in 1.2 mL of methanol and loaded equally on two SCX cartridges pre-eluted with 3 column volumes of methanol. The columns were washed with 3 column volumes of methanol (no traces of product in washes according to LC-MS). The product was let sitting on the column overnight. The desired product was eluted with 2 column volumes of 1 N triethylamine in methanol. After concentration under reduced pressure, the residue was then purified by reverse phase chromatography (Method V) to provide after lyophilization 12.9 mg (26%) of the desired product. LC-MS m/z 1349.4 [M+H⁺], retention time=0.74 minutes. Analytical HPLC retention time=5.813 minutes.

Example 41

Preparation of N~2~-[(2R)-2-hydroxypropanoyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (60)

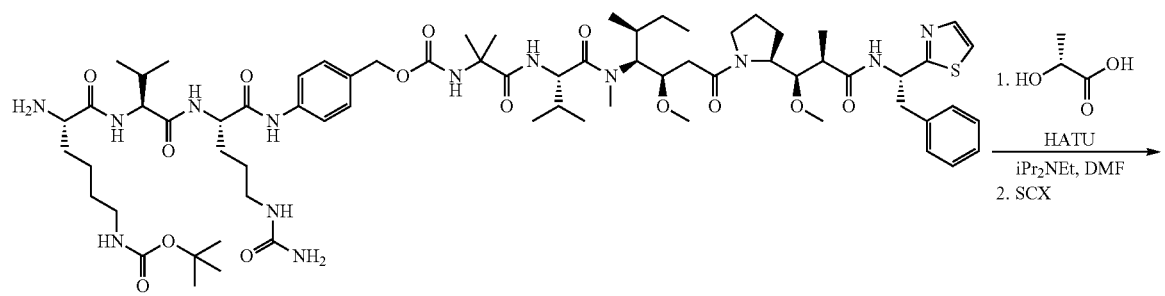

56

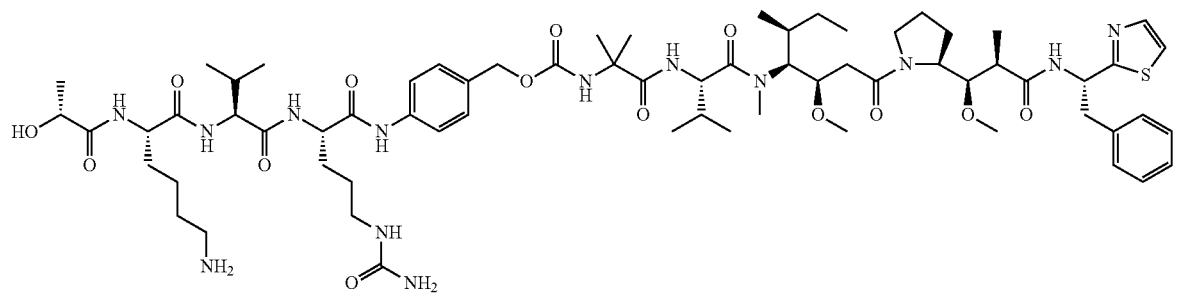

60

In an iced water bath, to a solution of N~6~-(tert-butoxycarbonyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (56, 50.0 mg, 0.0335 mmol) in 0.5 mL of N,N-dimethylacetamide were added (2R)-2-hydroxypropanoic acid (3.01 mg, 0.0334 mmol) in 0.1 mL of N,N-dimethylacetamide, O-(7-azabenzotriazol-1-yl)-N,N,N',N'-tetramethyluronium hexafluorophosphate (HATU, 15.3 mg, 0.0402 mmol mmol) in 0.1 mL of N,N-dimethylacetamide and N,N-diisopropylethylamine (17.9 uL, 13.4 mg, 0.101 mmol). The mixture was monitored by LC-MS and allowed to stir for 45 minutes at room temperature then concentrated under a strong flow of nitrogen to give the crude (LC-MS m/z 1449.4 [M+H⁺], retention time=0.90 minutes). The residue was then purified by reverse phase chromatography (Method V) to provide after lyophilization 29.6 mg (60%) of the desired product. LC-MS m/z 1349.4 [M+H⁺], retention time=0.75 minutes. Analytical HPLC retention time=5.740 minutes.

Example 42

Preparation of N~2~-[(2S)-2,3-dihydroxypropanoyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (62)

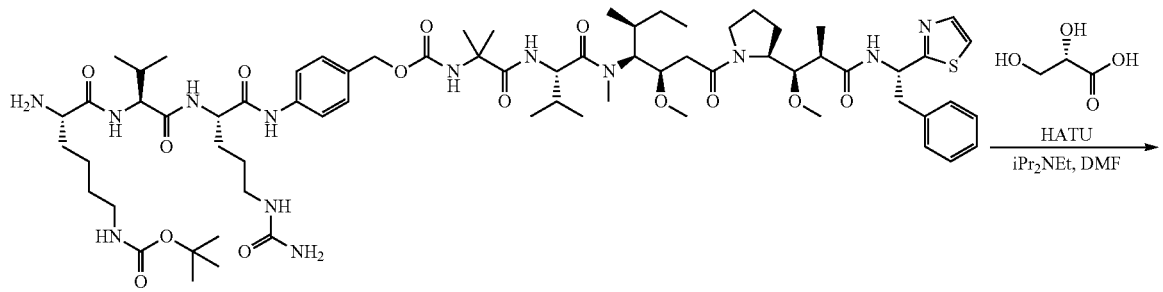

56

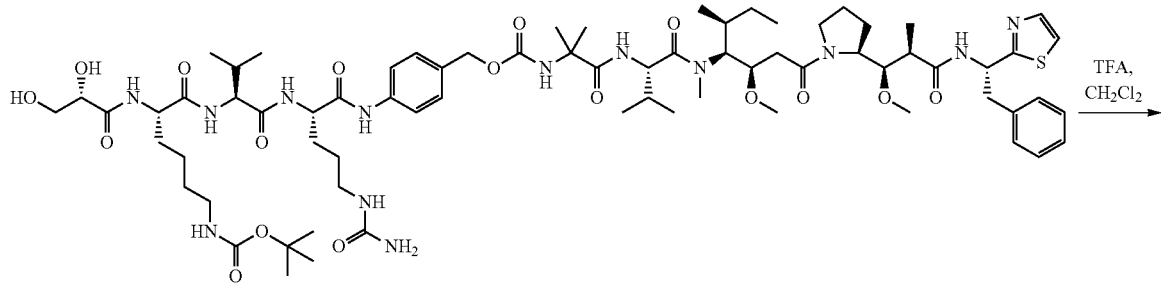

61

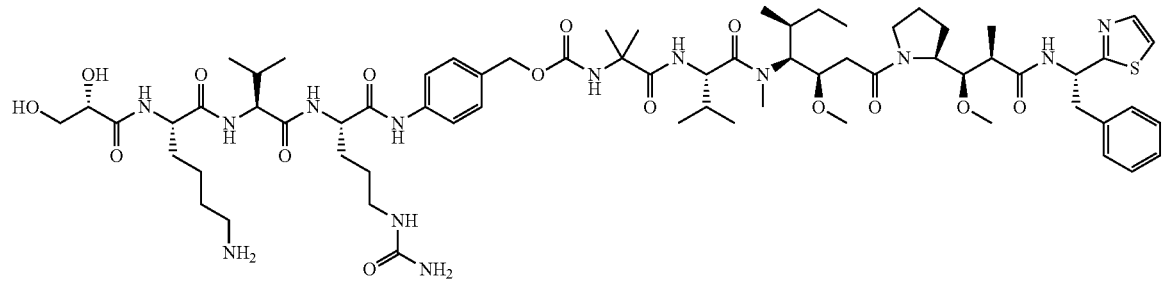

62

Step 1: Synthesis of N~6~-(tert-butoxycarbonyl)-N~2~-[(2S)-2,3-dihydroxypropanoyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (61). In an iced water bath, to a solution of N~6~-(tert-butoxycarbonyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (56, 50.0 mg, 0.0335 mmol) in 0.5 mL of N,N-dimethylacetamide were added (2S)-2,3-dihydroxypropanoic acid$^y$ (4.02 mg, 0.0379 mmol) in 0.1 mL of N,N-dimethylacetamide, O-(7-azabenzotriazol-1-yl)-N,N,N',N'-tetramethyluronium hexafluorophosphate (HATU, 15.3 mg, 0.0402 mmol mmol) in 0.1 mL of N,N-dimethylacetamide and N,N-diisopropylethylamine (l7.9 uL, 13.4 mg, 0.101 mmol). The mixture was monitored by LC-MS and allowed to stir for 45 minutes at room temperature then concentrated under a strong flow of nitrogen. The yellow residue was then purified by reverse phase chromatography (Method U) to provide after lyophilization 10.8 mg (22%) of the desired product. LC-MS m/z 1465.5 [M+H$^+$], retention time=0.89 minutes. Analytical HPLC retention time=6.607 minutes.

Step 2: Synthesis of N~2~-[(2S)-2,3-dihydroxypropanoyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (62). To a suspension of N~6~-(tert-butoxycarbonyl)-N~2~-[(2S)-2,3-dihydroxypropanoyl]-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (61, 10.8 mg, 0.0074 mmol) in 1 mL of dichloromethane was added 0.5 mL of trifluoroacetic acid. The mixture was monitored by LC-MS and allowed to stir for 20 minutes at room temperature. The reaction was then concentrated and purified by reverse phase chromatography (Method V) to provide after lyophilization 3.6 mg (33%). LC-MS m/z 1365.4 [M+H$^+$]; retention time=0.74 minutes. Analytical HPLC retention time=5.749 minutes.

Example 43

Preparation of N~2~-(3-hydroxypropanoyl)-L-lysyl-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (64)

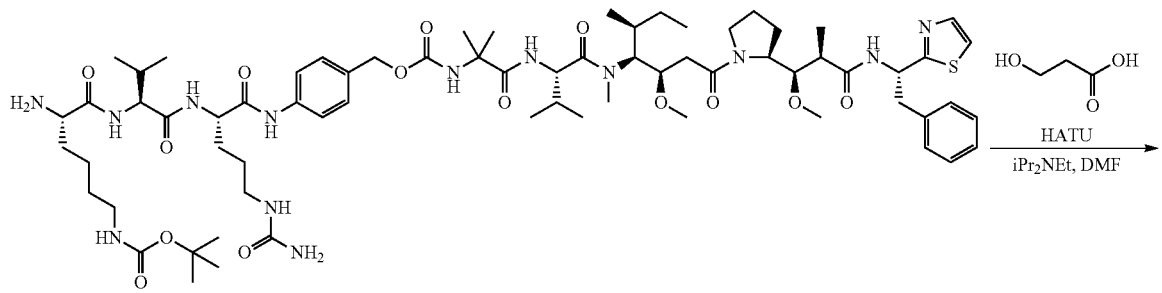

56

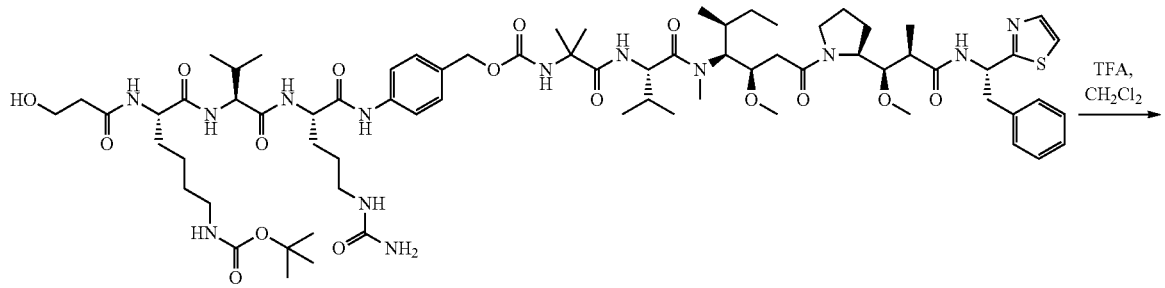

63

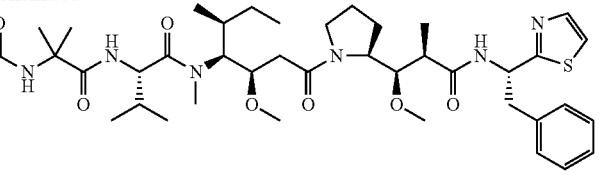
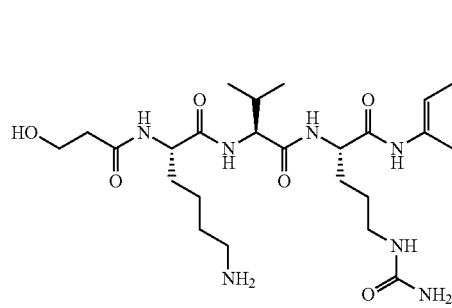

64

Step 1: Synthesis of N~6~-(tert-butoxycarbonyl)-N~2~-(3-hydroxypropanoyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (63). In an iced water bath, to a solution of N~6~-(tert-butoxycarbonyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (56, 50.0 mg, 0.0335 mmol) in 0.5 mL of N,N-dimethylacetamide were added 3-hydroxypropanoic acid (4.01 mg, 0.0445 mmol) in 0.1 mL of N,N-dimethylacetamide, O-(7-azabenzotriazol-1-yl)-N,N,N',N'-tetramethyluronium hexafluorophosphate (HATU, 15.3 mg, 0.0402 mmol mmol) in 0.1 mL of N,N-dimethylacetamide and N,N-diisopropylethylamine (17.9 uL, 13.4 mg, 0.101 mmol). The mixture was monitored by LC-MS and allowed to stir for 45 minutes at room temperature then concentrated under a strong flow of nitrogen. The yellow residue was then purified by reverse phase chromatography (Method U) to provide after lyophilization 13.9 mg (29%) of the desired product. LC-MS m/z 1449.6 [M+H⁺], retention time=0.91 minutes. Analytical HPLC retention time=6.721 minutes.

Step 2: Synthesis of N~2~-(3-hydroxypropanoyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (64). To a suspension of N~6~-(tert-butoxycarbonyl)-N~2~-(3-hydroxypropanoyl)-L-lysylvalyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide (63, 13.9 mg, 0.0096 mmol) in 1 mL of dichloromethane was added 0.5 mL of trifluoroacetic acid. The mixture was monitored by LC-MS and allowed to stir for 20 minutes at room temperature. The reaction was then concentrated and purified by reverse phase chromatography (Method V) to provide after lyophilization 4.1 mg (29%). LC-MS m/z 1349.4 [M+H⁺]; retention time=0.75 minutes. Analytical HPLC retention time=5.758 minutes.

Example 44

Preparation of N~2~-(methylsulfonyl)lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide, trifluoroacetic salt (70)

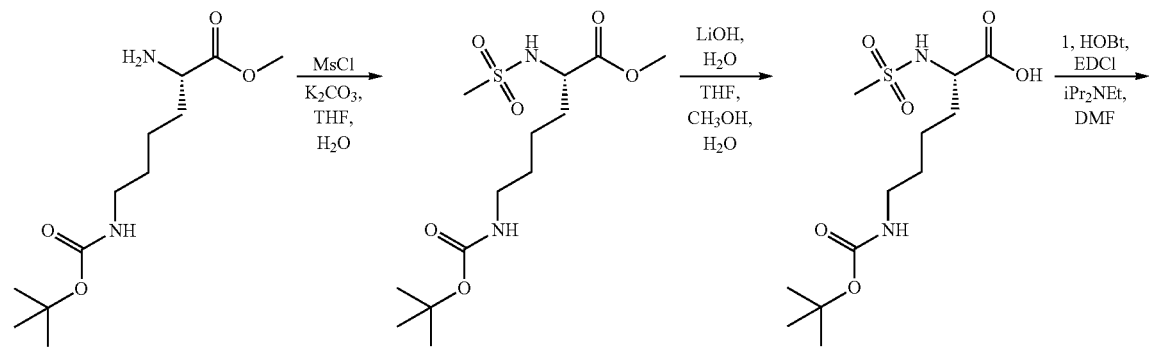

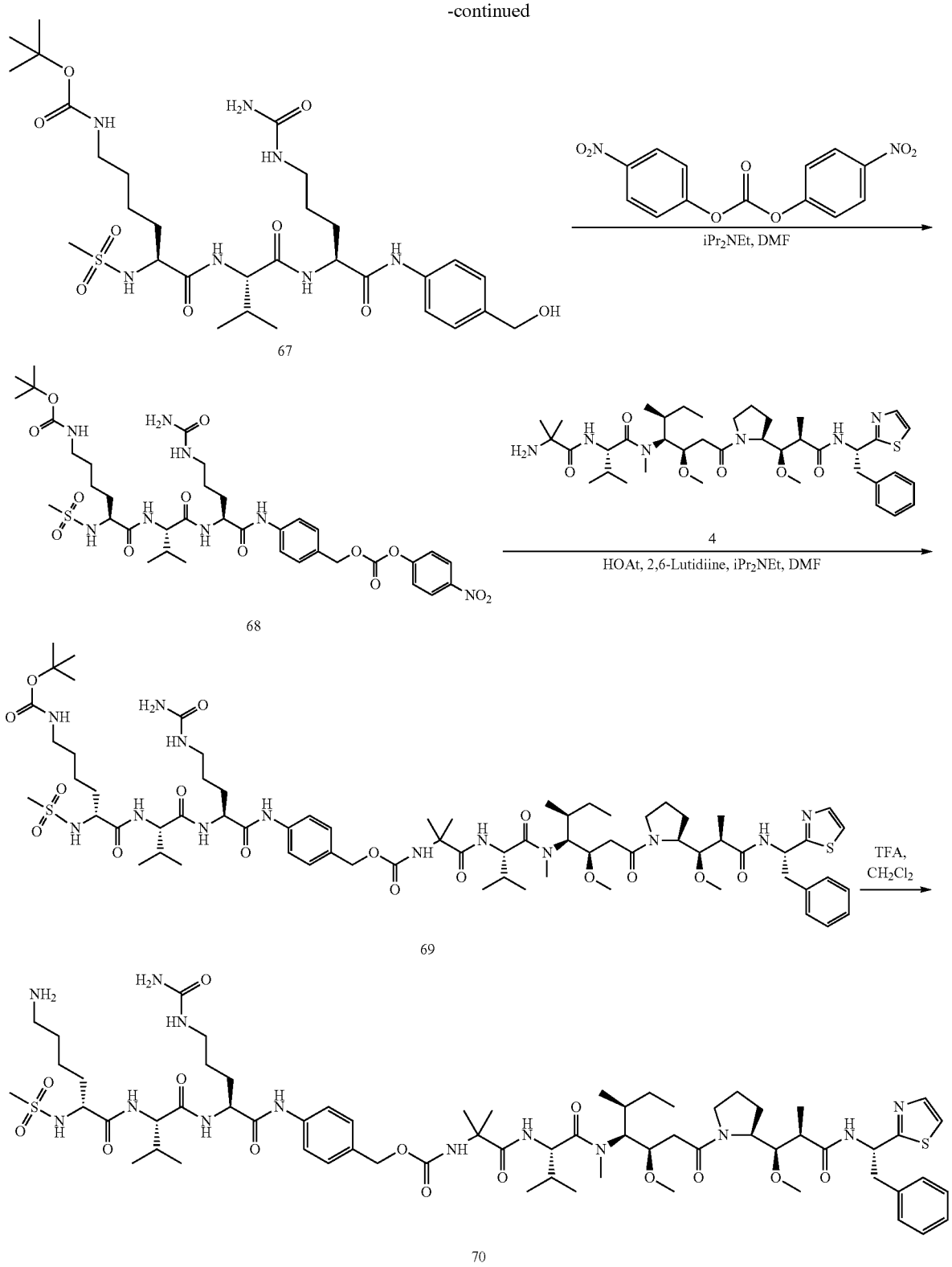

Step 1: Synthesis of methyl N~6~-(tert-butoxycarbonyl)-N~2~-(methylsulfonyl)-L-lysinate (65). To an ice cold solution of methyl N~6~-(tert-butoxycarbonyl)-L-lysinate (2.0 g, 6.73 mmol) in tetrahydrofuran:water (1:1, 20 mL) was added potassium carbonate (4.6 g, 33.7 mmol) followed by dropwise addition of mesyl chloride (0.62 mL, 8.08 mmol). The mixture was stirred at room temperature for 3 hours and the mixture was then filtered. The filtrate was extracted with ethyl acetate three times. The combined extracts were washed with brine, dried over sodium sulfate and concentrated under educed pressure. The residue was purified by silica gel chromatography using a gradient elution of 0% to 2% methanol in dichloromethane to provide 2.0 g (87%) of the desired product as colorless oil. $^1$H NMR (400 MHz, CHLOROFORM-d) δ=5.23 (d, J=9.0 Hz, 1H), 4.62 (br. s., 1H), 4.10 (dt, J=5.0, 8.5 Hz, 1H), 3.78 (s, 3H), 3.16-3.04 (m, 2H), 2.95 (s, 3H), 1.88-1.78 (m, 2H), 1.77-1.64 (m, 1H), 1.59-1.47 (m, 3H), 1.45 (s, 9H).

Step 2: Synthesis of N~6~-(tert-butoxycarbonyl)-N~2~-(methylsulfonyl)-L-lysine (66). To a stirred solution of methyl N~6~-(tert-butoxycarbonyl)-N~2~-(methylsulfonyl)-L-lysinate (65, 2.0 g, 5.90 mmol) in tetrahydrofuran: water:methanol (1:1:1, 30 mL) was added lithium hydroxide monohydrate (496 mg, 11.8 mmol). The mixture was stirred at room temperature for 3 hours. The mixture was concentrated under reduced pressure. The remaining aqueous layer was extracted twice with ethyl acetate. The aqueous was acidified to pH 3 with a 1N aqueous solution of hydrochloric acid and then extracted twice with isopropyl alcohol:ethyl acetate (1:5). The combined organic extracts were washed with brine, dried over sodium sulfate and concentrated under reduced pressure to provide 1.3 g (68%) of the desired product as a white solid. MS m/z 323.1 [M−H$^+$]; $^1$H NMR (400 MHz, CHLOROFORM-d) δ=6.40 (br. s., 1H), 5.81-5.66 (m, 1H), 4.79 (br. s., 1H), 3.23-3.06 (m, 2H), 2.99 (s, 3H), 1.96-1.71 (m, 2H), 1.55-1.39 (m, 13H).

Step 3: Synthesis of N~6~-(tert-butoxycarbonyl)-N~2~-(methylsulfonyl)-L-lysyl-L-valyl-N~5~-carbamoyl-N-[4-(hydroxymethyl)phenyl]ornithinamide (67). To an ice cold solution of N~6~-(tert-butoxycarbonyl)-N~2~-(methylsulfonyl)-L-lysine (66, 1.0 g, 3.09 mmol) and L-valyl-N~5~-carbamoyl-N-[4-(hydroxymethyl)phenyl]-L-ornithinamide (1, 1.28 g, 3.40 mmol) in 20 mL N,N-dimethylformamide were added N,N-diisopropylethylamine (600 uL, 438 mg, 3.40 mmol), N-(3-dimethylaminopropyl)-N'-ethylcarbodiimide hydrochloride (649 mg, 3.40 mmol) and 1-hydroxybenzotriazole hydrate (459 mg, 3.40 mmol). The mixture was allowed to warm to room temperature and was stirred for 16 hours. The mixture was then added dropwise to 150 mL of tert-Butyl methyl ether. The solid was purified by reverse phase HPLC. Product containing fractions were lyophilized to provide 580 mg (28%) of the desired product as a white solid.

Step 4: Synthesis of N~6~-(tert-butoxycarbonyl)-N~2~-(methylsulfonyl)-L-lysyl-L-valyl-N~5~-carbamoyl-N-[4-({[(4-nitrophenoxy)carbonyl]oxy}methyl)phenyl]ornithinamide (68). To a stirred solution of N~6~-(tert-butoxycarbonyl)-N~2~-(methylsulfonyl)-L-lysyl-L-valyl-N~5~-carbamoyl-N-[4-(hydroxymethyl)phenyl]ornithinamide (67, 580 mg, 0.85 mmol) and p-nitrophenyl carbonate (770 mg, 2.56 mmol) in 10 mL of N,N-dimethylformamide was added N,N-diisopropylethylamine (451 ul, 330 mg, 2.56 mmol). The mixture was stirred at room temperature for 16 hours. The mixture was added dropwise to 150 mL of tert-Butyl methyl ether. The solid was purified by reverse phase HPLC (Method XXX). Product containing fractions were lyophilized to provide 200 mg (28%) of the desired product as a white solid. MS m/z 851.4 [M+H$^+$]. $^1$H NMR (400 MHz, DMSO-d$_6$) δ=10.16 (s, 1H), 8.32 (d, J=9.5 Hz, 2H), 8.26 (d, J=6.5 Hz, 1H), 7.95 (t, J=7.4 Hz, 1H), 7.65 (d, J=8.5 Hz, 2H), 7.58 (t, J=5.9 Hz, 2H), 7.45 (d, J=9.0 Hz, 1H), 7.42 (d, J=8.5 Hz, 2H), 6.79 (t, J=5.5 Hz, 1H), 6.00 (t, J=5.8 Hz, 1H), 5.45 (s, 2H), 4.40 (d, J=5.0 Hz, 1H), 4.33-4.06 (m, 1H), 3.84 (d, J=4.5 Hz, 1H), 3.30 (br. s., 1H), 3.09-2.99 (m, 1H), 2.98-2.93 (m, 1H), 2.93-2.86 (m, 2H), 2.83 (s, 3H), 2.01 (d, J=6.5 Hz, 1H), 1.59 (br. s., 3H), 1.47 (d, J=13.1 Hz, 2H), 1.38 (s, 13H), 0.89 (d, J=7.0 Hz, 3H), 0.85 (d, J=7.0 Hz, 3H).

Step 5: Synthesis of N~6~-(tert-butoxycarbonyl)-N~2~-(methylsulfonyl)-D-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (69). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (4, 52.0 mg, 0.070 mmol) and N~6~-(tert-butoxycarbonyl)-N~2~-(methylsulfonyl)-L-lysyl-L-valyl-N~5~-carbamoyl-N-[4-({[(4-nitrophenoxy)carbonyl]oxy}methyl)phenyl]ornithinamide (68, 60.6 mg, 0.0710 mmol) in 2 mL of N,N-dimethylacetamide were added 2,6-lutidine (31 uL, 28.3 mg, 0.264 mmol) N,N-diisopropylethylamine (46 uL, 34.1 mg, 0.264 mmol) and 3H-[1,2,3]triazolo[4,5-b]pyridin-3-ol (9 mg, 0.066 mmol). The mixture was allowed to stir for 16 hours at 45° C. The reaction was then purified by reverse phase HPLC (Method S) to provide after lyophilization 70 mg (69%) of the desired product as a white solid. LC-MS m/z 1455.09 [M+H$^+$], 1453.77 [M−H$^+$]; retention time=1.80 minutes.

Step 6: Synthesis of N~2~-(methylsulfonyl)lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide, trifluoroacetic salt (70). To a solution of N~6~-(tert-butoxycarbonyl)-N~2~-(methylsulfonyl)-D-lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (69, 30 mg, 0.021 mmol) in 0.8 mL of dichloromethane was added 0.2 mL of trifluoroacetic acid. The mixture was monitored by LC-MS and allowed to stir for 30 minutes at room temperature. The solution was then directly purified by reverse phase HPLC (Method B). Product containing fractions were lyophilized to provide after lyophilization 15 mg (48%). LC-MS m/z 1355.4 [M+H$^+$], 1353.3 [M−H$^+$]; retention time=1.42 minutes.

Example 45
Preparation of N~2~-(phenylsulfonyl)lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide, trifluoroacetic salt (75)
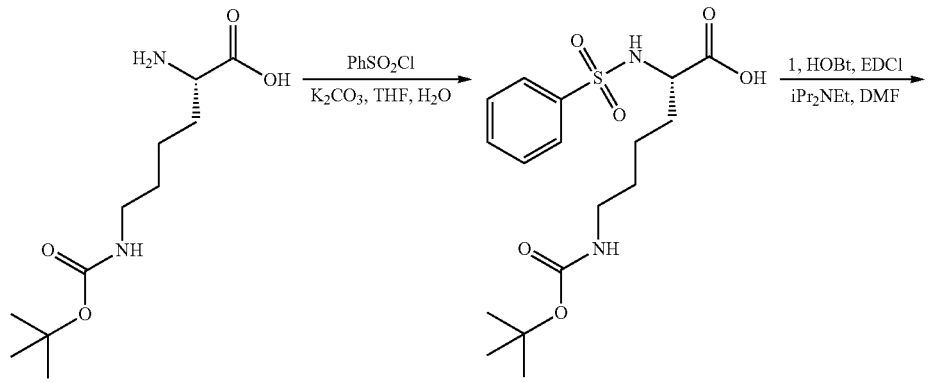
71
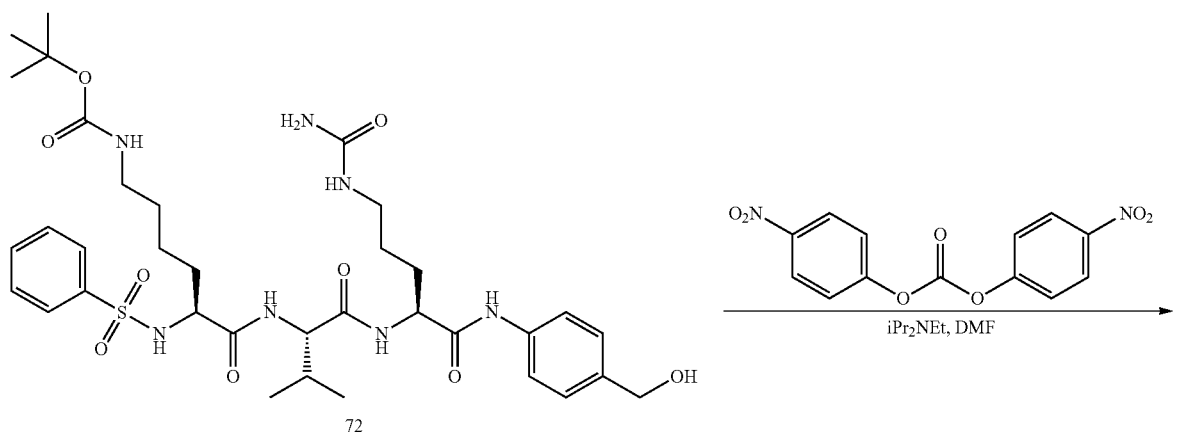
72
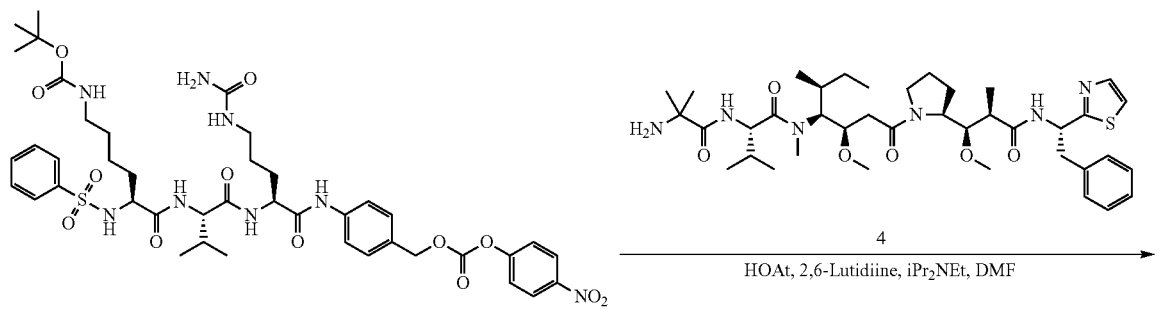
73

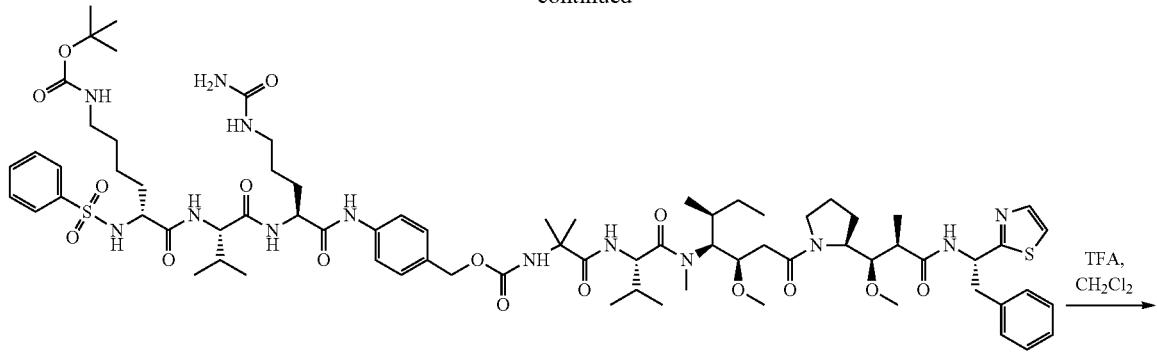

74

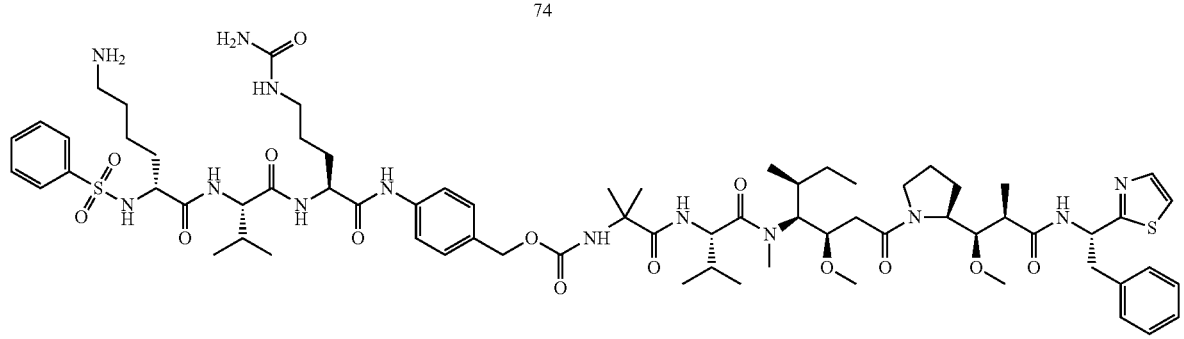

75

Step 1: Synthesis of N~6~-(tert-butoxycarbonyl)-N~2~-(phenylsulfonyl)-L-lysine (71). To an ice cold solution of N~6~-(tert-butoxycarbonyl)-L-lysine (3.0 g, 12.2 mmol) in tetrahydrofuran:water (1:1, 100 mL) was added potassium carbonate (8.4 g, 61.0 mmol) followed by dropwise addition of benzenesulfonyl chloride (1.86 mL, 14.6 mmol). The mixture was stirred at room temperature for 3 hours and the mixture was then filtered. The filtrate was extracted three times with ethyl acetate: isopropyl alcohol 10:1. The combined extracts were washed with brine, dried over sodium sulfate and concentrated under reduced pressure. To the residue was added 100 mL of tert-Butyl methyl ether and the mixture was stirred for 30 minutes. The solid was collected by filtration and purified by reverse phase HPLC. Product containing fractions were lyophilized to provide 538 mg (11%) of the desired product as a white solid. MS m/z 408.9 [M+Na$^+$]. $^1$H NMR (400 MHz, DMSO-d$_6$) δ=7.76 (d, J=7.5 Hz, 2H), 7.63-7.50 (m, 3H), 3.61-3.53 (m, 1H), 2.82-2.73 (m, 2H), 1.61-1.40 (m, 2H), 1.35 (s, 9H), 1.28-1.06 (m, 4H).

Step 2: Synthesis of N~6~-(tert-butoxycarbonyl)-N~2~-(phenylsulfonyl)-L-lysyl-L-valyl-N~5~-carbamoyl-N-[4-(hydroxymethyl)phenyl]ornithinamide (72). To an ice cold solution of N~6~-(tert-butoxycarbonyl)-N~2~-(phenylsulfonyl)-L-lysine (71, 1.2 g, 3.10 mmol) and L-valyl-N~5~-carbamoyl-N-[4-(hydroxymethyl)phenyl]-L-ornithinamide (1, (1.30 g, 3.41 mmol) in 20 mL N,N-dimethylformamide were added N,N-diisopropylethylamine (600 uL, 438 mg, 3.40 mmol), N-(3-Dimethylaminopropyl)-N'-ethylcarbodiimide hydrochloride (650 mg, 3.41 mmol) and 1-Hydroxybenzotriazole hydrate (460 mg, 3.41 mmol). The mixture was allowed to warm to room temperature and was stirred for 16 hours. The mixture was added dropwise to 150 mL of tert-Butyl methyl ether. The solid was isolated by filtration and then purified by reverse phase HPLC. Product containing fractions were lyophilized to provide 850 mg (37%) of the desired product as a white solid.

Step 3: Synthesis of N~6~-(tert-butoxycarbonyl)-N~2~-(phenylsulfonyl)-L-lysyl-L-valyl-N~5~-carbamoyl-N-[4-({[(4-nitrophenoxy)carbonyl]oxy}methyl)phenyl]ornithinamide (73). To a stirred solution of N~6~-(tert-butoxycarbonyl)-N~2~-(phenylsulfonyl)-L-lysyl-L-valyl-N~5~-carbamoyl-N-[4-(hydroxymethyl)phenyl]ornithinamide (72, 850 mg, 1.14 mmol) and p-nitrophenyl carbonate (853 mg, 2.85 mmol) in 15 mL of N,N-dimethylformamide was added N,N-diisopropylethylamine (501 ul, 365 mg, 2.85 mmol). The mixture was stirred at room temperature for 16 hours. The mixture was added dropwise to 150 mL of tert-Butyl methyl ether. The solid was purified by reverse phase HPLC. Product containing fractions were lyophilized to provide 450 mg (43%) of the desired product as a white solid. MS m/z 935.1 [M+Na$^+$]; $^1$H NMR (400 MHz, DMSO-d$_6$) δ=10.11 (s, 1H), 8.35-8.27 (m, 2H), 8.10 (d, J=7.0 Hz, 1H), 7.94 (d, J=8.5 Hz, 1H), 7.83 (d, J=8.5 Hz, 1H), 7.76 (d, J=7.5 Hz, 2H), 7.63 (d, J=8.5 Hz, 2H), 7.60-7.48 (m, 5H), 7.40 (t, J=5.8 Hz, 2H), 6.70 (s, J=5.6, 5.6 Hz, 1H), 6.01-5.93 (m, 1H), 5.43 (s, 2H), 4.36 (d, J=6.0 Hz, 1H), 4.01 (t, J=7.5 Hz, 1H), 3.78 (d, J=5.0 Hz, 1H), 3.01 (d, J=6.0 Hz, 1H), 2.97-2.88 (m, 1H), 2.76 (q, J=6.5 Hz, 2H), 1.86 (d, J=6.5 Hz, 1H), 1.44 (d, J=5.5 Hz, 4H), 1.41-1.40 (m, 1H), 1.36 (s, 9H), 1.31-1.13 (m, 3H), 1.05 (br. s., 1H), 0.75 (d, J=7.0 Hz, 3H), 0.73 (d, J=7.0 Hz, 3H).

Step 4: Synthesis of N~6~-(tert-butoxycarbonyl)-N~2~-(phenylsulfonyl)lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (74). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]

pyrrolidin-1-yl}-5-methyl-1-oxoheptan-4-yl]-N-methyl-L-valinamide (4, 52.0 mg, 0.070 mmol) and N~6~-(tert-butoxycarbonyl)-N~2~-(phenylsulfonyl)-L-lysyl-L-valyl-N~5~-carbamoyl-N-[4-({[(4-nitrophenoxy)carbonyl]oxy}methyl)phenyl]ornithinamide (73, 60.4 mg, 0.066 mmol) in 2 mL of N,N-dimethylacetamide were added 2,6-lutidine (31 uL, 28.3 mg, 0.264 mmol) N,N-diisopropylethylamine (46 uL, 34.1 mg, 0.264 mmol) and 3H-[1,2,3]triazolo[4,5-b]pyridin-3-ol (9 mg, 0.066 mmol). The mixture was allowed to stir for 16 hours at 45° C. The reaction was then purified by reverse phase HPLC (Method S) to provide after lyophilization 85 mg (85%) of the desired product as a white solid. LC-MS m/z 1518.4 [M+H⁺], 1516.3 [M−H⁺]; retention time=1.93 minutes.

Step 5: Synthesis of N~2~-(phenylsulfonyl)lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide, trifluoroacetic salt (75). To a solution of N~6~-(tert-butoxycarbonyl)-N~2~-(phenylsulfonyl)lysyl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (75, 82 mg, 0.054 mmol) in 0.8 mL of dichloromethane was added 0.2 mL of trifluoroacetic acid. The mixture was monitored by LC-MS and allowed to stir for 30 minutes at room temperature. The solution was then directly purified by reverse phase HPLC (Method B). Product containing fractions were lyophilized to provide after lyophilization 35 mg (42%). LC-MS m/z 1416.87 [M+H⁺]; retention time=1.35 minutes.

Example 46

Preparation of N-acetyl-O-(2-aminoethyl)-D-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide, trifluoroacetic acid salt (83)

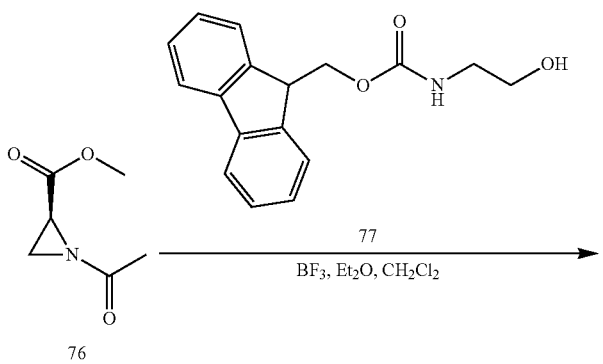

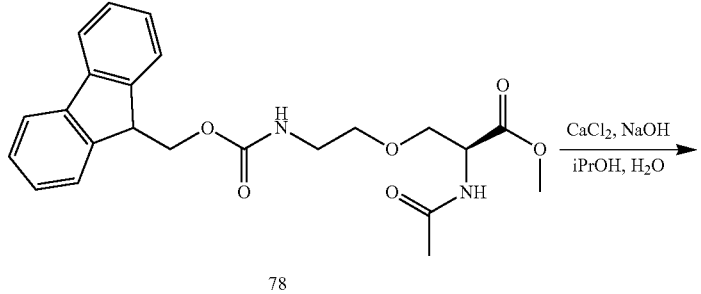

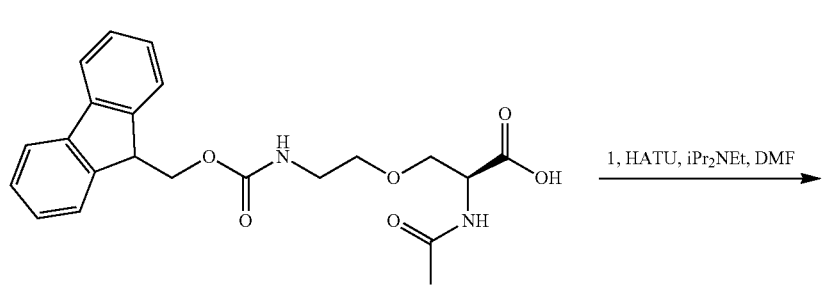

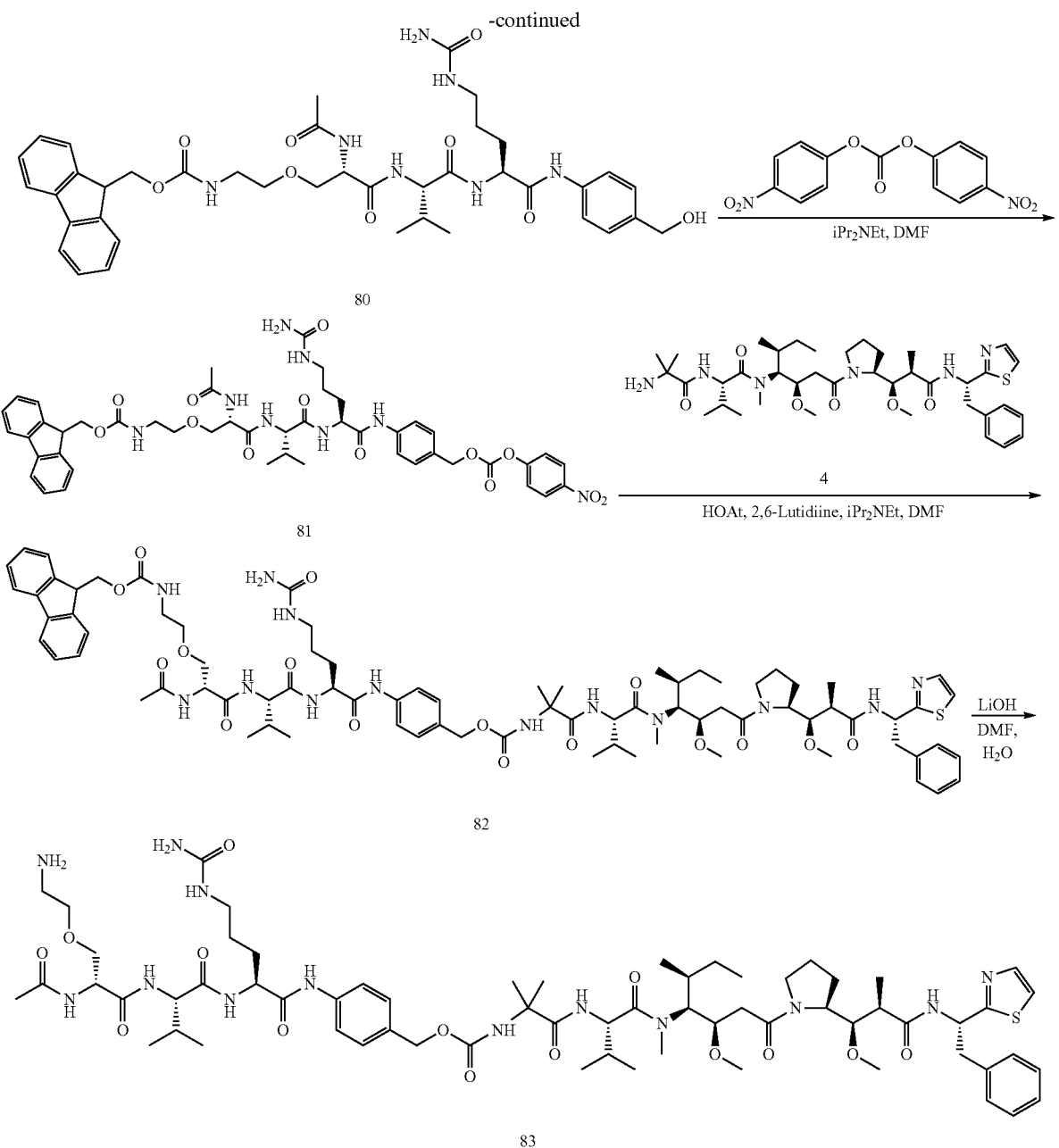

Step 1: Synthesis of methyl N-acetyl-O-(2-{[(9H-fluoren-9-ylmethoxy)carbonyl]amino}ethyl)-L-serinate (78). To a suspension of 9H-fluoren-9-ylmethyl (2-hydroxyethyl)carbamate (1000 mg, 3.53 mmol) and methyl (2S)-1-acetylaziridine-2-carboxylate (US 20110021482, 758 mg, 5.29 mmol) in 20 mL of dichloromethane at −30° C. was added dropwise boron trifluoride diethyl etherate (532 uL, 601 mg, 4.24 mmol). The mixture was stirred at that temperature for 2 hours then allowed to warm up to room temperature. After another hour, to the reaction was added a saturated aqueous solution of sodium bicarbonate and diluted with dichloromethane (80 mL). The organic phase was separated and washed with brine, dried over sodium sulfate and concentrated under reduced pressure. The residue was purified by reverse phase HPLC (Method W). The appropriate fractions were combined and the organic solvents were removed under reduced pressure. The remaining aqueous mixture was extracted with ethyl acetate (2×100 mL). The combined extracts were washed with brine, dried over sodium sulfate and concentrated. The residue was co-evaporated with dichloromethane (50 mL) once to give the title compound 160 mg (11%) as a light yellow gum. MS m/z 448.9 [M+Na$^+$]; $^1$H NMR (400 MHz, CHLOROFORM-d) δ=7.78 (d, J=7.5 Hz, 2H), 7.60 (d, J=7.5 Hz, 2H), 7.42 (t, J=7.5 Hz, 2H), 7.37-7.31 (m, 2H), 6.66 (br. s., 1H), 5.07 (br. s., 1H), 4.89-4.72 (m, 1H), 4.45 (d, J=6.5 Hz, 2H), 4.23 (d, J=6.5 Hz, 1H), 3.88 (d, J=6.5 Hz, 1H), 3.72 (br. s., 4H), 3.54 (br. s., 2H), 3.36 (br. s., 2H), 2.09 (s, 3H).

Step 2: Synthesis of N-acetyl-O-(2-{[(9H-fluoren-9-ylmethoxy)carbonyl]amino}ethyl)-L-serine (79). To a solution of N-acetyl-O-(2-{[(9H-fluoren-9-ylmethoxy)carbonyl]amino}ethyl)-L-serinate (78, 160 mg, 0.375 mmol)

isopropanol:water (7:3, 10 mL) was added calcium chloride (833 g, 7.5 mmol). Once the mixture became clear, sodium hydroxide (18 mg, 0.450 mmol) was added. The resulting mixture was stirred at room temperature for 3 hours. The mixture was then acidified to pH ~1-2 with a 3M aqueous solution of hydrochloric acid and diluted with water (10 mL). The mixture was extracted with ethyl acetate (20 mL) and the organic was isolated and concentrated under reduced pressure to remove most of the isopropanol. The aqueous phase was extracted with ethyl acetate (2×100 mL). The combined organic layers were washed with brine, dried over sodium sulfate and concentrated to provide 107 mg (96%) the desired compound as a blue solid, which will be used as is in the next step without further purification. MS m/z 434.8 [M+Na$^+$]; $^1$H NMR (400 MHz, CHLOROFORM-d) δ=8.48 (d, J=9.0 Hz, 1H), 7.78 (d, J=7.5 Hz, 2H), 7.56 (d, J=7.5 Hz, 2H), 7.47-7.37 (m, 2H), 7.35-7.29 (m, 2H), 7.15 (t, J=6.1 Hz, 1H), 5.03 (d, J=9.0 Hz, 1H), 4.51 (dd, J=6.8, 10.8 Hz, 1H), 4.41 (dd, J=7.0, 10.5 Hz, 2H), 4.30-4.23 (m, 1H), 4.32-4.21 (m, 1H), 4.21-4.09 (m, 1H), 3.57 (t, J=8.3 Hz, 3H), 3.53-3.45 (m, 2H), 3.40 (br. s., 1H), 3.31 (d, J=9.0 Hz, 1H), 2.00 (s, 3H).

Step 3: Synthesis of N-acetyl-O-(2-{[(9H-fluoren-9-yl-methoxy)carbonyl]amino}ethyl)-L-serylvalyl-N~5~-carbamoyl-N-[4-(hydroxymethyl)phenyl]-L-ornithinamide (80). To a solution of N-acetyl-O-(2-{[(9H-fluoren-9-yl-methoxy)carbonyl]amino}ethyl)-L-serine (79, 105 mg, 0.255 mmol) and L-valyl-N~5~-carbamoyl-N-[4-(hydroxymethyl)phenyl]-L-ornithinamide (1, 96.6 mg, 0.255 mmol) in 3 mL of N,N-dimethylformamide was added O-(7 azabenzotriazol 1 yl) N,N,N',N' tetramethyluronium hexafluorophosphate (106 mg, 0.280 mmol) followed by N,N diisopropylethylamine (98.7 mg, 0.764 mmol). The yellow clear mixture was stirred at room temperature for 2 hours. The mixture was diluted with tert-butyl methyl ether (60 mL) and stirred for 30 minutes. The solid was isolated by filtration and then purified by reverse phase HPLC (Method X). Product containing fractions were lyophilized to provide 84 mg (43%) of the desired product as a white solid. MS m/z 774.2 [M+H$^+$].

Step 4: Synthesis of N-acetyl-O-(2-{[(9H-fluoren-9-yl-methoxy)carbonyl]amino}ethyl) serylvalyl-N~5~-carbamoyl-N-[4-({[(4-nitrophenoxy)carbonyl]oxy}methyl)phenyl]-L-ornithinamide (81). To a stirred solution of N-acetyl-O-(2-{[(9H-fluoren-9-ylmethoxy)carbonyl]amino}ethyl)-L-serylvalyl-N~5~-carbamoyl-N-[4-(hydroxymethyl)phenyl]-L-ornithinamide (80, 200 mg, 0.258 mmol) and p-nitrophenyl carbonate (853 mg, 2.85 mmol) in 5 mL of N,N-dimethylformamide was added N,N-diisopropylethylamine (100.8 ul, 73.5 mg, 0.569 mmol). The mixture was stirred at room temperature for 3 hours then more p-nitrophenyl carbonate (78.6 mg, 0.258 mmol) was added. After an extra hour, the mixture was added dropwise to 100 mL of tert-butyl methyl ether. The solid was isolated by filtration, washed with some tert-butyl methyl ether to provide after air drying 180 mg (74%) of the desired product as a yellow solid. MS m/z 939.2 [M+H$^+$] 961.1 [M+Na$^+$].

Step 5: Synthesis of N-acetyl-O-(2-{[(9H-fluoren-9-yl-methoxy)carbonyl]amino}ethyl)-D-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (82). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (4, 60.0 mg, 0.081 mmol) and N-acetyl-O-(2-{[(9H-fluoren-9-yl-methoxy)carbonyl]amino}ethyl) serylvalyl-N~5~-carbamoyl-N-[4-({[(4-nitrophenoxy)carbonyl]oxy}methyl)phenyl]-L-ornithinamide (81, 121 mg, 0.188 mmol) in 2.5 mL of N,N-dimethylacetamide were added 2,6-lutidine (37.4 uL, 34.6 mg, 0.323 mmol) N,N-diisopropylethylamine (42.2 uL, 31.3 mg, 0.242 mmol) and 3H-[1,2,3]triazolo[4,5-b]pyridin-3-ol (11.0 mg, 0.081 mmol). The mixture was allowed to stir for 6 hours at 45° C. The reaction was then purified by reverse phase HPLC (Method G) to provide after lyophilization 62 mg (50%) of the desired product as a white solid. LC-MS m/z 1543.3 [M+H$^+$]; retention time=2.25 minutes. Analytical HPLC retention time=7.435 minutes.

Step 6: Synthesis of N-acetyl-O-(2-aminoethyl)-D-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide, trifluoroacetic acid salt (83) To a solution of N-acetyl-O-(2-{[(9H-fluoren-9-ylmethoxy)carbonyl]amino}ethyl)-D-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (82, 42 mg, 0.027 mmol) in 2.5 mL of N,N-dimethylformamide was added an aqueous solution of lithium hydroxide (3.26 mg, 0.136 mmol) and the mixture was stirred at room temperature for an hour. The solution was then concentrated and purified by reverse phase HPLC (Method L). Product containing fractions were lyophilized to provide 29 mg (74%) of the desired product. LC-MS m/z 1321.2 [M+H$^+$]; retention time=1.30 minutes. Analytical HPLC retention time=5.804 minutes.

Example 47
N-acetyl-O-[2-(2-aminoethoxy)ethyl]-L-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide, trifluoroacetic acid salt (90)
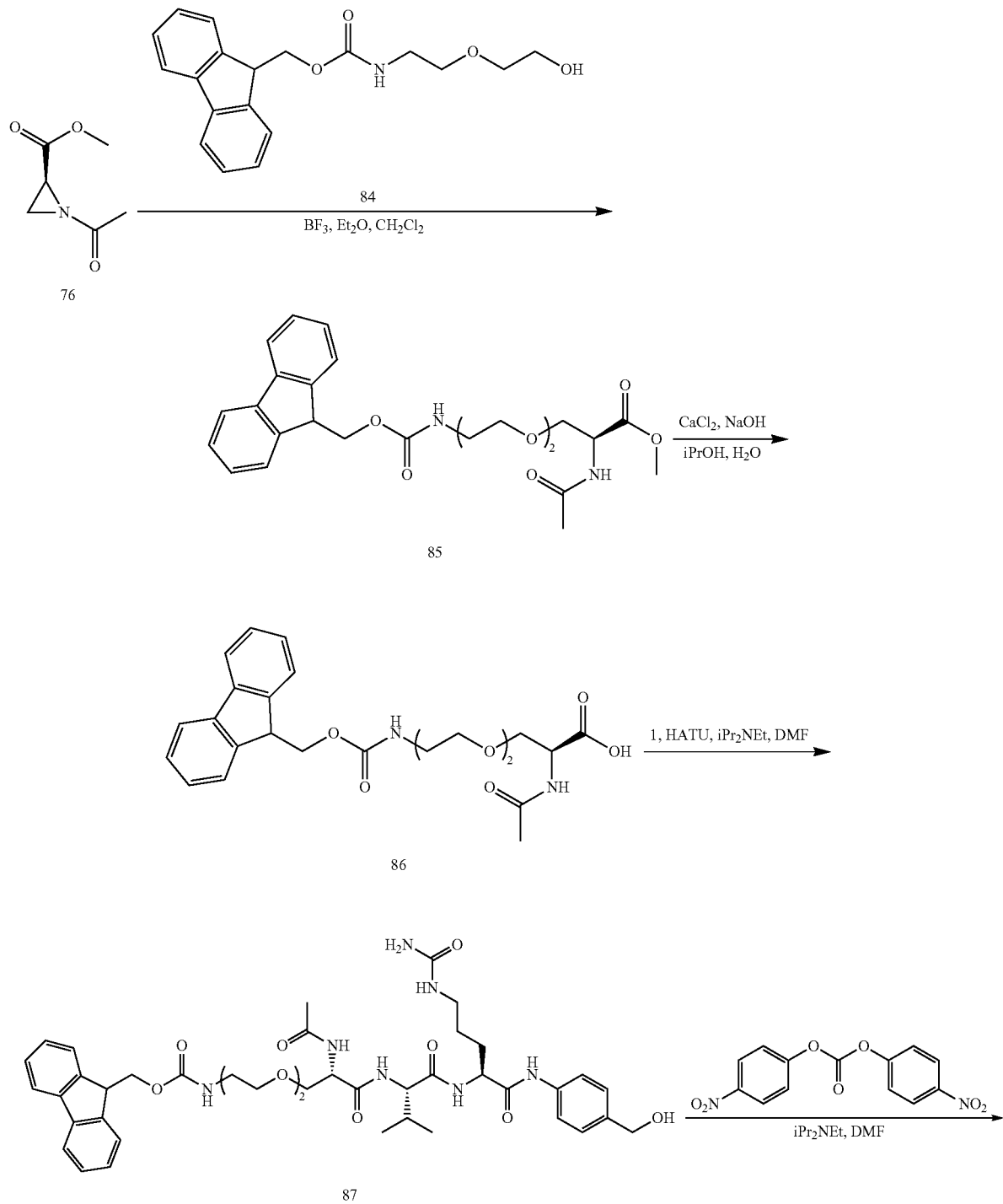

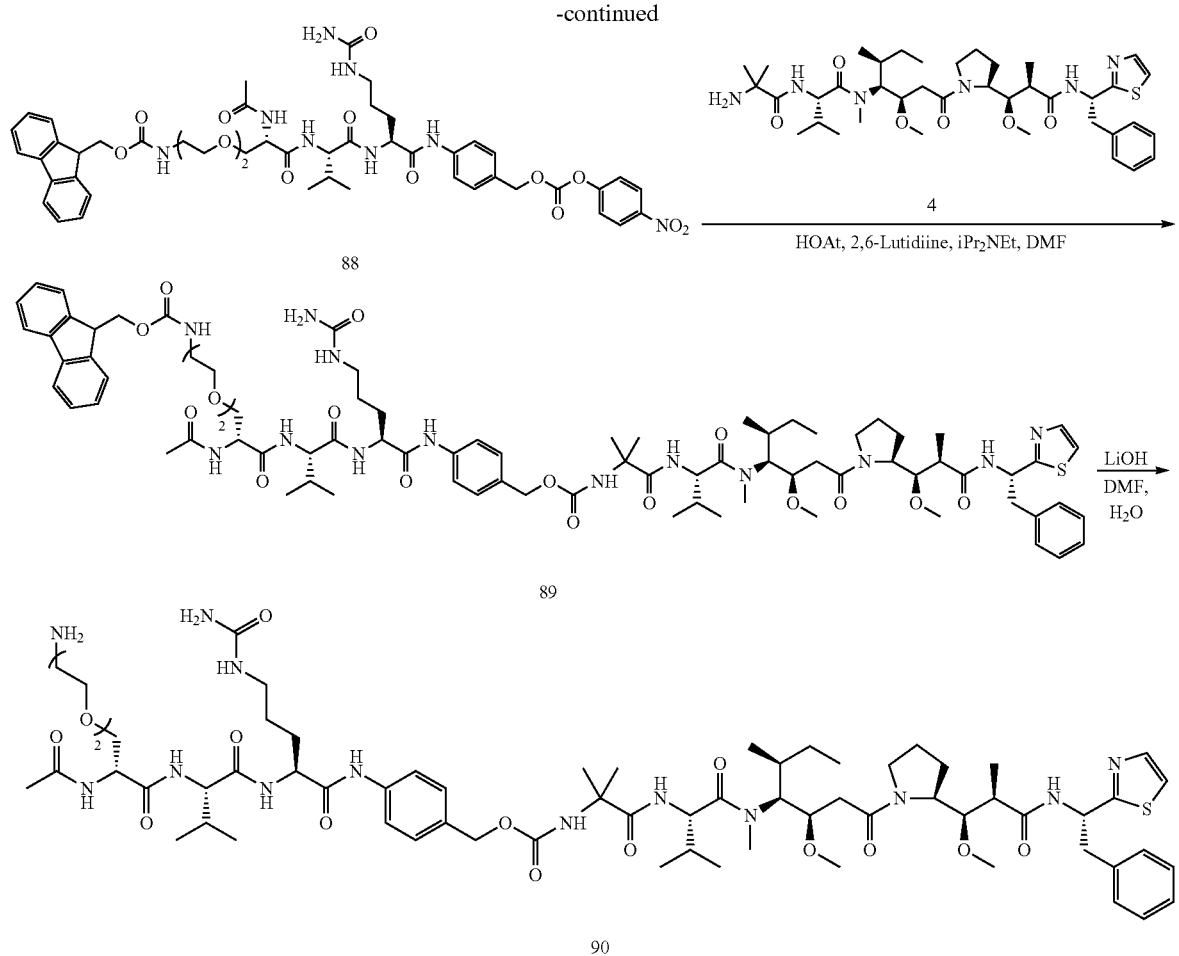

Step 1: Synthesis of methyl N-acetyl-O-[2-(2-{[(9H-fluoren-9-ylmethoxy)carbonyl]amino}ethoxy)ethyl]-L-serinate (85). To a solution of 9H-fluoren-9-ylmethyl [2-(2-hydroxyethoxy)ethyl]carbamate (84, 7.55 g, 23.1 mmol) and methyl (2S)-1-acetylaziridine-2-carboxylate (758 mg, 5.29 mmol) in 130 mL of dichloromethane was added dropwise boron trifluoride diethyl etherate (3.94 mL, 4.46 g, 31.4 mmol). After an hour, to the reaction was added a saturated aqueous solution of sodium bicarbonate. The organic phase was separated and washed with brine, dried over sodium sulfate and concentrated under reduced pressure. The residue was purified by reverse phase HPLC (Method Y). The appropriate fractions were combined and the organic solvents were removed under reduced pressure. The remaining aqueous mixture was extracted with dichloromethane (2×100 mL). The combined extracts were washed with brine, dried over sodium sulfate and concentrated under reduced pressure to give the title compound 3.8 g (26%) as a colorless oil. MS m/z 493.0 [M+Na$^+$]; $^1$H NMR (400 MHz, CHLOROFORM-d) δ=7.77 (d, J=7.5 Hz, 2H), 7.62 (d, J=7.0 Hz, 2H), 7.44-7.37 (m, 2H), 7.35-7.29 (m, 2H), 6.69 (d, J=6.5 Hz, 1H), 5.49 (br. s., 1H), 4.78 (d, J=8.0 Hz, 1H), 4.42 (d, J=6.5 Hz, 2H), 4.25 (d, J=7.0 Hz, 1H), 3.95 (d, J=10.0 Hz, 1H), 3.75 (s, 3H), 3.66-3.50 (m, 6H), 3.41 (br. s., 2H), 2.04 (s, 3H).

Step 2: Synthesis of N-acetyl-O-[2-(2-{[(9H-fluoren-9-ylmethoxy)carbonyl]amino}ethoxy)ethyl]-L-serine (86). To a solution of methyl N-acetyl-O-[2-(2-{[(9H-fluoren-9-ylmethoxy)carbonyl]amino}ethoxy)ethyl]-L-serinate (85, 3200 mg, 6.8 mmol) in 90 mL of isopropanol and 40 mL of water was added calcium chloride (15.1 g, 136 mmol). Once the mixture became clear, sodium hydroxide (326 mg, 8.16 mmol) was added. After 2 hours, the mixture was then acidified to pH ~1-2 with a 3M aqueous solution of hydrochloric acid and diluted with water (300 mL). The mixture was extracted with ethyl acetate (3×250 mL) and the organic was isolated and concentrated under reduced pressure to provide 3000 mg (97%) the desired compound as a white solid, which was used as is in the next step without further purification. MS m/z 456.9 [M+H$^+$]; $^1$H NMR (400 MHz, CHLOROFORM-d) δ=7.77 (d, J=7.5 Hz, 2H), 7.63-7.53 (m, 2H), 7.44-7.38 (m, 2H), 7.36-7.30 (m, 2H), 6.65 (d, J=6.0 Hz, 1H), 4.77 (br. s., 1H), 4.51 (br. s., 1H), 4.43 (d, J=6.5 Hz, 1H), 4.26 (d, J=6.0 Hz, 1H), 3.95 (br. s., 1H), 3.76 (br. s., 1H), 3.70-3.57 (m, 3H), 3.54 (d, J=7.5 Hz, 2H), 3.41 (d, J=13.1 Hz, 2H), 3.29 (br. s., 1H), 2.05 (br. s., 3H).

Step 3: Synthesis of N-acetyl-O-[2-(2-{[(9H-fluoren-9-ylmethoxy)carbonyl]amino}ethoxy)ethyl]-L-serylvalyl-N~5~-carbamoyl-N-[4-(hydroxymethyl)phenyl]-L-ornithinamide (87). To a solution of N-acetyl-O-[2-(2-{[(9H-fluoren-9-ylmethoxy)carbonyl]amino}ethoxy)ethyl]-L-serine (86, 3000 mg, 6.57 mmol) in 45 mL of N,N-dimethylformamide was added O-(7-azabenzotriazol-1-yl)-N,N,N',N'-tetramethyluronium hexafluorophosphate (HATU, 3000 mg, 7.89 mmol). After 20 minutes, L-valyl-N~5~-carbamoyl-N-[4-(hydroxymethyl)phenyl]-L-ornithinamide (1, 2490 mg, 6.57 mmol) was added followed by N,N-diisopropylethylamine (2550 mg, 19.7 mmol). After 3 hours, the mixture was poured into a mixture of tert-butyl methyl ether (500 mL) and petroleum ether (200 mL) and stirred for 20 minutes. The solid was isolated by filtration and then purified by silica gel chromatography using a gradient elution of 1% to 20% methanol in dichloromethane to provide 3100 mg (58%) of the desired product as a white solid. MS m/z 818.1[M+H$^+$].

Step 4: Synthesis of N-acetyl-O-[2-(2-{[(9H-fluoren-9-ylmethoxy)carbonyl]amino}ethoxy)ethyl]-L-serylvalyl-N~5~-carbamoyl-N-[4-({[(4-nitrophenoxy)carbonyl]oxy}methyl)phenyl]-L-ornithinamide (88). To an ice cold stirred solution of N-acetyl-O-[2-(2-{[(9H-fluoren-9-ylmethoxy)carbonyl]amino}ethoxy)ethyl]-L-serylvalyl-N~5~-carbamoyl-N-[4-(hydroxymethyl)phenyl]-L-ornithinamide (87, 500 mg, 0.611 mmol) and p-nitrophenyl carbonate (279 mg, 0.917 mmol) in 6 mL of N,N-dimethylformamide was added N,N-diisopropylethylamine (216.7 ul, 158 mg, 1.22 mmol). The mixture was stirred at room temperature for 5 hours then more and p-nitrophenyl carbonate (100 mg, 0.538 mmol) was added. After an extra 12 hours, the mixture was was poured into a mixture of tert-butyl methyl ether (60 mL) and petroleum ether (20 mL) and stirred for 15 minutes. The solid was isolated by filtration then purified by silica gel chromatography using a gradient elution of 1% to 10% methanol in dichloromethane to provide 300 mg (50%) of the desired product as a white solid. MS m/z 983.5 [M+H$^+$].

Step 5: Synthesis of N-acetyl-O-[2-(2-{[(9H-fluoren-9-ylmethoxy)carbonyl]amino}ethoxy)ethyl]-L-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (89). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5-methyl-1-oxoheptan-4-yl]-N-methyl-L-valinamide (4, 60.0 mg, 0.081 mmol) and N-acetyl-O-[2-(2-{[(9H-fluoren-9-ylmethoxy)carbonyl]amino}ethoxy)ethyl]-L-serylvalyl-N~5~-carbamoyl-N-[4-({[(4-nitrophenoxy)carbonyl]oxy}methyl)phenyl]-L-ornithinamide (88, 75.4 mg, 0.077 mmol) in 2.5 mL of N,N-dimethylacetamide were added 2,6-lutidine (37.4 uL, 34.6 mg, 0.323 mmol) N,N-diisopropylethylamine (42.2 uL, 31.3 mg, 0.242 mmol) and 3H-[1,2,3]triazolo[4,5-b]pyridin-3-ol (HOAt, 11.0 mg, 0.081 mmol). The mixture was allowed to stir for 16 hours at 45° C. The reaction was then purified by reverse phase HPLC (Method G) to provide after lyophilization 76 mg (58%) of the desired product as a white solid. LC-MS m/z 1587.3 [M+H$^+$]; retention time=2.26 minutes. Analytical HPLC retention time=7.459 minutes.

Step 6: Synthesis of N-acetyl-O-[2-(2-aminoethoxy)ethyl]-L-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide, trifluoroacetic acid salt (90) To a solution of N-acetyl-O-[2-(2-{[(9H-fluoren-9-ylmethoxy)carbonyl]amino}ethoxy)ethyl]-L-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (89, 40 mg, 0.025 mmol) in 2.5 mL of N,N-dimethylformamide was added an aqueous solution of lithium hydroxide (3.02 mg, 0.126 mmol) and the mixture was stirred at room temperature for 30 minutes. The solution was then purified by reverse phase HPLC (Method D). Product containing fractions were lyophilized to provide 27 mg (72%) of the desired product. LC-MS m/z 1365.2 [M+H$^+$]; retention time=1.26 minutes. Analytical HPLC retention time=5.768 minutes.

Example 48

Preparation of N~2~-(3-hydroxypropanoyl)-L-lysyl-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoyl-L-ornithinamide, trifluoroacetic acid salt (97)

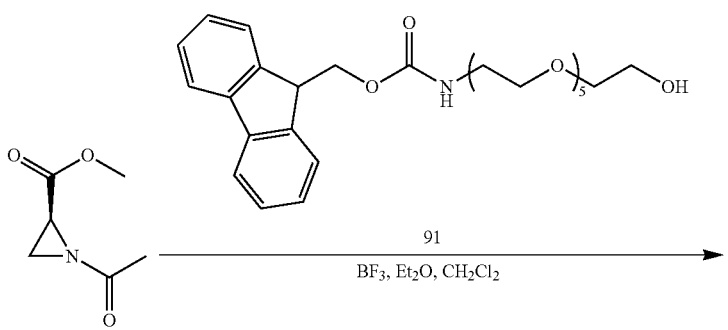

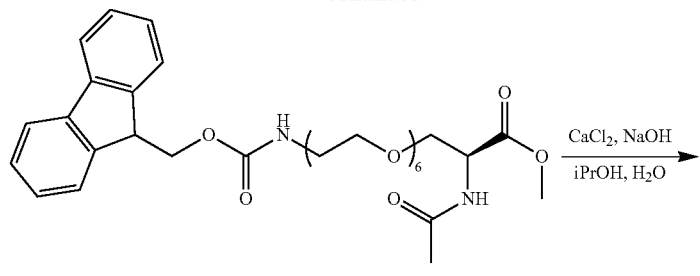
92
CaCl₂, NaOH
iPrOH, H₂O
→
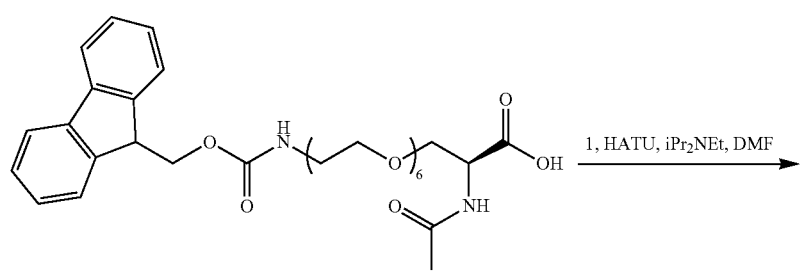
93
1, HATU, iPr₂NEt, DMF
→
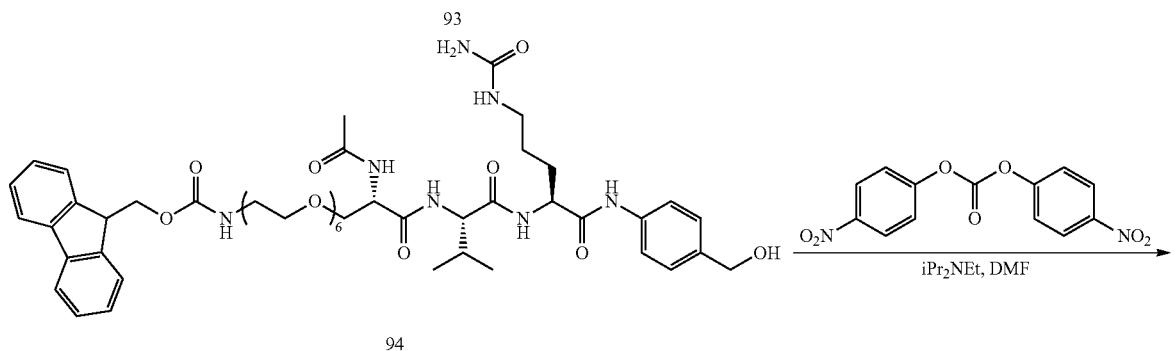
94
iPr₂NEt, DMF
→
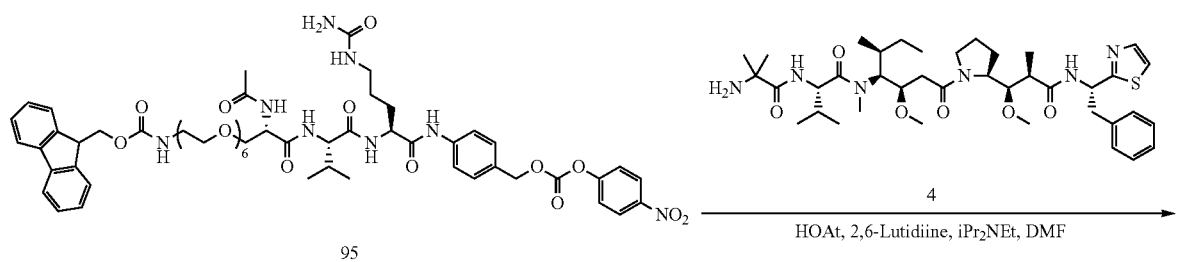
95
4
HOAt, 2,6-Lutidiine, iPr₂NEt, DMF
→
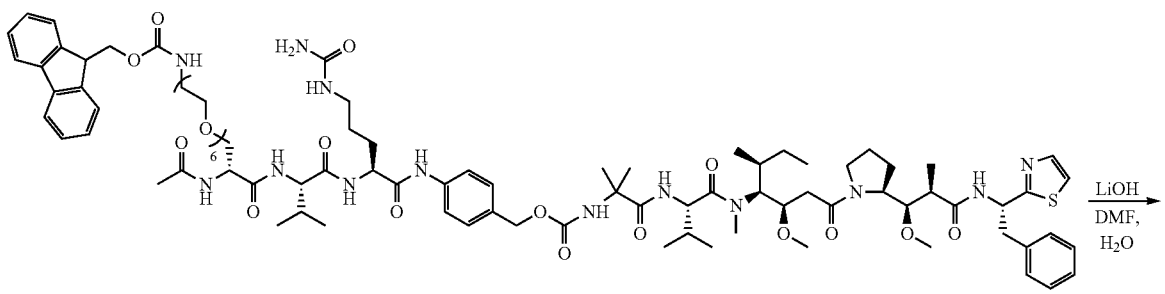
96
LiOH
DMF,
H₂O
→

-continued

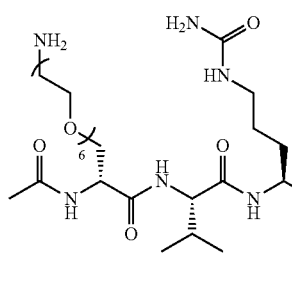

97

Step 1: Synthesis of methyl N-acetyl-O-[1-(9H-fluoren-9-yl)-3-oxo-2,7,10,13,16,19-hexaoxa-4-azahenicosan-21-yl]-L-serinate (92). To a solution of 9H-fluoren-9-ylmethyl (17-hydroxy-3,6,9,12,15-pentaoxaheptadec-1-yl)carbamate (91, 7600 mg, 15.09 mmol) and methyl (2S)-1-acetylaziridine-2-carboxylate (4320 mg, 30.2 mmol) in 150 mL of dichloromethane was added dropwise boron trifluoride diethyl etherate (2.84 mL, 3210 mg, 22.6 mmol). After 2.5 hours, the reaction was washed with a saturated aqueous solution of sodium bicarbonate then brine, dried over sodium sulfate and concentrated under reduced pressure. The residue was purified by reverse phase HPLC (Method Z). The appropriate fractions were combined and the organic solvents were removed under reduced pressure. The remaining aqueous mixture was extracted with ethyl acetate (2×100 mL). The combined extracts were dried over sodium sulfate and concentrated to give the title compound 5 g (51%) as an oil. MS m/z 647.1 [M+H$^+$]; $^1$H NMR (400 MHz, CHLOROFORM-d) δ=7.76 (d, J=7.5 Hz, 2H), 7.61 (d, J=7.5 Hz, 2H), 7.40 (t, J=7.5 Hz, 2H), 7.31 (t, J=7.4 Hz, 2H), 6.72 (d, J=7.5 Hz, 1H), 5.47 (br. s., 1H), 4.73 (td, J=3.5, 8.0 Hz, 1H), 4.41 (d, J=7.0 Hz, 2H), 4.26-4.19 (m, 1H), 3.94 (dd, J=3.5, 10.0 Hz, 1H), 3.75 (s, 3H), 3.70 (dd, J=3.5, 10.0 Hz, 1H), 3.67-3.56 (m, 22H), 3.40 (q, J=5.2 Hz, 2H), 2.07 (s, 3H).

Step 2: Synthesis of N-acetyl-O-[1-(9H-fluoren-9-yl)-3-oxo-2,7,10,13,16,19-hexaoxa-4-azahenicosan-21-yl]-L-serine (93). To a solution of methyl N-acetyl-O-[1-(9H-fluoren-9-yl)-3-oxo-2,7,10,13,16,19-hexaoxa-4-azahenicosan-21-yl]-L-serinate (92, 4200 mg, 6.49 mmol) in isopropanol:water (7:3, 170 mL) was added calcium chloride (14.4 g, 130 mmol). Once the mixture became clear, sodium hydroxide (312 mg, 7.79 mmol) was added. The resulting mixture was stirred at room temperature for 3 hours. The mixture was then acidified to pH ~1-2 with a 3M aqueous solution of hydrochloric acid and diluted with water (100 mL). The mixture was extracted with ethyl acetate (100 mL) and the organic was isolated and concentrated under reduced pressure to remove most of the isopropanol. The aqueous phase was extracted with ethyl acetate (2×100 mL). The combined organic layers were washed with brine, dried over sodium sulfate and concentrated under reduced pressure. The residue was then purified by silica gel chromatography using a gradient elution of 0% to 15% methanol in dichloromethane to provide 3.4 g (83%) the desired compound as a yellow oil. MS m/z 633.1 [M+H$^+$].

Step 3: Synthesis of N-acetyl-O-[1-(9H-fluoren-9-yl)-3-oxo-2,7,10,13,16,19-hexaoxa-4-azahenicosan-21-yl]-L-serylvalyl-N~5~-carbamoyl-N-[4-(hydroxymethyl)phenyl]-L-ornithinamide (94). To an ice cold solution of N-acetyl-O-[1-(9H-fluoren-9-yl)-3-oxo-2,7,10,13,16,19-hexaoxa-4-azahenicosan-21-yl]-L-serine (93, 1.20 g, 1.90 mmol) and L-valyl-N~5~-carbamoyl-N-[4-(hydroxymethyl)phenyl]-L-ornithinamide (1, 720 mg, 1.90 mmol) in 15 mL of N,N-dimethylformamide was added O-(7 azabenzotriazol 1 yl) N,N,N',N' tetramethyluronium hexafluorophosphate (794 mg, 2.09 mmol) followed by N,N diisopropylethylamine (736 mg, 5.69 mmol). The yellow clear mixture was stirred at room temperature for 2 hours. The mixture was diluted with ethyl acetate (3×30 mL), washed with water (60 mL) and dried over sodium sulfate and concentrated under reduced pressure. The residue was then purified by silica gel chromatography using a gradient elution of 0% to 15% methanol in dichloromethane to provide 1.5 g (80%) of the desired product as a colorless glass. MS m/z 994.8 [M+H$^+$].

Step 4: Synthesis of N-acetyl-O-[2-(2-aminoethoxy)ethyl]-L-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (95). In an iced bath, to a stirred solution N-acetyl-O-[1-(9H-fluoren-9-yl)-3-oxo-2,7,10,13,16,19-hexaoxa-4-azahenicosan-21-yl]-L-serylvalyl-N~5~-carbamoyl-N-[4-(hydroxymethyl)phenyl]-L-ornithinamide (94, 1.5 g, 1.5 mmol) and p-nitrophenyl carbonate (918 mg, 3.02 mmol) in 15 mL of N,N-dimethylformamide was added N,N-diisopropylethylamine (402 ul, 293 mg, 2.26 mmol). The mixture was stirred at room temperature for 16 hours then more p-nitrophenyl carbonate (918 mg, 3.02 mmol) was added. After an extra 3 hours, the mixture was diluted with ethyl acetate (30 mL), washed with water (40 mL). The aqueous phase was extracted with ethyl acetate (30 mL). The combined organic layers were concentrated under reduced pressure then purified by silica gel chromatography using a gradient elution of 0% to 15% methanol in dichloromethane then by purified by reverse phase HPLC (Method AA) to provide after lyophilization 944 mg (54%) of the desired product as a white solid. MS m/z 1159.8[M+H$^+$].

Step 5: Synthesis of N-acetyl-O-[1-(9H-fluoren-9-yl)-3-oxo-2,7,10,13,16,19-hexaoxa-4-azahenicosan-21-yl]-L-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (96). To a solution of 2-methylalanyl-N-[(3R,4S,5S)-3-methoxy-1-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-5- methyl-1-oxoheptan-4-yl]-N-methyl-L-valinamide (4, 55.0 mg, 0.074 mmol) and N-acetyl-O-[2-(2-aminoethoxy)ethyl]-L-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino} propyl] pyrrolidin-1-yl}-2-oxoethyl)-5,5,10-trimethyl-3,6,9-trioxo-8-(propan-2-yl)-2,13-dioxa-4,7,10-triazatetradec-1-yl] phenyl}-N~5~-carbamoylornithinamide (95, 85.8 mg, 0.074 mmol) in 2.5 mL of N,N-dimethylacetamide were added 2,6-lutidine (34.3 uL, 31.7 mg, 0.296 mmol) N,N-diisopropylethylamine (38.7 uL, 28.7 mg, 0.222 mmol) and 3H-[1,2,3]triazolo[4,5-b]pyridin-3-ol (10.1 mg, 0.074 mmol). The mixture was allowed to stir for 6 hours at 45° C. The reaction was then purified by reverse phase HPLC (Method G) to provide after lyophilization 90 mg (69%) of the desired product as a white solid. LC-MS m/z 1764.4 [M+H$^+$]; retention time=1.99 minutes. Analytical HPLC retention time=7.476 minutes.

Step 6: Synthesis of N-acetyl-O-(17-amino-3,6,9,12,15-pentaoxaheptadec-1-yl)-L-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide, trifluoroacetic acid salt (97) To a solution of N-acetyl-O-[1-(9H-fluoren-9-yl)-3-oxo-2,7,10,13,16,19-hexaoxa-4-azahenicosan-21-yl]-L-seryl-L-valyl-N-{4-[(8S,11S,12R)-11-[(2S)-butan-2-yl]-12-(2-{(2S)-2-[(1R,2R)-1-methoxy-2-methyl-3-oxo-3-{[(1S)-2-phenyl-1-(1,3-thiazol-2-yl)ethyl]amino}propyl]pyrrolidin-1-yl}-2-oxoethyl)-5,5,10-trimethyl-3,6,9-trioxo-8-(propan-2-yl)-2,13-dioxa-4,7,10-triazatetradec-1-yl]phenyl}-N~5~-carbamoylornithinamide (96, 46 mg, 0.026 mmol) in 2.5 mL of N,N-dimethylformamide was added an aqueous solution of lithium hydroxide (3.1 mg, 0.130 mmol) and the mixture was stirred at room temperature for 20 minutes. The solution was then concentrated and purified by reverse phase HPLC (Method D then Method H). Product containing fractions were lyophilized to provide 15 mg (35%) of the desired product. LC-MS m/z 1542.2 [M+H$^+$]; retention time=1.41 minutes. Analytical HPLC retention time=5.836 minutes.

The following additional ADCs (attached at various positions and on various tags on the Trop2 antibody, as indicated on Tables 2 through 7) were made using the above described conjugation technique (bracketed portion indicates a glutamine residue, with wavy lines showing attachments points to the remainder of the Anti-Trop2 antibody):

Example 49

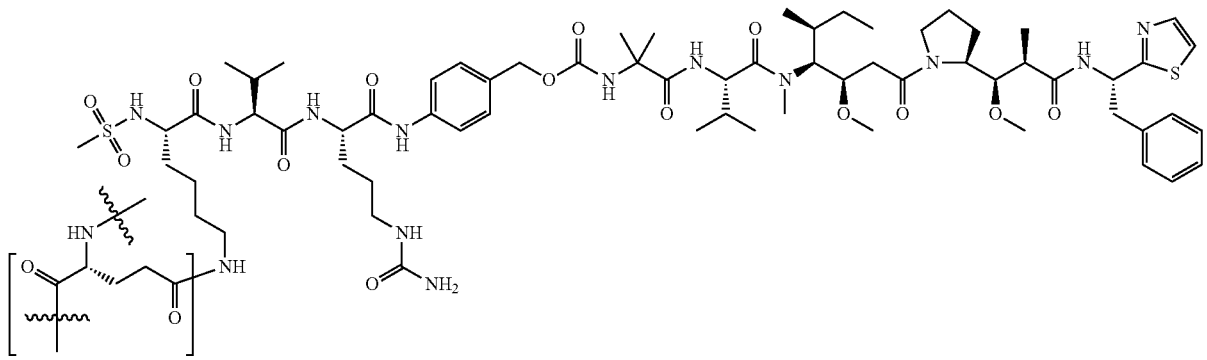

Example 50

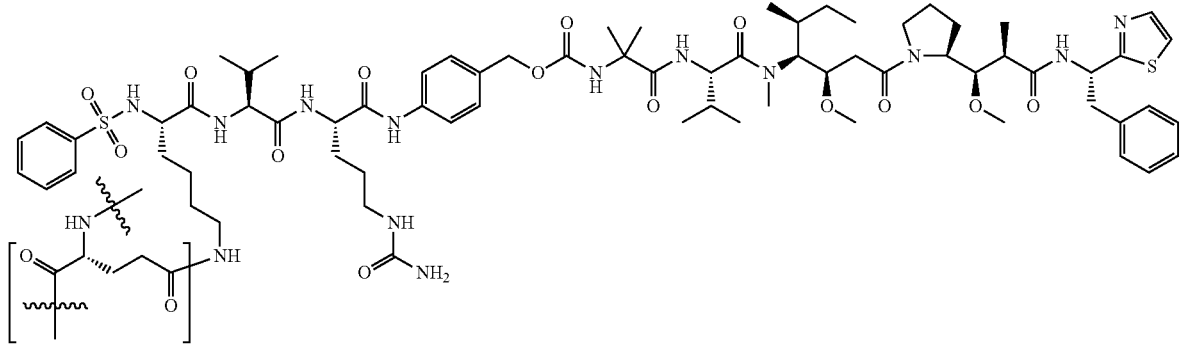

Example 51
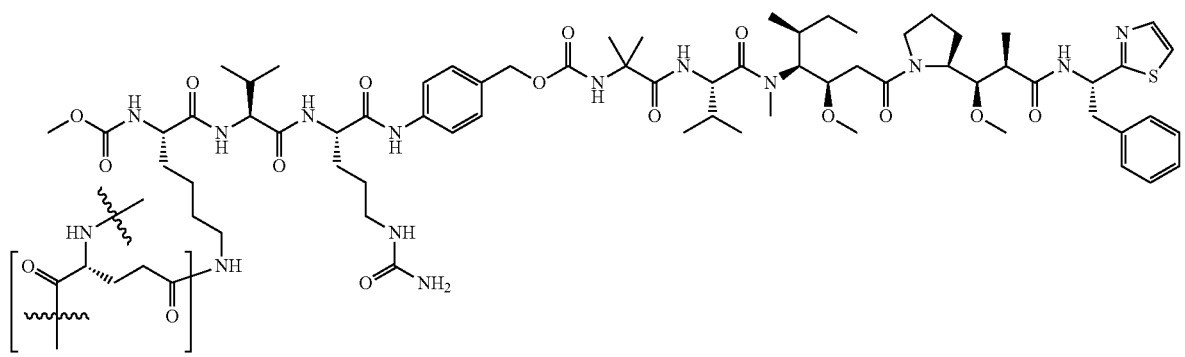
Example 52
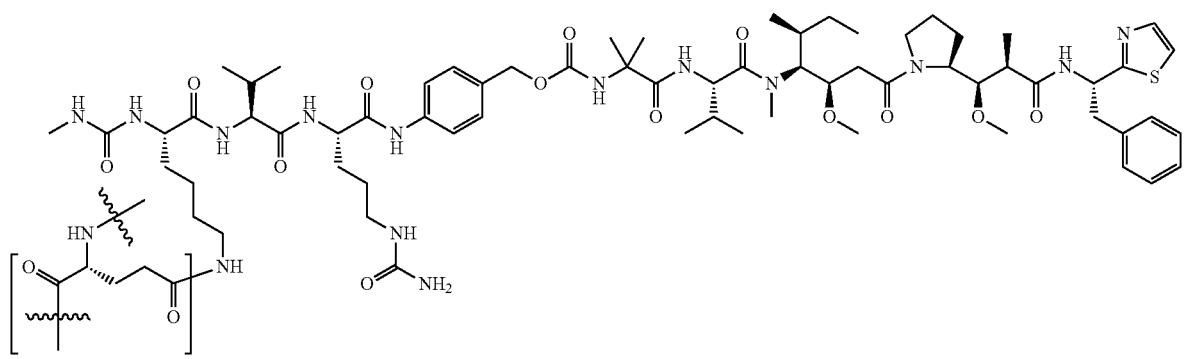
Example 53
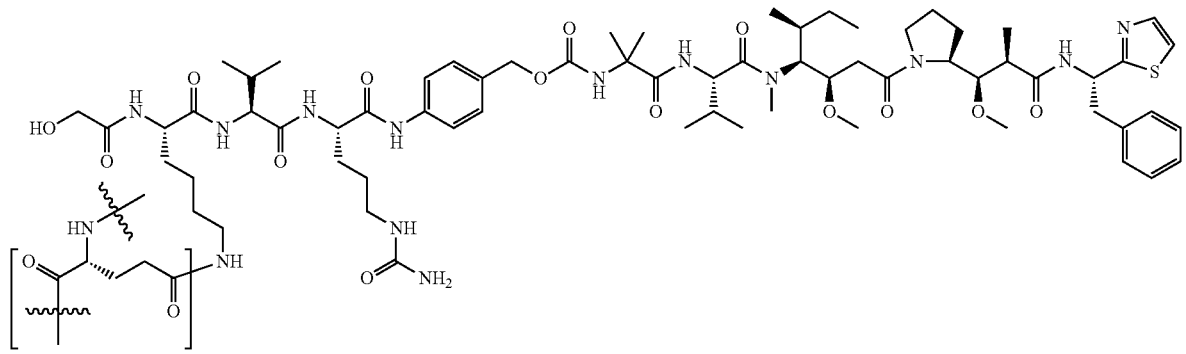

Example 54
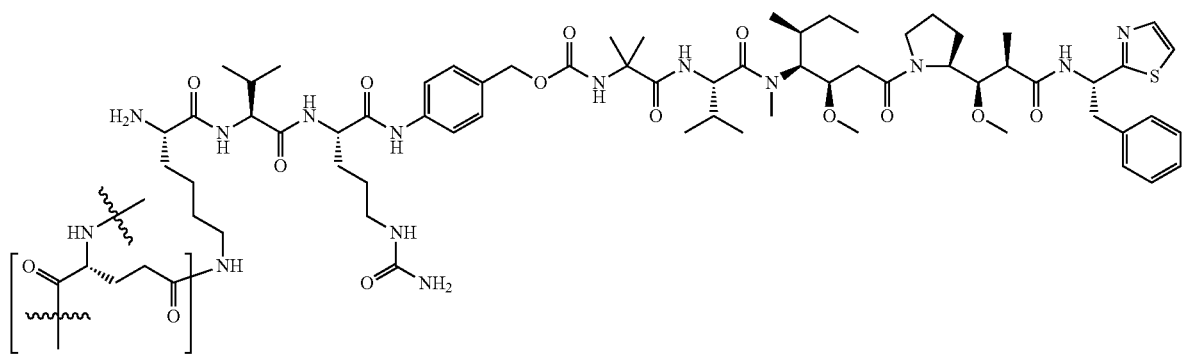
Example 55
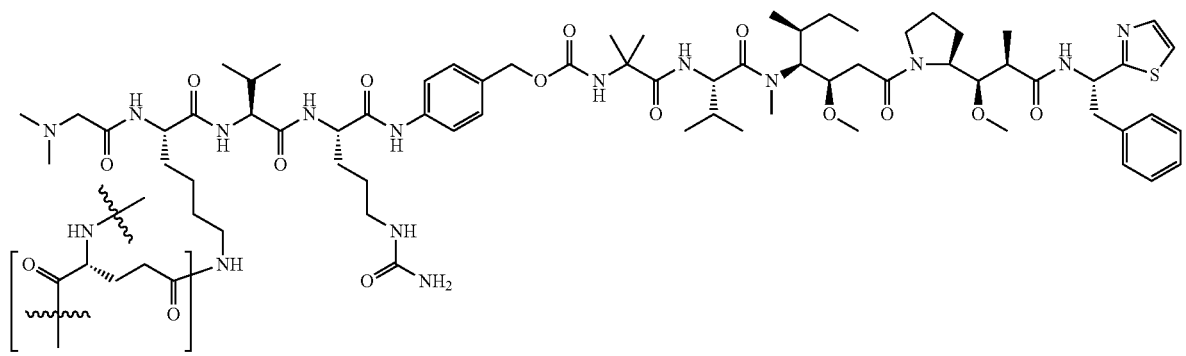
Example 56
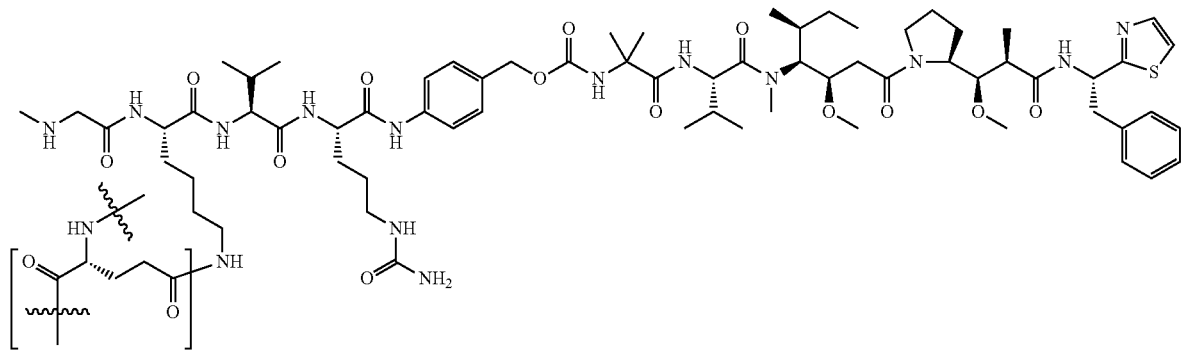

Example 57
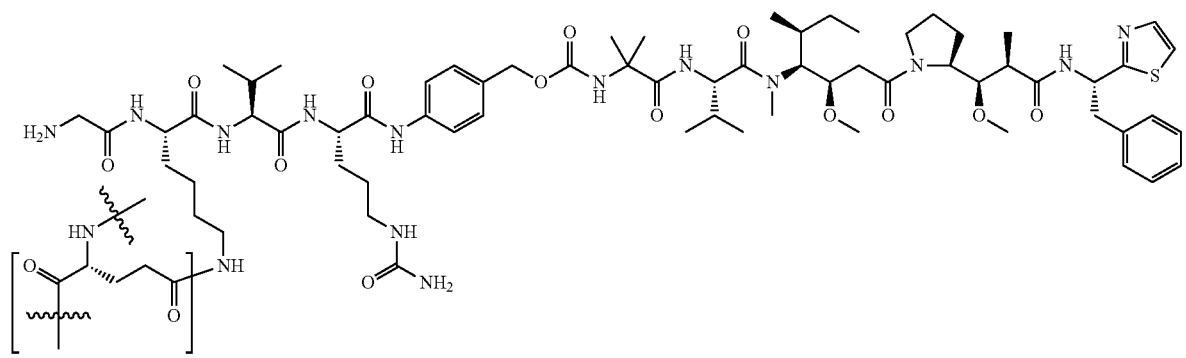
Example 58
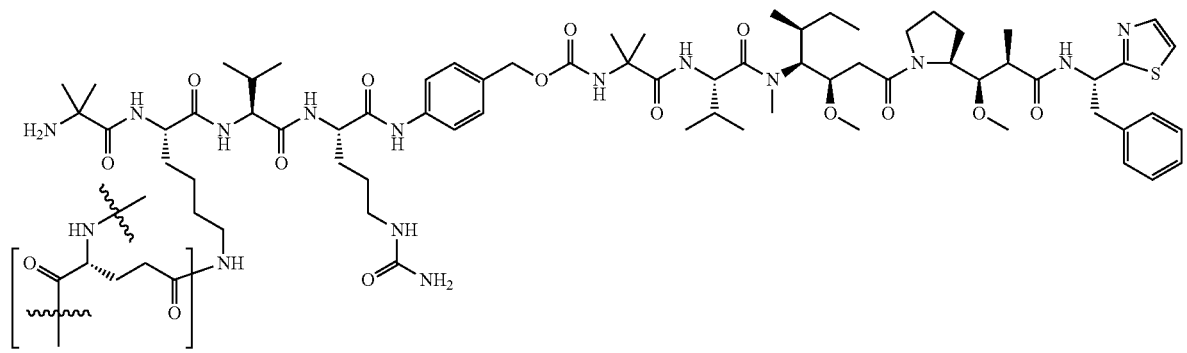
Example 59
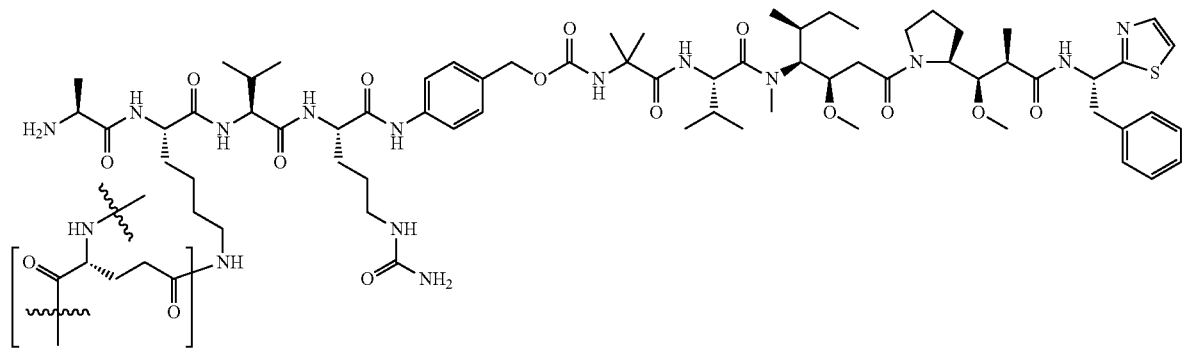

Example 60
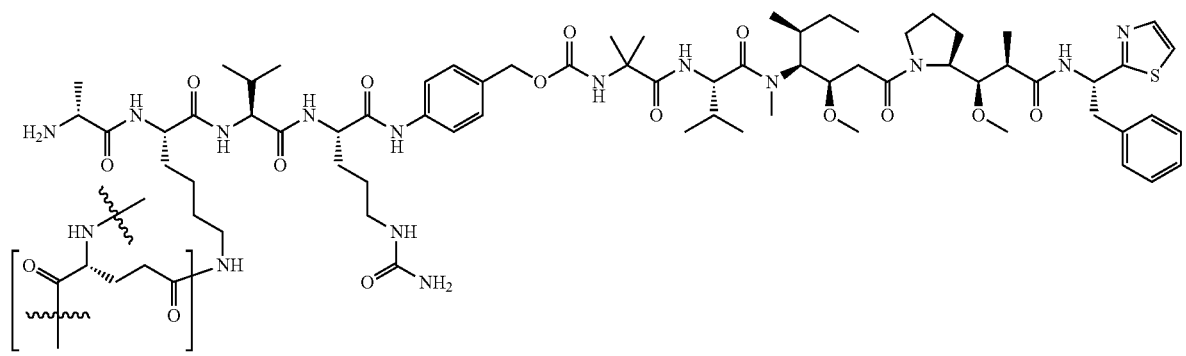
Example 61
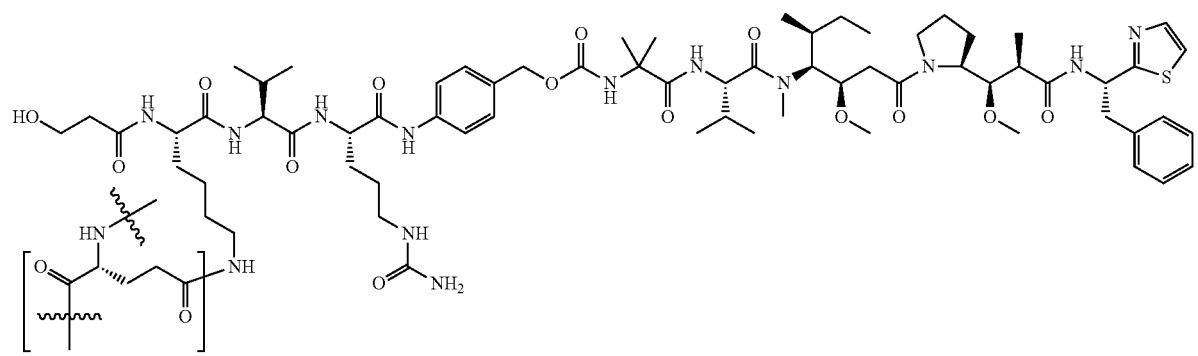
Example 62
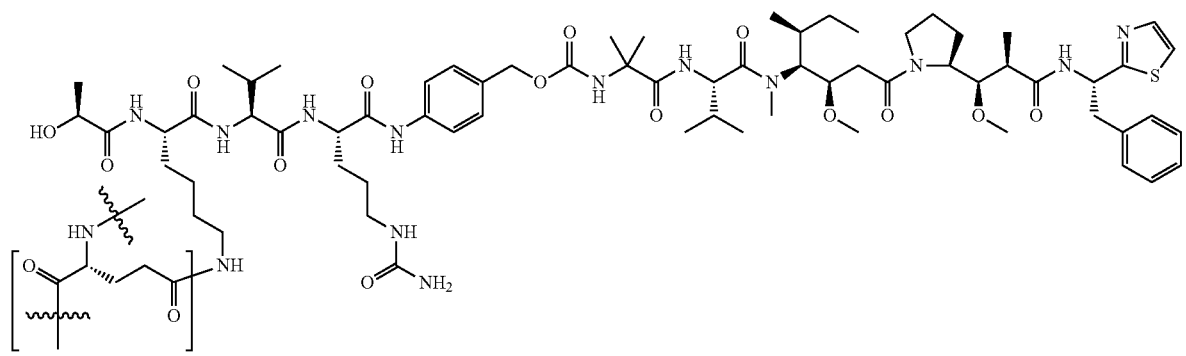

Example 63
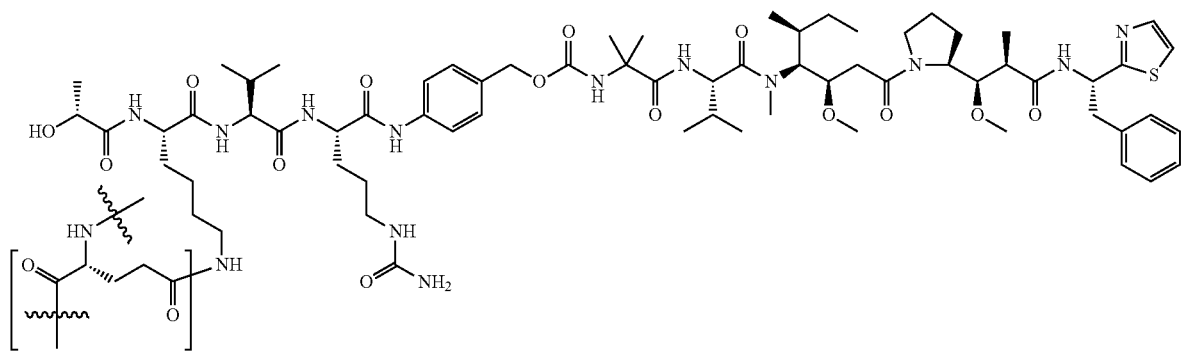
Example 64
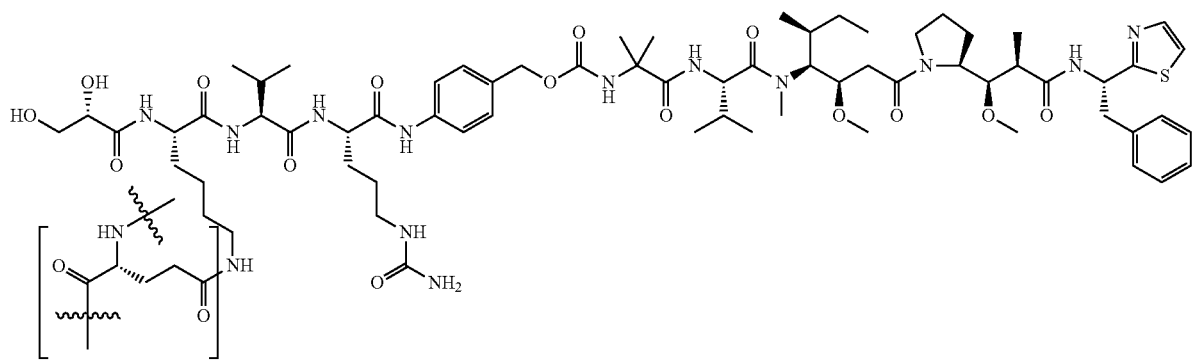
Example 65
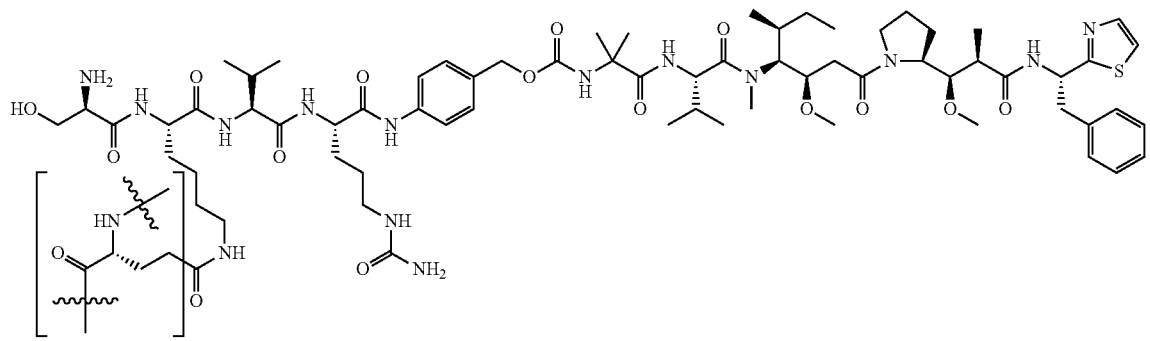

Example 66
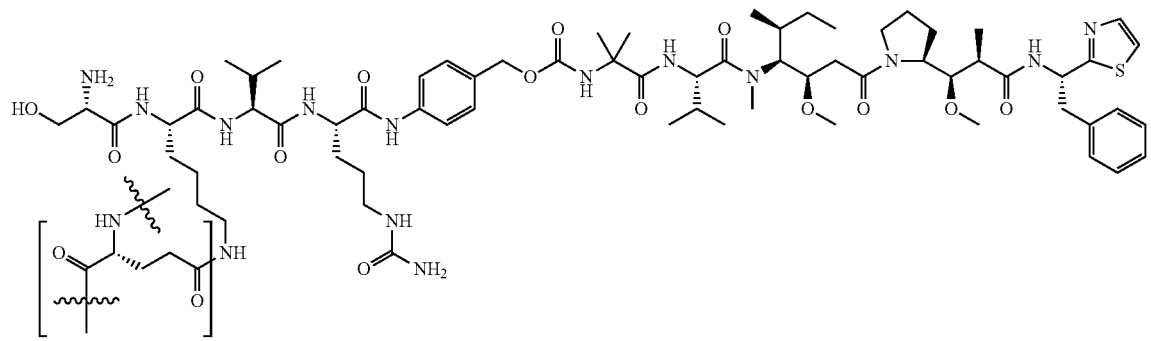
Example 67
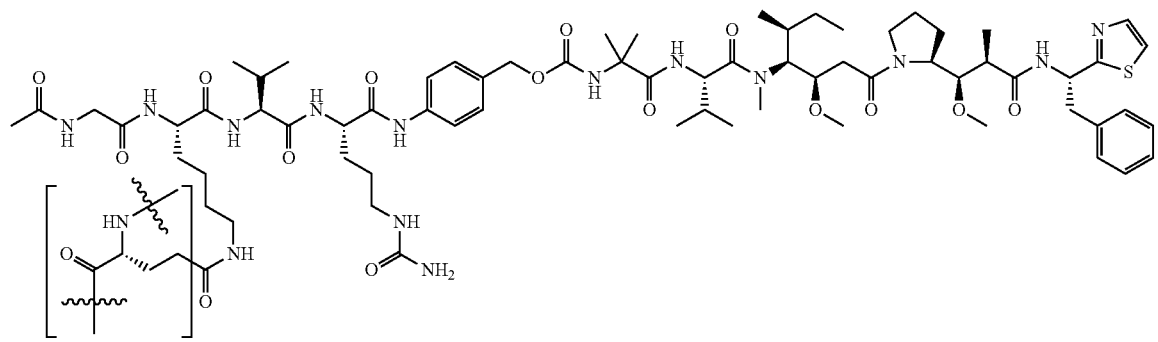
Example 68
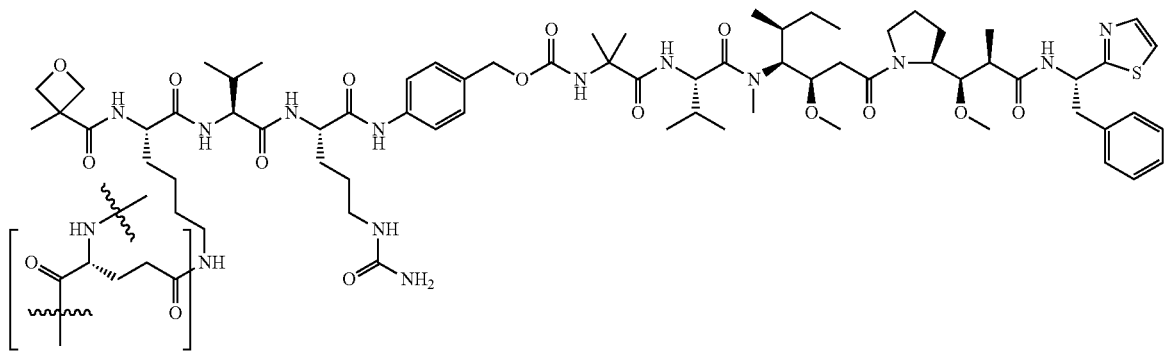

Example 69
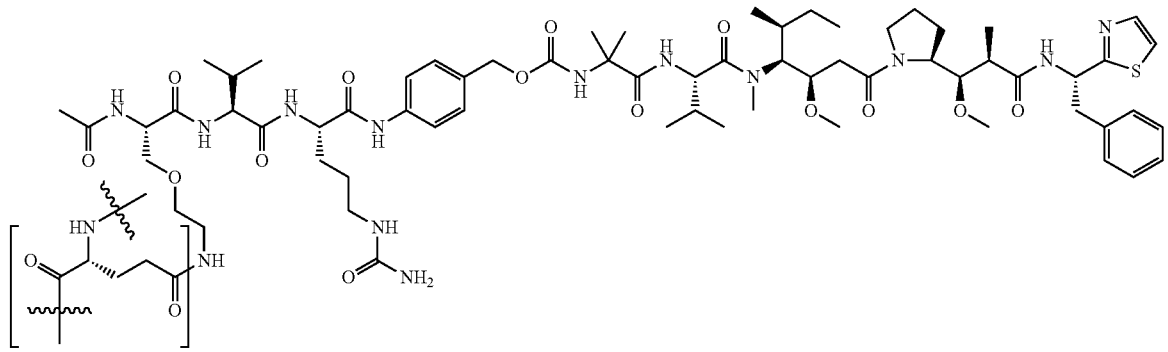
Example 70
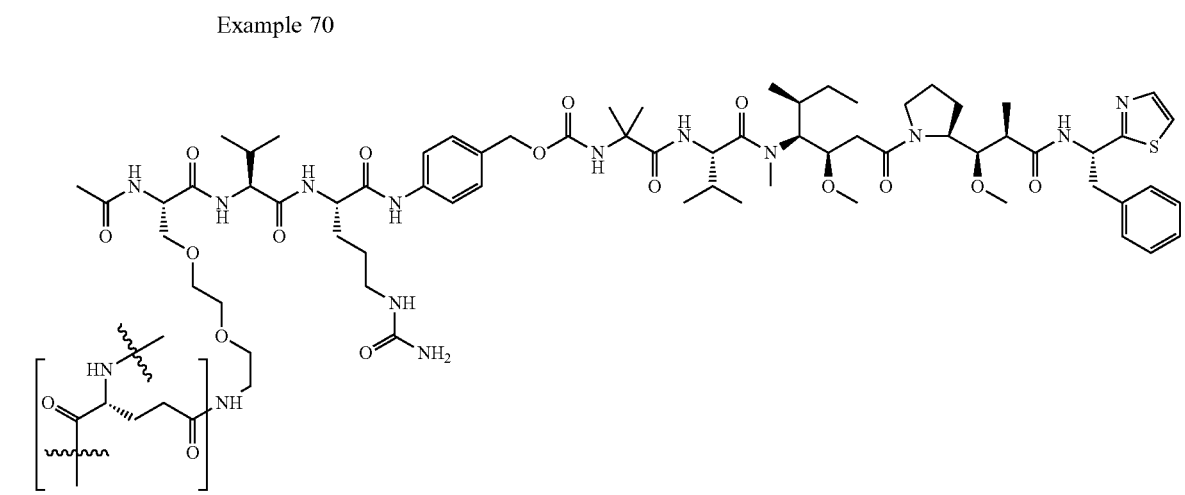
Example 71
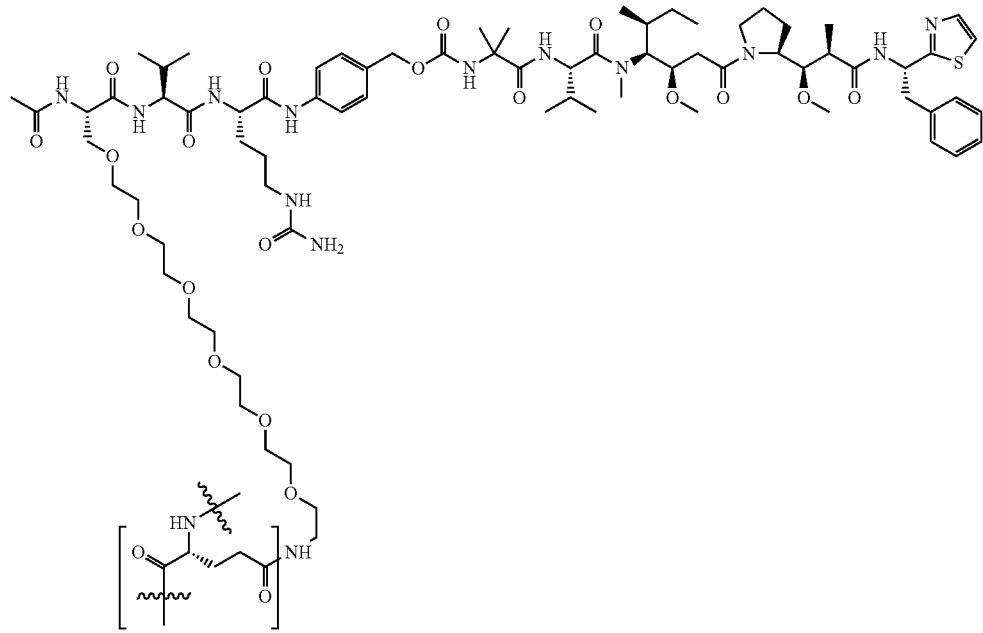

Example 72

Figure 3:
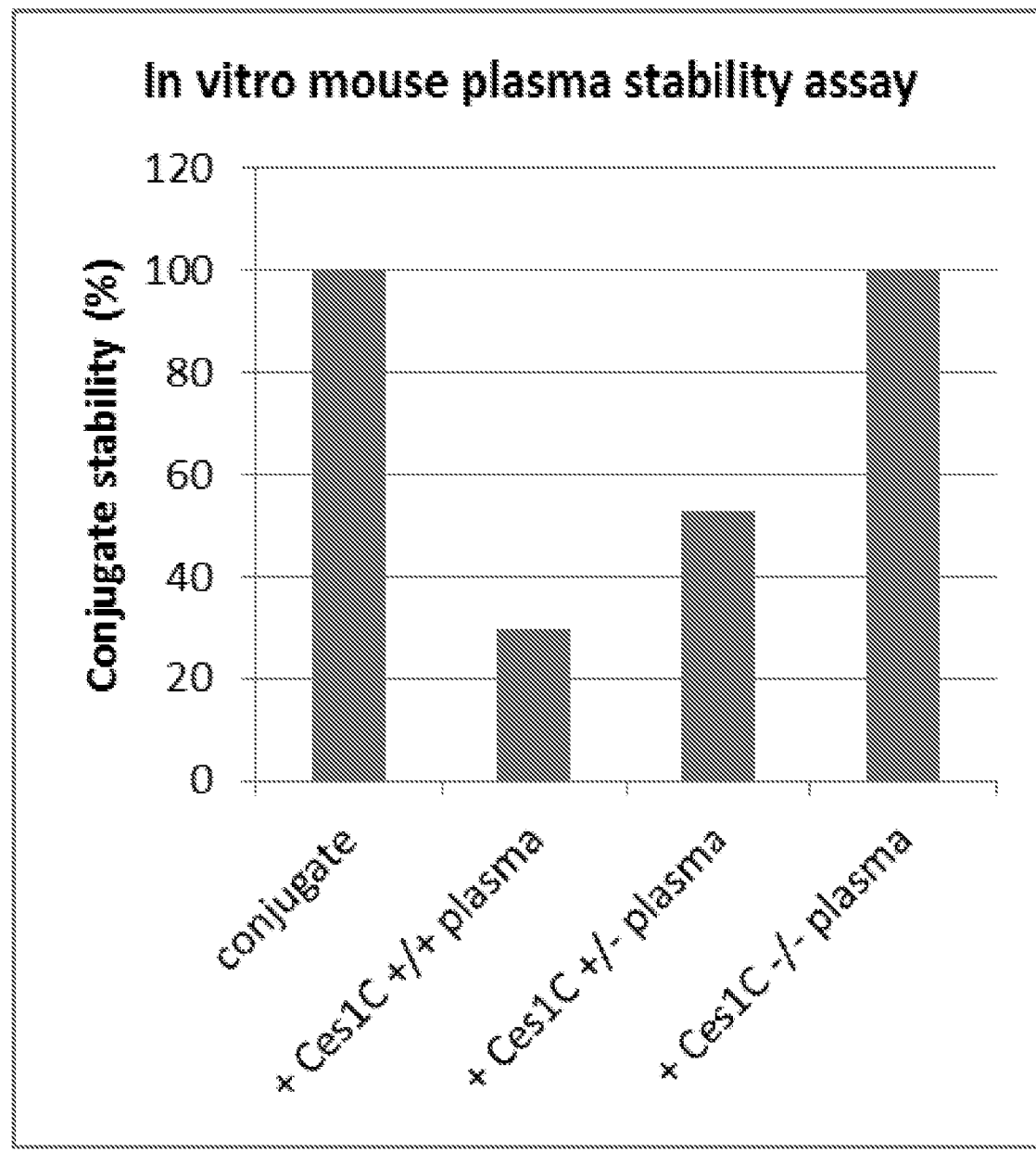
FIG. 3. provides confirmation of mouse carboxylesterase 1c as the enzyme responsible for vc-pabc linker cleavage in the plasma by comparison of mouse knockout strain c56/bl6 ces1c-/-, heterozygous strain c56/bl6 ces1c+/-, and wild type strain c56/bl6 ces1c+/+.

Confirmation of Mouse Carboxylesterase 1C as the Enzyme Responsible for VC-PABC Linker Cleavage in the Plasma Plasma samples from mouse knockout strain C56/BL6 Ces1C−/−, heterozygous strain C56/BL6 Ces1C+/−, and wild type strain C56/BL6 Ces1C+/+ were used to test stability of the anti-Trop2 L11B-C6-VC-PABC-Aur0101 conjugate. 56 ug of ADC were incubated in the plasma in 35% plasma supplemented with 1×PBS to the final ADC concentration of 0.125 mg/mL. Following incubation for 18 hours, ADCs were isolated using M1S1 antigen coupled to CNBr-activated Sepharose (GE Healthcare) using standard protocols. DAR values were assessed before and after incubation using HIC analysis. Conjugate stability (%) is calculated as % DAR remaining after incubation. See FIG. 3.

BIOLOGICAL DATA

The stability data generated in the procedures outlined in Examples 8 through 18 are summarized in Tables 2 through 7.

TABLE 2

Conjugate Stability In Vivo in Mouse

| | | | | Glutamine-Containing Tag on Trop2 Antibody | | | | | | | | |
|---|---|---|---|---|---|---|---|---|---|---|---|---|
| | Ex. # | TG6 | H7C | H8A | H10 | H12C | H13A | H16 | L11B/C | LCQ04 | N297A | N297Q |
| ADC Structure | 8 | | | | 0 (3 d) | | | | | | 1 (3 d) | |
| | 9 | 83 (4 d) | | | | | | | | 89** (4 d) | | |
| | 10 | | | | | | | | | 72, 24 (3 & 10 d) | | |
| | 11 | | | | | | | | | 95, 80 (3 & 10 d) | | |
| | 12 | | | | | | | | | 3 (3 d) | | |
| | 13 | | | | | | | | | 3 (3 d) | | |
| | 14 | | | | | | | | | 0 (3 d) | | |
| | 15 | | | | | | | | | 82, 45 (3 & 10 d) | | |
| | 16 | | | | | | | | | 38 (3 d) | | |
| | 17 | | | | | | | | | 89, 72 (3 & 10 d) | | |
| | 18 | | | | | | | | | 99, 82 (3 & 10 d) | | |

Conjugate stability in vivo in the mouse. DAR values for conjugates purified from animals dosed at 9 mg/kg were compared to DAR values prior to in vivo exposure. Stability values above are expressed as % DAR remaining after given exposure period (shown in brackets).

TABLE 3

Conjugate Stability In Vivo in Rat

| | | | | Glutamine-Containing Tag on Trop2 Antibody | | | | | | | | |
|---|---|---|---|---|---|---|---|---|---|---|---|---|
| | Ex. # | TG6 | H7C | H8A | H10 | H12C | H13A | H16 | L11B/C | LCQ04 | N297A | N297Q |
| ADC Structure | 8 | | | | | | | | | | | |
| | 9 | | | | | | | | | | | |
| | 10 | | | | | | | | | | | |
| | 11 | | | 94 (14 d) | 98 (14 d) | | | | 88 (14 d) | 94 (14 d) | | ~100 (14 d) |
| | 12 | | | | | | | | | | | |
| | 13 | | | | | | | | | | | |
| | 14 | | | | | | | | | | | |
| | 15 | | | | | | | | | | | |
| | 16 | | | | | | | | | | | |
| | 17 | | | | | | | | | | | |
| | 18 | | | | | | | | | | | |

Conjugate stability in vivo in the rat. DAR values for conjugates purified from animals dosed at 9 mg/kg were compared to DAR values prior to in vivo exposure. Stability values above are expressed as % DAR remaining after given exposure period (shown in brackets).

TABLE 4

Conjugate Stability In Vitro in Mouse Plasma

Glutamine-Containing Tag on Trop2 Antibody

| | Ex. # | TG6 | H7C | H8A | H10 | H12C | H13A | H16 | L11B/C | LCQ04 | N297A | N297Q |
|---|---|---|---|---|---|---|---|---|---|---|---|---|
| ADC Structure | 8 | 51 (3 d) | 26 (3 d) | 18 (3 d) | 37 (3 d) | 96 (3 d) | 0 (3 d) | 99 (3 d) | 9/5 (3 d) | 66*, 75** (3 d) | 77 (3 d) | 96 (3 d) |
| | 9 | 88 (3 d) | | | | | | | | 90*, 97** (3 d) | | |
| | 10 | 64, 54 (3 d) 44, 34 (4.5 d) | 22 (4.5 d) | 6 (4.5 d) | 42, 42 (4.5 d) | | | 100 (4.5 d) | 4, 5 (4.5 d) | 88, 86 (4.5 d) | 89 (4.5 d) | 100 (4.5 d) |
| | 11 | 93, 94 (3 d) 92, 94 (4.5 d) | 85 (4.5 d) | 73 (4.5 d) | 92 (4.5 d) | | | 100 (4.5 d) | 65 (4.5 d) | 99 (4.5 d) | 100 (4.5 d) | |
| | 12 | 5 (3 d) | | | | | | | 0 (4.5 d) | 49 (4.5 d) | | |
| | 13 | 19 (3 d) | | | | | | | | 61 (4.5 d) | | |
| | 14 | 0 (3 d) | | | | | | | 0 (4.5 d) | 9 (4.5 d) | | |
| | 15 | 80 (3 d) | | | | | | | 6 (4.5 d) | 95 (4.5 d) | | |
| | 16 | 34 (3 d) | | | | | | | 0 (4.5 d) | 71 (4.5 d) | | |
| | 17 | 85 (3 d) 84 (4.5 d) | 86 (4.5 d) | 68 (4.5 d) | 90 (4.5 d) | | | 100 (4.5 d) | 67 (4.5 d) | 94 (4.5 d) | 95 (4.5 d) | |
| | 18 | 94 (3 d) 95 (4.5 d) | 88 (4.5 d) | 77 (4.5 d) | 91 (4.5 d) | | | 100 (4.5 d) | 61 (4.5 d) | 97 (4.5 d) | 100 (4.5 d) | |
| | 49 | 47 (4.5 d) | | | | | | | 17 (4.5 d) | | | |
| | 50 | 3 (4.5 d) | | | | | | | 0 (4.5 d) | | | |
| | 55 | | | | | | | | 4 (4.5 d) | | | |
| | 53 | | | | | | | | 84 (4.5 d) | | | |
| | 56 | | | | | | | | 57 (4.5 d) | | | |
| | 52 | | | | | | | | 60 (4.5 d) | | | |
| | 57 | | | | | | | | 81 (4.5 d) | | | |
| | 54 | | | | | | | | 34 (4.5 d) | | | |
| | 68 | | | | | | | | 5 (4.5 d) | | | |
| | 58 | | | | | | | | 2 (4.5 d) | | | |
| | 59 | | | | | | | | 50 (4.5 d) | | | |
| | 51 | | | | | | | | 5 (4.5 d) | | | |
| | 60 | | | | | | | | 58 (4.5 d) | | | |
| | 67 | | | | | | | | 44 (4.5 d) | | | |
| | 69 | | | | | | | | 51 (4.5 d) | | | |
| | 70 | | | | | | | | 20 (4.5 d) | | | |
| | 71 | | | | | | | | 0 (4.5 d) | | | |
| | 66 | | | | | | | | 90 (4.5 d) | | | |

TABLE 4-continued

Conjugate Stability In Vitro in Mouse Plasma

Glutamine-Containing Tag on Trop2 Antibody

| Ex. # | TG6 | H7C | H8A | H10 | H12C | H13A | H16 | L11B/C | LCQ04 | N297A | N297Q |
|---|---|---|---|---|---|---|---|---|---|---|---|
| 65 | | | | | | | | 82 (4.5 d) | | | |
| 62 | | | | | | | | 58 (4.5 d) | | | |
| 64 | | | | | | | | 85 (4.5 d) | | | |
| 61 | | | | | | | | 76 (4.5 d) | | | |
| 63 | | | | | | | | 49 (4.5 d) | | | |

Conjugate stability in vitro in the mouse plasma. DAR values for conjugates purified after plasma incubation were compared to DAR values prior to plasma treatment. Stability values above are expressed as % DAR remaining after given incubation period (shown in brackets).

TABLE 5

Conjugate Stability In Vitro in Rat Plasma

Glutamine-Containing Tag on Trop2 Antibody

| | Ex. # | TG6 | H7C | H8A | H10 | H12C | H13A | H16 | L11B/C | LCQ04 | N297A | N297Q |
|---|---|---|---|---|---|---|---|---|---|---|---|---|
| ADC Structure | 8 | | | | | | | | | | | |
| | 9 | | | | | | | | | | | |
| | 10 | 97 (4.5 d) | 97 (4.5 d) | 99 (4.5 d) | 97 (4.5 d) | | | 100 (4.5 d) | 94 (4.5 d) | 99 (4.5 d) | 100 (4.5 d) | 100 (4.5 d) |
| | 11 | 99 (4.5 d) | 98 (4.5 d) | 100 (4.5 d) | 98 (4.5 d) | | | 100 (4.5 d) | 96 (4.5 d) | 99 (4.5 d) | 100 (4.5 d) | |
| | 12 | | | | | | | | 75 (4.5 d) | 92, 100 (4.5 d) | | |
| | 13 | | | | | | | | | 95 (4.5 d) | | |
| | 14 | | | | | | | | 48 (4.5 d) | 91 (4.5 d) | | |
| | 15 | | | | | | | | 95 (4.5 d) | 98 (4.5 d) | | |
| | 16 | | | | | | | | 83 (4.5 d) | 96 (4.5 d) | | |
| | 17 | 96 (4.5 d) | 97 (4.5 d) | 93 (4.5 d) | 97 (4.5 d) | | | 100 (4.5 d) | 94 (4.5 d) | 95 (4.5 d) | 96 (4.5 d) | |
| | 18 | 99 (4.5 d) | 100 (4.5 d) | 98 (4.5 d) | 97 (4.5 d) | | | 100 (4.5 d) | 97 (4.5 d) | 98 (4.5 d) | 100 (4.5 d) | |

Conjugate stability in vitro in the rat plasma. DAR values for conjugates purified after plasma incubation were compared to DAR values prior to plasma treatment. Stability values above are expressed as % DAR remaining after given incubation period (shown in brackets).

TABLE 6

Conjugate stability In Vitro in Cyno Plasma

Glutamine-Containing Tag on Trop2 Antibody

| | Ex. # | TG6 | H7C | H8A | H10 | H12C | H13A | H16 | L11B/C | LCQ04 | N297A | N297Q |
|---|---|---|---|---|---|---|---|---|---|---|---|---|
| ADC Structure | 8 | | | | | | | | | | | |
| | 9 | | | | | | | | | | | |
| | 10 | 99 (4.5 d) | 98 (4.5 d) | 101 (4.5 d) | 97 (4.5 d) | | | 100 (4.5 d) | 99 (4.5 d) | 100 (4.5 d) | 99 (4.5 d) | 100 (4.5 d) |
| | 11 | 99 (4.5 d) | 99 (4.5 d) | 100 (4.5 d) | 99 (4.5 d) | | | 100 (4.5 d) | 97 (4.5 d) | 100 (4.5 d) | 100 (4.5 d) | |
| | 12 | | | | | | | | 95 (4.5 d) | 100 (4.5 d) | | |

TABLE 6-continued

Conjugate stability In Vitro in Cyno Plasma

Glutamine-Containing Tag on Trop2 Antibody

| Ex. # | TG6 | H7C | H8A | H10 | H12C | H13A | H16 | L11B/C | LCQ04 | N297A | N297Q |
|---|---|---|---|---|---|---|---|---|---|---|---|
| 13 | | | | | | | | | 102 (4.5 d) | | |
| 14 | | | | | | | | 95 (4.5 d) | 99 (?) (4.5 d) | | |
| 15 | | | | | | | | 98 (4.5 d) | 100 (4.5 d) | | |
| 16 | | | | | | | | 96 (4.5 d) | 99 (4.5 d) | | |
| 17 | 96 (4.5 d) | 95 (4.5 d) | 95 (4.5 d) | 98 (4.5 d) | | | 100 (4.5 d) | 95 (4.5 d) | 95 (4.5 d) | 94 (4.5 d) | |
| 18 | 99 (4.5 d) | 100 (4.5 d) | 100 (4.5 d) | 97 (4.5 d) | | | 100 (4.5 d) | 100 (4.5 d) | 99 (4.5 d) | 100 (4.5 d) | |

Conjugate stability in vitro in the cyno plasma. DAR values for conjugates purified after plasma incubation were compared to DAR values prior to plasma treatment. Stability values above are expressed as % DAR remaining after given incubation period (shown in brackets).

TABLE 7A

Experimental DAR Values with Calculated % Stability
All DAR values were determined by assessing the number of drugs attached to the antibody using HIC or mass spectrometry analysis. Conjugate stability is calculated as the % DAR remaining after incubation in plasma for 3 or 4.5 days.

| Trop-2 Antibody Attachment Position | Pay load (with linker) From Example # | DAR | DAR after plasma incubation for 3 to 4.5 days | Conjugate stability (%) |
|---|---|---|---|---|
| TG6 | 10 | 1.98 | 0.67 | 34 |
| TG6 | 9 | 1.97 | 1.80 | 92 |
| TG6 | 17 | 1.90 | 1.59 | 84 |
| TG6 | 18 | 1.97 | 1.88 | 95 |
| TG6 | 16 | 1.90 | 0.65 | 34 |
| TG6 | 14 | 1.38 | 0 | 0 |
| TG6 | 15 | 1.90 | 1.53 | 80 |
| TG6 | 12 | 1.41 | 0.08 | 5 |
| TG6 | 13 | 1.61 | 0.31 | 19 |
| H7C | 10 | 1.52 | 0.34 | 22 |
| H7C | 11 | 1.90 | 1.61 | 85 |
| H7C | 17 | 1.69 | 1.45 | 86 |
| H7C | 18 | 1.90 | 1.67 | 88 |
| H8A | 10 | 1.78 | 0.11 | 6 |
| H8A | 11 | 1.82 | 1.34 | 73 |
| H8A | 17 | 1.50 | 1.03 | 68 |
| H8A | 18 | 1.84 | 1.41 | 77 |
| H10 | 10 | 1.72 | 0.71 | 42 |
| H10 | 11 | 1.62 | 1.50 | 92 |
| H10 | 17 | 1.59 | 1.43 | 90 |
| H10 | 18 | 1.73 | 1.58 | 91 |
| H16 | 10 | 2.00 | 2.00 | 100 |
| L11B | 10 | 1.88 | 0.09 | 5 |
| L11B | 11 | 1.87 | 1.22 | 65 |
| L11B | 17 | 1.67 | 1.11 | 67 |
| L11B | 18 | 1.87 | 1.14 | 61 |
| LCQ04 | 10 | 1.90 | 1.63 | 86 |
| LCQ04 | 11 | 1.88 | 1.85 | 99 |
| LCQ04 | 17 | 1.68 | 1.57 | 94 |
| LCQ04 | 18 | 1.97 | 1.91 | 97 |
| LCQ04 | 16 | 1.87 | 1.34 | 71 |
| LCQ04 | 14 | 1.38 | 0.13 | 9 |
| LCQ04 | 15 | 1.93 | 1.83 | 95 |
| LCQ04 | 12 | 1.47 | 0.72 | 49 |
| LCQ04 | 13 | 1.31 | 0.79 | 61 |
| N297A | 10 | 1.89 | 1.64 | 87 |
| N297Q | 10 | 3.94 | 3.93 | 100 |

TABLE 7B

Additional Experimental DAR Values with Calculated % Stability
All DAR values were determined by assessing the number of drugs attached to the antibody using HIC or mass spectrometry analysis. Conjugate stability is calculated as the % DAR remaining after incubation in plasma for 3 or 4.5 days.

| Trop-2 Antibody Attachment Position | Linker-Payload Example # | DAR | DAR after plasma incubation for 3 to 4.5 days | Conjugate stability (%) |
|---|---|---|---|---|
| TG6 | 44 | 1.74 | 0.82 | 47 |
| TG6 | 45 | 1.42 | 0.04 | 3 |
| H16 | Ac-Lys-Val-Cit-PABC-0101* | 1.94 | 1.96 | 100 |
| H16 | 4 | 1.84 | 1.89 | 100 |
| H16 | 5 | 1.96 | 2.0 | 100 |
| L11B | 3 | 1.66 | 0 | 0 |
| L11B | 2 | 1.54 | 0 | 0 |
| L11B | 7 | 1.51 | 0 | 0 |
| L11B | 44 | 1.50 | 0.25 | 17 |
| L11B | 45 | 0.66 | 0 | 0 |
| L11B | 28 | 1.83 | 0.07 | 4 |
| L11B | 25 | 1.91 | 1.61 | 84 |
| L11B | 27 | 1.72 | 0.98 | 57 |
| L11B | 26 | 1.92 | 1.16 | 60 |
| L11B | 29 | 1.80 | 1.46 | 81 |
| L11B | 33 | 1.53 | 0.52 | 34 |
| L11B | 30 | 1.27 | 0.06 | 5 |
| L11B | 31 | 1.77 | 0.03 | 2 |
| L11B | 34 | 1.72 | 0.86 | 50 |
| L11B | 32 | 1.53 | 0.08 | 5 |
| L11B | 35 | 1.82 | 1.07 | 58 |
| L11B | 37 | 1.94 | 0.85 | 44 |
| L11B | 46 | 1.36 | 0.69 | 51 |
| L11B | 47 | 1.96 | 0.40 | 20 |
| L11B | 48 | 1.94 | 0 | 0 |

TABLE 7B-continued

Additional Experimental DAR Values with Calculated % Stability
All DAR values were determined by assessing the number of drugs attached to the antibody using HIC or mass spectrometry analysis. Conjugate stability is calculated as the % DAR remaining after incubation in plasma for 3 or 4.5 days.

| Trop-2 Antibody Attachment Position | Linker-Payload Example # | DAR | DAR after plasma incubation for 3 to 4.5 days | Conjugate stability (%) |
|---|---|---|---|---|
| L11B | 38 | 1.47 | 1.32 | 90 |
| L11B | 39 | 1.87 | 1.53 | 82 |
| L11B | 40 | 1.87 | 1.08 | 58 |
| L11B | 42 | 1.87 | 1.60 | 85 |
| L11B | 43 | 1.62 | 1.23 | 76 |
| L11B | 41 | 1.86 | 0.91 | 49 |

*Produced as described in WO2012/059882 and WO2015/015448.

TABLE 8

Additional Experimental DAR Values with Calculated % Stability, Linker-Payloads Conjugated to the Combo_Rd4_0.6nM_C29 Antibody with the LCQ05 Glutamine-Containing Tag
Conjugation methods were as described herein for anti-Trop2 antibodies. Combo_Rd4_0.6nM_C29 antibody is the anti-BCMA antibody as described in U.S. Provisional Pat. application No. 62/146,843. Following incubation in SCID mouse plasma, compounds were purified using MabSelect Protein A resin (GE Healthcare) according to standard methods. All DAR values were determined by assessing the number of drugs attached to the antibody using HIC analysis. Conjugate stability is calculated as the % DAR remaining after incubation in SCID mouse plasma for 4.5 days.

| Antibody Attachment Position | Payload (with linker) | DAR | DAR after plasma incubation for 4.5 days | Conjugate stability (%) |
|---|---|---|---|---|
| LCQ05 | Ac-Lys-Val-Cit-PABC-0101 | 2.0 | 1.98 | 99 |
| LCQ05 | 6835 vc0101 | 1.92 | 1.71 | 89 |
| LCQ05 | 1516 vc0101 | 1.94 | 1.90 | 98 |

Although the disclosed teachings have been described with reference to various applications, methods, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A compound of Formula (III):

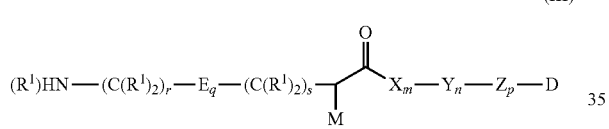

(III)

or a pharmaceutically acceptable salt or solvate thereof; wherein:

M is a stability modulator -$M^1$-$M^2$, where $M^1$ is —$NR^1$—C(O)—, —$NR^1$—S(O)$_2$—, or is absent, and $M^2$ is selected from the group consisting of:

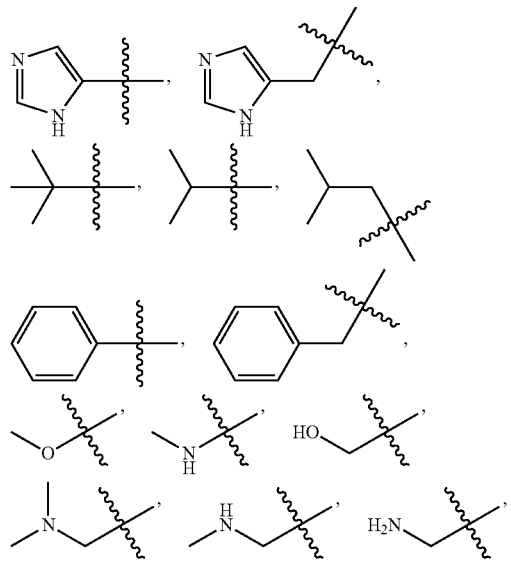

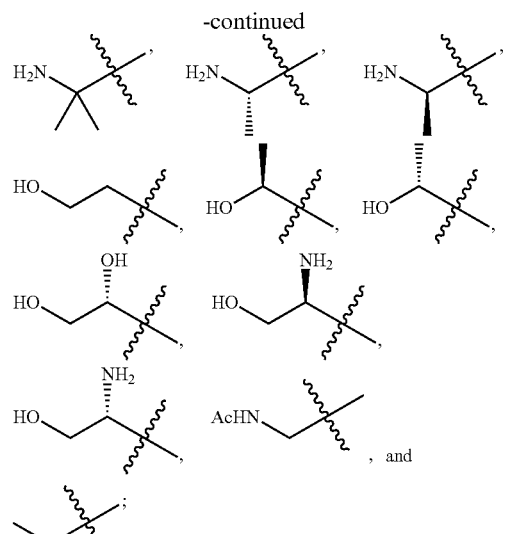

, and

;

each E is independently selected from the group consisting of: 1) —C($R^1$)$_2$—, 2) —O—C($R^1$)$_2$—C($R^1$)$_2$—, and 3) —C($R^1$)$_2$—C($R^1$)$_2$—O, wherein when E is —O—C($R^1$)$_2$—C($R^1$)$_2$, r is 2, and wherein when E is —C($R^1$)$_2$—C($R^1$)$_2$—O—, s is at least 1;

each $R^1$ is independently selected from the group consisting of: H, and $C_1$-$C_6$ straight or branched alkyl;

wherein —$X_m$—$Y_n$— is -X-Y- and where X-Y is selected from the group consisting of Gly, β-Ala, Val-Cit, Phe-Lys, Val-Lys, Phe-Phe-Lys, Ala-Lys, Phe-Cit, Leu-Cit, Ala-Cit, Trp-Cit, Phe-Ala, Gly-Phe-Leu-Gly (SEQ ID NO: 38), Ala-Leu-Ala-Leu (SEQ ID NO: 39), Phe-N9-tosyl-Arg, Phe-N9-Nitro-Arg, Val-Ala, and Ala-Ala-Asn;

each Z is PABC (p-aminobenzyl-carbamoyl);

p is 0-2, q is 0-10, r is 0-2, and s is 0-2, where q+r+s=2 or more; and

D is a cytotoxic agent.

2. A compound selected from the group consisting of:
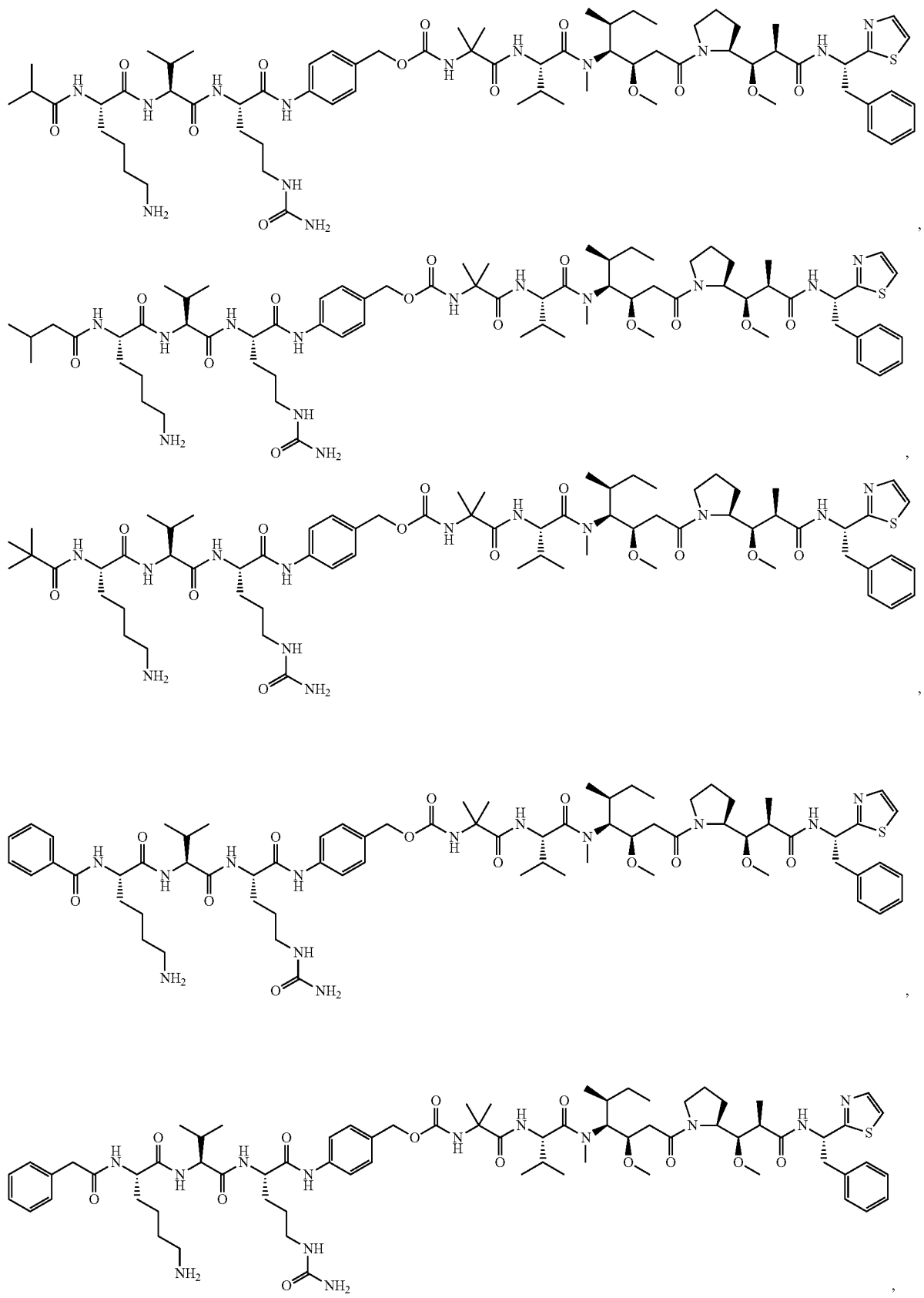

197 198
-continued
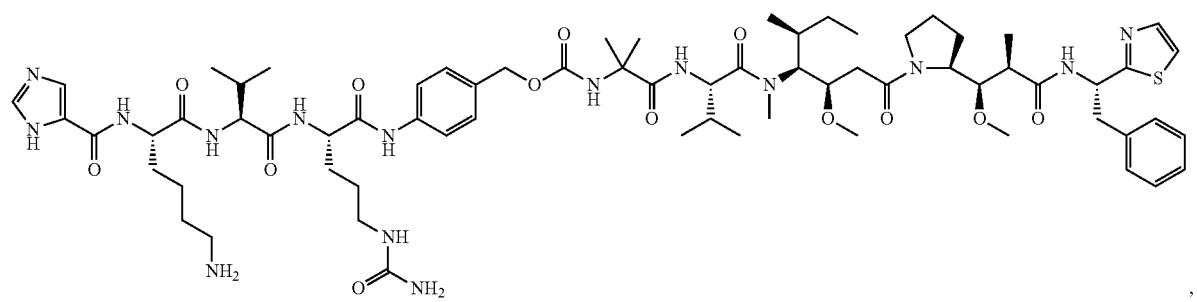
,
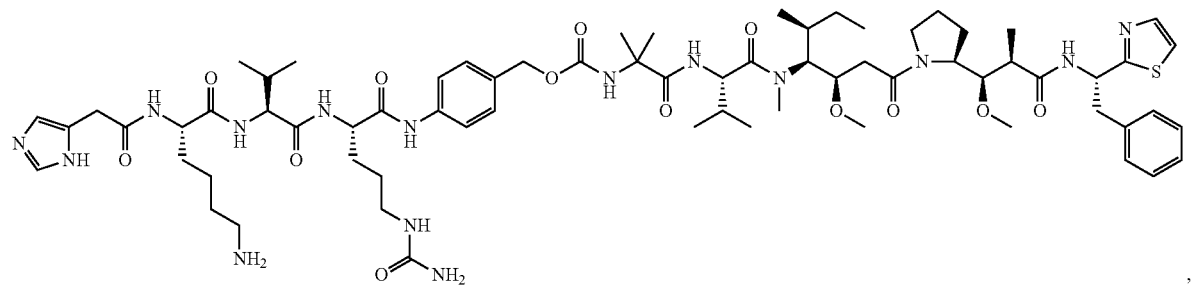
,
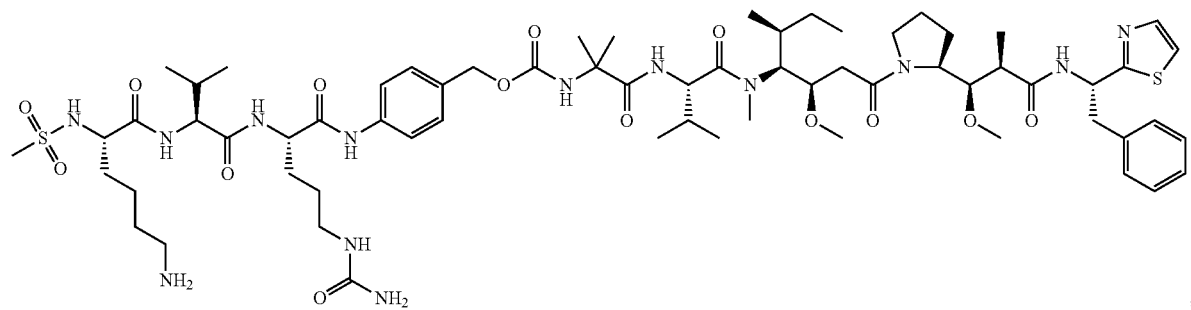
,
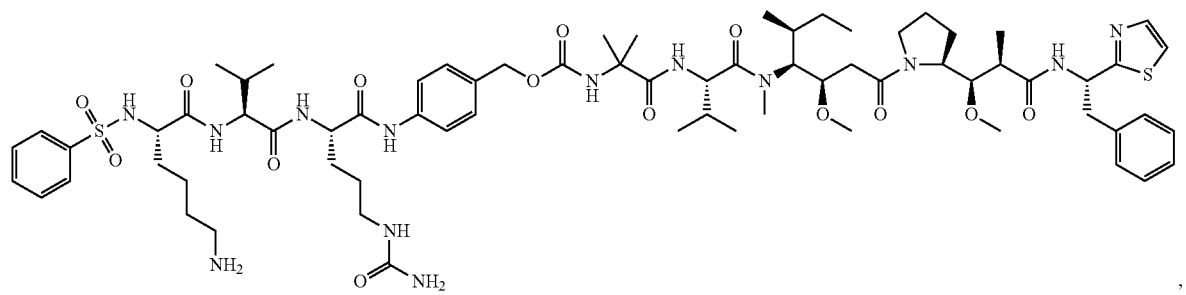
,
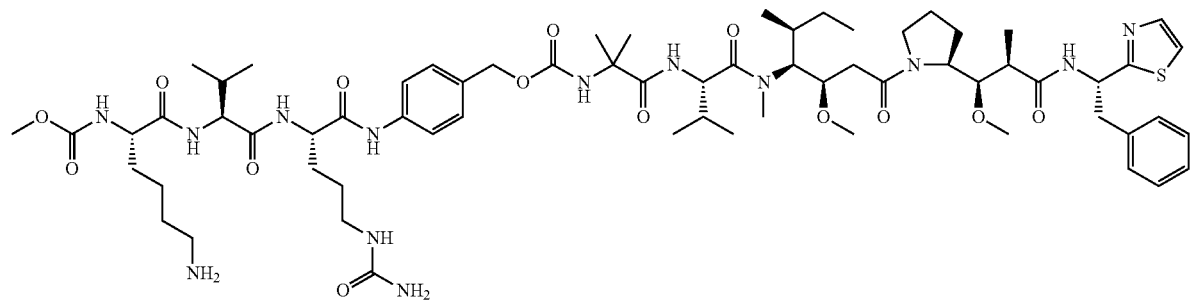
, -continued
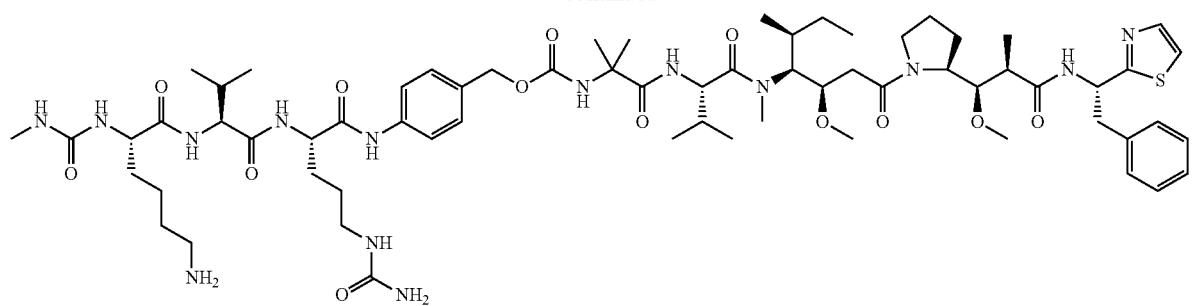
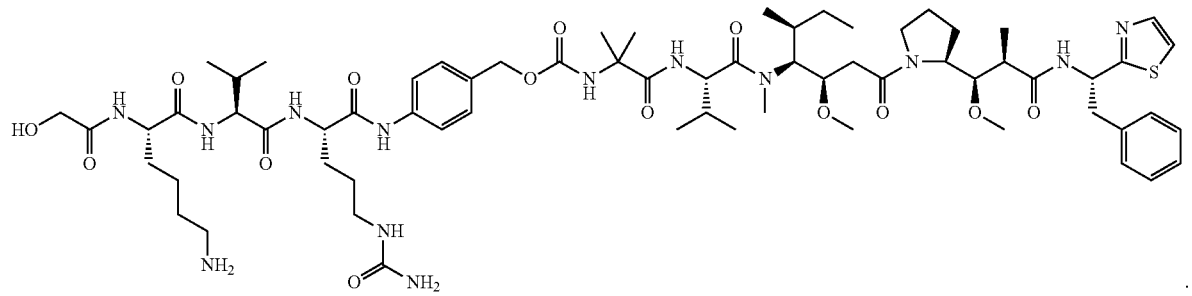
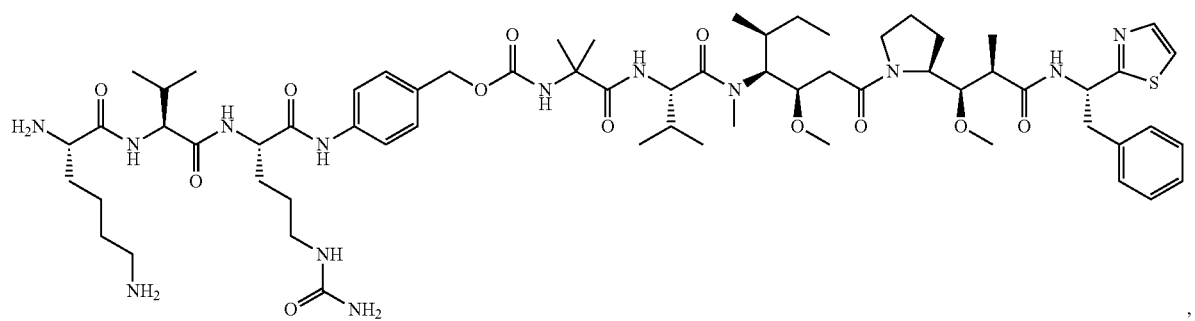
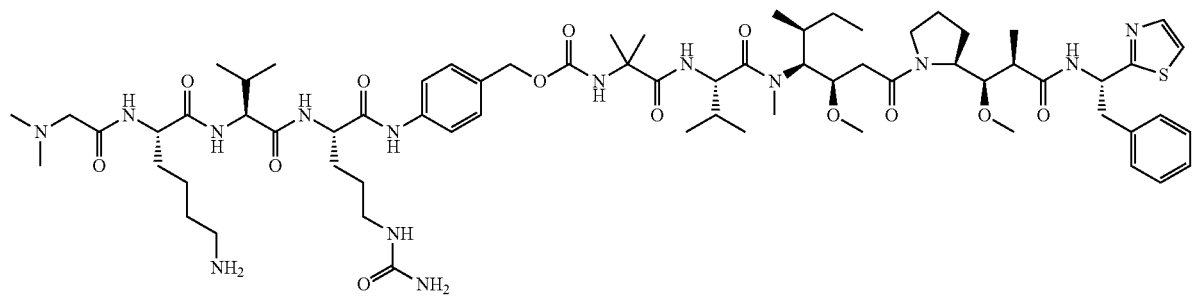
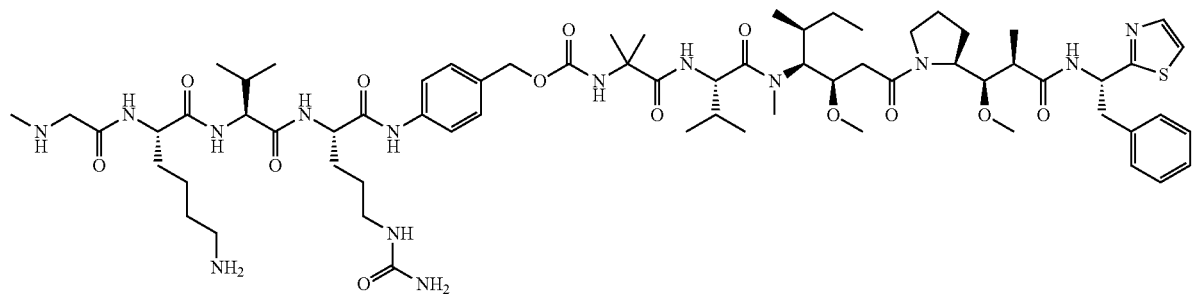

201 202
-continued
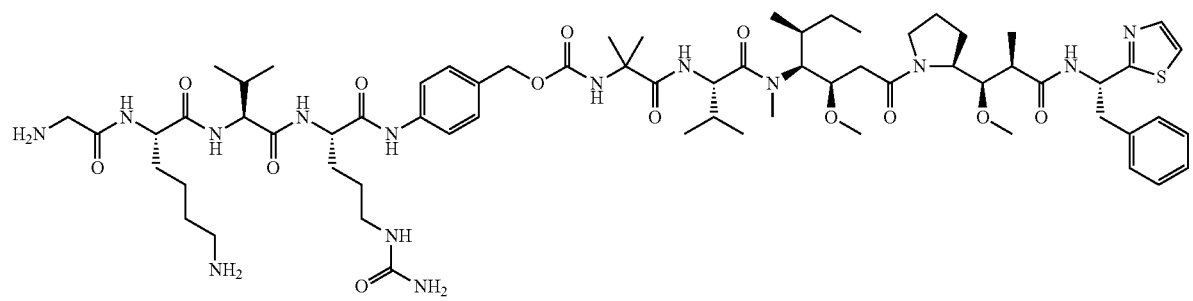
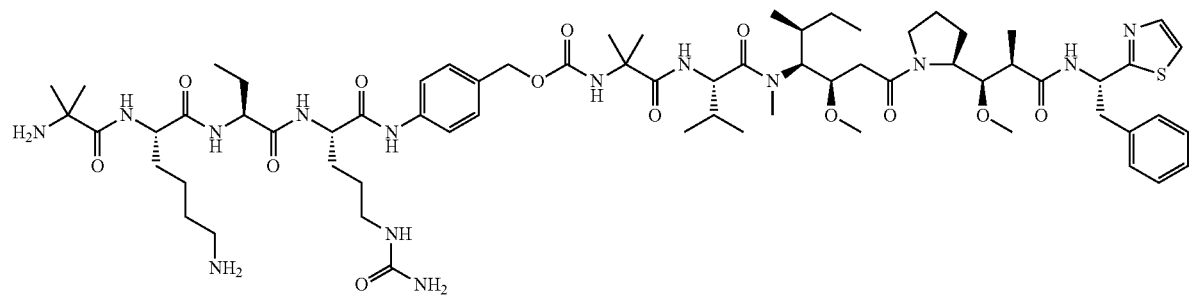
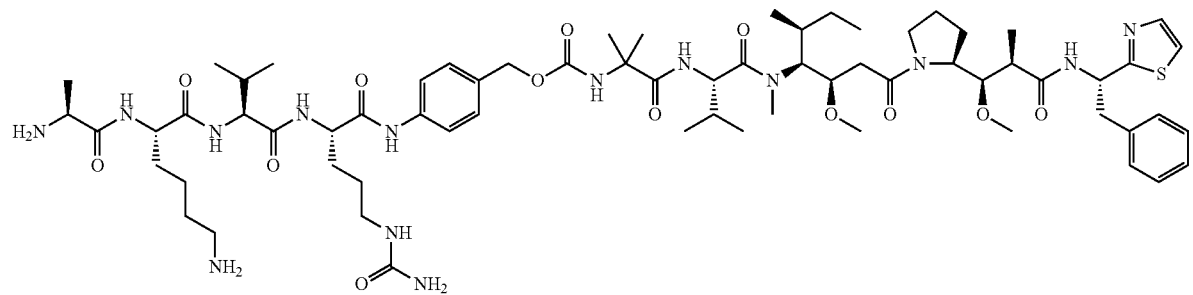
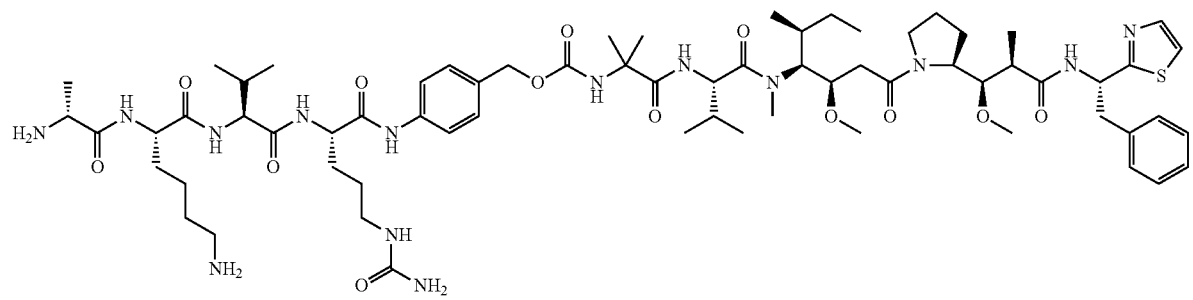
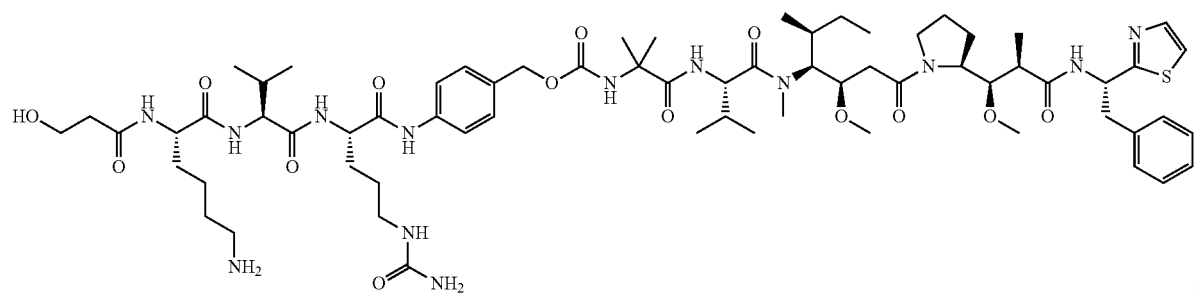

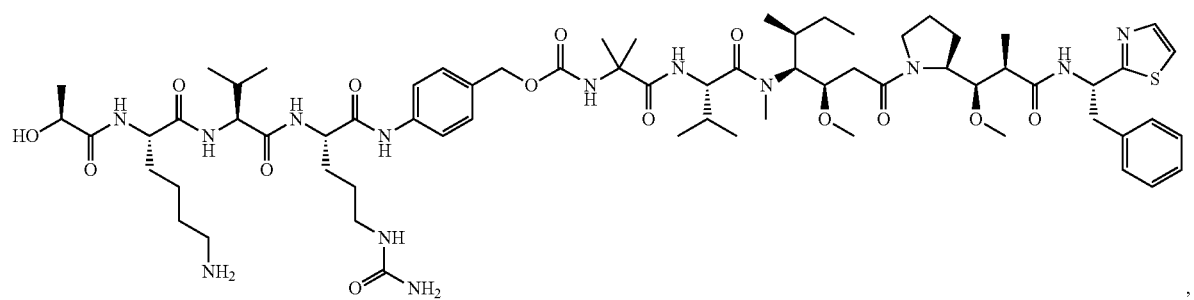
,
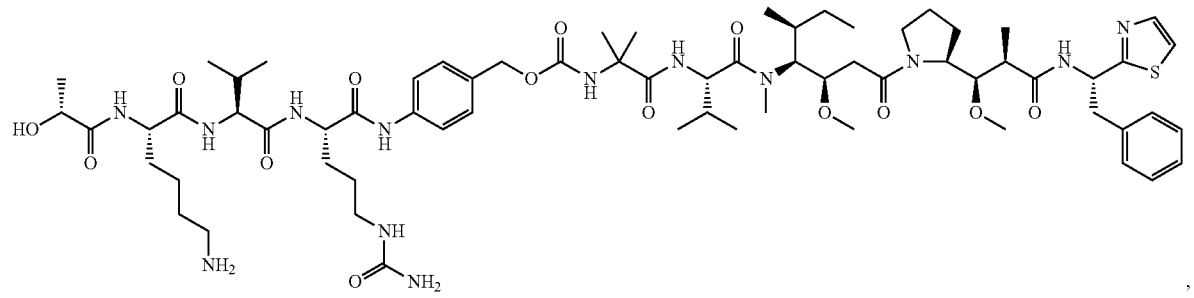
,
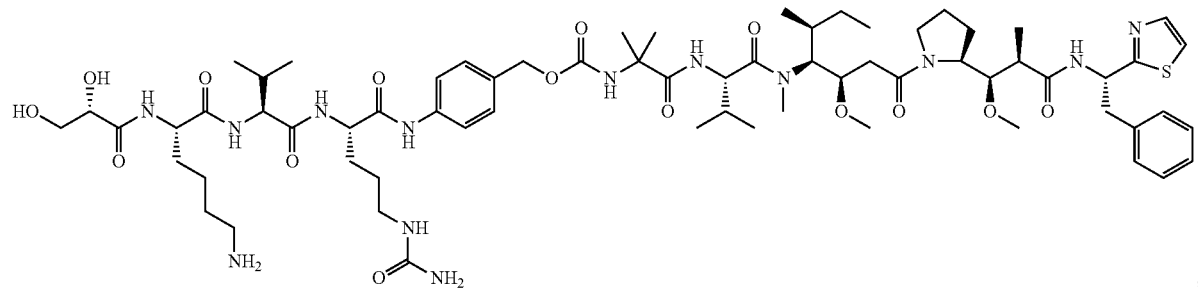
,
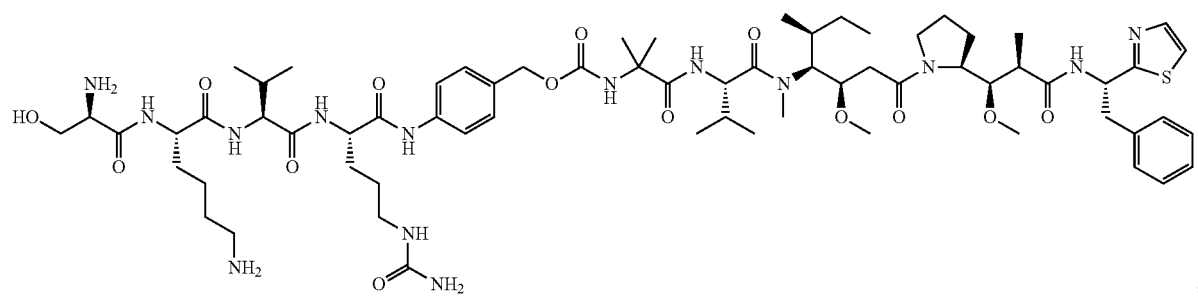
,
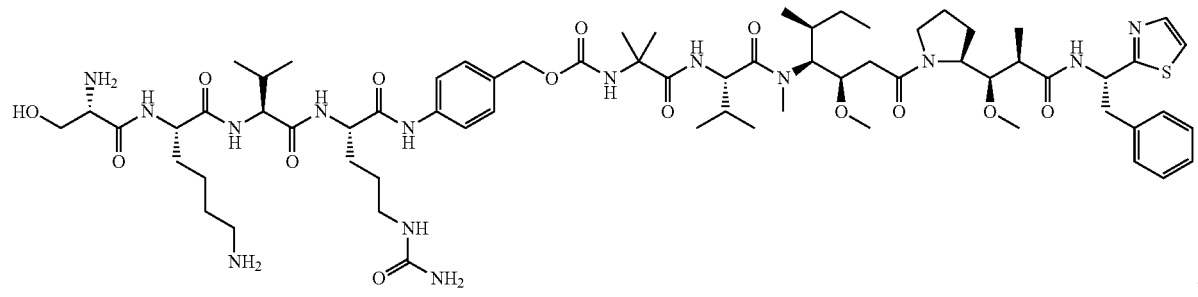
,

205
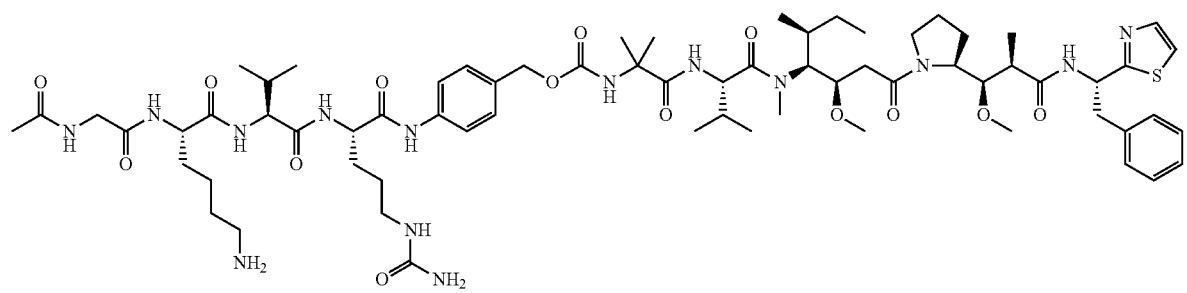
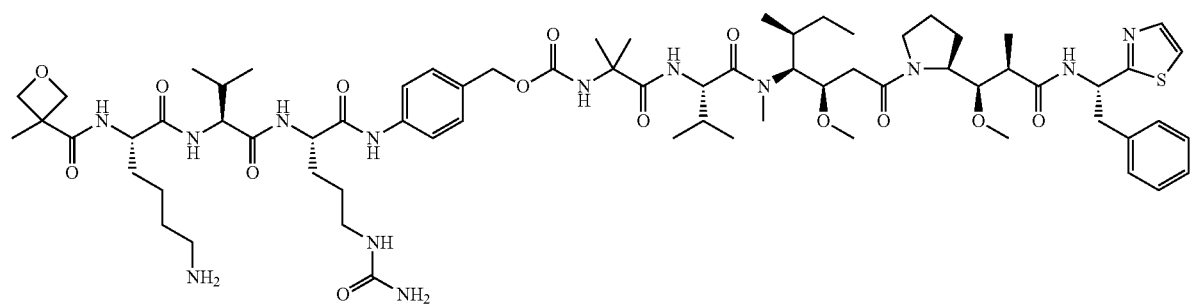
206
-continued
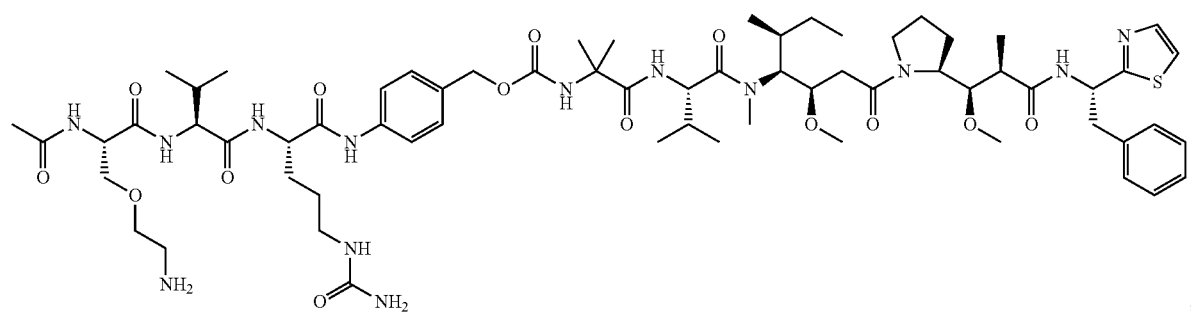
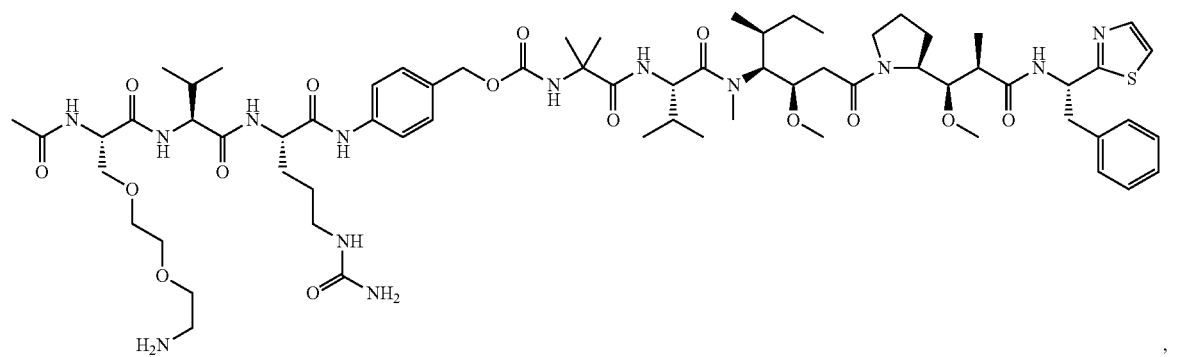
, and

-continued
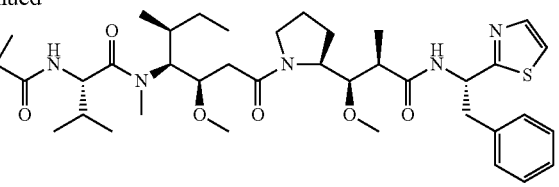
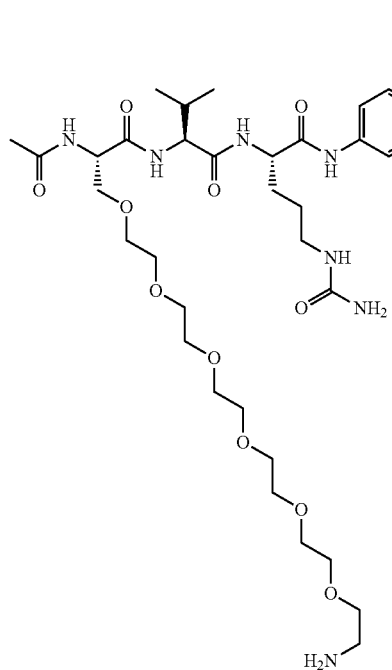
or a pharmaceutically acceptable salt or solvate thereof.
* * * * *